United States Patent [19]

Kanda et al.

[11] Patent Number: 5,733,924

[45] Date of Patent: Mar. 31, 1998

[54] DC 107 DERIVATIVES AND TREATMENT METHODS

[75] Inventors: Yutaka Kanda; Yutaka Saitoh, both of Tokyo; Hiromitsu Saito, Kanagawa; Tadashi Ashizawa, Shizuoka; Kazuyo Sugiyama, Shizuoka; Katsushige Gomi, Shizuoka; Shingo Kakita, Tokyo; Yuichi Takahashi, Shizuoka; Chikara Murakata, Shizuoka, all of Japan

[73] Assignee: Kyowa Hakko Kogyo Co., Ltd., Tokyo, Japan

[21] Appl. No.: 776,938

[22] PCT Filed: Jun. 14, 1996

[86] PCT No.: PCT/JP96/01646

§ 371 Date: Apr. 17, 1997

§ 102(e) Date: Apr. 17, 1997

[87] PCT Pub. No.: WO97/00260

PCT Pub. Date: Mar. 1, 1997

[30] Foreign Application Priority Data

Jun. 16, 1995 [JP] Japan ................... 7-150141

[51] Int. Cl.⁶ ...................................... A61K 37/00
[52] U.S. Cl. .................. 514/431; 540/450; 540/451; 540/467; 540/471; 540/472; 540/473; 540/476; 540/477; 540/482; 549/1; 549/9; 549/10; 514/1; 514/23; 514/183; 514/430; 514/461; 514/471; 514/473; 514/478; 514/480
[58] Field of Search ................... 540/450, 451, 540/467, 471, 472, 473, 476, 477, 482; 549/1, 9, 10; 514/1, 23, 183, 430, 431, 461, 471, 473, 478, 480

[56] References Cited

U.S. PATENT DOCUMENTS 4,999,196  3/1991  Nakano et al. ................... 424/116

FOREIGN PATENT DOCUMENTS 0300294  1/1989  European Pat. Off. .

OTHER PUBLICATIONS

Chemical Abstracts, vol. 112, No. 11 (Mar. 12, 1990) 96887z.

Hara et al., J. Antibiot., vol. 42, No. 12 (1989) 1768-74.

*Primary Examiner*—Ardin H. Marschel
*Attorney, Agent, or Firm*—Fitzpatrick, Cella, Harper & Scinto

[57] ABSTRACT

DC107 derivatives represented by the formula (I):

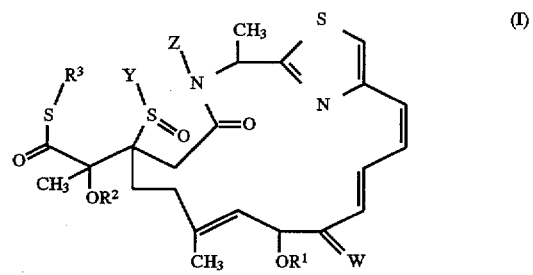

or pharmacologically acceptable slats thereof, [wherein $R^1$ is hydrogen, lower alkoxyalkyl, aralkyloxyalkyl, lower alkoxyalkoxyalkyl, lower alkoxyalkoxyalkoxyalkyl, aralkyl, tetrahydropyranyl, $COR^4$ or the like; $R^2$ represents hydrogen or $COR^5$; $R^3$ represents lower alkyl, lower alkenyl, aralkyl which may be substituted with substituted or unsubstituted aryl, lower alkoxyalkyl, aralkyloxyalkyl, substituted or unsubstituted aryloxyalkyl, lower alkoxycarbonylalkyl, lower alkanoyloxyalkyl, alicyclic alkanoyloxyalkyl or the like, or bonds to Y to represent a single bond; Y bonds to $R^3$ to represent a single bond, or bonds to Z to represent a single bond; Z represents hydrogen or bonds to Y to represent a single bond; W represents oxygen or $NR^6$, with the proviso that the compound wherein $R^1$, $R^2$ and Z each represents hydrogen, $R^3$ bonds to Y to represent a single bond, and W represents oxygen (DC107) is excluded.]

14 Claims, No Drawings

DC 107 DERIVATIVES AND TREATMENT METHODS

TECHNICAL FIELD

This invention relates to novel DC107 derivatives having an antibacterial activity and an antitumor activity.

BACKGROUND ART

DC107 (leinamycin) is a compound produced by a microorganism belonging to the genus Streptomyces and disclosed in Japanese Published Unexamined Patent Application No. 112988/89. DC107 exhibits an antibacterial activity against various bacteria and also an antitumor activity and has a chemical structure represented by the formula (I) described below wherein $R^1$, $R^2$ and Z each represents a hydrogen atom, $R^3$ bonds to Y to represent a single bond, and W represents an oxygen atom.

DISCLOSURE OF THE INVENTION

The present invention relates to the DC107 derivatives represented by the formula (I):

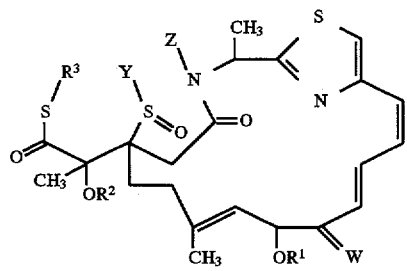

or pharmacologically acceptable salts thereof, wherein $R^1$ represents hydrogen, a lower alkoxyalkyl group, an aralkyloxyalkyl group, a lower alkoxyalkoxyalkyl group, a lower alkoxyalkoxyalkoxyalkyl group, an aralkyl group, a tetrahydropyranyl group,

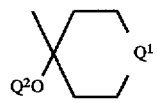

{wherein $Q^1$ represents $CH_2$, O, S, SO, $SO_2$ or N—$Q^3$ (wherein $Q^3$ represents a substituted or unsubstituted aryl group or a lower alkoxycarbonyl group), and $Q^2$ represents a lower alkyl group}, $COR^4$ [wherein $R^4$ represents an alkyl group, an alicyclic alkyl group, an aralkyl group, a substituted or unsubstituted aryl group, a substituted or unsubstituted heterocyclic group, a lower alkoxy group, an alicyclic alkoxy group, a 9-fluorenylmethoxy, an aralkyloxy group, a substituted or unsubstituted aryloxy group, $(CH_2)_m R^{4A}$ <wherein m represents an integer of from 1 to 6, $R^{4A}$ represents hydroxy, a lower alkoxy group, a carboxyl group, a lower alkoxycarbonyl group, a substituted or unsubstituted aryl group, a substituted or unsubstituted heterocyclic group, a substituted or unsubstituted aralkyloxy group, $NR^{4B}COR^{4C}$ {wherein $R^{4B}$ represents hydrogen or a lower alkyl group, and $R^{4C}$ represents hydrogen, a lower alkyl group, a lower alkoxy group, an aralkyloxy group, an aryl group, an aryloxy group, a 9-fluorenylmethoxy group, $(CH_2)_n NHCOR^{4D}$ (wherein n represents an integer of from 1 to 6, $R^{4D}$ represents an alkyl group, a lower alkoxy group, an aralkyloxy group, an aryl group, an aryloxy group or a 9-fluorenylmethyloxy group) or $CHR^{4E}NHCOR^{4F}$ (wherein $R^{4E}$ represents a lower alkyl group or a hydroxy lower alkyl group, and $R^{4F}$ has the same meaning as $R^{4D}$)}> or $CHR^{4G}NHCOR^{4H}$ (wherein $R^{4G}$ has the same meaning as $R^{4E}$, and $R^{4H}$ has the same meaning as $R^{4C}$)]; $R^2$ represents hydrogen or $COR^5$ (wherein $R^5$ represents a lower alkyl group, an aralkyl group, a substituted or unsubstituted aryl group or a substituted or unsubstituted heterocyclic group); $R^3$ represents a lower alkyl group, a lower alkenyl group, a substituted or unsubstituted aralkyl group in which aryl may be substituted, a lower alkoxyalkyl group, an aralkyloxyalkyl group, a substituted or unsubstituted aryloxyalkyl group, a lower alkoxycarbonylalkyl group, a lower alkanoyloxyalkyl group, an alicyclic alkanoyloxyalkyl group or

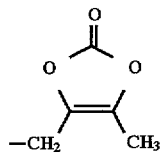

or $R^3$ bonds to Y to represent a single bond; Y bonds to $R^3$ to represent a single bond or bonds to Z to represent a single bond; Z represents hydrogen or bonds to Y to represent a single bond; W represents oxygen or $NR^6$ (wherein $R^6$ represents a hydroxyl group, a lower alkoxy group, a lower alkenyloxy group, an aralkyloxy group, a substituted or unsubstituted arylsulfonylamino group or a lower alkoxycarbonylamino group), with the proviso that the compound wherein $R^1$, $R^2$ and Z each represents hydrogen, $R^3$ bonds to Y to represent a single bond, and W represents oxygen (DC107) is excluded.

In the present invention, the compounds represented by the formula (I) above are hereinafter referred to as compound (I). Other formula numbers are also applied to the corresponding compounds in the same manner.

In the definition of each of the groups in the formula (I), the alkyl group includes a straight chain or branched chain alkyl group having from 1 to 20 carbon atoms, for example, methyl, ethyl, propyl, isopropyl, butyl, isobutyl, sec-butyl, tert-butyl, pentyl, isopentyl, hexyl, heptyl, octyl, nonyl, decyl, undecyl, dodecyl, pentadecyl and the like. The alkyl group contained in the lower alkoxyalkyl group, the aralkyloxyalkyl group, the lower alkoxyalkoxyalkyl group, the lower alkoxyalkoxyalkoxyalkyl group, the lower alkoxycarbonylalkyl group, the substituted or unsubstituted aryloxyalkyl group, the lower alkanoyloxyalkyl group and the alicyclic alkanoyloxyalkyl group has the same meaning as the above-described alkyl group. The alicyclic alkyl group includes those having from 3 to 8 carbon atoms, for example, cyclopropyl, cyclobutyl, cyclopentyl, cyclohexyl, cycloheptyl, cyclooctyl and the like. The alicyclic alkyl group contained in the alicyclic alkoxy group and the alicyclic alkanoyloxyalkyl group has the same meaning as the above-described alicyclic alkyl group.

The lower alkyl group represents the above-described alkyl group in which the group has from 1 to 8 carbon atoms. The lower alkyl group contained in the lower alkoxy group, the lower alkoxyalkyl group, the lower alkoxyalkoxyalkyl group, the lower alkoxyalkoxyalkoxyalkyl group, the lower alkoxycarbonyl group, the hydroxy lower alkyl group, the lower alkoxycarbonylalkyl group, the lower alkanoyloxyalkyl group and the lower alkoxycarbonylamino group has the same meaning as the above-described lower alkyl group.

The lower alkenyl group and the lower alkenyl moiety in the lower alkenyloxy group include a straight chain or branched group having from 3 to 6 carbon atoms, for example, allyl, crotyl, prenyl and the like.

The aralkyl group and the aralkyl moiety in the aralkyloxy group and the aralkyloxyalkyl group include those having from 7 to 15 carbon atoms, for example, benzyl, phenethyl, benzhydryl, naphthylmethyl and the like.

The aryl group and the aryl moiety in the aryloxy group, the aryloxyalkyl group and the arylsulfonylamino group include phenyl, naphthyl and the like.

The heterocyclic group represents a 3-membered to 8-membered aliphatic or aromatic group which is composed of cyclic compound containing at least one hetero atom selected from oxygen, sulfur, nitrogen and the like, or a condensed cyclic compound group in which said cyclic compound group is condensed with the same or a different cyclic compound or a benzene ring, and preferred examples include a 5-membered or 6-membered nitrogen-containing aromatic heterocyclic group such as imidazolyl, pyridyl, indolyl, quinolyl, isoquinolyl, quinoxalinyl, quinazolinyl and the like, or a 5-membered or 6-membered nitrogen-containing alicyclic heterocyclic group such as pyrrolidinyl, oxopyrrolidinyl, piperidinyl, piperidino, piperadinyl, morpholino, thiomorpholino, homopiperidinyl, homopiperadinyl, tetrahydropyridinyl and the like.

Substituents on the aryl group, the aryloxy group, the aralkyl group, the aralkyloxy group, the aryloxyalkyl group, the arylsulfonylamino group and the heterocyclic group are the same or different and include, for example, from 1 to 3 substituents selected from halogen, nitro, lower alkyl, hydroxyl, lower alkoxy, lower aroyloxy, lower alkoxycarbonyl, N,N-di-lower alkylcarbamoyloxy, N-acetylhexahydroisonicotinyloxy and the like. In the substituents, the halogen includes fluorine, chlorine, bromine and iodine, and the lower alkyl and the lower alkyl moiety contained in the lower alkoxy, the lower aroyloxy, the lower alkoxycarbonyl and the di-lower alkylcarbamoyloxy have the same meanings as the above-described lower alkyl.

The pharmacologically acceptable salts of the compounds (I) include, for example, acid addition salts such as hydrochloride, hydrobromide, sulfate, formate, acetate, benzoate, maleate, fumarate, succinate, tartarate, citrate, oxalate, methanesulfonate, p-toluenesulfonate, aspartate, glutamate and the like.

Processes for preparing the compounds (I) are described hereinafter.

Preparation Process 1

Of the compounds (I), the compound (I) wherein $R^1$ is a group other than hydrogen, $R^2$ and Z each is hydrogen, $R^3$ bonds to Y to represent a single bond, and W is oxygen is referred to as compound (Ia), the compound (I) wherein $R^1$ and $R^2$ are groups other than hydrogen, Z is hydrogen, $R^3$ bonds to Y to represent a single bond, and W is oxygen is referred to as compound (Ib), the compound (I) wherein $R^1$ and $R^2$ each is hydrogen, Y bonds to Z to represent a single bond, and W is oxygen is referred to as compound (Ic), the compound (I) wherein $R^2$ is hydrogen, $R^1$ is a group other than hydrogen, Y bonds to Z to represent a single bond, and W is oxygen is referred to as compound (Id), and the compound (I) wherein $R^1$ and $R^2$ each is a group other than hydrogen, Y bonds to Z to represent a single bond, and W is oxygen is referred to as compound (Ie). These compounds (I) wherein W is oxygen can be prepared, for example, from DC107 as a starting material via the following synthetic route:

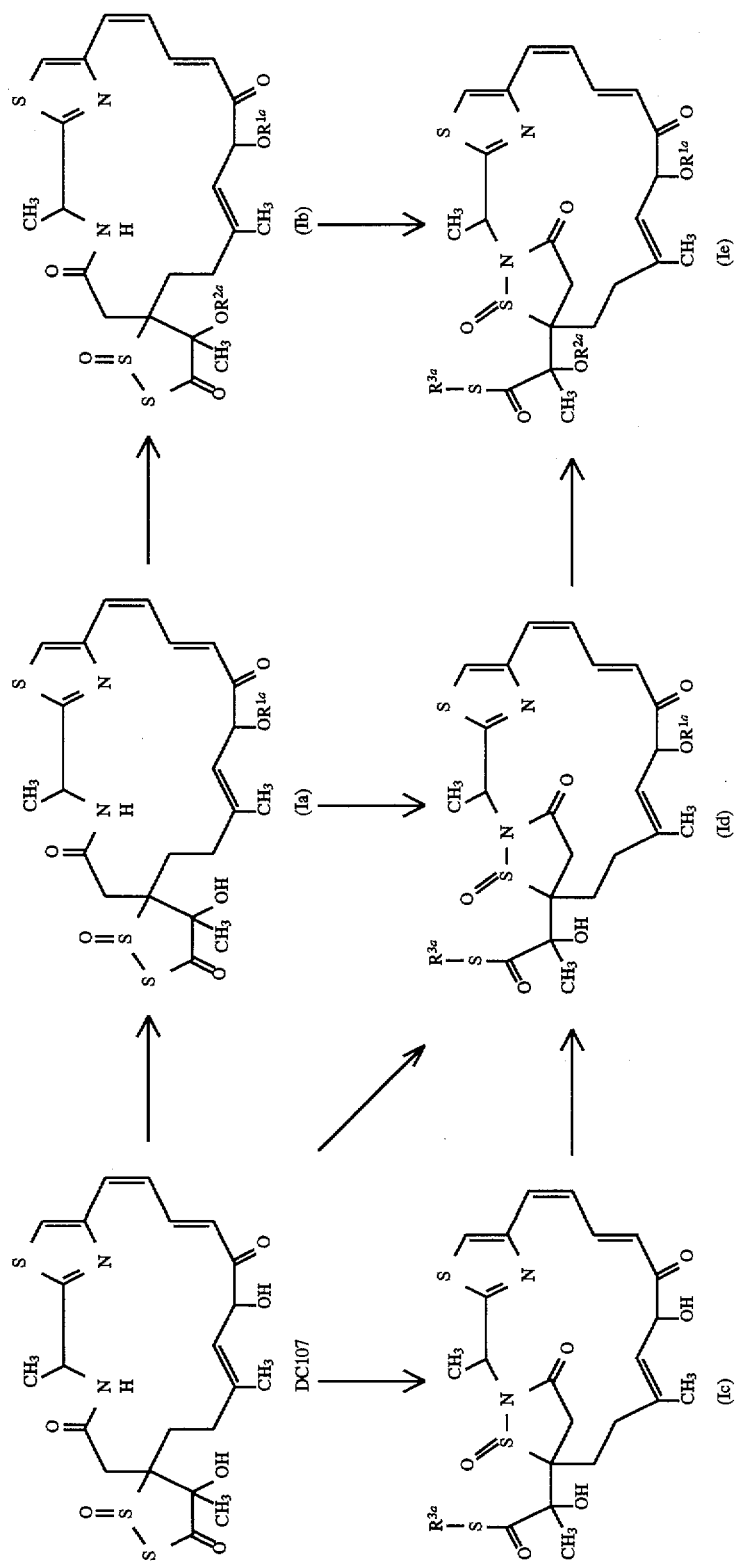

{wherein R¹ᵃ represents a group defined as the above-described R¹ excluding hydrogen, R²ᵃ represents COR⁵ (wherein R⁵ has the same meaning as defined above), R³ᵃ represents a lower alkyl group, a lower alkenyl group, a substituted or unsubstituted aralkyl group in which aryl may be substituted, a lower alkoxyalkyl group, an aralkyloxyalkyl group, a substituted or unsubstituted aryloxyalkyl group, a lower alkoxycarbonylalkyl group, a lower alkanoyloxyalkyl group, an alicyclic alkanoyloxyalkyl group or

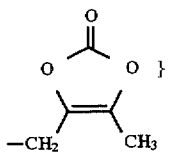

}

Compounds (Ia), (Ib), (Ic), (Id) and (Ie) can be prepared by, for example, the following steps based on the above-described synthetic route, depending upon the type of R¹ᵃ, R²ᵃ and R³ᵃ.

Step 1

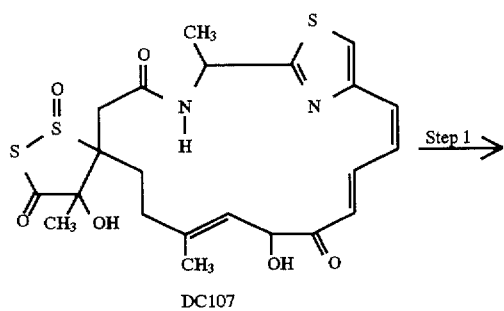

DC107

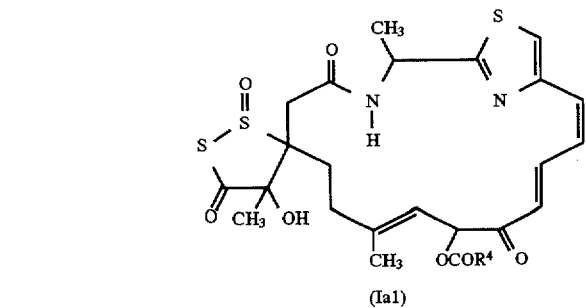

(Ia1)

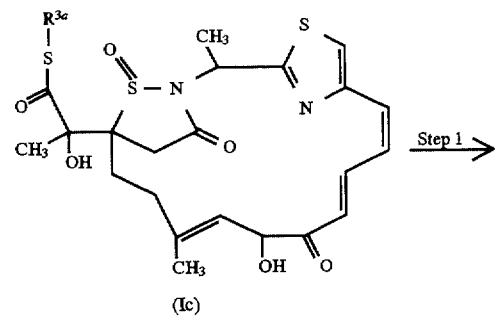

(Ic)

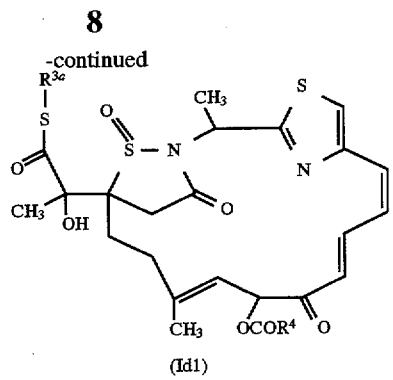

(Id1)

(wherein R³ᵃ and R⁴ have the same meanings as defined above.)

Of the compounds (Ia) or (Id), the compound (Ia1) or (Id1) wherein R¹ represents COR⁴ (wherein R⁴ has the same meaning as defined above) can be obtained by reacting DC107, which is disclosed in Japanese Published Unexamined Patent Application No. 112988/89 or compound (Ic) with the compound (II) represented by the following formula:

$$(R^4CO)_2O \quad (II)$$

(wherein R⁴ has the same meaning as defined above) or the compound (III) represented by the following formula:

$$R^4COX \quad (III)$$

(wherein R⁴ has the same meaning as defined above and X represents chlorine, bromine or iodine) in a solvent which is inert to the reaction and in the presence of a base. In the above reaction, when DC107 is used, the compound (Ia1) is produced and, when the compound (Ic) is used, the compound (Id1) is produced. The compound (II) or the compound (III) is generally used in an amount of one equivalent or more, preferably from 1 to 100 equivalents, to DC107 or the compound (Ic).

The solvent used in the reaction may be any solvent which is inert to the reaction, and examples thereof include chloroform, dichloromethane, ether, tetrahydrofuran, acetone, dimethylformamide and acetonitrile which can be used singly or as a mixture thereof. As the base, for example, pyridine, triethylamine or diisopropylethylamine may be used singly or as a mixture thereof, and the reaction can be promoted by further adding dimethylaminopyridine, etc. to the reaction system in an amount of from 0.1 to 2 equivalents. The base is generally used in an amount of one equivalent or more, preferably from 1 to 200 equivalents, to DC107 or the compound (Ic). The reaction is generally completed within from 5 minutes to 24 hours at a reaction temperature in the range of from −20° to 50° C.

Step 2

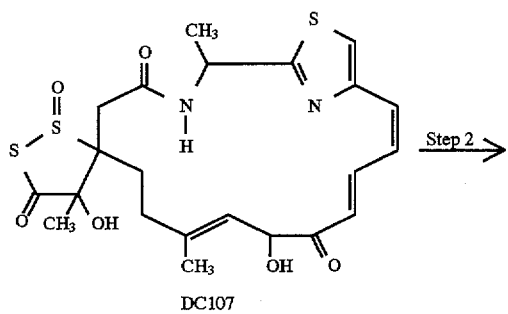

DC107

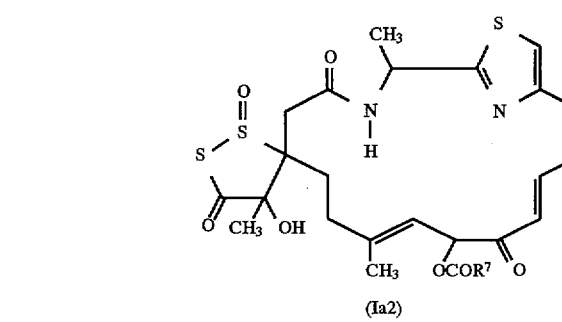

(Ia2)

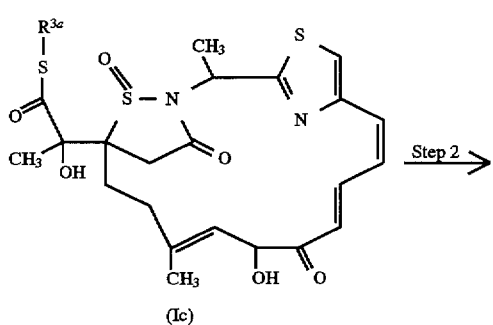

(Ic)

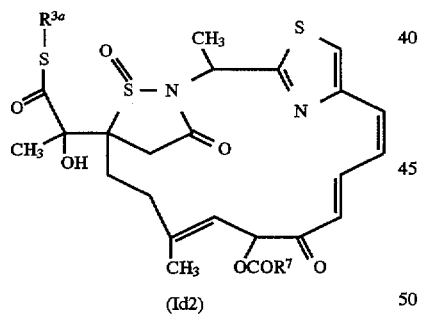

(Id2)

(wherein $R^{3a}$ has the same meaning as defined above, and $R^7$ represents a group defined as the above-described $R^4$ excluding a lower alkoxy group, an alicyclic alkoxy group, a 9-fluorenylmethoxy group, an aralkyloxy group and a substituted or unsubstituted aryloxy group.)

Of the compounds (Ia) or (Id), the compound (Ia2) or (Id2) wherein $R^{1a}$ represents $COR^7$ (wherein $R^7$ has the same meaning as defined above) can also be prepared by reacting DC107 or the compound (Ic) with the compound (IV) represented by the following formula:

$R^7CO_2H$          (IV)

(wherein $R^7$ has the same meaning as defined above) in an inert solvent in the presence of a condensing agent. The solvent used in the reaction may be any of the above-described inert solvents, but chloroform and dichloromethane are preferred. The condensing agent may be any of those generally used for the condensation of a carboxylic acid and an alcohol, for example, dicyclohexylcarbodiimide, 1-ethyl-3-(3-dimethylaminopropyl)carbodiimide hydrochloride and the like, and dimethylaminopyridine and the like can be further added to the reaction system in an amount of from 0.1 to 10 equivalents. The compound (IV) and the condensing agent are generally used in an amount of from 1 to 100 equivalents to DC107 or the compound (Ic). The reaction is generally completed within from 10 minutes to 24 hours at a reaction temperature of from 0° to 30° C.

Step 3

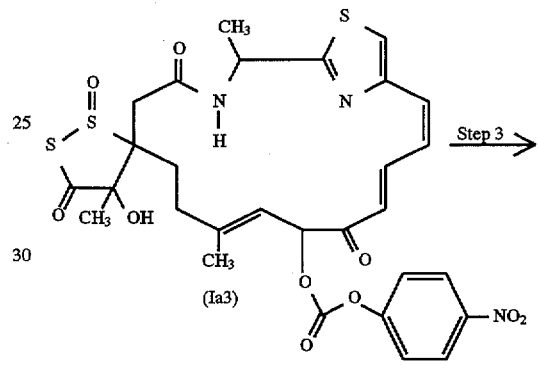

(Ia3)

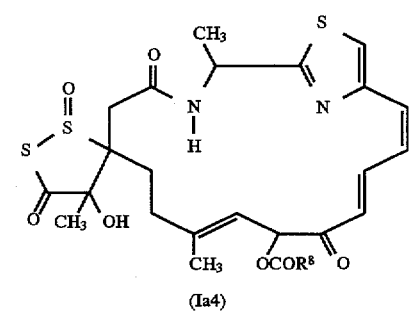

(Ia4)

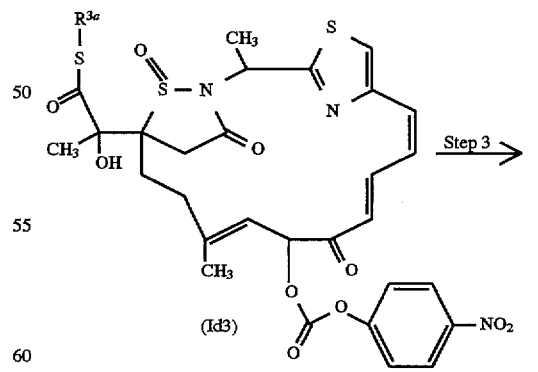

(Id3)

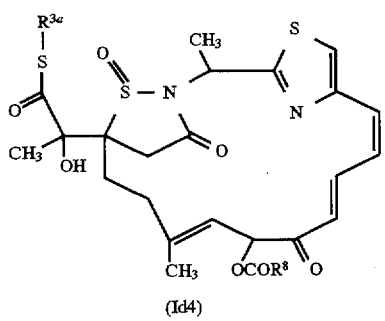

(Id4)

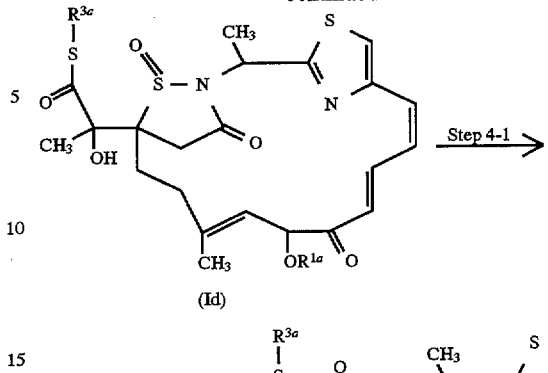

(Id)

(wherein $R^{3a}$ has the same meaning as defined above, and $R^8$ represents a nitrogen-containing alicyclic heterocyclic group.)

Of the compounds (Ia) or (Id), the compound (Ia4) or (Id4) wherein $R^{1a}$ represents $COR^8$ (wherein $R^8$ has the same meaning as defined above) can be prepared by reacting the compound (Ia3) or the compound (Id3) wherein $R^{1a}$ is p-nitrophenyloxycarbonyl with a nitrogen-containing alicyclic heterocyclic group in an inert solvent. The solvent used for the reaction may be any of the above-described inert solvents, but chloroform and dichloromethane are preferably used. The nitrogen-containing alicyclic heterocyclic group is generally used in an amount of from 1 to 10 equivalents. The reaction is generally completed within from 10 minutes to 24 hours at a reaction temperature of from 0° to 30° C.

Step 4-1

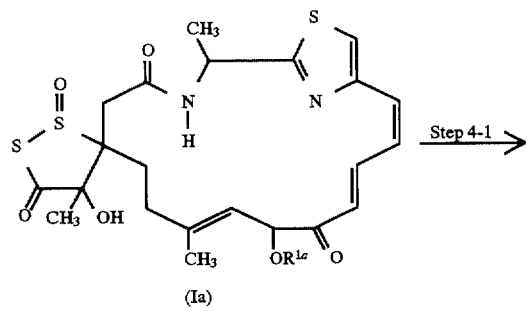

(Ia)

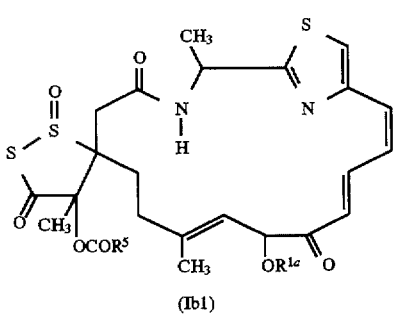

(Ib1)

(Ie1)

(wherein $R^{1a}$, $R^{3a}$ and $R^5$ have the same meanings as defined above.)

The compound (Ib1) or the compound (Ie1) can be prepared by reacting the compound (Ia) or (Id) with the compound (V) represented by the following formula:

$$(R^5CO)_2O \qquad (V)$$

(wherein $R^5$ has the same meaning as defined above) or the compound (VI) represented by the following formula:

$$R^5COX \qquad (VI)$$

(wherein $R^5$ and X have the same meanings as defined above) in a solvent which is inert to the reaction in the presence of a base. When the compound (Ia) is used, the compound (Ib1) is produced and, when the compound (Id) is used, the compound (Ie1) is produced.

The solvent for use in the reaction may be any solvent which is inert to the reaction, and examples thereof include chloroform, dichloromethane, ether, tetrahydrofuran, acetone, dimethylformamide, acetonitrile and the like which can be used singly or as a mixture thereof. As the base, for example, pyridine, triethylamine, diisopropylethylamine and the like may be used singly or as a mixture thereof, and dimethylaminopyridine and the like may further be added to the reaction system in an amount of from 0.1 to 10 equivalents.

The compound (V) or the compound (VI) is generally used in an amount of one equivalent or more, preferably from 1 to 100 equivalents, to the compound (Ia) or the compound (Id), and the base is generally used in an amount of one equivalent or more, preferably from 1 to 500 equivalents, to the compound (Ia) or the compound (Id). The reaction is generally completed within from 5 minutes to 20 hours at a reaction temperature in the range of from −20° to 50° C.

Step 4-2

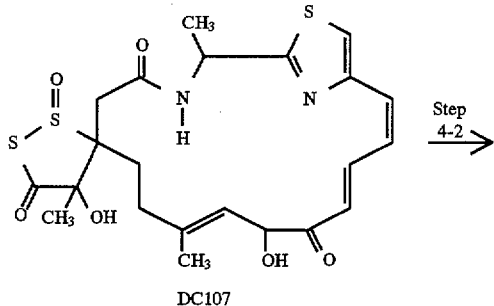

DC107

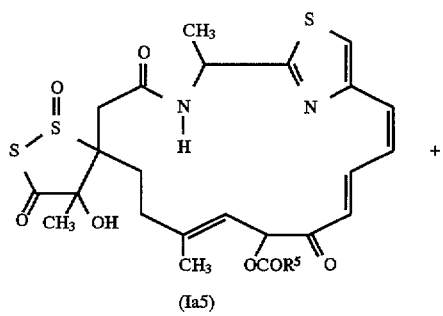

(Ia5)

+

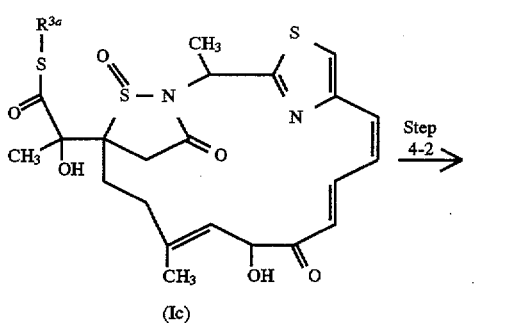

(Ib2)

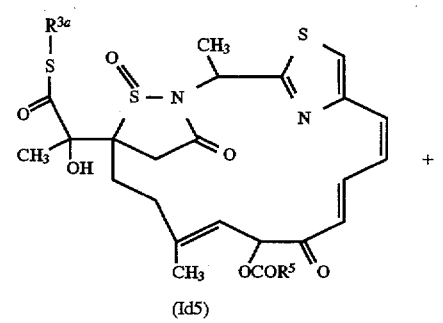

(Ic)

Step 4-2 →

+

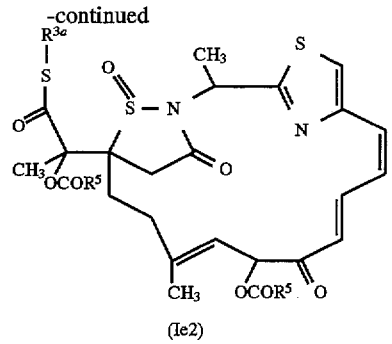

(Ie2)

(wherein $R^{3a}$ and $R^5$ have the same meanings as defined above.)

In a similar manner as Step 4-1, when DC107 or the compound (Ic) is used as a starting material in Step 4-2, the compound (Ib2) or (Ie2) having the same substituent in $R^{2a}$ as $R^{1a}$ ($R^{1a}=R^{2a}=COR^5$) can also be obtained, together with the compound (Ia5) or the compound (Id5). In this case, the production ratio of (Ia5) and (Ib2), or (Id5) and (Ie2) varies depending upon the reaction conditions such as the type of the compound (V) or the compound (VI), the amount thereof, and the solvent used.

Step 5

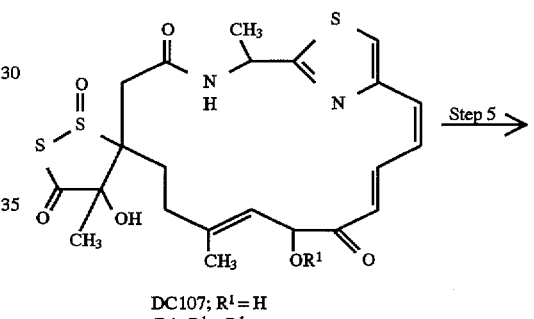

DC107; $R^1 = H$
(Ia); $R^1 = R^{1a}$

Step 5 →

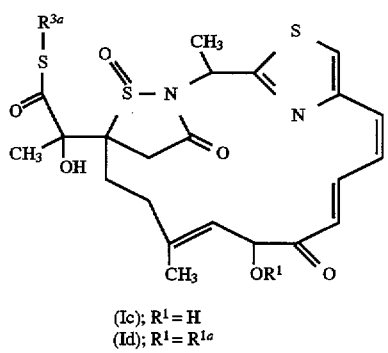

(Ic); $R^1 = H$
(Id); $R^1 = R^{1a}$ (wherein $R^{1a}$ and $R^{3a}$ have the same meanings as defined above.)

The compound (Ic) and the compound (Id) can be prepared by reacting DC107 or the compound (Ia) with the compound (VII) represented by the following formula:

$$R^{3a}X \qquad (VII)$$

(wherein $R^{3a}$ and X have the same meanings as defined above) in a solvent which is inert to the reaction in the presence of a base.

The solvent used in the reaction may be any solvent which is inert to the reaction, and examples thereof include chloroform, dichloromethane, ether, tetrahydrofuran, acetone, dimethylformamide, acetonitrile and the like which can be used singly or as a mixture thereof. As the base, for example, amines such as pyridine, imidazole, triethylamine, diisopropyl ethylamine and the like, and a carbonate or bicarbonate of an alkali metal or alkaline earth metal such as sodium carbonate, potassium carbonate, calcium carbonate, sodium bicarbonate and the like may be used, and dimethylaminopyridine and the like may be used as a catalyst. Further, the reaction can be promoted by adding potassium iodide, sodium iodide, tetrabutylammonium iodide and the like to the reaction system in an amount of from 1 to 100 equivalents.

The compound (VII) is generally used in an amount of one equivalent or more, preferably from 1 to 100 equivalents, to DC107 or the compound (Ia). The base is generally used in an amount of one equivalent or more, preferably from 1 to 200 equivalents, to DC107 or the compound (Ia). The reaction is generally completed within from 10 minutes to 24 hours at a reaction temperature in the range of from 0° to 50° C.

Step 6-1

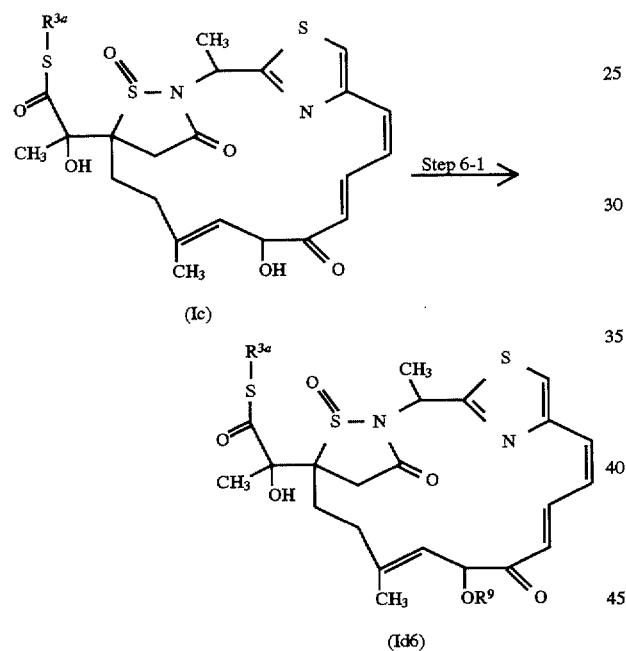

(wherein $R^{3a}$ has the same meaning as defined above, and $R^9$ represents lower alkoxyalkyl, aralkyloxyalkyl, lower alkoxyalkoxyalkyl or lower alkoxyalkoxyalkoxyalkyl.)

Of the compounds (Id), the compound (Id6) wherein $R^{1a}$ is lower alkoxyalkyl, aralkyloxyalkyl, lower alkoxyalkoxyalkyl or lower alkoxyalkoxyalkoxyalkyl can be prepared by reacting the compound (Ic) with the compound (VIII) represented by the following formula:

$$R^9X \qquad (VIII)$$

(wherein $R^9$ and X have the same meanings as defined above.) The reaction is conducted in a solvent which is inert to the reaction, such as chloroform, dichloromethane, dimethylformamide, acetonitrile, ether, tetrahydrofuran and the like, in the presence of a tertiary amine such as triethylamine, diisopropylethylamine, N-methylpiperidine and the like. The compound (VIII) is generally used in an amount of from 1 to 100 equivalents, and the tertiary amine is generally used in an amount of from 1 to 200 equivalents.

The reaction is generally completed within from 1 to 24 hours at a reaction temperature of from 0° to 50° C.

Step 6-2

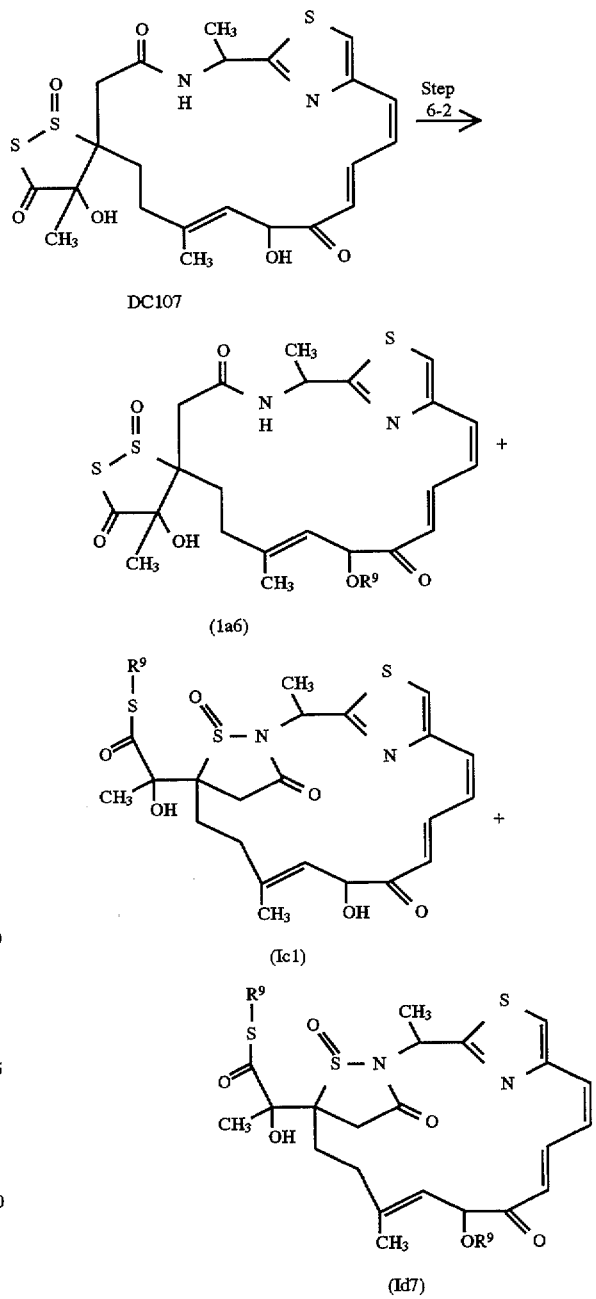

(wherein $R^9$ has the same meaning as defined above.)

In a similar manner as Step 6-1, when DC107 is used as a starting material in Step 6-2, the compound (Ia6) or the compound (Ic1) wherein one of $R^{1a}$ and $R^{3a}$ represents lower alkoxyalkyl, aralkyloxyalkyl or lower alkoxyalkoxyalkyl, and the compound (Id7) wherein both $R^{1a}$ and $R^{3a}$ represent lower alkoxyalkyl, aralkyloxyalkyl, lower alkoxyalkoxyalkyl or lower alkoxyalkoxyalkoxyalkyl may be obtained. The production ratio of the compounds (Ia6), (Ic1) and (Id7) varies depending upon the reaction conditions used such as the type of base, the equivalent, the solvent, the reaction temperature, and the like.

Step 7

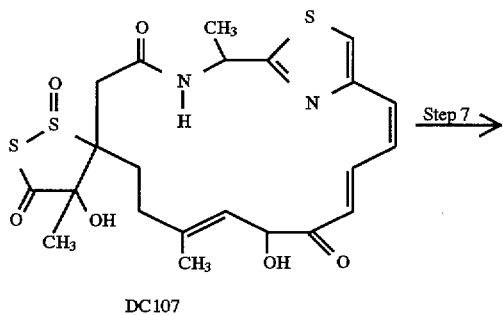

DC107

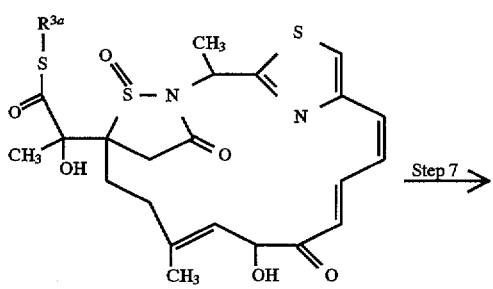

(Ia7)

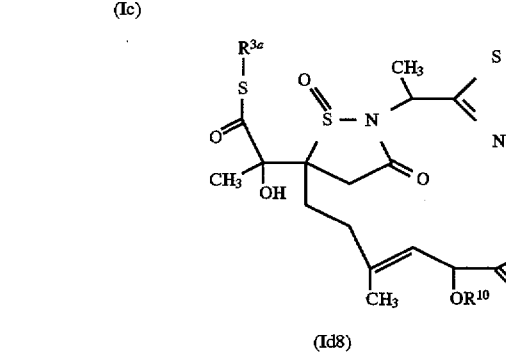

(Ic)

(Id8)

[wherein $R^{3a}$ has the same meaning as defined above, and $R^{10}$ represents tetrahydropyranyl, lower alkoxyalkyl, aralkyl or

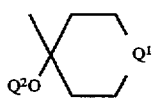

(wherein $Q^1$ and $Q^2$ have the same meanings as defined above)].

The compound (Ia7) or the compound (Id8) can be prepared by reacting DC107 or the compound (Ic) with 3,4-dihydro-2H-pyran in the case where $R^{10}$ represents tetrahydropyranyl, with aralkyl 2,2,2-trichloroacetimidate in the case where $R^{10}$ is aralkyl, or with lower alkoxyalkyl in the case where $R^{10}$ is lower alkoxyalkyl, with

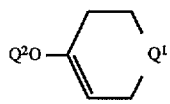

(wherein $Q^1$ and $Q^2$ have the same meanings as defined above) in the case where $R^{10}$ is

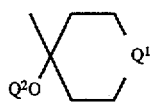

(wherein $Q^1$ and $Q^2$ have the same meanings as defined above) each in an amount of from 1 to 300 equivalents to DC107 or the compound (Ic), in a solvent which is inert to the reaction in the presence of an acid.

The solvent used in the reaction can be any solvent which is inert to the reaction such as chloroform, dichloromethane, ether, tetrahydrofuran, acetone, dimethylformamide, acetonitrile and the like which can be used singly or as a mixture thereof. Examples of the acid used in the reaction include organic acids such as p-toluenesulfonic acid, camphorsulfonic acid, pyridinium p-toluenesulfonate, trifluoroacetic acid, trifluoromethanesulfonic acid and the like, inorganic acids such as hydrochloric acid, sulfuric acid and the like, and Lewis acids such as titanium tetrachloride and a complex of boron trifluoride and diethyl etherate. The acid is generally used in an amount of from 0.1 to 5 equivalents to DC107 or the compound (Ic). The reaction is generally completed within from 5 minutes to 24 hours at a reaction temperature of from −30° to 30° C.

Preparation Process 2

Of the compounds (I), the compounds (I) wherein $R^1$ is hydrogen, $R^2$ represents $COR^5$ (wherein $R^5$ has the same meaning as defined above), and W is oxygen are referred to as compound (If) or compound (Ig). The compound (If) or the compound (Ig) can be prepared by, for example, the following step.

Step 8

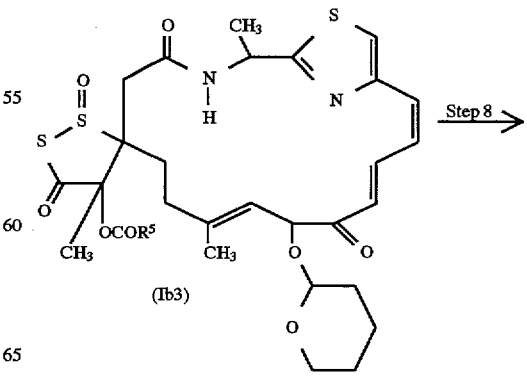

(Ib3)

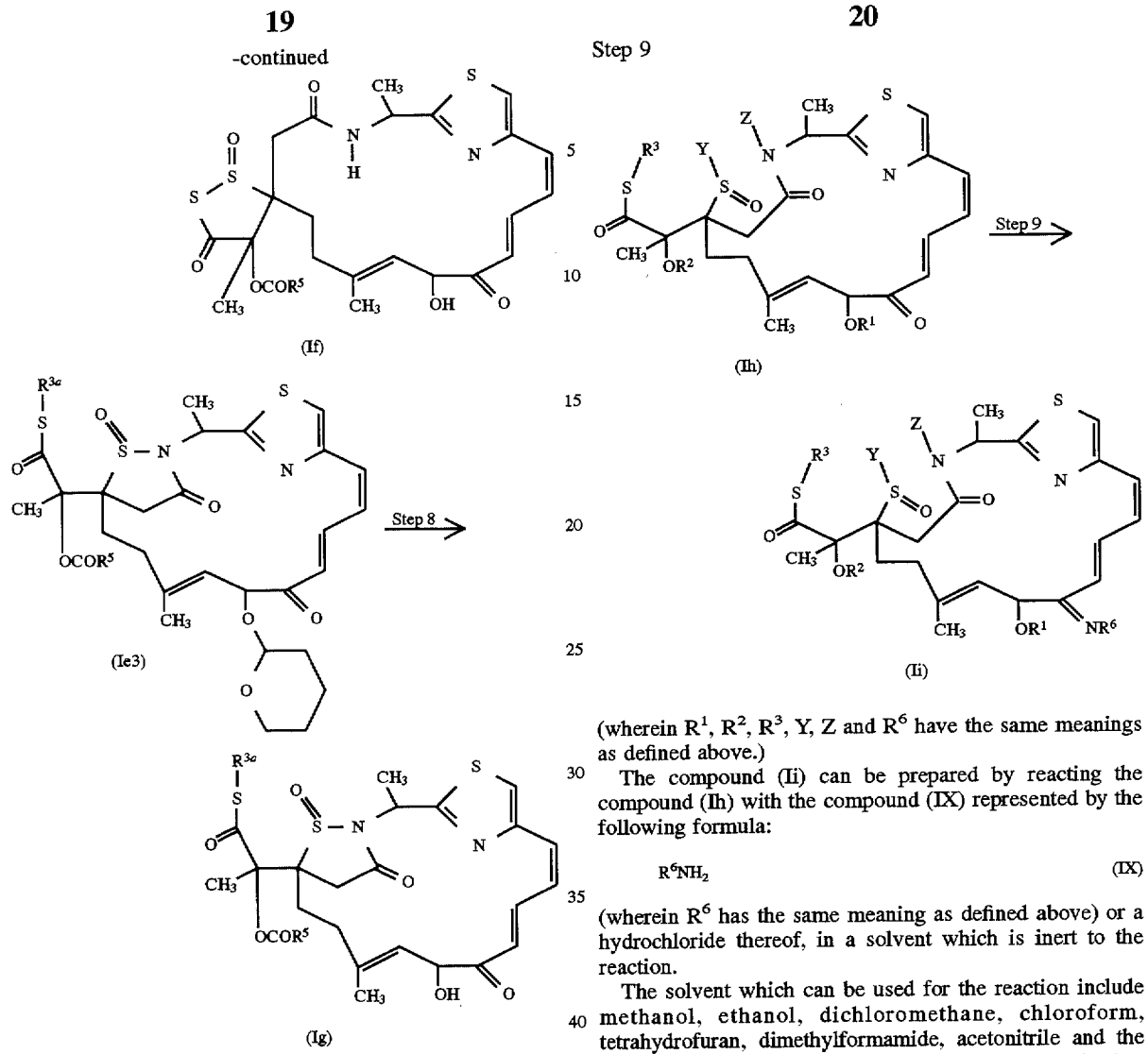

(wherein $R^{3a}$ and $R^5$ have the same meanings as defined above.)

The compound (If) or the compound (Ig) can be prepared by treating the compound (Ib3) or the compound (Ie3) with an organic acid such as p-toluenesulfonic acid, camphorsulfonic acid and the like or an inorganic acid such as hydrochloric acid, sulfuric acid and the like in an amount of from 0.1 to 100 equivalents in a solvent such as methanol, ethanol and the like. The reaction is generally completed within from 5 minutes to 24 hours at a reaction temperature of from −30° to 30° C.

Preparation Process 3

Of the compounds (I), the compounds (I) wherein W represents oxygen or $NR^6$ (wherein $R^6$ has the same meaning as defined above) are referred to as compound (Ih) and compound (Ii), respectively. The compound (Ii) can be prepared from the compound (Ih) by, for example, the following step.

(wherein $R^1$, $R^2$, $R^3$, Y, Z and $R^6$ have the same meanings as defined above.)

The compound (Ii) can be prepared by reacting the compound (Ih) with the compound (IX) represented by the following formula:

$$R^6NH_2 \qquad (IX)$$

(wherein $R^6$ has the same meaning as defined above) or a hydrochloride thereof, in a solvent which is inert to the reaction.

The solvent which can be used for the reaction include methanol, ethanol, dichloromethane, chloroform, tetrahydrofuran, dimethylformamide, acetonitrile and the like which can be used singly or as a mixture thereof. Also, the reaction can be promoted by adding pyridine or an acid to the reaction system. The acid is preferably an organic acid such as p-toluenesulfonic acid, camphorsulfonic acid, pyridinium p-toluenesulfonate and the like, but an inorganic acid such as hydrochloric acid, sulfuric acid and the like may also be used.

The compound (IX) is generally used in an amount of from 1 to 50 equivalents to the compound (I), and pyridine or an acid may be used in an amount of from 1 to 100 equivalents. The reaction is generally completed within from 5 minutes to 24 hours at a reaction temperature of from 0° to 30° C.

The object compounds in the above-described preparation processes can be isolated and purified by purification procedures ordinary used in the organic synthetic chemistry, for example, neutralization, filtration, extraction, washing, drying, concentration, recrystallization, various types of chromatography and the like.

Further, the compounds (I) may exist in the form of adducts with water and various solvents, and it is to be understood that these adducts are also included within the scope of the compounds according to the present invention.

Specific examples of the compound (I) obtained by the above-described preparation processes are shown in Table 1 below.

TABLE 1

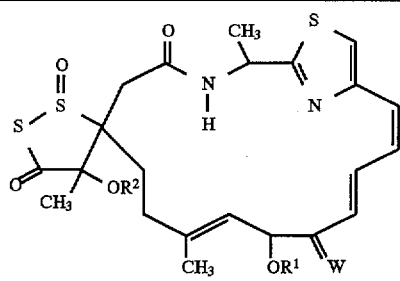

| Compound | R¹ | R² | W |
|---|---|---|---|
| | Specific Examples (1) of Compound (I) | | |
| 1 | COCH₃ | H | O |
| 2 | COCH₂CH₃ | H | O |
| 3 | COC(CH₃)₃ | H | O |
| 4 | CO(CH₂)₁₀CH₃ | H | O |
| 5 | CO(CH₂)₁₄CH₃ | H | O |
| 6 | CO-cyclohexyl | H | O |
| 7 | COPh | H | O |
| 8 | CO-C₆H₄-F | H | O |
| 9 | CO-quinoxalinyl | H | O |
| 10 | CO₂CH₂CH₃ | H | O |
| 11 | CO₂CH₂CH(CH₃)₂ | H | O |
| 12 | CO₂Ph | H | O |
| 13 | CO₂-C₆H₄-NO₂ | H | O |
| 14 | CO₂CH₂Ph | H | O |
| 15 | CO₂CH₂-fluorenyl | H | O |
| 16 | CO-N-piperidinyl | H | O |
| 17 | CO-N-pyrrolidinyl | H | O |
| 18 | THP | H | O |
| 19 | CH(CH₃)OCH₂CH₃ | H | O |
| 20 | CH₂Ph | H | O |
| | Specific Examples (2) of Compound (I) | | |
| 21 | COCH₃ | COCH₃ | O |
| 22 | COC(CH₃)₃ | COC(CH₃)₃ | O |

TABLE 1-continued

| # | Col A | Col B | Col C |
|---|---|---|---|
| 23* | THP | COCH$_3$ | O |
| 24* | THP | COCH$_3$ | O |
| 25 | H | COCH$_3$ | O |
| 30 | CH$_2$OCH$_3$ | H | O |
| 65 | H | H | NOH |
| 66** | H | H | NOCH$_3$ |
| 67** | H | H | NOCH$_3$ |
| 68** | H | H | NOCH$_2$Ph |
| 69** | H | H | NOCH$_2$Ph |
| 70** | H | H | NOCH$_2$CH=CH$_2$ |
| 71** | H | H | NOCH$_2$CH=CH$_2$ |
| 74 | H | H | NNHSO$_2$-C$_6$H$_4$-CH$_3$ |
| 75 | H | H | NNHCO$_2$CH$_3$ |
| 76 | COPh | COPh | O |
| 90 | 4-methoxy-4-methyltetrahydropyran-yl | H | O |
| 91 | 1-methoxy-1-methylcyclohexyl | H | O |
| 92 | 4-methoxy-4-methyltetrahydrothiopyran-yl | H | O |
| 93 | 4-methoxy-4-methyl-1-(ethoxycarbonyl)piperidin-yl | H | O |

Specific Examples (3) of Compound (I)

| # | Col A | Col B | Col C |
|---|---|---|---|
| 94 | CO-pyrazinyl | H | O |
| 95 | CO-(N-Boc-pyrrolidin-2-yl) | H | O |
| 96 | COCH$_2$NHCO$_2$C(CH$_3$)$_3$ | H | O |
| 97 | COCH$_2$NHCO$_2$CH$_2$Ph | H | O |
| 98 | COCH$_2$NHCO$_2$CH$_2$-(9H-fluoren-9-yl) | H | O |
| 99 | COCH$_2$NHCHO | H | O |
| 100 | COCH$_2$NHCOCH$_3$ | H | O |
| 101 | COCH$_2$N(CH$_3$)CO$_2$CH$_2$Ph | H | O |
| 102 | COCH(CH$_3$)NHCO$_2$C(CH$_3$)$_3$ | H | O |
| 103 | COCH(CH$_3$)NHCO$_2$CH$_2$Ph | H | O |
| 104 | COCH(CH$_2$OH)NHCO$_2$CH$_2$Ph | H | O |
| 105 | CO(CH$_2$)$_2$NHCO$_2$CH$_2$Ph | H | O |
| 106 | CO(CH$_2$)$_3$NHCO$_2$CH$_2$Ph | H | O |
| 107 | COCH$_2$NHCOCH$_2$NHCO$_2$C(CH$_3$)$_3$ | H | O |
| 108 | COCH$_2$NHCOCH$_2$NHCO$_2$CH$_2$Ph | H | O |
| 109 | COCH$_2$NHCOCH$_2$NHCOPh | H | O |
| 110 | COCH$_2$NHCOCH(CH$_3$)NHCO$_2$CH$_2$Ph | H | O |
| 111 | COCH$_2$NHCO(CH$_2$)$_2$NHCO$_2$CH$_2$Ph | H | O |
| 112 | COCH$_2$NHCO(CH$_2$)$_2$NHCO$_2$C(CH$_3$)$_3$ | H | O |

TABLE 1-continued

| 113 | COCH$_2$NHCO(CH$_2$)$_3$NHCO$_2$CH$_2$Ph | H | O |
| 114 | COCH$_2$NHCOCH$_2$N(CH$_3$)CO$_2$CH$_2$Ph | H | O |
| 115 | COCH$_2$NHCOCH(CH$_2$CH(CH$_3$)$_2$)NHCO$_2$CH$_2$Ph | H | O |
| 116 | COCH$_2$NHCOCH(CH$_2$OH)NHCO$_2$CH$_2$Ph | H | O |
| 117 | COCH$_2$N(CH$_3$)CO(CH$_2$)$_2$NHCO$_2$CH$_2$Ph | H | O |
| 118 | CO(CH$_2$)$_2$NHCOCH$_2$NHCO$_2$CH$_2$Ph | H | O |
| 119 | CO(CH$_2$)$_2$NHCO(CH$_2$)$_2$NHCO$_2$CH$_2$Ph | H | O |

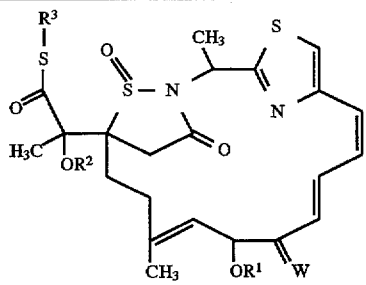

| Compound | R$^1$ | R$^2$ | R$^3$ | W |
|---|---|---|---|---|
| Specific Examples (4) of Compound (I) | | | | |
| 26 | H | H | CH$_3$ | O |
| 27 | H | H | CH$_2$CH=CH$_2$ | O |
| 28 | H | H | CH$_2$OCH$_3$ | O |
| 29 | CH$_2$OCH$_3$ | H | CH$_2$OCH$_3$ | O |
| 31 | CH$_2$OCH$_2$CH$_3$ | H | CH$_2$OCH$_2$CH$_3$ | O |
| 32 | H | H | CH$_2$OCH$_2$Ph | O |
| 33 | H | H | CH$_2$CO$_2$CH$_2$CH$_3$ | O |
| 34 | H | H | CH$_2$OCOC(CH$_3$)$_3$ | O |
| 35 | H | H | DMDO | O |
| 36 | COCH$_3$ | H | CH$_2$OCH$_3$ | O |
| 37* | THP | H | CH$_2$OCH$_3$ | O |
| 38* | THP | H | CH$_2$OCH$_3$ | O |
| 39 | COCH$_3$ | H | CH$_2$OCOC(CH$_3$)$_3$ | O |
| 40 | COCH$_2$CH$_3$ | H | CH$_2$OCOC(CH$_3$)$_3$ | O |
| 41 | CO$_2$CH$_2$CH$_3$ | H | CH$_2$OCOC(CH$_3$)$_3$ | O |
| 42 | CO$_2$Ph | H | CH$_2$OCOC(CH$_3$)$_3$ | O |
| 43 | CH$_2$OCH$_3$ | H | CH$_2$OCOC(CH$_3$)$_3$ | O |
| 44 | THP | H | CH$_2$OCOC(CH$_3$)$_3$ | O |
| 45 | COCH$_3$ | H | DMDO | O |
| 46 | COCH$_3$ | COCH$_3$ | DMDO | O |
| 47 | COCH$_2$CH$_3$ | H | DMDO | O |
| Specific Examples (5) of Compound (I) | | | | |
| 48 | CO-cyclohexyl | | H | DMDO | O |
| 49 | CO-1-naphthyl | | H | DMDO | O |
| 50 | CO-2-naphthyl | | H | DMDO | O |
| 51 | CO-quinolinyl | | H | DMDO | O |
| 52 | CO-quinoxalinyl | | H | DMDO | O |

TABLE 1-continued

| | | | | |
|---|---|---|---|---|
| 53 | CO$_2$CH$_2$CH$_3$ | H | DMDO | O |
| 54 | CO$_2$CH$_2$CH(CH$_3$)$_2$ | H | DMDO | O |
| 55 | CO$_2$Ph | H | DMDO | O |
| 56 | CO$_2$CH$_2$Ph | H | DMDO | O |
| 57 | fluorenyl-CO$_2$CH$_2$– | H | DMDO | O |
| 58 | CH$_2$OCH$_3$ | H | DMDO | O |
| 59 | CH$_2$OCH$_2$CH$_3$ | H | DMDO | O |
| 60 | CH$_2$O(CH$_2$)$_7$CH$_3$ | H | DMDO | O |
| 61 | CH$_2$OCH$_2$Ph | H | DMDO | O |
| 62 | CH$_2$O(CH$_2$)$_2$OCH$_3$ | H | DMDO | O |
| 63* | THP | H | DMDO | O |
| 64* | THP | H | DMDO | O |

Specific Examples (6) of Compound (I)

| | | | | |
|---|---|---|---|---|
| 72** | H | H | DMDO | NOCH$_2$Ph |
| 73** | H | H | DMDO | NOCH$_2$Ph |
| 77 | H | H | CH$_2$OCO–cyclopropyl | O |
| 78 | H | H | CH$_2$OCO–cyclobutyl | O |
| 79 | H | H | CH$_2$OCO–cyclopentyl | O |
| 80 | H | H | CH$_2$OCO–cyclohexyl | O |
| 81 | H | H | CH$_2$OCOCH(CH$_3$)$_2$ | O |
| 82 | H | H | CH$_2$OCOCH$_2$CH(CH$_3$)$_2$ | O |
| 83 | H | H | CH$_2$OCO(CH$_2$)$_3$CH$_3$ | O |
| 84 | H | H | CH$_2$OCO(CH$_2$)$_6$CH$_3$ | O |
| 85 | THP | H | CH$_2$OCO–cyclohexyl | O |
| 86 | THP | H | CH$_2$OCOCH$_2$CH(CH$_3$)$_2$ | O |
| 87 | CH(CH$_3$)OCH$_2$CH$_3$ | H | DMDO | O |
| 88** | THP | H | DMDO | NOCH$_3$ |
| 89** | THP | H | DMDO | NOCH$_3$ |
| 120 | C(CH$_3$)$_2$OCH$_3$ | H | CH$_2$OCO–cyclohexyl | O |
| 121 | C(CH$_3$)$_2$OCH$_3$ | H | DMDO | O |
| 122 | MTHP | H | DMDO | O |
| 123** | MTHP | H | DMDO | NOH |
| 124** | MTHP | H | DMDO | NOH |
| 125 | THP | H | DMDO | NOH |

Specific Examples (7) of Compound (I)

| | | | | |
|---|---|---|---|---|
| 126 | 1-methoxy-1-cyclohexyl (CH$_3$O–) | H | DMDO | O |

TABLE 1-continued

| | | | | |
|---|---|---|---|---|
| 127 | [cyclohexane with CH3O and S substituents] | H | DMDO | O |
| 128 | [cyclohexane with CH3O and S=O substituents] | H | DMDO | O |
| 129 | [cyclohexane with CH3O and SO2 substituents] | H | DMDO | O |
| 130 | [cyclohexane with CH3O and NCO2Et substituents] | H | DMDO | O |
| 131 | [cyclohexane with CH3O and NPh substituents] | H | DMDO | O |
| 132 | H | H | CH2—C6H4—NO2 | O |
| 133 | MTHP | H | CH2—C6H4—NO2 | O |
| 134 | H | H | CH2—C6H4—OCOCH3 | O |
| 135 | THP | H | CH2—C6H4—OCOCH3 | O |
| 136 | MTHP | H | CH2—C6H4—OCOCH3 | O |
| 137 | H | H | CH2—C6H4—OH | O |
| 138 | H | H | CH2—C6H4—OCON(CH3)2 | O |
| 139 | MTHP | H | CH2—C6H4—OCON(CH3)2 | O |
| 140 | H | H | CH2—C6H4—OCO—[piperidine]—NCOCH3 | O |
| 141 | THP | H | CH2—C6H4—OCO—[piperidine]—NCOCH3 | O |

TABLE 1-continued

| 142 | MTHP | H | [structure: CH$_2$—C$_6$H$_4$—OCO—(piperidine)—NCOCH$_3$] | O |

*Specific Examples (8) of Compound (I)*

| 143 | CO—(2-pyridyl) | H | DMDO | O |
| 144 | CO—(3-pyridyl) | H | DMDO | O |
| 145 | CO—(pyrazinyl) | H | DMDO | O |
| 146 | CO—C$_6$H$_4$—CO$_2$H (ortho) | H | DMDO | O |
| 147 | COCH$_2$—(3-pyridyl) | H | DMDO | O |
| 148 | CO—(N-CO$_2$C(CH$_3$)$_3$-pyrrolidinyl) | H | DMDO | O |
| 149 | CO—(pyrrolidinone) | H | DMDO | O |
| 150 | CO(CH$_2$)$_2$CO$_2$H | H | DMDO | O |
| 151 | COCH$_2$CO$_2$CH$_3$ | H | DMDO | O |
| 152 | COCH$_2$CO$_2$H | H | DMDO | O |
| 153 | COCH$_2$OCH$_2$—C$_6$H$_4$—OCH$_3$ | H | DMDO | O |
| 154 | COCH$_2$OH | H | DMDO | O |
| 155 | CH$_2$O(CH$_2$CH$_2$O)$_2$CH$_3$ | H | DMDO | O |

*Specific Examples (9) of Compound (I)*

| 156 | COCH$_2$NHCO$_2$C(CH$_3$)$_3$ | H | DMDO | O |
| 157 | COCH$_2$NHCO$_2$CH$_2$Ph | H | DMDO | O |
| 158 | COCH$_2$NHCO$_2$CH$_2$—(9-fluorenyl) | H | DMDO | O |
| 159 | COCH$_2$NHCHO | H | DMDO | O |
| 160 | COCH$_2$NHCOCH$_3$ | H | DMDO | O |
| 161 | COCH$_2$N(CH$_3$)CO$_2$C(CH$_3$)$_3$ | H | DMDO | O |
| 162 | COCH$_2$N(CH$_3$)CO$_2$CH$_2$Ph | H | DMDO | O |
| 163 | COCH(CH$_3$)NHCO$_2$CH$_2$Ph | H | DMDO | O |
| 164 | COCH(CH$_2$OH)NHCO$_2$CH$_2$Ph | H | DMDO | O |
| 165 | COCH$_2$NHCOCH$_2$NHCO$_2$C(CH$_3$)$_3$ | H | DMDO | O |

TABLE 1-continued

| | | | | | |
|---|---|---|---|---|---|
| 166 | $COCH_2NHCOCH_2NHCO_2CH_2Ph$ | H | DMDO | | O |
| 167 | $COCH_2NHCOCH_2NHCOPh$ | H | DMDO | | O |
| 168 | $COCH_2NHCOCH(CH_3)NHCO_2CH_2Ph$ | H | DMDO | | O |
| 169 | $COCH_2NHCO(CH_2)_2NHCO_2CH_2Ph$ | H | DMDO | | O |
| 170 | $COCH_2NHCO(CH_2)_2NHCO_2C(CH_3)_3$ | H | DMDO | | O |
| 171 | $COCH_2NHCO(CH_2)_3NHCO_2CH_2Ph$ | H | DMDO | | O |
| 172 | $COCH_2NHCOCH_2N(CH_3)CO_2CH_2Ph$ | H | DMDO | | O |
| 173 | $COCH_2NHCOCH(CH_2CH(CH_3)_2)NHCO_2CH_2Ph$ | H | DMDO | | O |
| 174 | $COCH_2NHCOCH(CH_2OH)NHCO_2CH_2Ph$ | H | DMDO | | O |
| 175 | $COCH_2N(CH_3)CO(CH_2)_2NHCO_2CH_2Ph$ | H | DMDO | | O |
| 176 | $CO(CH_2)_2NHCOCH_2NHCO_2CH_2Ph$ | H | DMDO | | O |
| 177 | $CO(CH_2)_2NHCO(CH_2)_2NHCO_2CH_2Ph$ | H | DMDO | | O |

*A diastereomer due to asymmetric carbon on the tetrahydropyranyl group in $R^1$.
**A geometrical isomer relative to the C=N bond in W.

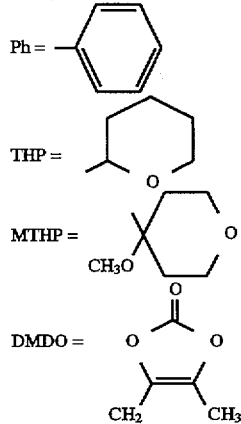

The antibacterial activity and the antitumor activity of typical compounds (I) are hereinafter described with reference to test examples.

Test Example 1
Antibacterial Activity

The antibacterial activity as determined by the agar dilution method using a medium prepared by dissolving 3 g of Bacto-Tryptone (a product of Difco Laboratories), 3 g of a meat extract, 1 g of an yeast extract, 1 g of glucose and 16 g of agar in one liter of water (pH 7). The antibacterial activities of typical compounds in terms of the minimum growth inhibitory concentration (MIC) are shown in Table 2 below.

TABLE 2

| Compound | Name of Bacteria and MIC (μg/ml) | | | | |
|---|---|---|---|---|---|
| | EF | SA | BS | KP | EC |
| Antibacterial Activities (1) | | | | | |
| 1 | 0.52 | 0.52 | 0.26 | 17 | — |
| 2 | 0.081 | 0.041 | 0.33 | 0.65 | 1.3 |
| 6 | 0.91 | 0.91 | 0.028 | 7.3 | 3.7 |
| 8 | 0.081 | 0.081 | 0.020 | 1.3 | 1.3 |
| 10 | 0.26 | 0.26 | 0.13 | 4.2 | 4.2 |
| 15 | 0.081 | 0.16 | 0.041 | — | — |
| 18 | 0.16 | 0.16 | 0.041 | 2.6 | 1.3 |
| 25 | 2.6 | 1.3 | 10 | 10 | 42 |
| 30 | 0.065 | 0.13 | 0.033 | 1.0 | 8.3 |
| 52 | 0.72 | 0.72 | 2.9 | 23 | 92 |
| 54 | 0.13 | 0.13 | — | — | 0.018 |
| 58 | 0.72 | 0.72 | 0.72 | 2.9 | 46 |
| 59 | 1.3 | 1.3 | 0.65 | 5.2 | 21 |
| 61 | 0.65 | 0.65 | 0.081 | — | 2.6 |
| 63 | 0.65 | 0.65 | 0.081 | 5.2 | 21 |
| 64 | 1.3 | 0.65 | 0.16 | 5.2 | 5.2 |

TABLE 2-continued

| Compound | Name of Bacteria and MIC (μg/ml) | | | | |
|---|---|---|---|---|---|
| | EF | SA | BS | KP | EC |
| 69 | 0.028 | 0.057 | 0.028 | 0.23 | 1.8 |
| 78 | 9.4 | 4.7 | 0.073 | 2.3 | — |
| 80 | 5.2 | 2.6 | 0.041 | — | — |
| 84 | 0.39 | 0.39 | 0.049 | 0.098 | — |
| 87 | 54 | 0.85 | 0.11 | 1.7 | 6.8 |
| Antibacterial Activities (2) | | | | | |
| 90 | 0.041 | 0.041 | 0.020 | 0.16 | 0.65 |
| 97 | 0.041 | 0.041 | 0.33 | 0.81 | 0.65 |
| 99 | 0.041 | 0.041 | 0.041 | 0.041 | 2.6 |
| 100 | 0.041 | 0.041 | 0.081 | 0.041 | 2.6 |
| 103 | 0.081 | 42 | 0.041 | 1.3 | 10 |
| 106 | 0.16 | 0.16 | 0.041 | 1.3 | 10 |
| 108 | 0.081 | 0.16 | 0.041 | 0.33 | 21 |
| 109 | 0.081 | 0.081 | 0.35 | 0.041 | 3.2 |
| 111 | 0.16 | 0.33 | 0.081 | 0.041 | 2.6 |
| 114 | 0.037 | 0.037 | 0.037 | 1.2 | 11 |
| 116 | 0.033 | 0.033 | 0.033 | 0.033 | 4.2 |
| 117 | 0.23 | 0.13 | 0.13 | 0.057 | 0.46 |
| 121 | 0.78 | 0.78 | 0.26 | 0.39 | — |
| 122 | 1.3 | 0.65 | 0.16 | 2.6 | 42 |
| 126 | 1.0 | 1.0 | 0.033 | 4.2 | — |
| 127 | 0.65 | 0.65 | 0.041 | 2.6 | — |
| 143 | 0.33 | 0.16 | 0.16 | 0.65 | 5.2 |
| 167 | 2.1 | 2.1 | 2.1 | 2.1 | — |
| 170 | 2.3 | 2.3 | 2.3 | 2.3 | 75 |
| 172 | 1.0 | 2.1 | 1.0 | 1.0 | — |

EF: *Enterococcus faecium* ATCC 10541
SA: *Staphylococcus aureus* ATCC 6538P
BS: *Bacillus subtilis* No. 10707
KP: *Klebsiella pneumoniae* ATCC 10031
EC: *Escherichia coli* ATCC 26

Test Example 2
Antitumor Activity of Test Compounds Against P388 Leukemia Ascites were collected from the abdominal cavity of P388 ascites tumor-bearing cancer mice (DBA/2) on the 7th day after transplantation. A number of P388 cells in the ascites was counted, and a tumor cell floating liquid of $5 \times 10^6$ cells/ml was prepared using a physiological saline solution. Then, 0.2 ml of the solution containing $1 \times 10^6$ cells was transplanted into the abdominal cavity of $CDF_1$ mice having a body weight of from 20 to 25 g.

The test compound was dissolved in a physiological saline solution containing polyoxyethylene sorbitan monooleate, and 0.2 ml of the solution was administered intraperitoneally to $CDF_1$ mice (five mice per group) on the 24 hours after the tumor transplantation, and thereafter a number of survival days of mice was observed for a period of 30 days.

The effect of the test compound was determined in terms of the ratio of average survival days of the group administered with the test compound to average survival days of the control group (non-medicated group) (i.e., an increased life span, ILS%). The results obtained are shown in Table 3 below.

TABLE 3

| Compound | Dose (mg/kg) | ILS (%) |
|---|---|---|
| *Antitumor Activity against P388 Leukemia (1)* | | |
| 2 | 2.0 | 42 |
| 6 | 4.0 | 49 |
| 9 | 2.0 | 44 |
| 11 | 2.0 | 50 |
| 12 | 1.0 | 44 |
| 14 | 1.0 | 42 |
| 15 | 16.0 | 63 |
| 34 | 2.0 | 48 |
| 35 | 2.0 | 65 |
| 41 | 2.0 | 40 |
| 48 | 8.0 | 47 |
| 53 | 2.0 | 43 |
| 54 | 2.0 | 42 |
| 55 | 1.0 | 40 |
| 56 | 1.0 | 63 |
| 57 | 4.0 | 53 |
| 59 | 2.0 | 47 |
| 63 | 2.0 | 48 |
| 73 | 4.0 | 43 |
| *Antitumor Activity against P388 Leukemia (2)* | | |
| 91 | 8.0 | 48 |
| 92 | 8.0 | 48 |
| 96 | 2.0 | 46 |
| 97 | 8.0 | 54 |
| 99 | 8.0 | 56 |
| 100 | 4.0 | 66 |
| 101 | 4.0 | 48 |
| 102 | 4.0 | 49 |
| 103 | 4.0 | 52 |
| 105 | 4.0 | 53 |
| 106 | 16 | 62 |
| 108 | 4.0 | 72 |
| 109 | 8.0 | 78 |
| 110 | 8.0 | 58 |
| 111 | 16 | 76 |
| 112 | 8.0 | 67 |
| 113 | 16 | 58 |
| 114 | 4.0 | 70 |
| 115 | 8.0 | 67 |
| 117 | 16 | 73 |
| 118 | 16 | 71 |
| 119 | 16 | 63 |
| *Antitumor Activity against P388 Leukemia (3)* | | |
| 122 | 2.0 | 52 |
| 125 | 16 | 54 |
| 127 | 16 | 52 |
| 128 | 4.0 | 84 |
| 129 | 1.0 | 64 |
| 131 | 8.0 | 60 |
| 143 | 0.5 | 49 |
| 144 | 2.0 | 49 |
| 147 | 2.0 | 60 |
| 148 | 8.0 | 49 |
| 149 | 4.0 | 55 |
| 154 | 2.0 | 48 |
| 157 | 8.0 | 98 |
| 159 | 8.0 | 50 |
| 160 | 4.0 | 62 |
| 161 | 4.0 | 65 |
| 162 | 8.0 | 57 |
| 163 | 2.0 | 46 |
| 166 | 8.0 | 64 |
| 167 | 16 | 90 |
| 168 | 4.0 | 58 |
| 169 | 16 | 91 |
| 170 | 8.0 | 70 |
| 171 | 16 | 63 |
| 172 | 4.0 | 65 |
| 173 | 8.0 | 64 |
| 175 | 16 | 65 |
| 176 | 16 | 75 |
| 177 | 32 | 52 |

The compound according to the present invention is useful as an antibacterial agent and an antitumor agent and can be used as it is or in various dosage forms. For example, when the compound (I) is used as an injectable preparation, it can be used after dissolving in a diluting agent which is ordinary used in the art, for example, a physiological saline solution, a glucose injectable solution, a lactose injectable solution, a mannitol injectable solution or the like, or it may be used as a freeze-dried injectable preparation based on the Japanese Pharmacopeia, or a powdery injectable preparation mixed with sodium chloride. Also, an auxiliary agent such as polyethylene glycol, HCO-60 (a surface active agent; a product of Nikko Chemical Co., Ltd.) and the like or a carrier such as ethanol and/or liposome, cyclodextrin and the like may be added to the injectable preparation. These injectable preparations are generally administered intravenously, but may be administered intraarterially, intraperitoneally or intrathoracically.

The compound (I) can be used as an oral preparation by mixing and formulating the compound (I) into a dosage form such as tablets, granules, powders, syrup and the like with appropriate excipients, disintegrating agents, binders, lubricating agents and the like in a usual manner.

The dosage level varies depending upon the administration method, the type of the compound (I) as well as the age and the severity of conditions, and the method for administration can also be varied by the severity of conditions and the dosage level, but the compound (I) can be generally administered parenterally as an injectable preparation or orally. For example, it can be administered at a dose in the range of from 0.06 to 6 mg/kg once a week or once at an interval of three weeks.

The present invention is further illustrated by the following Examples.

BEST MODE FOR CARRYING OUT THE INVENTION

In the following examples, the physical and chemical properties of each of the compounds were determined by the following apparatus:

| | |
|---|---|
| MS | JEOL HX/HX110A (measurement by the FAB method) |
| | Hitachi M-80B (measurement by the SI method) |
| $^1$HNMR | Bruker AM500 (500 MHz) |
| | JEOL α400 (400 MHz) |
| | JEOL FX-100 (100 MHz) |
| IR | Nippon Bunko IR-810 |

In the physical data of the compounds in the following examples, "HRFABMAS" means a high resolution MS measurement by the FAB method; "Anal" means an elemental analysis; "calcd" means a theoretical value based on the molecular formula; and "found" means a measured value. In the examples, "Cbz" means carbobenzyloxy, "Boc" means tert-butoxycarbonyl, and "Fmoc" means 9-fluorenylmethylcarbonyl.

Also, in the following examples, the term "usual post-treatment" as used therein means the following treatment was conducted after the reaction.

First, that treatment includes, after completion of the reaction in each step, adding, if necessary, water, an acid, a buffering solution or the like to the reaction solution, and extracting the mixture with a water-insoluble solvent such as ethyl acetate, ether, chloroform, dichloromethane and the like. Next, the resulting extract is washed with water, an aqueous sodium chloride solution or the like, dried over anhydrous sodium sulfate or the like, and the solvent is distilled off under reduced pressure.

EXAMPLE 1
Synthesis of Compound 1

DC107 (52 mg, 0.102 mmol) was dissolved in dichloromethane (2.0 ml) and pyridine (0.1 ml, 1.2 mmol), and then acetic anhydride (0.05 ml, 0.53 mmol) and 4-dimethylaminopyridine (2.0 mg, 0.016 mmol) were added thereto, followed by stirring at 25° C. for 1.5 hours. After subjecting the resulting mixture to the usual post-treatment, the mixture was purified by thin layer chromatography (developed with ether/hexane=10/1) to obtain Compound 1 (46 mg, 82% yield).

IR (KBr) 3400, 2950, 1720, 1660, 1615, 1540, 1450, 1450, 1370, 1230, 1100, 1030, 1000, 950, 900, 805 cm$^{-1}$ $^1$H NMR (CDCl$_3$, 400 MHz) δ ppm; 8.80 (dd, J=16.5, 11.6 Hz, 1H), 7.28 (s, 1H), 6.67 (br d, J=6.6 Hz, 1H), 6.65 (d, J=11.6 Hz, 1H), 6.36 (dd, J=11.6, 11.6 Hz, 1H), 6.03 (d, J=16.5 Hz, 1H), 5.79 (br s, 2H), 5.36 (dq, J=6.6, 6.6 Hz, 1H), 4.45 (br s, 1H), 3.06 (br s, 2H), 2.35 (dt, J=12.8, 3.9 Hz, 1H), 2.06 (dt, J=12.8, 5.2 Hz, 1H), 2.00 (s, 3H), 1.88 (dt, J=12.8, 5.2 Hz, 1H), 1.78 (s, 3H), 1.77 (d, J=6.6 Hz, 3H), 1.75 (m, 1H), 1.72 (s, 3H)

SIMS m/z 553 (M+H)$^+$

HRFABMS calcd for C$_{24}$H$_{29}$N$_2$O$_7$S$_3$ (M+H)$^+$ 553.1137, found 553.1160

EXAMPLE 2
Synthesis of Compound 2

According to the procedure as described in Example 1, Compound 2 (34 mg, 76% yield) was obtained from DC107 (40.7 mg, 0.080 mmol), chloroform (4.0 ml), pyridine (0.162 ml, 2.0 mmol), propionic anhydride (0.051 ml, 0.40 mmol) and 4-dimethylaminopyridine (3.0 mg, 0.024 mmol).

IR (KBr) 3420, 3350, 2926, 1718, 1653, 1615, 1540, 1448, 1373, 1271, 1185, 1082, 1003, 947, 893, 799 cm$^{-1}$ $^1$H NMR (CDCl$_3$, 500 MHz) δ ppm; 8.83 (dd, J=16.6, 11.3 Hz, 1H), 7.28 (s, 1H), 6.68 (br d, J=6.4 Hz, 1H), 6.64 (d, J=11.3 Hz, 1H), 6.35 (dd, J=11.3, 11.3 Hz, 1H), 6.02 (d, J=16.6 Hz, 1H), 5.81 (br d, J=9.8 Hz, 1H), 5.78 (d, J=9.8 Hz, 1H), 5.36 (dq, J=6.4, 6.4 Hz, 1H), 4.50 (br s, 1H), 3.08 (d, J=15.3 Hz, 1H), 3.03 (d, J=15.3 Hz, 1H), 2.34 (dt, J=12.8, 4.0 Hz, 1H), 2.27 (dq, J=7.6, 1.5 Hz, 2H), 2.07 (ddd, J=13.4, 12.8, 5.5 Hz, 1H), 1.88 (ddd, J=14.3, 12.8, 5.5 Hz, 1H), 1.79 (ddd, J=14.3, 13.4, 4.0 Hz, 1H), 1.79 (s, 3H), 1.77 (d, J=6.4 Hz, 3H), 1.73 (s, 3H), 1.04 (t, J=7.6 Hz, 3H)

FABMS m/z 567 (M+H)$^+$.

HRFABMS calcd for C$_{25}$H$_{31}$N$_2$O$_7$S$_3$ (M+H)$^+$ 567.1293, found 567.1313

EXAMPLE 3
Synthesis of Compound 3

According to the procedure as described in Example 1, Compound 3 (23 mg, 51% yield) was obtained from DC107 (40.0 mg, 0.078 mmol), dichloromethane (1.0 ml), pyridine (0.82 ml, 10.1 mmol), pivaloyl chloride (0.63 ml, 5.15 mmol) and 4-dimethylaminopyridine (2.0 mg, 0.016 mmol).

IR (KBr) 3400, 2936, 1718, 1654, 1617, 1540, 1460, 1364, 1149, 1100, 1000, 950 cm$^{-1}$ $^1$H NMR (CDCl$_3$, 400 MHz) δ ppm; 8.83 (dd, J=16.6, 11.3 Hz, 1H), 7.28 (s, 1H), 6.80 (br d, J=6.6 Hz, 1H), 6.62 (d, J=11.6 Hz, 1H), 6.33 (dd, J=11.6, 11.3 Hz, 1H), 5.97 (d, J=16.6 Hz, 1H), 5.88 (br d, J=9.5 Hz, 1H), 5.66 (d, J=9.5 Hz, 1H), 5.36 (dq, J=6.6, 6.6 Hz, 1H), 4.61 (br s, 1H), 3.12 (d, J=15.0 Hz, 1H), 3.00 (d, J=15.0 Hz, 1H), 2.40–2.33 (m, 1H), 2.13–2.06 (m, 1H), 1.93–1.62 (m, 2H), 1.82 (s, 3H), 1.80 (d, J=6.6 Hz, 3H), 1.74 (d, J=1.2 Hz, 3H), 1.08 (s, 9H)

FABMS m/z 595 (M+H)$^+$

HRFABMS calcd for C$_{27}$H$_{35}$N$_2$O$_7$S$_3$ (M+H)$^+$ 595.1606, found 595.1603

EXAMPLE 4
Synthesis of Compound 4

According to the procedure as described in Example 1, Compound 4 (23 mg, 51% yield) was obtained from DC107 (40.2 mg, 0.079 mmol), dichloromethane (4.0 ml), pyridine (0.034 ml, 0.42 mmol) and lauroyl chloride (0.048 ml, 0.21 mmol).

IR (KBr) 3450, 3330, 2926, 2856, 1714, 1646, 1615, 1521, 1447, 1368, 1190, 1100, 1000, 947, 890, 799 cm$^{-1}$ $^1$H NMR (CDCl$_3$, 500 MHz) δ ppm; 8.81 (dd, J=16.8, 11.3 Hz, 1H), 7.27 (s, 1H), 6.73 (br d, J=6.3 Hz, 1H), 11.3 (d, J=11.3 Hz, 1H), 6.02 (d, J=16.8 Hz, 1H), 5.80 (br d, J=9.9 Hz, 1H), 5.76 (d, J=9.9 Hz, 1H), 5.36 (dq, J=6.7, 6.3 Hz, 1H), 4.52 (br s, 1H), 3.09 (d, J=15.1 Hz, 1H), 3.03 (d, J=15.1 Hz, 1H), 2.38–2.32 (m, 1H), 2.22 (t, J=7.3 Hz, 2H), 2.06 (dt, J=12.8, 5.2 Hz, 1H), 1.93–1.10 (m, 20H), 1.80 (s, 3H), 1.77 (d, J=6.7 Hz, 3H), 1.72 (s, 3H), 0.88 (t, J=6.7 Hz, 3H)

FABMS m/z 693 (M+H)$^+$

HRFABMS calcd for C$_{34}$H$_{49}$N$_2$O$_7$S$_3$ (M+H)$^+$ 693.2702, found 93.2675

EXAMPLE 5
Synthesis of Compound 5

According to the procedure as described in Example 1, Compound 5 (55 mg, 72% yield) was obtained from DC107 (52 mg, 0.102 mmol), dichloromethane (2.5 ml), pyridine (0.050 ml, 0.62 mmol) and palmitoyl chloride (100 mg, 0.36 mmol).

IR (KBr) 3420, 3330, 2928, 2856, 1713, 1647, 1614, 1529, 1453, 1371, 1263, 1200, 1101, 1000, 948, 892, 808, 720 cm$^{-1}$ $^1$H NMR (CDCl$_3$, 400 MHz) δ ppm; 8.97 (dd, J=16.9, 11.5 Hz, 1H), 7.27 (s, 1H), 6.72 (br d, J=6.3 Hz, 1H), 6.63 (d, J=11.3 Hz, 1H), 6.34 (dd, J=11.5, 11.3 Hz, 1H), 6.00 (d, J=16.9 Hz, 1H), 5.81 (br d, J=10.0 Hz, 1H), 5.74 (d, J=10.0 Hz, 1H), 5.35 (dq, J=6.6, 6.3 Hz, 1H), 4.59 (br s, 1H), 3.09 (d, J=15.2 Hz, 1H), 3.01 (d, J=15.2 Hz, 1H), 2.34 (ddd, J=13.0, 12.2, 4.4 Hz, 1H), 2.21 (t, J=7.5 Hz, 2H), 2.07 (ddd, J=13.0, 12.2, 5.6 Hz, 1H), 1.94—1.75 (m, 2H), 1.80 (s, 3H), 1.77 (d, J=6.6 Hz, 3H), 1.73 (d, j=1.0 Hz, 3H), 1.54–1.05 (m, 26H), 0.88 (t, J=6.8 Hz, 3H)

FABMS m/z 749 (M+H)$^+$

HRFABMS calcd for $C_{38}H_{57}N_2O_6S_3$ (M+H)$^+$ 749.3328, found 749.3331

EXAMPLE 6

Synthesis of Compound 6

According to the procedure as described in Example 1, Compound 6 (50 mg, 81% yield) was obtained from DC107 (51 mg, 0.099), dichloromethane (5.0 ml), pyridine (0.16 ml, 1.99 mmol) and cyclohexanecarbonyl chloride (0.134 ml, 1.0 mmol).

IR (KBr) 3450, 3350, 2932, 2858, 1730, 1652, 1612, 1530, 1447, 1369, 1247, 1193, 1166, 1130, 1100, 1001, 940, 892 cm$^{-1}$ $^1$H NMR (CDCl$_3$, 400 MHz) δ ppm; 8.81 (dd, J=16.7, 11.5 Hz, 1H), 7.28 (s, 1H), 6.75 (br d, J=6.3 Hz, 1H), 6.64 (d, J=11.5 Hz, 1H), 6.35 (dd, J=11.5, 11.5 Hz, 1H), 6.00 (dd, J=16.7, 0.6 Hz, 1H), 5.83 (br d, J=9.4 Hz, 1H), 5.69 (d, J=9.4 Hz, 1H), 5.36 (dq, J=6.6, 6.3 Hz, 1H), 4.37 (br s, 1H), 3.11 (d, J=15.2 Hz, 1H), 3.02 (d, J=15.2 Hz, 1H), 2.35 (ddd, J=13.0, 12.2, 4.7 Hz, 1H), 2.21 (tt, J=11.2, 3.6 Hz, 1H),2.08 (ddd, J=13.0, 12.2, 5.4 Hz, 1H), 1.94–1.50 (m, 6H), 1.82 (s, 3H), 1.78 (d, J=6.6 Hz, 3H), 1.73 (d, J=1.2 Hz, 3H), 1.39–1.11 (m, 6H)

FABMS m/z 621 (M+H)$^+$

HRFABMS calcd for $C_{29}H_{37}N_2O_7S_3$ (M+H)$^+$ 621.1763, found 621.1742

EXAMPLE 7

Synthesis of Compound 7

According to the procedure as described in Example 1, Compound 7 (17 mg, 84% yield) was obtained from DC107 (17 mg, 0.033 mmol), dichloromethane (0.8 ml), pyridine (0.10 ml, 1.2 mmol), benzoyl chloride (0.040 ml, 0.34 mmol) and 4-dimethylaminopyridine (5.0 mg, 0.041 mmol), IR (KBr) 3400, 2934, 1718, 1653, 1620, 1520, 1457, 1380, 1320, 1266, 1100, 1069, 799, 712 cm$^{-1}$ $^1$H NMR (CDCl$_3$, 500 MHz) δ ppm; 9.01 (dd, J=16.8, 11.6 Hz, 1H), 7.87 (dd, J=8.5, 1.2 Hz, 2H), 7.48 (dt, J=7.6, 1.2 Hz, 1H), 7.30 (s, 1H), 7.27 (dd, J=8.5, 7.6 Hz, 2H), 6.78 (br d, J=6.4 Hz, 1H), 6.67 (d, J=11.9 Hz, 1H), 6.37 (dd, J=11.6, 11.3 Hz, 1H), 6.08 (dd, J=9.8, 1.1 Hz, 1H), 6.07 (d, J=16.8 Hz, 1H), 5.95 (br d, J=9.8 Hz, 1H), 5.32 (dq, J=6.7, 6.4 Hz, 1H), 4.54 (br s, 1H), 3.09 (d, J=14.9 Hz, 1H), 3.03 (d, J=14.9 Hz, 1H), 2.39 (dt, J=13.1, 4.0 Hz, 1H), 2.11 (dt, J=13.1, 5.2 Hz, 1H), 1.92–1.81 (m, 2H), 1.82 (d, J=1.1 Hz, 3H), 1.79 (s, 3H), 1.60 (d, J=6.4 Hz, 3H)

SIMS m/z 615 (M+H)$^+$

HRFABMS calcd for $C_{29}H_{31}N_2O_7S_3$ (M+H)$^+$ 615.1293, found 615.1307

EXAMPLE 8

Synthesis of Compound 8

According to the procedure as described in Example 1, Compound 8 (21 mg, 56% yield) was obtained from DC107 (30 mg, 0.060 mmol), dichloromethane (3.0 ml), pyridine (0.14 ml, 1.78 mmol) and p-fluorobenzoyl chloride (0.105 ml, 0.89 mmol).

IR (KBr) 3420, 2930, 1721, 1653, 1604, 1520, 1506, 1448, 1411, 1370, 1266, 1155, 1104, 1091, 992, 950, 894, 854, 799, 764 cm$^{-1}$ $^1$H NMR (CDCl$_3$, 500 MHz) δ ppm; 8.90 (dd, J=16.6, 11.6 Hz, 1H), 7.95–7.88 (m, 2H), 7.31 (s, 1H), 6.97–6.91 (m, 2H), 6.66 (d, J=11.3 Hz, 1H), 6.66 (br d, J=6.4 Hz, 1H), 6.39 (dd, J=11.6, 11.3 Hz, 1H), 6.10 (d, J=9.6 Hz, 1H), 6.09 (d, J=16.6 Hz, 1H), 5.92(br d, J=9.6 Hz, 1H), 5.36 (dq, J=6.7, 6.4 Hz, 1H), 4.31 (br s, 1H), 3.07 (br s, 2H), 2.39 (dt, J=13.0, 4.0 Hz, 1H), 2.13 (dt, J=13.0, 5.2 Hz, 1H), 1.95–1.75 (m, 2H), 1.82 (d, J=0.9 Hz, 3H), 1.79 (s, 3H), 1.62 (d, J=6.7 Hz, 3H)

FABMS m/z 633 (M+H)$^+$

HRFABMS calcd for $C_{29}H_{30}FN_2O_7S_3$ (M+H)$^+$ 633.1199, found 633.1203

EXAMPLE 9

Synthesis of Compound 9

According to the procedure as described in Example 1, Compound 9 (40 mg, 75% yield) was obtained from DC107 (40 mg, 0.079 mmol), dichloromethane (4.0 ml), pyridine (0.16 ml, 2.0 mmol) and 2-quinoxaloyl chloride (46 mg, 0.24 mmol).

IR (KBr) 3420, 2932, 1716, 1659, 1613, 1546, 1493, 1446, 1367, 1341, 1269, 1231, 1156, 1104, 980, 895, 799, 774 cm$^{-1}$ $^1$H NMR (CDCl$_3$, 400 MHz) δ ppm; 9.41 (s, 1H), 8.96 (dd, J=16.9, 11.2 Hz, 1H), 8.14 (dd, J=8.3, 1.3 Hz, 1H), 7.92 (dd, J=8.3, 1.3 Hz, 1H), 7.86 (ddd, J=8.3, 6.9, 1.3 Hz, 1H), 7.78 (ddd, J=8.3, 6.9, 1.3 Hz, 1H), 7.31 (s, 1H), 6.68 (d, J=11.2 Hz, 1H), 6.64 (br d, J=6.4 Hz, 1H), 6.39 (dd, J=11.2, 11.2 Hz, 1H), 6.26 (d, J=9.7 Hz, 1H), 6.13 (d, J=16.6 Hz, 1H), 6.00 (br d, J=9.7 Hz, 1H), 5.36 (dq, J=6.6, 6.4 Hz, 1H), 4.28 (br s, 1H), 3.11 (d, J=15.3 Hz, 1H), 3.05 (d, J=15.3 Hz, 1H), 2.44 (dt, J=12.9, 4.2 Hz, 1H), 2.14 (dt, J=13.7, 5.0 Hz, 1H), 1.98–1.72 (m, 2H), 1.86 (d, J=1.2 Hz, 3H), 1.77 (s, 3H), 1.66 (d, J=6.6 Hz, 3H)

FABMS m/z 667 (M+H)$^+$

HRFABMS calcd for $C_{31}H_{31}N_4O_7S_3$ (M+H)$^+$ 667.1355, found 667.1360

EXAMPLE 10

Synthesis of Compound 10

According to the procedure as described in Example 1, Compound 10 (48 mg, 85% yield) was obtained from DC107 (50 mg, 0.098 mmol), dichloromethane (5.0 ml), pyridine (0.16 ml, 1.96 mmol) and ethyl chloroformate (0.094 ml, 0.98 mmol).

IR (KBr) 3400, 2930, 1735, 1660, 1615, 1540, 1450, 1374, 1256, 1202, 1095, 998, 784 cm$^{-1}$ $^1$H NMR (CDCl$_3$, 400 MHz) δ ppm; 8.76 (dd, J=16.6, 11.4 Hz, 1H), 7.27 (s, 1H), 6.66 (br d, J=6.5 Hz, 1H), 6.66 (d, J=11.4 Hz, 1H), 6.37 (dd, J=11.4, 11.4 Hz, 1H), 6.07 (d, J=16.6 Hz, 1H), 5.78 (br d, J=10.0 Hz, 1H), 5.73 (d, J=10.0 Hz, 1H), 5.36 (dq, J=6.5, 6.5 Hz, 1H), 4.41 (br s, 1H), 4.14 (q, J=7.1 Hz, 2H), 3.04 (s, 2H), 2.34 (dt, J=12.7, 4.0 Hz, 1H), 2.06 (ddd, J=13.0, 12.7, 5.3 Hz, 1H), 1.89 (ddd, J=12.7, 12.4, 5.3 Hz, 1H), 1.77 (s, 3H), 1.76 (ddd, J=13.0, 12.4, 4.0 Hz, 1H), 1.75 (d, J=1.2 Hz, 3H), 1.74 (d, J=6.5 Hz, 3H), 1.23 (t, J=7.1 Hz, 3H)

FABMS m/z 583 (M+H)$^+$

HRFABMS calcd for $C_{25}H_{31}N_2O_8S_3$ (M+H)$^+$ 583.1242, found 583.1259

EXAMPLE 11

Synthesis of Compound 11

According to the procedure as described in Example 1, Compound 11 (50 mg, 84% yield) was obtained from DC107 (50 mg, 0.098mmol), dichloromethane (5.0 ml), pyridine (0.080 ml, 0.98 mmol) and isobutyl chloroformate (0.089 ml, 0.69 mmol).

IR (KBr) 3400, 3340, 2966, 1740, 1660, 1615, 1530, 1448, 1378, 1252, 1202, 1099, 996, 968, 946, 894, 808,785 cm$^{-1}$

¹H NMR (CDCl₃, 400 MHz) δ ppm; 8.82 (dd, J=16.2, 11.3 Hz, 1H), 7.26 (s, 1H), 6.71 (br d, J=6.6 Hz, 1H), 6.65 (d, J=11.5 Hz, 1H), 6.37 (dd, J=11.5, 11.3 Hz, 1H), 6.06 (d, J=16.2 Hz, 1H), 5.78 (br d, J=9.7 Hz, 1H), 5.68 (d, J=9.7 Hz, 1H), 5.35 (dq, J=6.6, 6.4 Hz, 1H), 4.52 (br s, 1H), 3.89 (dd, J=10.5, 6.6 Hz, 1H), 3.82 (dd, J=10.5, 6.6 Hz, 1H), 3.09 (d, J=15.3 Hz, 1H), 3.03 (d, J=15.3 Hz, 1H), 2.35 (dt, J=12.7, 3.7 Hz, 1H), 2.07 (dt, J=12.7, 5.2 Hz, 1H), 2.03–1.70 (m, 2H), 1.86 (dq, J=6.8, 6.6 Hz, 1H), 1.79 (s, 3H), 1.75 (d, J=6.4 Hz, 3H), 1.75 (d, J=1.0 Hz, 3H), 0.83 (d, J=6.8 Hz, 3H), 0.88 (t, J=6.8 Hz, 3H)

FABMS m/z 611 (M+H)⁺

HRFABMS calcd for $C_{27}H_{35}N_2O_8S_3$ (M+H)⁺ 611.1555, found 611.1568

EXAMPLE 12
Synthesis of Compound 12

According to the procedure as described in Example 1, Compound 12 (40 mg, 81% yield) was obtained from DC107 (40 mg, 0.079mmol), dichloromethane (4.0 ml), pyridine (0.064 ml, 0.79 mmol) and phenyl chloroformate (0.030 ml, 0.24 mmol).

IR (KBr) 3400, 2924, 1761, 1720, 1660, 1612, 1522, 1490, 1448, 1369, 1251, 1206, 1101, 1022, 949, 894, 767 cm⁻¹

¹H NMR (CDCl₃, 500 MHz) δ ppm; 8.83 (dd, J=16.5, 11.3 Hz, 1H), 7.32 (ddd, J=8.5, 7.3, 1.2 Hz, 2H), 7.29 (s, 1H), 7.20 (dt, J=7.3, 1.2 Hz, 1H), 7.08 (dt, J=8.5, 1.2 Hz, 2H), 6.69 (br d, J=6.7 Hz, 1H), 6.68 (d, J=11.3 Hz, 1H), 6.40 (dd, J=11.3, 11.3 Hz, 1H), 6.11 (d, J=16.5 Hz, 1H), 5.85 (d, J=10.2 Hz, 1H), 5.83 (d, J=10.2 Hz, 1H), 5.38 (dq, J=6.7, 6.7 Hz, 1H), 4.43 (br s, 1H), 3.09 (d, J=12.5 Hz, 1H), 3.05 (d, J=12.5 Hz, 1H), 2.38 (ddd, J=13.1, 12.8, 4.0 Hz, 1H), 2.09 (dt, J=13.1, 4.9 Hz, 1H), 1.91 (ddd, J=12.8, 12.5, 4.9 Hz, 1H), 1.80 (ddd, J=13.1, 12.5, 4.0 Hz, 1H), 1.77 (d, J=6.7 Hz, 3H), 1.76 (s, 3H), 1.76 (s, 3H)

FABMS m/z 631 (M+H)⁺

HRFABMS calcd for $C_{29}H_{31}N_2O_8S_3$ (M+H)⁺ 631.1242, found 631.1258

EXAMPLE 13
Synthesis of Compound 13

According to the procedure as described in Example 1, Compound 13 (64 mg, 96% yield) was obtained from DC107 (51 mg, 0.99 mmol), dichloromethane (5.0 ml), pyridine (0.080 ml, 0.98 mmol) and p-nitrophenyl chloroformate (59.8 mg, 0.30 mmol).

IR (KBr) 3370, 2936, 1764, 1718, 1654, 1616, 1570, 1526, 1491, 1458, 1348, 1250, 1216, 1106, 164, 949, 897, 861, 799, 751 cm⁻¹

¹H NMR (CDCl₃, 400 MHz) δ ppm; 8.73 (dd, J=16.6, 11.2 Hz, 1H), 8.23 (ddd, J=9.0, 3.2, 2.2 Hz, 2H), 7.32 (ddd, J=9.0, 3.2, 2.2 Hz, 2H), 7.30 (s, 1H), 6.68 (d, J=11.3 Hz, 1H), 6.52 (br d, J=6.6 Hz, 1H), 6.38 (dd, J=11.3, 11.2 Hz, 1H), 6.12 (d, J=16.6 Hz, 1H), 5.89 (d, J=9.8 Hz, 1H), 5.85 (br d, J=9.8 Hz, 1H), 5.42 (dq, J=6.8, 6.6 Hz, 1H), 4.11 (br s, 1H), 3.17(d, J=15.6 Hz, 1H), 2.99 (d, J=15.6 Hz, 1H), 2.40 (dt, J=13.0, 4.1 Hz, 1H), 2.11 (dt, J=13.0, 4.5 Hz, 1H), 1.92 (dt, J=14.4, 4.5 Hz, 1H), 1.72–1.70 (m, 1H), 1.76 (d, J=6.8 Hz, 3H), 1.76 (d, J=0.7 Hz, 3H), 1.72 (s, 3H)

FABMS m/z 676 (M+H)⁺

HRFABMS calcd for $C_{29}H_{30}N_3O_{10}S_3$ (M+H)⁺ 676.1093, found 676.1093

EXAMPLE 14
Synthesis of Compound 14

According to the procedure as described in Example 1, Compound 14 (29 mg, 74% yield) was obtained from DC107 (31 mg, 0.060 mmol), dichloromethane (3.0 ml), pyridine (0.66 ml, 8.17 mmol) and benzyl chloroformate (1.18 ml, a 30% toluene solution, 2.47 mmol).

IR (KBr) 3330, 2934, 1744, 1720, 1655, 1614, 1530, 1455, 1382, 1255, 1099, 1000, 949, 895, 799, 783, 697 cm⁻¹

¹H NMR (CDCl₃, 400 MHz) δ ppm; 8.84 (dd, J=16.3, 11.2 Hz, 1H), 7.35–7.22 (m, 5H), 7.30 (s, 1H), 6.64 (d, J=11.2 Hz, 1H), 6.62 (br d, J=6.6 Hz, 1H), 6.34 (dd, J=11.2, 11.2 Hz, 1H), 6.05 (d, J=16.3 Hz, 1H), 5.79 (br d, J=9.6 Hz, 1H), 5.72 (d, J=9.6 Hz, 1H), 5.32 (dq, J=6.6, 6.6 Hz, 1H), 5.10 (s, 2H), 4.50 (br s, 1H), 3.08 (d, J=15.2 Hz, 1H), 3.01 (d, J=15.2 Hz, 1H), 2.33 (dt, J=12.7, 3.9 Hz, 1H), 2.08 (dt, J=12.7, 5.6 Hz, 1H), 1.93–1.72 (m, 2H), 1.79 (s, 3H), 1.74 (d, J=1.0 Hz, 3H), 1.69 (d, J=6.6 Hz, 3H)

FABMS m/z 645 (M+H)⁺

HRFABMS calcd for $C_{30}H_{33}N_2O_8S_3$ (M+H)⁺ 645.1399, found 645.1415

EXAMPLE 15
Synthesis of Compound 15

According to the procedure as described in Example 1, Compound 15 (18.5 mg, 43% yield) was obtained from DC107 (30 mg, 0.059 mmol), dichloromethane (2.5 ml), pyridine (0.029 ml, 0.35 mmol) and 9-fluorenylmethyl chloroformate (45 mg, 0.17 mmol).

IR (KBr) 3410, 2930, 1746, 1718, 1654, 1612, 1520, 1449, 1383, 1323, 1260, 1102, 949, 805, 758, 740 cm⁻¹

¹H NMR (CDCl₃, 400 MHz) δ ppm; 9.01 (dd, J=16.6, 11.3 Hz, 1H), 7.72–7.09 (m, 8H), 7.30 (s, 1H), 6.65 (d, J=11.3 Hz, 1H), 6.62 (br d, J=6.6 Hz, 1H), 6.35 (dd, J=11.3, 11.3 Hz, 1H), 6.06 (d, J=16.6 Hz, 1H), 5.84 (br d, J=9.6 Hz, 1H), 5.69 (d, J=9.6 Hz, 1H), 5.32 (dq, J=6.6, 6.6 Hz, 1H), 4.64 (br s, 1H), 4.46 (dd, J=10.5, 7.0 Hz, 1H), 4.24 (dd, J=10.5, 7.4 Hz, 1H), 4.14 (dd, J=7.4, 7.0 Hz, 1H), 3.14 (d, J=15.3 Hz, 1H), 2.99 (d, J=15.3 Hz, 1H), 2.35 (ddd, J=13.0, 12.0, 4.0 Hz, 1H), 2.11 (ddd, J=13.5, 13.0, 6.1 Hz, 1H), 1.95–1.60 (m, 2H), 1.83 (s, 3H), 1.78 (br s, 3H), 1.72 (d, J=6.6 Hz, 3H)

FABMS m/z 733 (M+H)⁺

HRFABMS calcd for $C_{37}H_{37}N_2O_8S_3$ (M+H)⁺ 733.1712, found 733.1734

EXAMPLE 16
Synthesis of Compound 16

Compound 13 (4.3 mg, 0.0063 mmol) was dissolved in chloroform (0.5 ml), and piperidine (0.0025 ml, 0.025 mmol) was added thereto, followed by stirring at 25° C. for 30 minutes. The reaction mixture was purified by thin layer chromatography (developed with ether/methanol=97/3) to obtain Compound 16 (1.0 mg, 26% yield).

IR (KBr) 3430, 2938, 2860, 1700, 1671, 1617, 1540, 1433, 1371, 1258, 1233, 1151, 1100, 1023, 949, 894, 854, 799, 760 cm⁻¹

¹H NMR (CDCl₃, 500 MHz) δ ppm; 8.73 (dd, J=16.4, 11.6 Hz, 1H), 7.28 (s, 1H), 6.84 (br s, 1H), 6.63 (d, J=11.1 Hz, 1H), 6.38 (dd, J=11.6, 11.1 Hz, 1H), 6.04 (d, J=16.4 Hz, 1H), 5.79 (br d, J=9.5 Hz, 1H), 5.73 (d, J=9.5 Hz, 1H), 5.37 (dq, J=6.7, 6.4 Hz, 1H), 4.52 (br s, 1H), 3.55–3.10 (m, 4H), 3.11 (d, J=15.1 Hz, 1H), 3.03 (d, j=15.1 Hz, 1H), 2.34 (ddd, J=13.1, 11.9, 5.2 Hz, 1H), 2.06 (ddd, J=12.8, 11.9, 5.2 Hz, 1H), 1.93–1.80 (m, 2H), 1.81 (s, 3H), 1.80–1.38 (m, 6H), 1.75 (d, J=6.7 Hz, 3H), 1.74 (s, 3H)

FABMS m/z 622 (M+H)⁺

HRFABMS calcd for $C_{28}H_{36}N_3O_7S_3$ (M+H)⁺ 622.1715, found 622.1730

EXAMPLE 17

Synthesis of Compound 17

According to the procedure as described in Example 16, Compound 17 (1.5 mg, 9% yield) was obtained from Compound 13 (18 mg, 0.027 mmol), chloroform (1.5 ml) and pyrrolidine (0.0045 ml, 0.054 mmol).

IR (KBr) 3420, 2938, 1703, 1670, 1612, 1521, 1424, 1375, 1260, 1200, 1181, 1098, 1000, 861, 762 cm$^{-1}$ $^1$H NMR (CDCl$_3$, 100 MHz) δ ppm; 8.80 (dd, J=16.5, 11.5 Hz, 1H), 7.28 (s, 1H), 6.88 (br d, J=6.2 Hz, 1H), 6.62 (d, J=11.5 Hz, 1H), 6.30 (dd, J=11.5, 11.5 Hz, 1H), 6.04 (d, J=16.5 Hz, 1H), 5.80 (br s, 2H), 5.36 (dq, J=6.2, 6.5 Hz, 1H), 3.5–3.0 (m, 6H), 2.5–1.4 (m, 8H), 1.78 (s, 3H), 1.75 (s, 3H), 1.72 (d, J=6.5 Hz, 3H)

FABMS m/z 608 (M+H)$^+$

HRFABMS calcd for C$_{27}$H$_{34}$N$_3$O$_7$S$_3$ (M+H)$^+$ 608.1559, found 608.1586

EXAMPLE 18

Synthesis of Compound 18

DC107 (71 mg, 0.14 mmol) was dissolved in dichloromethane (9.0 ml), and then 3,4-dihydro-2H-pyran (0.164 ml, 1.81 mmol) and camphorsulfonic acid (77 mg, 0.33 mmol) were added thereto, followed by stirring at 0° C. for 4 hours. After subjecting the resulting mixture to the usual post-treatment, the mixture was purified by silica gel column chromatography (eluted with chloroform/methanol=99/1) to obtain Compound 18 (49 mg, 58% yield). From $^1$H NMR data, Compound 18 was found to be a mixture of diastereomers at about 5:4 due to the asymmetric carbon of the tetrahydropyranyl group.

IR (KBr) 3400, 3320, 2930, 2850, 1715, 1651, 1612, 1538, 1450, 1373, 1260, 1098, 1025, 970, 890, 867, 808 cm$^{-1}$ $^1$H NMR (CDCl$_3$, 500 MHz) δ ppm; major isomer: 9.25 (dd, J=16.5, 11.6 Hz, 1H), 7.25 (s, 1H), 6.88 (br d, J=6.4 Hz, 1H), 6.63 (d, J=11.6 Hz, 1H), 6.36 (dd, J=11.6, 11.6 Hz, 1H), 6.01 (d, J=16.5 Hz, 1H), 5.94 (d, J=9.7 Hz, 1H), 5.30 (dq, J=6.7, 6.4 Hz, 1H), 5.08 (dd, J=9.7, 1.2 Hz, 1H), 5.00 (br s, 1H), 4.58 (t, J=4.6 Hz, 1H), 3.78–3.74 (m, 1H), 3.50–3.45 (m, 1H), 3.25 (d, J=15.0 Hz, 1H), 2.90 (d, J=15.0 Hz, 1H), 2.35–2.28 (m, 1H), 2.12–2.06 (m, 1H), 1.95–1.44 (m, 8H), 1.88 (s, 3H), 1.79 (d, J=6.7 Hz, 3H), 1.72 (d, J=1.2 Hz, 3H); minor isomer: 9.04 (dd, J=16.5, 11.6 Hz, 1H), 7.25 (s, 1H), 6.86 (br d, J=6.4 Hz, 1H), 6.63 (d, J=11.6 Hz, 1H), 6.39 (dd, J=11.6, 11.6 Hz, 1H), 6.05 (d, J=16.5 Hz, 1H), 5.87 (d, J=9.8 Hz, 1H), 5.27 (dq, J=6.4, 6.4 Hz, 1H), 4.93 (br s, 1H), 4.91 (dd, J=9.8, 1.2 Hz, 1H), 4.63 (br s, 1H), 3.72–3.67 (m, 1H), 3.45–3.39 (m, 1H), 3.22 (d, J=14.6 Hz, 1H), 2.88 (d, J=14.6 Hz, 1H), 2.35–2.28 (m, 1H), 2.14–2.06 (m, 1H), 1.90–1.40 (m, 8H), 1.90 (s, 3H), 1.72 (d, J=6.4 Hz, 3H), 1.72 (s, 3H)

FABMS m/z 595 (M+H)$^+$

HRFABMS calcd for C$_{27}$H$_{35}$N$_2$O$_7$S$_3$ (M+H)$^+$ 595.1606, found 595.1606

EXAMPLE 19

Synthesis of Compound 19

DC107 (10 mg, 0.020 mmol) was dissolved in dichloromethane (1.0 ml), and then ethyl vinyl ether (0.224 ml, 2.35 mmol) and pyridinium p-toluenesulfonate (5.3 mg, 0.021 mmol) were added thereto, followed by stirring at 25° C. for 1 hour. After subjecting the resulting mixture to the usual post-treatment, the mixture was purified by separation thin layer chromatography (developed with chloroform/methanol=99/1) to obtain Compound 19 (5.0 mg, 43% yield). From $^1$H NMR data, Compound 19 was found to be a mixture of diastereomers at about 3:2 due to the asymmetric carbon of the 1-ethoxyethyl group.

IR (KBr) 3420, 3350, 2990, 1721, 1645, 1613, 1540, 1460, 1367, 1096, 957, 810 cm$^{-1}$ $^1$H NMR (CDCl$_3$, 400 MHz) δ ppm; major isomer: 9.18 (dd, J=16.6, 11.5 Hz, 1H), 7.25 (s, 1H), 6.84 (br d, J=6.4 Hz, 1H), 6.63 (d, J=11.5 Hz, 1H), 6.37 (d, J=11.5 Hz, 1H), 6.02 (d, J=16.6 Hz, 1H), 5.90 (br d, J=9.5 Hz, 1H), 5.26 (dq, J=6.4, 6.4 Hz, 1H), 5.10 (br s, 1H), 4.83 (dd, J=9.5, 1.2 Hz, 1H), 4.69 (q, J=5.4 Hz, 1H), 3.52–3.25 (m, 2H), 3.24 (d, J=14.6 H, 1H), 2.86 (d, J=14.6 Hz, 1H), 2.35–1.80 (m, 4H), 1.91 (s, 3H), 1.76 (d, J=6.4 Hz, 3H); 1.73 (s, 3H), 1.18 (d, J=5.4 Hz, 3H), 1.07 (t, J=7.0 Hz, 3H), minor isomer: 9.31 (dd, J=16.6, 11.5 Hz, 1H), 7.25 (s, 1H), 6.83 (br d, J=6.4 Hz, 1H), 6.64 (d, J=11.5 Hz, 1H), 6.37 (dd, J=11.5, 11.5 Hz, 1H), 6.01 (d, J=16.6 Hz, 1H), 5.91 (br d, J=9.8 Hz, 1H), 5.27 (dq, J=6.4, 6.4 Hz, 1H), 5.08 (br s, 1H), 4.98 (dd, J=9.8, 1.2 Hz, 1H), 4.64 (q, J=5.4 Hz, 1H), 3.52–3.25 (m, 2H), 3.24 (d, J=14.6 Hz, 1H), 2.87 (d, J=14.6 Hz, 1H), 2.35–1.80 (m, 4H), 1.90 (s, 3H), 1.78 (d, J=6.6 Hz, 3H), 1.73 (br s, 3H), 1.14 (t, J=7.1 Hz, 3H), 1.12 (d, J=5.4 Hz, 3H)

FABMS m/z 583 (M+H)$^+$

HRFABMS calcd for C$_{25}$H$_{35}$N$_2$O$_7$S$_3$ (M+H)$^+$ 583.1606, found 583.1600

EXAMPLE 20

Synthesis of Compound 20

DC107 (44 mg, 0.085 mmol) was dissolved in dichloromethane (5.0 ml), and then benzyl 2,2,2-trichloroacetimidate (0.22 ml, 1.18 mmol) and trifluoromethanesulfonic acid (0.011 ml, 0.13 mmol) were added thereto, followed by stirring at 25° C. for 1 hour. After subjecting the resulting mixture to the usual post-treatment, the mixture was purified by thin layer chromatography (developed with ether/methanol=97/3) to obtain Compound 20 (7.0 mg, 14% yield).

IR (KBr) 3420, 2926, 1711, 1653, 1612, 1532, 1451, 1369, 1199, 1095, 1067, 997, 945, 799, 736, 697 cm$^{-1}$ $^1$H NMR (CDCl$_3$, 400 MHz) δ ppm; 9.46 (dd, J=16.3, 11.5 Hz, 1H), 7.25–7.03 (m, 5H), 7.27 (s, 1H), 6.84 (br d, J=6.2 Hz, 1H), 6.68 (d, J=11.5 Hz, 1H), 6.41 (dd, J=11.5, 11.5 Hz, 1H), 6.06 (d, J=16.3 Hz, 1H), 5.93 (br d, J=9.5 Hz, 1H), 5.20 (dq, J=6.5, 6.2 Hz, 1H), 5.08 (br s, 1H), 4.68 (dd, J=9.5, 1.0 Hz, 1H), 4.49 (d, J=11.6 Hz, 1H), 4.40 (d, J=11.6 Hz, 1H), 3.24 (d, J=14.5 Hz, 1H), 2.86 (d, J=14.5 Hz, 1H), 2.32–1.45 (m, 4H), 1.90 (s, 3H), 1.67 (d, J=1.0 Hz, 3H), 1.53 (d, J=6.5 Hz, 3H)

FABMS m/z 601 (M+H)$^+$

HRFABMS calcd for C$_{29}$H$_{33}$N$_2$O$_6$S$_3$ (M+H)$^+$ 601.1501, found 601.1490

EXAMPLE 21

Synthesis of Compound 21

DC107 (50 mg, 0.098 mmol) was dissolved in dichloromethane (1.0 ml), and then pyridine (0.79 ml, 9.8 mmol), acetyl chloride (0.35 ml, 4.9 mmol) and 4-dimethylaminopyridine (2.4 mg, 0.020 mmol) were added thereto, followed by stirring at 25° C. for 20 minutes. After subjecting the resulting mixture to the usual post-treatment, the mixture was purified by thin layer chromatography (developed with ether/methanol=99/1) to obtain Compound 21 (43 mg, 74% yield).

IR (KBr) 3450, 2932, 1735, 1652, 1620, 1558, 1520, 1456, 1369, 1218, 1109, 1020, 950 cm$^{-1}$ $^1$H NMR (CDCl$_3$, 400 MHz) δ ppm; 8.33 (dd, J=16.6, 11.5 Hz, 1H), 7.28 (s, 1H), 6.66 (d, J=11.3 Hz, 1H), 6.39 (br d, J=6.6 Hz, 1H), 6.38 (dd, J=11.5, 11.3 Hz, 1H), 6.08 (d, J=16.6 Hz, 1H), 5.99 (d, J=9.3 Hz, 1H), 5.68 (br d, J=9.3 Hz, 1H), 5.50 (dq, J=6.6, 6.6 Hz, 1H), 3.39 (d, J=16.4 Hz, 1H), 2.95 (d, J=16.3 Hz, 1H), 2.12 (s, 3H), 2.10 (s, 3H), 2.10–1.72 (m, 4H), 2.01 (s, 3H), 1.75 (d, J=6.6 Hz, 3H), 1.68 (d, J=1.2 Hz, 3H)

FABMS m/z 595 (M+H)$^+$
HRFABMS calcd for $C_{26}H_{31}N_2O_8S_3$ (M+H)$^+$ 595.1242, found 595.1224

EXAMPLE 22
Synthesis of Compound 22

DC107 (50 mg, 0.098 mmol) was dissolved in dichloromethane (1.0 ml) and pyridine (0.79 ml, 9.8 mmol), and then pivaloyl chloride (0.84 ml, 6.85 mmol) and 4-dimethylaminopyridine (2.4 mg, 0.020 mmol) were added thereto, followed by stirring at 25° C. for 24 hours. After subjecting the resulting mixture to the usual post-treatment, the mixture was purified by silica gel column chromatography (eluted with chloroform) to obtain Compound 22 (16 mg, 24% yield).

IR (KBr) 3420, 2976, 2936, 1730, 1653, 1620, 1520, 1479, 1447, 1395, 1368, 1277, 1146, 1101, 1030, 857 cm$^{-1}$ $^1$H NMR (CDCl$_3$, 500 MHz) δ ppm; 8.64 (br dd, J=16.8, 11.3 Hz, 1H), 7.29 (s, 1H), 6.63 (d, J=11.3 Hz, 1H), 6.38 (br s, 1H), 6.34 (dd, J=11.3, 11.3 Hz, 1H), 6.02 (d, J=16.8 Hz, 1H), 5.84 (br s, 2H), 5.45 (dq, J=6.7, 6.4 Hz, 1H), 3.33 (d, J=15.9 Hz, 1H), 2.91 (br d, J=15.9 Hz, 1H), 2.20–1.60 (m, 4H), 1.89 (s, 3H), 1.76 (d, J=6.7 Hz, 3H), 1.75 (br s, 3H), 1.21 (s, 9H), 1.16 (s, 9H)

FABMS m/z 679 (M+H)$^+$
HRFABMS calcd for $C_{32}H_{43}N_2O_8S_3$ (M+H)$^+$ 679.2181, found 679.2164

EXAMPLE 23
Synthesis of Compounds 23 and 24

Compound 18 (77 mg, 0.13 mmol) was dissolved in chloroform (4.0 ml) and pyridine (2.9 ml, 35.9 mmol), and then acetic anhydride (0.68 ml, 7.2 mmol) and 4-dimethylaminopyridine (2.7 mg, 0.024 mmol) were added thereto, followed by stirring at 25° C. for 5 hours. After subjecting the resulting mixture to the usual post-treatment, a mixture of Compounds 23 and 24 (76 mg, 91% yield) was obtained. Then, 36 mg of the resulting mixture was purified by thin layer chromatography (developed with ether/methanol=97/3) to obtain Compound 23 (13 mg) and Compound 24 (11 mg) which is a diastereomer of Compound 23.

Compound 23

IR (KBr) 3420, 3332, 3100, 2942, 2856, 1763, 1716, 1670, 1612, 1521, 1447, 1368, 1212, 1112, 1078, 1021, 969, 912, 867, 808 cm$^{-1}$ $^1$H NMR (CDCl$_3$, 500 MHz) δ ppm; 8.76 (br dd, J=16.5, 11.6 Hz, 1H), 7.24 (s, 1H), 6.63 (d, J=11.3 Hz, 1H), 6.59 (br d, J=7.0 Hz, 1H), 6.35 (dd, J=11.6, 11.3 Hz, 1H), 6.02 (d, J=16.5 Hz, 1H), 5.83 (br d, J=9.2 Hz, 1H), 5.44 (dq, J=7.0, 6.7 Hz, 1H), 5.18 (d, J=9.2 Hz, 1H), 4.56 (dd, J=4.9, 2.7 Hz, 1H), 3.87–3.82 (m, 1H), 3.50–3.47 (m, 1H), 3.19 (d, J=15.5 Hz, 1H), 2.94 (br d, J=15.5 Hz, 1H), 2.22–1.45 (m, 10H), 2.10 (s, 3H), 2.07 (s, 3H), 1.74 (d, J=1.2 Hz, 3H), 1.73 (d, J=6.7 Hz, 3H)

FABMS m/z 637 (M+H)$^+$
HRFABMS calcd for $C_{29}H_{37}N_2O_8S_3$ (M+H)$^+$ 637.1712, found 637.1723

Compound 24

IR (KBr) 3450, 3330, 3100, 2942, 2860, 1759, 1718, 1653, 1615, 1522, 1447, 1368, 1212, 1104, 1078, 1019, 972, 910, 866, 799 cm$^{-1}$ $^1$H NMR (CDCl$_3$, 500 MHz) δ ppm; 8.57 (br dd, J=16.5, 11.6 Hz, 1H), 7.24 (s, 1H), 6.62 (d, J=11.1 Hz, 1H), 6.49 (br d, J=6.6 Hz, 1H), 6.36 (dd, J=11.6, 11.1 Hz, 1H), 6.08 (d, J=16.5 Hz, 1H), 5.70 (br d, J=9.3 Hz, 1H), 5.42 (dq, J=6.7, 6.7 Hz, 1H), 5.11 (d, J=9.3 Hz, 1H), 4.68 (t, J=3.5 Hz, 1H), 3.78–3.74 (m, 1H), 3.46–3.42 (m, 1H), 3.22 (d, J=15.7 Hz, 1H), 2.81 (br d, J=15.7 Hz, 1H), 2.25–1.45 (m, 10H), 2.23 (s, 3H), 2.21 (s, 3H), 1.73 (d, J=1.2 Hz, 3H), 1.70 (d, J=6.7 Hz, 3H)

FABMS m/z 637 (M+H)$^+$
HRFABMS calcd for $C_{29}H_{37}N_2O_8S_3$ (M+H)$^+$ 637.1712, found 637.1738

EXAMPLE 24
Synthesis of Compound 25

The unpurified mixture of Compounds 23 and 24 (30 mg, 0.047 mmol) obtained in Example 23 was dissolved in methanol (4.0 ml), and camphorsulfonic acid (22 mg, 0.094 mmol) was added thereto, followed by stirring at 0° C. for 40 minutes. After subjecting the mixture to the usual post-treatment, the resulting mixture was purified by thin layer chromatography (developed with chloroform/methanol=99/3) to obtain Compound 25 (14 mg, 53% yield).

IR (KBr) 3450, 3300, 2930, 1760, 1716, 1654, 1614, 1528, 1446, 1372, 1218, 1104, 1066, 1010, 949, 842, 808 cm$^{-1}$ $^1$H NMR (CDCl$_3$, 400 MHz) δ ppm; 8.08 (ddd, J=16.5, 11.5, 1.0 Hz, 1H), 7.26 (s, 1H), 6.72 (dd, J=11.2, 1.0 Hz, 1H), 6.40 (dd, J=11.5, 11.2 Hz, 1H), 6.24 (br d, J=7.2 Hz, 1H), 6.20 (d, J=16.5 Hz, 1H), 5.51 (dq, J=7.2, 6.8 Hz, 1H), 5.48 (br d, J=9.0 Hz, 1H), 5.05 (d, J=9.0 Hz, 1H), 3.97 (br s, 1H), 3.46 (d, J=16.6 Hz, 1H), 3.00 (d, J=16.6 Hz, 1H), 2.12–1.82 (m, 3H), 2.09 (s, 3H), 1.98 (s, 3H), 1.75–1.65 (m, 1H), 1.74 (d, J=6.8 Hz, 3H), 1.64 (d, J=1.2 Hz, 3H)

FABMS m/z 553 (M+H)$^+$
HRFABMS calcd for $C_{24}H_{29}N_2O_7S_3$ (M+H)$^+$ 553.1137, found 553.1143

EXAMPLE 25
Synthesis of Compound 26

DC107 (51 mg, 0.10 mmol) was dissolved in dichloromethane (10 ml), and N,N-diisopropylethylamine (0.69 ml, 4.0 mmol) and iodomethane (0.19 ml, 3.0 mmol) were added thereto, followed by stirring at 25° C. for 5 hours. After subjecting the mixture to the usual post-treatment, the mixture was purified by thin layer chromatography (developed with chloroform/methanol=97/3) to obtain Compound 26 (17 mg, 34% yield).

IR (KBr) 3430, 2930, 1720, 1680, 1610, 1448, 1364, 1264, 1155, 1089, 997, 753 cm$^{-1}$ $^1$H NMR (CDCl$_3$, 500 MHz) δ ppm; 8.45 (ddd, J=16.5, 11.6, 1.0 Hz, 1H), 7.47 (s, 1H), 6.58 (d, J=11.6 Hz, 1H), 6.23 (dd, J=11.6, 11.6 Hz, 1H), 6.17 (d, J=16.5 Hz, 1H), 5.73 (br d, J=8.5 Hz, 1H), 5.46 (br s, 1H), 5.41 (q, J=6.7 Hz, 1H), 4.94 (d, J=8.5 Hz, 1H), 3.93 (d, J=17.8 Hz, 1H), 2.28 (d, J=17.8 Hz, 1H), 2.38–1.92 (m, 4H), 2.23 (s, 3H), 2.03 (d, J=6.7 Hz, 3H), 1.78 (s, 3H), 1.75 (d, J=1.2 Hz, 3H)

FABMS m/z 525 (M+H)$^+$
HRFABMS calcd for $C_{23}H_{29}N_2O_6S_3$ (M+H)$^+$ 525.1189, found 525.1187

EXAMPLE 26
Synthesis of Compound 27

DC107 (51 mg, 0.10 mmol) was dissolved in dimethylformamide (4.0 ml), and N,N-diisopropylethylamine (0.35 ml, 1.98 mmol), allyl bromide (0.086 ml, 0.99 mmol) and potassium iodide (82 mg, 0.50 mmol) were added thereto, followed by stirring at 25° C. for 16 hours. After subjecting the mixture to the usual post-treatment, the mixture was purified by thin layer chromatography (developed with chloroform/methanol=95/5) to obtain Compound 27 (26 mg, 49% yield).

IR (KBr) 3420, 2930, 1720, 1675, 1610, 1450, 1370, 1262, 1153, 1090, 987, 923 cm$^{-1}$ $^1$H NMR (CDCl$_3$, 400 MHz) δ ppm; 8.38 (dd, J=16.4, 11.3 Hz, 1H), 7.27 (s, 1H), 6.51 (br d, J=11.7 Hz, 1H), 6.16 (dd, J=11.7, 11.3 Hz, 1H), 6.10 (d, J=16.4 Hz, 1H), 5.68 (ddt, J=16.8, 10.1, 6.8 Hz, 1H), 5.65 (br d, J=9.0 Hz, 1H), 5.39 (br s, 1H), 5.34 (q, J=6.8 Hz, 1H), 5.17 (dd, J=16.8, 1.2 Hz, 1H), 5.04 (br d, J=10.1 Hz, 1H), 4.87 (d, J=9.0 Hz, 1H), 3.87 (d, J=18.0 Hz, 1H), 3.67 (br s, 1H), 3.40 (dd, J=14.2, 6.8 Hz, 1H), 3.35 (dd, J=14.2, 6.8 Hz, 1H), 2.28–1.72 (m, 4H), 2.21 (d, J=18.0 Hz, 1H), 1.95 (d, J=6.8 Hz, 3H), 1.71 (s, 3H), 1.68 (d, J=0.5 Hz, 3H)

FABMS m/z 551 (M+H)$^+$

HRFABMS calcd for $C_{25}H_{31}N_2O_6S_3$ (M+H)$^+$ 551.1344, found 551.1336

EXAMPLE 27
Synthesis of Compounds 28 and 29

DC107 (100 mg, 0.20 mmol) was dissolved in dichloromethane (20 ml), and N,N-diisopropylethylamine (1.4 ml, 7.9 mmol) and chloromethyl methyl ether (0.30 ml, 4.0 mmol) were added thereto, followed by stirring at 25° C. for 3 hours. After subjecting the mixture to the usual post-treatment, the mixture was purified by silica gel column chromatography (eluted with chloroform/methanol=99/1) to obtain Compound 28 (47 mg, 43% yield) and Compound 29 (37 mg, 31% yield). Compound 28 (Monomethoxymethyl compound)

IR (KBr) 3430, 2930, 1685, 1653, 1610, 1447, 1363, 1264, 1185, 1154, 1093, 1020, 982 cm$^{-1}$ $^1$H NMR (CDCl$_3$, 400 MHz) δ ppm; 8.46 (ddd, J=16.4, 11.2, 1.0 Hz, 1H), 7.34 (s, 1H), 6.58 (d, J=12.0 Hz, 1H), 6.23 (dd, J=12.0, 11.2 Hz, 1H), 6.17 (d, J=16.4 Hz, 1H), 5.73 (br d, J=8.5 Hz, 1H), 5.49 (br s, 1H), 5.42 (q, J=6.9 Hz, 1H), 5.00 (d, J=11.0 Hz, 1H), 4.94 (d, J=11.0 Hz, 1H), 4.94 (d, J=8.5 Hz, 1H), 3.95 (d, J=17.8 Hz, 1H), 3.70 (br s, 1H), 3.31 (s, 3H), 2.35–1.85 (m, 4H), 2.30 (d, J=17.8 Hz, 1H), 2.03 (d, J=6.9 Hz, 3H), 1.79 (s, 3H), 1.75 (d, J=1.5 Hz, 3H)

FABMS m/z 555 (M+H)$^+$

HRFABMS calcd for $C_{24}H_{31}N_2O_7S_3$ (M+H)$^+$ 555.1293, found 555.1285

Compound 29 (Dimethoxymethyl compound)

IR (KBr) 3450, 2928, 1683, 1651, 1608, 1443, 1380, 1260, 1150, 1094, 1024, 982 cm$^{-1}$ $^1$H NMR (CDCl$_3$, 400 MHz) δ ppm; 9.53 (ddd, J=16.6, 11.4, 1.0 Hz, 1H), 7.40 (s, 1H), 6.62 (d, J=11.5 Hz, 1H), 6.36 (dd, J=11.5, 11.4 Hz, 1H), 6.03 (d, J=16.6 Hz, 1H), 5.83 (br d, J=9.5 Hz, 1H), 5.59 (q, J=6.7 Hz, 1H), 5.52 (br s, 1H), 5.03 (d, J=11.0 Hz, 1H), 4.93 (d, J=11.0 Hz, 1H), 4.80 (dd, J=9.5, 1.2 Hz, 1H), 4.63 (d, J=6.9 Hz, 1H), 4.59 (d, J=6.9 Hz, 1H), 4.10 (d, J=17.8 Hz, 1H), 3.33 (s, 3H), 3.29 (s, 3H), 2.43–2.30 (m, 2H), 2.33 (d, J=17.8 Hz, 1H), 1.92–1.38 (m, 2H), 1.90 (d, J=6.7 Hz, 3H), 1.75 (d, J=1.2 Hz, 3H), 1.72 (s, 3H)

FABMS m/z 599 (M+H)$^+$

HRFABMS calcd for $C_{26}H_{35}N_2O_8S_3$ (M+H)$^+$ 599.1555, found 599.1553

EXAMPLE 28
Synthesis of Compound 30

DC107 (16 mg, 0.032 mmol) was dissolved in chloroform (1.0 ml), and N,N-diisopropylethylamine (0.20 ml, 1.2 mmol) and chloromethyl methyl ether (0.070 ml, 0.92 mmol) were added thereto, followed by stirring at 0° C. for 1 hour. After subjecting the mixture to the usual post-treatment, the mixture was purified by thin layer chromatography (developed with chloroform/methanol=98/2) to obtain Compound 30 (8.3 mg, 48% yield). In this reaction, Compound 28 and Compound 29 were also produced.

IR (KBr) 3310, 2928, 1717, 1646, 1613, 1541, 1449, 1373, 1263, 1194, 1149, 1097, 1025, 946, 894, 808 cm$^{-1}$ $^1$H NMR (CDCl$_3$, 500 MHz) δ ppm; 9.10 (dd, J=16.5, 11.6 Hz, 1H), 7.26 (s, 1H), 6.85 (br d, J=6.4 Hz, 1H), 6.64 (d, J=11.6 Hz, 1H), 6.38 (t, J=11.6 Hz, 1H), 6.03 (d, J=16.5, 1.0 Hz, 1H), 5.88 (br d, J=9.4 Hz, 1H), 5.30 (dq, J=6.4, 6.4 Hz, 1H), 4.95 (br s, 1H), 4.92 (dd, J=9.4, 1.2 Hz, 1H), 4.59 (d, J=6.7 Hz, 1H), 4.54 (d, J=6.7 Hz, 1H), 3.25 (s, 3H), 3.21 (d, J=15.5 Hz, 1H), 2.92 (d, J=15.5 Hz, 1H), 2.33 (m, 1H), 2.09 (m, 1H), 1.88 (m, 2H), 1.87 (s, 3H), 1.74 (d, J=6.4 Hz, 3H), 1.73 (d, J=1.2 Hz, 3H)

SIMS m/z 555 (M+H)$^+$

HRFABMS calcd for $C_{24}H_{31}N_2O_7S_3$ (M+H)$^+$ 555.1293, found 555.1305

EXAMPLE 29
Synthesis of Compound 31

DC107 (51 mg, 0.10 mmol) was dissolved in dichloromethane (3.0 ml), and N,N-diisopropylethylamine (1.1 ml, 6.0 mmol) and chloromethyl ethyl ether (0.28 ml, 3.0 mmol) were added thereto, followed by stirring at 25° C. for 3 hours. After subjecting the mixture to the usual post-treatment, the mixture was purified by silica gel column chromatography (eluted with chloroform/methanol=99/1) to obtain Compound 31 (34 mg, 55% yield).

IR (KBr) 3440, 2980, 2920, 1684, 1652, 1610, 1455, 1362, 1263, 1150, 1096, 1022, 985 cm$^{-1}$ $^1$H NMR (CDCl$_3$, 500 MHz) δ ppm; 9.52 (ddd, J=16.5, 11.6, 0.9 Hz, 1H), 7.40 (s, 1H), 6.61 (d, J=11.3 Hz, 1H), 6.36 (dd, J=11.6, 11.3 Hz, 1H), 6.02 (d, J=16.5 Hz, 1H), 5.82 (dd, J=9.2, 0.9 Hz, 1H), 5.59 (q, J=6.7 Hz, 1H), 5.50 (br s, 1H), 5.06 (d, J=11.0 Hz, 1H), 4.98 (d, J=11.0 Hz, 1H), 4.81 (dd, J=9.2, 1.2 Hz, 1H), 4.67 (d, J=7.0 Hz, 1H), 4.63 (d, J=7.0 Hz, 1H), 4.09 (d, J=17.7 Hz, 1H), 3.56–3.46 (m, 4H), 2.45–2.30 (m, 3H), 2.32 (d, J=17.7 Hz, 1H), 1.89 (d, J=6.7 Hz, 3H), 1.74 (d, J=1.2 Hz, 3H), 1.71 (s, 3H), 1.45–1.40 (m, 1H), 1.20 (t, J=7.0 Hz, 3H), 1.14 (t, J=7.0 Hz, 3H)

FABMS m/z 627 (M+H)$^+$

HRFABMS calcd for $C_{28}H_{39}N_2O_8S_3$ (M+H)$^+$ 627.1868, found 627.1861

EXAMPLE 30
Synthesis of Compound 32

DC107 (5.5 mg, 0.011 mmol) was dissolved in dichloromethane (0.5 ml), and N,N-diisopropylethylamine (0.019 ml, 0.11 mmol) and chloromethyl benzyl ether (0.0075 ml, 0.055 mmol) were added thereto, followed by stirring at 25° C. for 6 hours. After subjecting the mixture to the usual post-treatment, the mixture was purified by thin layer chromatography (developed with chloroform/methanol=97/3) to obtain Compound 32 (2.2 mg, 32% yield).

IR (KBr) 3400, 2934, 1684, 1652, 1611, 1453, 1375, 1264, 1089, 1018, 981, 807, 741, 698 cm$^{-1}$ $^1$H NMR (CDCl$_3$, 500 MHz) δ ppm; 8.46 (ddd, J=16.2, 11.3, 1.0 Hz, 1H), 7.35–7.25 (m, 5H), 7.34 (s, 1H), 6.58 (d, J=11.6 Hz, 1H), 6.23 (dd, J=11.6, 11.3 Hz, 1H), 6.17 (d, J=16.2 Hz, 1H), 5.73 (br d, J=8.6 Hz, 1H), 5.43 (br s, 1H), 5.41 (q, J=7.0 Hz, 1H), 5.08 (d, J=11.0 Hz, 1H), 5.03 (d, J=11.0 Hz, 1H), 4.94 (d, J=8.6 Hz, 1H), 4.53 (s, 2H), 3.94 (d, J=17.7 Hz, 1H), 3.74 (br s, 1H), 2.36–1.70 (m, 4H), 2.27 (d, J=17.7 Hz, 1H), 2.02 (d, J=7.0 Hz, 3H), 1.79 (s, 3H), 1.74 (d, J=1.0 Hz, 3H)

FABMS m/z 631 (M+H)$^+$

HRFABMS calcd for $C_{30}H_{35}N_2O_7S_3$ (M+H)$^+$ 631.1606, found 631.1624

EXAMPLE 31
Synthesis of Compound 33

DC107 (40 mg, 0.079 mmol) was dissolved in dimethylformamide (4.0 ml), and N,N-diisopropylethylamine (0.27 ml, 1.6 mmol), ethyl bromoacetate (0.088 ml, 0.79 mmol) and tetra-n-butylammonium iodide (291 mg, 0.79 mmol)

were added thereto, followed by stirring at 25° C. for 8 hours. After subjecting the resulting mixture to the usual post-treatment, the mixture was purified by silica gel column chromatography (eluted with chloroform) to obtain Compound 33 (36 mg, 77% yield).

IR (KBr) 3420, 2984, 2938, 1715, 1684, 1647, 1610, 1448, 1368, 1264, 1155, 1092, 1020, 991, 860 cm$^{-1}$ $^1$H NMR (CDCl$_3$, 400 MHz) δ ppm; 8.46 (ddd, J=16.5, 11.2, 1.0 Hz, 1H), 7.35 (s, 1H), 6.59 (d, J=11.7 Hz, 1H), 6.24 (dd, J=11.7, 11.2 Hz, 1H), 6.17 (d, J=16.5 Hz, 1H), 5.72 (dd, J=8.8, 1.0 Hz, 1H), 5.65 (br s, 1H), 5.42 (q, J=6.8 Hz, 1H), 4.93 (d, J=8.8 Hz, 1H), 4.16 (m, 2H), 3.98 (d, J=18.1 Hz, 1H), 3.69 (d, J=16.4 Hz, 1H), 3.50 (d, J=16.4 Hz, 1H), 2.47 (d, J=18.1 Hz, 1H), 2.35–1.75 (m, 4H), 2.03 (d, J=6.8 Hz, 3H), 1.80 (s, 3H), 1.73 (d, J=1.0 Hz, 3H), 1.26 (t, J=7.1 Hz, 3H)

FABMS m/z 597 (M+H)$^+$

HRFABMS calcd for C$_{26}$H$_{33}$N$_2$O$_8$S$_3$ (M+H)$^+$ 597.1399, found 597.1398

EXAMPLE 32
Synthesis of Compound 34

DC107 (48 mg, 0.093 mmol) was dissolved in acetonitrile (7.0 ml), and potassium carbonate (1.6 g, 11.2 mmol), chloromethyl pivalate (1.0 ml, 6.9 mmol) and potassium iodide (310 mg, 1.9 mmol) were added thereto, followed by stirring at 25° C. for 2 hours. After subjecting the mixture to the usual post-treatment, the mixture was purified by silica gel column chromatography (eluted with n-hexane/ethyl acetate=1/1) to obtain Compound 34 (34 mg, 59% yield).

IR (KBr) 3430, 3098, 2980, 2940, 2874, 1715, 1698, 1652, 1611, 1480, 1449, 1369, 1268, 1129, 974, 847, 807, 769 cm$^{-1}$ $^1$H NMR (CDCl$_3$, 400 MHz) δ ppm; 8.48 (ddd, J=16.4, 11.2, 1.0 Hz, 1H), 7.35 (s, 1H), 6.58 (d, J=11.6 Hz, 1H), 6.24 (dd, J=11.6, 11.2 Hz, 1H), 6.17 (d, J=16.4 Hz, 1H), 5.75 (dd, J=8.6, 1.2 Hz, 1H), 5.51 (br s, 1H), 5.42 (q, J=7.1Hz, 1H), 5.41 (d, J=11.8 Hz, 1H), 5.35 (d, J=11.8 Hz, 1H), 4.93 (d, J=8.6 Hz, 1H), 3.59 (d, J=18.0 Hz, 1H), 2.33–2.15 (m, 3H), 2.25 (d, J=18.0 Hz, 1H), 2.02 (d, J=7.1 Hz, 3H), 2.02–1.93 (m, 1H), 1.78 (s, 3H), 1.74 (d, J=1.2 Hz, 3H), 1.16 (s, 9H)

FABMS m/z 625 (M+H)$^+$

HRFABMS calcd for C$_{28}$H$_{37}$N$_2$O$_8$S$_3$ (M+H)$^+$ 625.1712, found 625.1708

EXAMPLE 33
Synthesis of Compound 35

DC107 (150 mg, 0.29 mmol) was dissolved in dimethylformamide (10 ml), and potassium carbonate (1.2 g, 8.9 mmol), 4-chloromethyl-5-methyl-2-oxo-1,3-dioxolene (0.86 g, 5.8 mmol) and potassium iodide (245 mg, 1.47 mmol) were added thereto, followed by stirring at 25° C. for 1 hour. After subjecting the mixture to the usual post-treatment, the mixture was purified by silica gel column chromatography (eluted with chloroform) to obtain Compound 35 (125 mg, 69% yield).

IR (KBr) 3420, 2936, 1819, 1680, 1647, 1611, 1450, 1375, 1265, 1208, 1150, 1092, 980, 768 cm$^{-1}$ $^1$H NMR (CDCl$_3$, 400 MHz) δ ppm; 8.37 (ddd, J=16.3, 11.7, 1.0 Hz, 1H), 7.28 (s, 1H), 6.52 (d, J=11.7 Hz, 1H), 6.17 (dd, J=11.7, 11.7 Hz, 1H), 6.11 (d, J=16.3 Hz, 1H), 5.66 (br d, J=8.5 Hz, 1H), 5.34 (q, J=6.9 Hz, 1H), 4.88 (d, J=8.5 Hz, 1H), 3.83 (d, J=17.9 Hz, 1H), 3.69 (br s, 2H), 2.23–1.60 (m, 4H), 2.18 (d, J=17.9 Hz, 1H), 2.07 (s, 3H), 1.95 (d, J=6.9 Hz, 3H), 1.71 (s, 3H), 1.68 (d, J=1.2 Hz, 3H)

FABMS m/z 623 (M+H)$^+$

HRFABMS calcd for C$_{27}$H$_{31}$N$_2$O$_9$S$_3$ (M+H)$^+$ 623.1192, found 623.1174

EXAMPLE 34
Synthesis of Compound 36

Compound 1 (20 mg, 0.036 mmol) was dissolved in dichloromethane (1.5 ml), and N,N-diisopropylethylamine (0.25 ml, 1.43 mmol) and chloromethyl methyl ether (0.054 ml, 0.71 mmol) were added thereto, followed by stirring at 25° C. for 2 hours. After subjecting the mixture to the usual post-treatment, the mixture was purified by thin layer chromatography (developed twice with chloroform/methanol=7/3) to obtain Compound 36 (16 mg, 76% yield).

IR (KBr) 3430, 2932, 1730, 1684, 1609, 1446, 1372, 1262, 1230, 1184, 1092, 1022, 983 cm$^{-1}$ $^1$H NMR (CDCl$_3$, 400 MHz) δ ppm; 9.28 (ddd, J=16.6, 11.4, 1.0 Hz, 1H), 7.42 (s, 1H), 6.62 (d, J=11.6 Hz, 1H), 6.33 (dd, J=11.6, 11.4 Hz, 1H), 6.03 (dd, J=16.6, 1.0 Hz, 1H), 5.77 (br d, J=9.6 Hz, 1H), 5.66 (dd, J=9.6, 1.0 Hz, 1), 5.60 (q, J=6.7 Hz, 1H), 5.47 (br s, 1H), 5.03 (d, J=11.0 Hz, 1H), 4.94 (d, J=11.0 Hz, 1H), 4.09 (d, J=17.7 Hz, 1H), 3.33 (s, 3H), 2.46–2.33 (m, 3H), 2.33 (d, J=17.7 Hz, 1H), 2.02 (s, 3H), 1.93 (d, J=6.7 Hz, 3H), 1.78 (d, J=1.2 Hz, 3H), 1.73 (s, 3H), 1.51–1.43 (m, 1H)

FABMS m/z 597 (M+H)$^+$

HRFABMS calcd for C$_{26}$H$_{33}$N$_2$O$_8$S$_3$ (M+H)$^+$ 597.1399, found 597.1407

EXAMPLE 35
Synthesis of Compounds 37 and 38

Compound 18 (a mixture of diastereomers, 48.5 mg, 0.082 mmol) was dissolved in dichloromethane (4.0 ml), and N,N-diisopropylethylamine (0.285 ml, 1.64 mmol), and chloromethyl methyl ether (0.062 ml, 0.82 mmol) were added thereto, followed by stirring at 25° C. for 1.5 hours. After subjecting the mixture to the usual post-treatment, the mixture was purified by thin layer chromatography (developed with chloroform/methanol=98/2) to obtain Compound 37 (21 mg, 39% yield) and Compound 38 (23 mg, 45% yield) which is a diastereomer thereof.

Compound 37

IR (KBr) 3404, 3096, 2940, 1690, 1648, 1607, 1442, 1374, 1259, 1186, 1152, 1094, 1023, 975, 894, 868, 810 cm$^{-1}$ $^1$H NMR (CDCl$_3$, 500 MHz) δ ppm; 9.59 (ddd, J=16.5, 11.6, 1.0 Hz, 1H), 7.40 (s, 1H), 6.61 (d, J=11.6 Hz, 1H), 6.34 (dd, J=11.6, 11.6 Hz, 1H), 6.00 (d, J=16.5 Hz, 1H), 5.83 (br d, J=9.2 Hz, 1H), 5.59 (q, J=6.7 Hz, 1H), 5.53 (br s, 1H), 5.03 (d, J=11.0 Hz, 1H), 5.02 (dd, J=9.2, 1.2 Hz, 1H), 4.93 (d, J=11.0 Hz, 1H), 4.57 (t, J=4.3 Hz, 1H), 4.10 (d, J=17.7 Hz, 1H), 3.84–3.80 (m, 1H), 3.52–3.48 (m, 1H), 3.33 (s, 3H), 2.41–1.41 (m, 10H), 2.33 (d, J=17.7 Hz, 1H), 1.94 (d, J=6.7 Hz, 3H), 1.76 (d, J=1.2 Hz, 3H), 1.71 (s, 3H)

FABMS m/z 639 (M+H)$^+$

HRFABMS calcd for C$_{29}$H$_{39}$N$_2$O$_8$S$_3$ (M+H)$^+$ 639.1868, found 639.1876

Compound 38

IR (KBr) 3404, 3100, 2938, 1685, 1648, 1609, 1442, 1375, 1261, 1183, 1153, 1093, 1022, 974, 898, 868, 808 cm$^{-1}$ $^1$H NMR (CDCl$_3$, 400 MHz) δ ppm; 9.39 (ddd, J=16.5, 11.5, 1.0 Hz, 1H), 7.39 (s, 1H), 6.60 (d, J=11.5 Hz, 1H), 6.37 (dd, J=11.5, 11.5 Hz, 1H), 5.80 (br d, J=9.3 Hz, 1H), 5.57 (q, J=6.6 Hz, 1H), 5.51 (br s, 1H), 5.03 (d, J=11.0 Hz, 1H), 4.93 (d, J=11.0 Hz, 1H), 4.74 (dd, J=9.3, 1.2 Hz, 1H), 4.70 (m, 1H), 4.09 (d, J=17.8 Hz, 1H), 3.77–3.71 (m, 1H), 3.47–3.42 (m, 1H), 3.34 (s, 3H), 2.40–1.41 (m, 10H), 2.34 (d, J=17.8 Hz, 1H), 1.88 (d, J=6.6 Hz, 3H), 1.73 (d, J=1.2 Hz, 3H), 1.71 (s, 3H)

FABMS m/z 639 (M+H)$^+$

HRFABMS calcd for C$_{29}$H$_{39}$N$_2$O$_8$S$_3$ (M+H)$^+$ 639.1868, found 639.1860

EXAMPLE 36

Synthesis of Compound 39

According to the procedure as described in Example 1, Compound 39 (7.2 mg, 57% yield) was obtained from Compound 34 (12 mg, 0.019 mmol) prepared in Example 32, chloroform (1.0 ml), pyridine (0.15 ml, 1.9 mmol), acetic anhydride (0.036 ml, 0.38 mmol) and 4-dimethylaminopyridine (1.8 mg, 0.015 mmol).

IR (KBr) 3440, 3974, 2940, 1734, 1705, 1653, 1609, 1460, 1369, 1273, 1230, 1131, 1020, 974 $cm^{-1}$ $^1$H NMR (CDCl$_3$, 400 MHz) δ ppm; 9.21 (dd, J=16.6, 11.4 Hz, 1H), 7.35 (s, 1H), 6.55 (d, J=11.4 Hz, 1H), 6.26 (dd, J=11.4, 11.4 Hz, 1H), 5.95 (d, J=16.6 Hz, 1H), 5.70 (br d, J=9.7 Hz, 1H), 5.59 (d, J=9.7 Hz, 1H), 5.53 (q, J=6.6 Hz, 1H), 5.39 (br s, 1H), 5.36 (d, J=10.9 Hz, 1H), 5.28 (d, J=10.9 Hz, 1H), 3.28 (d, J=17.7 Hz, 1H), 2.40–2.24 (m, 3H), 2.20 (d, J=17.7 Hz, 1H), 1.95 (s, 3H), 1.85 (d, J=6.6 Hz, 3H), 1.71 (d, J=1.2 Hz, 3H), 1.64 (s, 3H), 1.45–1.35 (m, 1H), 1.12 (s, 9H)

FABMS m/z 667 (M+H)$^+$

HRFABMS calcd for C$_{30}$H$_{39}$N$_2$O$_9$S$_3$ (M+H)$^+$ 667.1818, found 667.1818

EXAMPLE 37

Synthesis of Compound 40

According to the procedure as described in Example 1, Compound 40 (25 mg, 55% yield) was obtained from Compound 34 (42 mg, 0.067 mmol), dichloromethane (8.0 ml), pyridine (0.22 ml, 2.7 mmol), propionic anhydride (0.069 ml, 0.54 mmol) and 4-dimethylaminopyridine (4.9 mg, 0.040 mmol).

IR (KBr) 3430, 2982, 2940, 1735, 1700, 1654, 1610, 1457, 1363, 1273, 1130, 1073, 1016, 972, 806 $cm^{-1}$ $^1$H NMR (CDCl$_3$, 500 MHz) δ ppm; 9.27 (dd, J=16.8, 11.3 Hz, 1H), 7.42 (s, 1H), 6.61 (d, J=11.3 Hz, 1H), 6.33 (dd, J=11.3, 11.3 Hz, 1H), 6.02 (d, J=16.8 Hz, 1H), 5.77 (br d, J=10.0 Hz, 1H), 5.66 (d, J=10.0 Hz, 1H), 5.60 (q, J=6.4 Hz, 1H), 5.46 (br s, 1H), 5.43 (d, J=11.0 Hz, 1H), 5.35 (d, J=11.0 Hz, 1H), 4.03 (d, J=17.0 Hz, 1H), 2.43–2.30 (m, 3H), 2.29 (q, J=7.6 Hz, 2H), 2.28 (d, J=17.0 Hz, 1H), 1.92 (d, J=6.4 Hz, 3H), 1.78 (d, J=0.9 Hz, 3H), 1.71 (s, 3H), 1.55–1.45 (m, 1H), 1.19 (s, 9H), 1.08 (t, J=7.6 Hz, 3H)

FABMS m/z 681 (M+H)$^+$

HRFABMS calcd for C$_{31}$H$_{41}$N$_2$O$_9$S$_3$ (M+H)$^+$ 681.1974, found 681.1987

EXAMPLE 38

Synthesis of Compound 41

According to the procedure as described in Example 1, Compound 41 (31 mg, 50% yield) was obtained from Compound 34 (55 mg, 0.088 mmol), dichloromethane (6.0 ml), pyridine (0.14 ml, 1.8 mmol) and ethyl chloroformate (0.084 ml, 0.88 mmol).

IR (KBr) 3430, 2984, 2938, 1735, 1698, 1654, 1609, 1478, 1456, 1370, 1320, 1260, 1129, 971, 873, 785 $cm^{-1}$ $^1$H NMR (CDCl$_3$, 500 MHz) δ ppm; 9.34 (ddd, J=16.8, 11.3, 0.9 Hz, 1H), 7.41 (s, 1H), 6.63 (d, J=11.3 Hz, 1H), 6.34 (dd, J=11.3, 11.3 Hz, 1H), 6.05 (d, J=16.8, 0.9 Hz, 1H), 5.80 (dd, J=9.8, 1.2 Hz, 1H), 5.61 (dd, J=9.8, 0.9 Hz, 1H), 5.57 (q, J=6.4 Hz, 1H), 5.49 (br s, 1H), 5.43 (d, J=11.0 Hz, 1H), 5.35 (d, J=11.0 Hz, 1H), 4.14 (q, 2H), 4.03 (d, J=17.7 Hz, 1H), 2.43–2.30 (m, 3H), 2.26 (d, J=17.7 Hz, 1H), 1.89 (d, J=6.4 Hz, 3H), 1.82 (d, J=1.2 Hz, 3H), 1.71 (s, 3H), 1.48–1.42 (m, 1H), 1.23 (t, 3H), 1.18 (s, 9H)

FABMS m/z 697 (M+H)$^+$

HRFABMS calcd for C$_{31}$H$_{41}$N$_2$O$_{10}$S$_3$ (M+H)$^+$ 697.1923, found 697.1926

EXAMPLE 39

Synthesis of Compound 42

According to the procedure as described in Example 1, Compound 42 (27 mg, 73% yield) was obtained from Compound 34 (34 mg, 0.055 mmol), dichloromethane (3.0 ml), pyridine (0.044 ml, 0.54 mmol) and phenyl chloroformate (0.020 ml, 0.16 mmol).

IR (KBr) 3430, 2980, 1761, 1740, 1701, 1653, 1610, 1480, 1456, 1369, 1319, 1245, 1208, 1130, 1072, 1022, 973, 771 $cm^{-1}$ $^1$H NMR (CDCl$_3$, 400 MHz) δ ppm; 9.43 (dd, J=16.8, 11.5 Hz, 1H), 7.43 (s, 1H), 7.40–7.12 (m, 5H), 6.66 (d, J=11.5 Hz, 1H), 6.38 (dd, J=11.5, 11.5 Hz, 1H), 6.10 (d, J=16.8 Hz, 1H), 5.87 (br d, J=9.7 Hz, 1H), 5.73 (dd, J=9.7, 1.0 Hz, 1H), 5.59 (q, J=6.7 Hz, 1H), 5.48 (br s, 1H), 5.43 (d, J=11.0 Hz, 1H), 5.36 (d, J=11.0 Hz, 1H), 4.04 (d, J=17.8 Hz, 1H), 2.51–2.32 (m, 3H), 2.28 (d, J=17.8 Hz, 1H), 1.96 (d, J=6.7 Hz, 3H), 1.85 (d, J=1.2 Hz, 3H), 1.73 (s, 3H), 1.55–1.44 (m, 1H), 1.19 (s, 9H)

FABMS m/z 745 (M+H)$^+$

HRFABMS calcd for C$_{35}$H$_{41}$N$_2$O$_{10}$S$_3$ (M+H)$^+$ 745.1923, found 745.1924

EXAMPLE 40

Synthesis of Compound 43

According to the procedure as described in Example 28, Compound 43 (10 mg, 36% yield) was obtained from Compound 34 (26 mg, 0.042 mmol), dichloromethane (4.0 ml), N,N-diisopropylethylamine (2.6 ml, 14.8 mmol), and chloromethyl methyl ether (0.93 ml, 12.2 mmol).

IR (KBr) 3440, 2986, 2936, 1735, 1696, 1647, 1609, 1457, 1364, 1272, 1133, 1094, 1027, 972 $cm^{-1}$ $^1$H NMR (CDCl$_3$, 500 MHz) δ ppm; 9.53 (ddd, J=16.5, 11.3, 0.9 Hz, 1H), 7.40 (s, 1H), 6.62 (d, J=11.6 Hz, 1H), 6.36 (dd, J=11.6, 11.3 Hz, 1H), 6.03 (d, J=16.5 Hz, 1H), 5.83 (br d, J=9.5 Hz, 1H), 5.59 (q, J=6.7 Hz, 1H), 5.52 (br s, 1H), 5.43 (d, J=10.8 Hz, 1H), 5.36 (d, J=10.8 Hz, 1H), 4.80 (dd, J=9.5, 1.2 Hz, 1H), 4.63 (d, J=6.7 Hz, 1H), 4.59 (d, J=6.7 Hz, 1H), 4.04 (d, J=17.7 Hz, 1H), 3.29 (s, 3H), 2.42–2.32 (m, 3H), 2.28 (d, J=17.7 Hz, 1H), 1.90 (d, J=6.7 Hz, 3H), 1.76 (d, J=1.2 Hz, 3H), 1.71 (s, 3H), 1.50–1.40 (m, 1H), 1.19 (s, 9H)

FABMS m/z 669 (M+H)$^+$

HRFABMS calcd for C$_{30}$H$_{41}$N$_2$O$_9$S$_3$ (M+H)$^+$ 669.1974, found 669.1991

EXAMPLE 41

Synthesis of Compound 44

According to the procedure as described in Example 18, Compound 34 (54 mg, 0.86mmol) was dissolved in dichloromethane (10 ml), and 3,4-dihydro-2H-pyran (0.11 ml, 1.22 mmol) and camphorsulfonic acid (39 mg, 0.17 mmol) were added thereto, followed by stirring at 0° C. for 5 hours. After subjecting the mixture to the usual post-treatment, the mixture was purified by thin layer chromatography (developed with ether/methanol=99/1) to obtain Compound 44 (21 mg, 34% yield). From $^1$H NMR, Compound 44 was found to be a mixture of diastereomers at a ratio of about 2:1.

IR (KBr) 3430, 2942, 2872, 1735, 1697, 1651, 1609, 1478, 1454, 1370, 1274, 1124, 1072, 1028, 971, 867, 799, 769 $cm^{-1}$ $^1$H NMR (CDCl$_3$, 400 MHz) δ ppm; major isomer: 9.40 (dd, J=16.8, 11.7 Hz, 1H), 7.40 (s, 1H), 6.60 (d, J=11.4 Hz, 1H), 6.37 (dd, J=11.7, 11.4 Hz, 1H), 6.05 (d, J=16.8 Hz, 1H), 5.80 (br d, J=10.0 Hz, 1H), 5.57 (q, J=6.6 Hz, 1H), 5.51 (br s, 1H), 5.43 (d, J=10.7 Hz, 1H), 5.35 (d, J=10.7 Hz, 1H), 4.74 (dd, J=10.0, 1.0 Hz, 1H), 4.71 (m, 1H), 4.03 (d, J=17.8 Hz, 1H), 3.81–3.69 (m, 1H), 3.47–3.40 (m, 1H), 2.43–1.40

(m, 10H), 2.28 (d, J=17.8 Hz, 1H), 1.88 (d, J=6.6 Hz, 3H), 1.74 (d, J=1.0 Hz, 3H), 1.70 (s, 3H), 1.19 (s, 9H); minor isomer: 9.59 (dd, J=16.8, 11.7 Hz, 1H), 7.40 (s, 1H), 6.61 (d, J=11.0 Hz, 1H), 6.34 (dd, J=11.7, 11.0 Hz, 1H), 6.00 (d, J=16.8 Hz, 1H), 5.83 (br d, J=10.0 Hz, 1H), 5.58 (q, J=6.6 Hz, 1H), 5.52 (br s, 1H), 5.43 (d, J=10.7 Hz, 1H), 5.35 (d, J=10.7 Hz, 1H), 5.02 (dd, J=10.0, 1.0 Hz, 1H), 4.57 (m, 1H), 4.04 (d, J=17.8 Hz, 1H), 3.87–3.80 (m, 1H), 3.55–3.40 (m, 1H), 2.43–1.40 (m, 10H), 2.27 (d, J=17.8 Hz, 1H), 1.94 (d, J=6.6 Hz, 3H), 1.76 (d, J=1.0H, 3H), 1.70 (s, 3H), 1.19 (s, 9H)

FABMS m/z 709 (M+H)$^+$

HRFABMS calcd for $C_{33}H_{45}N_2O_9S_3$ (M+H)$^+$ 709.2287, found 709.2305

EXAMPLE 42
Synthesis of Compounds 45 and 46

Compound 35 (50 mg, 0.081 mmol) obtained in Example 33 was dissolved in chloroform (2.0 ml) and pyridine (0.66 ml, 8.1 mmol), and then acetic anhydride (0.15 ml, 1.6 mmol) and 4-dimethylaminopyridine (7.9 mg, 0.065 mmol) were added thereto, followed by stirring at 25° C. for 30 minutes. After subjecting the mixture to the usual post-treatment, the mixture was purified by thin layer chromatography (developed with chloroform/methanol=95/5) to obtain Compound 45 (10.5 mg, 20% yield) and Compound 46 (26 mg, 46% yield).

Compound 45 (Monoacetyl compound)

IR (KBr) 3430, 2932, 1821, 1735, 1682, 1650, 1610, 1440, 1370, 1262, 1231, 1152, 1094, 1027, 978, 768 cm$^{-1}$ $^1$H NMR (CDCl$_3$, 500 MHz) δ ppm; 9.26 (ddd, J=16.9, 11.3, 1.0 Hz, 1H), 7.42 (s, 1H), 6.62 (d, J=11.6 Hz, 1H), 6.33 (dd, J=11.6, 11.3 Hz, 1H), 6.02 (d, J=16.9 Hz, 1H), 5.77 (br d, J=9.5 Hz, 1H), 5.66 (d, J=6.8, 1.0 Hz, 1H), 5.60 (q, J=6.4 Hz, 1H), 5.44 (br s, 1H), 4.04 (d, J=17.7 Hz, 1H), 3.78 (d, J=15.9 Hz, 1H), 3.77 (d, J=15.9 Hz, 1H), 2.48–2.25 (m, 3H), 2.29 (d, J=17.7 Hz, 1H), 2.15 (s, 3H), 2.03 (s, 3H), 1.92 (d, J=6.4 Hz, 3H), 1.79 (d, J=1.0 Hz, 3H), 1.71 (s, 3H), 1.55–1.40 (m, 1H).

FABMS m/z 665 (M+H)$^+$

HRFABMS calcd for $C_{29}H_{33}N_2O_{10}S_3$ (M+H)$^+$ 665.1297, found 665.1312

Compound 46 (Diacetyl compound)

IR (KBr) 3430, 2936, 1824, 1735, 1720, 1685, 1611, 1440, 1369, 1268, 1231, 1122, 1019, 974, 942, 768 cm$^{-1}$ $^1$H NMR (CDCl$_3$, 500 MHz) δ ppm; 9.11 (dd, J=16.5, 11.4 Hz, 1H), 7.41 (s, 1H), 6.61 (d, J=11.4 Hz, 1H), 6.31 (dd, J=11.4, 11.4 Hz, 1H), 6.03 (d, J=16.5 Hz, 1H), 5.74 (br d, J=9.5 Hz, 1H), 5.67 (d, J=9.5 Hz, 1H), 5.53 (q, J=6.4 Hz, 1H), 3.94 (d, J=17.8 Hz, 1H), 3.89 (br s, 2H), 2.55 (d, J=17.8 Hz, 1H), 2.38–1.95 (m, 3H), 2.14 (s, 3H), 2.12 (s, 3H), 2.04 (s, 3H), 2.01 (s, 3H), 1.95 (d, J=6.4 Hz, 3H), 1.74 (d, J=1.0 Hz, 3H), 1.60–1.48 (m, 1H)

FABMS m/z 707 (M+H)$^+$

HRFABMS calcd for $C_{31}H_{35}N_2O_{11}S_3$ (M+H)$^+$ 707.1403, found 707.1389

EXAMPLE 43
Synthesis of Compound 47

According to the procedure as described in Example 1, Compound 47 (29 mg, 54% yield) was obtained from Compound 35 (50 mg, 0.080 mmol), dichloromethane (2.4 ml), pyridine (0.23 ml, 2.8 mmol) and propionic anhydride (0.061 ml, 0.48 mmol).

IR (KBr) 3420, 2928, 1821, 1734, 1685, 1652, 1609, 1455, 1363, 1268, 1208, 1170, 1074, 1016, 978, 755 cm$^{-1}$ $^1$H NMR (CDCl$_3$, 500 MHz) δ ppm; 9.26 (ddd, J=16.8, 11.3, 1.0 Hz, 1H), 7.42 (s, 1H), 6.61 (d, J=11.6 Hz, 1H), 6.33 (dd, J=11.6, 11.3 Hz, 1H), 6.02 (dd, J=16.8, 1.0 Hz, 1H), 5.77 (dd, J=9.5, 1.2 Hz, 1H), 5.66 (dd, J=9.5, 1.0 Hz, 1H), 5.60 (q, J=6.7 Hz, 1H), 5.44 (br s, 1H), 4.04 (d, J=17.7 Hz, 1H), 3.80 (d, J=15.3 Hz, 1H), 3.76 (d, J=15.3 Hz, 1H), 2.47–2.30 (m, 3H), 2.29 (q, J=7.6 Hz, 2H), 2.29 (d, J=17.7 Hz, 1H), 2.15 (s, 3H), 1.92 (d, J=6.7 Hz, 3H), 1.79 (s, 3H), 1.71 (s, 3H), 1.55–1.48 (m, 1H), 1.08 (t, J=7.6 Hz, 3H)

FABMS m/z 679 (M+H)$^+$

HRFABMS calcd for $C_{30}H_{35}N_2O_{10}S_3$ (M+H)$^+$ 679.1454, found 679.1480

EXAMPLE 44
Synthesis of Compound 48

According to the procedure as described in Example 1, Compound 48 (24 mg, 55% yield) was obtained from Compound 35 (36 mg, 0.058 mmol), dichloromethane (3.0 ml), pyridine (0.050 ml, 0.62 mmol) and cyclohexanecarbonyl chloride (0.039 ml, 0.29 mmol).

IR (KBr) 3430, 2934, 2858, 1823, 1732, 1684, 1611, 1449, 1374, 1264, 1209, 1162, 1131, 977, 768 cm$^{-1}$ $^1$H NMR (CDCl$_3$, 400 MHz) δ ppm; 9.19 (dd, J=16.5, 11.5 Hz, 1H), 7.41 (s, 1H), 6.60 (d, J=11.5 Hz, 1H), 6.32 (dd, J=11.5, 11.5 Hz, 1H), 6.00 (d, J=16.5 Hz, 1H), 5.76 (br d, J=9.5 Hz, 1H), 5.60 (d, J=9.5 Hz, 1H), 5.59 (q, J=6.6 Hz, 1H), 5.45 (br s, 1H), 4.04 (d, J=17.8 Hz, 1H), 3.80 (d, J=15.2 Hz, 1H), 3.76 (d, J=15.2 Hz, 1H), 2.47–1.10 (m, 15H), 2.30 (d, J=17.8 Hz, 1H), 2.15 (s, 3H), 1.93 (d, J=6.6 Hz, 3H), 1.77 (d, J=0.7 Hz, 3H), 1.71 (s, 3H)

FABMS m/z 733 (M+H)$^+$

HRFABMS calcd for $C_{34}H_{41}N_2O_{10}S_3$ (M+H)$^+$ 733.1923, found 733.1934

EXAMPLE 45
Synthesis of Compound 49

Compound 35 (51 mg 0.082 mmol), 1-naphthoic acid (42 mg, 0.24 mmol), 1-ethyl-3-(3-dimethylaminopropyl) carbodiimide hydrochloride (46 mg, 0.24 mmol) and 4-dimethylaminopyridine (2.0 mg, 0.016 mmol) were dissolved in dichloromethane (5.0 ml), followed by stirring at 25° C. for 20 hours. After subjecting the mixture to the usual post-treatment, the mixture was purified by thin layer chromatography (developed with chloroform/methanol=95/5) to obtain Compound 49 (18 mg, 28% yield).

IR (KBr) 3420, 2930, 1821, 1711, 1684, 1611, 1501, 1438, 1375, 1267, 1241, 1195, 1131, 978, 781 cm$^{-1}$ $^1$H NMR (CDCl$_3$, 500 MHz) δ ppm; 9.41 (dd, J=16.6, 11.3, 0.6 Hz, 1H), 8.80 (dd, J=8.7, 1.1 Hz, 1H), 8.12 (dd, J=7.5, 1.4 Hz, 1H), 7.96 (d, J=8.0 Hz, 1H), 7.84 (dd, J=8.0, 1.4 Hz, 1H), 7.57–7.47 (m, 2H), 7.42 (s, 1H), 7.29 (dd, J=8.2, 7.5 Hz, 1H), 6.63 (d, J=11.6 Hz, 1H), 6.37 (dd, J=11.6, 11.3 Hz, 1H), 6.14 (d, J=16.6 Hz, 1H), 6.06 (dd, J=9.5, 0.9 Hz, 1H), 5.94 (br d, J=9.5 Hz, 1H), 5.45 (q, J=6.7 Hz, 1H), 5.44 (br s, 1H), 4.01 (d, J=17.7 Hz, 1H), 3.78 (br s, 2H), 2.50–2.25 (m, 3H), 2.28 (d, J=17.7 Hz, 1H), 2.15 (s, 3H), 1.91 (d, J=1.2 Hz, 3H), 1.72 (s, 3H), 1.63–1.55 (m, 1H), 1.56 (d, J=6.7 Hz, 3H)

FABMS m/z 777 (M+H)$^+$

HRFABMS calcd for $C_{38}H_{37}N_2O_{10}S_3$ (M+H)$^+$ 777.1610, found 777.1639

EXAMPLE 46
Synthesis of Compound 50

According to the procedure as described in Example 45, Compound 50 (15 mg, 29% yield) was obtained from Compound 35 (40 mg, 0.065 mmol), 2-naphthoic acid (122 mg, 0.71 mmol), 1-ethyl-3-(3-dimethylaminopropyl) carbodiimide hydrochloride (137 mg, 0.71 mmol), dichloromethane (5.0 ml) and 4-dimethylaminopyridine (3.2 mg, 0.026 mmol).

IR (KBr) 3430, 2932, 1821, 1713, 1685, 1610, 1440, 1389, 1371, 1356, 1269, 1227, 1195, 1129, 1090, 977, 866, 777 cm$^{-1}$ $^1$H NMR (CDCl$_3$, 500 MHz) δ ppm; 9.51 (dd, J=16.5, 11.3 Hz, 1H), 8.55 (s, 1H), 7.98 (dd, J=8.5, 1.2 Hz, 1H), 7.82 (d, J=8.2 Hz, 1H), 7.78 (d, J=8.5 Hz, 1H), 7.59 (d, J=8.2 Hz, 1H), 7.55 (ddd, J=8.2, 7.0, 1.2 Hz, 1H), 7.46 (s, 1H), 7.46 (ddd, J=8.2, 7.0, 1.2 Hz, 1H), 6.65 (d, J=11.6 Hz, 1H), 6.38 (dd, J=11.6, 11.3 Hz, 1H), 6.12 (d, J=16.5 Hz, 1H), 6.08 (dd, J=9.5, 1.2 Hz, 1H), 5.96 (br d, J=9.5 Hz, 1H), 5.49 (q, J=6.4 Hz, 1H), 5.44 (br s, 1H), 4.02 (d, J=17.7 Hz, 1H), 3.78 (br s, 2H), 2.52–2.26 (m, 3H), 2.29 (d, J=17.7 Hz, 1H), 2.15 (s, 3H), 1.92 (d, J=1.2 Hz, 3H), 1.73 (s, 3H), 1.67 (d, J=6.7 Hz, 3H), 1.64–1.55 (m, 1H)

FABMS m/z 777 (M+H)$^+$

HRFABMS calcd for C$_{38}$H$_{37}$N$_2$O$_{10}$S$_3$ (M+H)$^+$ 777.1610, found 777.1612

EXAMPLE 47
Synthesis of Compound 51

According to the procedure as described in Example 45, Compound 51 (18 mg, 29% yield) was obtained from Compound 35 (51 mg, 0.082 mmol), quinaldic acid (28 mg, 0.16 mmol), 1-ethyl-3-(3-dimethylaminopropyl)carbodiimide hydrochloride (31 mg, 0.16 mmol), dichloromethane (5.0 ml) and 4-dimethylaminopyridine (1.3 mg, 0.011 mmol).

IR (KBr) 3420, 2930, 1821, 1719, 1678, 1610, 1501, 1458, 1375, 1269, 1210, 1133, 1106, 977, 844, 776 cm$^{-1}$ $^1$H NMR (CDCl$_3$, 500 MHz) δ ppm; 9.42 (dd, J=16.3, 11.3 Hz, 1H), 8.19 (d, J=8.5 Hz, 1H), 8.06 (d, J=8.5 Hz, 1H), 8.05 (dd, J=8.2, 1.0 Hz, 1H), 7.82 (dd, J=8.2, 1.0 Hz, 1H), 7.73 (ddd, J=8.2, 7.0, 1.0 Hz, 1H), 7.62 (ddd, J=8.2, 7.0, 1.0 Hz, 1H), 7.43 (s, 1H), 6.64 (d, J=11.6 Hz, 1H), 6.37 (dd, J=11.6, 11.3 Hz, 1H), 6.14 (d, J=16.3 Hz, 1H), 6.12 (d, J=8.8 Hz, 1H), 5.96 (br d, J=8.8 Hz, 1H), 5.45 (q, J=6.7 Hz, 1H), 5.45 (br s, 1H), 4.00 (d, J=17.7 Hz, 1H), 3.79 (d, J=15.3 Hz, 1H), 3.76 (d, J=15.3 Hz, 1H), 2.50–2.27 (m, 3H), 2.27 (d, J=17.7 Hz, 1H), 2.15 (s, 3H), 1.94 (d, J=1.2 Hz, 3H), 1.73 (s, 3H), 1.67 (d, J=6.7 Hz, 3H), 1.62–1.50 (m, 1H)

FABMS m/z 778 (M+H)$^+$

HRFABMS calcd for C$_{37}$H$_{36}$N$_3$O$_{10}$S$_3$ (M+H)$^+$ 778.1563, found 778.1565

EXAMPLE 48
Synthesis of Compound 52

According to the procedure as described in Example 1, Compound 52 (38 mg, 61% yield) was obtained from Compound 35 (50 mg, 0.080 mmol), dichloromethane (5.0 ml), pyridine (0.16 ml, 2.0 mmol) and 2-quinoxaloyl chloride (47 mg, 0.24 mmol).

IR (KBr) 3430, 2930, 1820, 1719, 1707, 1684, 1609, 1490, 1364, 1341, 1266, 1231, 1208, 1154, 1107, 977, 799, 775 cm$^{-1}$ $^1$H NMR (CDCl$_3$, 500 MHz) δ ppm; 9.44 (s, 1H), 9.41 (dd, J=16.8, 11.6 Hz, 1H), 8.13 (dd, J=8.2, 1.4 Hz, 1H), 8.09 (dd, J=8.2, 1.4 Hz, 1H), 7.88 (ddd, J=8.2, 6.7, 1.4 Hz, 1H), 7.82 (ddd, J=8.2, 6.7, 1.4 Hz, 1H), 7.44 (s, 1H), 6.65 (d, J=11.6 Hz, 1H), 6.37 (dd, J=11.6, 11.6 Hz, 1H), 6.17 (dd, J=9.8, 0.9 Hz, 1H), 6.14 (dd, J=16.8, 0.9 Hz, 1H), 5.97 (br d, J=9.8 Hz, 1H), 5.47 (q, J=6.4 Hz, 1H), 5.40 (br s, 1H), 4.01 (d, J=17.7 Hz, 1H), 3.78 (br s, 2H), 2.52–2.25 (m, 3H), 2.28 (d, J=17.7 Hz, 1H), 2.15 (s, 3H), 1.94 (d, J=1.2 Hz, 3H), 1.73 (s, 3H), 1.69 (d, J=6.4 Hz, 3H), 1.65–1.50 (m, 1H)

SIMS m/z 779 (M+H)$^+$

HRFABMS calcd for C$_{36}$H$_{35}$N$_4$O$_{10}$S$_3$ (M+H)$^+$ 779.1515, found 779.1522

EXAMPLE 49
Synthesis of Compound 53

According to the procedure as described in Example 1, Compound 53 (26 mg, 63% yield) was obtained from Compound 35 (38 mg, 0.060 mmol), dichloromethane (3.0 ml), pyridine (0.049 ml, 0.060 mmol) and ethyl chloroformate (0.029 ml, 0.30 mmol).

IR (KBr) 3440, 2926, 1822, 1736, 1690, 1660, 1610, 1437, 1372, 1262, 1208, 1160, 1093, 978, 880, 787, 768 cm$^{-1}$ $^1$H NMR (CDCl$_3$, 500 MHz) δ ppm; 9.32 (ddd, J=16.8, 11.3, 0.9 Hz, 1H), 7.41 (s, 1H), 6.63 (d, J=11.3 Hz, 1H), 6.34 (t, J=11.3 Hz, 1H), 6.06 (dd, J=16.7, 0.6 Hz, 1H), 5.79 (br d, J=9.5 Hz, 1H), 5.61 (dd, J=9.5, 0.9 Hz, 1H), 5.57 (q, J=6.7 Hz, 1H), 5.46 (br s, 1H), 4.15 (dq, J=7.2, 0.6 Hz, 2H), 4.03 (d, J=17.7 Hz, 1H), 3.78 (s, 2H), 2.27 (d, J=17.7 Hz, 1H), 2.48–1.45 (m, 4H), 2.15 (s, 3H), 1.89 (d, J=6.7 Hz, 3H), 1.82 (d, J=1.2 Hz, 3H), 1.71 (s, 3H), 1.24 (t, J=7.2 Hz, 3H)

FABMS m/z 695 (M+H)$^+$

HRFABMS calcd for C$_{30}$H$_{35}$N$_2$O$_{11}$S$_3$ (M+H)$^+$ 695.1403, found 695.0392

EXAMPLE 50
Synthesis of Compound 54

According to the procedure as described in Example 1, Compound 54 (39 mg, 68% yield) was obtained from Compound 35 (50 mg, 0.080 mmol), dichloromethane (5.0 ml), pyridine (0.065 ml, 0.80 mmol) and isobutyl chloroformate (0.052 ml, 0.40 mmol).

IR (KBr) 3430, 2980, 2934, 1823, 1733, 1694, 1651, 1608, 1460, 1380, 1260, 1240, 1209, 1072, 976, 770 cm$^{-1}$ $^1$H NMR (CDCl$_3$, 500 MHz) δ ppm; 9.36 (ddd, J=16.8, 11.3, 0.9 Hz, 1H), 7.41 (s, 1H), 6.62 (d, J=11.6 Hz, 1H), 6.34 (dd, J=11.6, 11.3 Hz, 1H), 6.05 (dd, J=16.8, 0.6 Hz, 1H), 5.78 (br d, J=9.5 Hz, 1H), 5.58 (q, J=6.7 Hz, 1H), 5.57 (dd, J=9.5, 1.2 Hz, 1H), 5.47 (br s, 1H), 4.04 (d, J=17.7 Hz, 1H), 3.91 (dd, J=10.4, 6.7 Hz, 1H), 3.84 (dd, J=10.4, 6.7 Hz, 1H), 3.78 (br s, 2H), 2.50–2.15 (m, 3H), 2.27 (d, J=17.7 Hz, 1H), 2.14 (s, 3H), 1.92–1.82 (m, 1H), 1.90 (d, J=6.7 Hz, 3H), 1.81 (d, J=1.2 Hz, 3H), 1.71 (s, 3H), 1.55–1.42 (m, 1H), 0.85 (d, J=6.7 Hz, 6H)

FABMS m/z 723 (M+H)$^+$

HRFABMS calcd for C$_{32}$H$_{39}$N$_2$O$_{11}$S$_3$ (M+H)$^+$ 723.1716, found 723.1715

EXAMPLE 51
Synthesis of Compound 55

According to the procedure as described in Example 1, Compound 55 (36 mg, 57% yield) was obtained from Compound 35 (53 mg, 0.085 mmol), dichloromethane (5.0 ml), pyridine (0.069 ml, 0.85 mmol) and phenyl chloroformate (0.032 ml, 0.26 mmol).

IR (KBr) 3420, 2934, 1821, 1759, 1720, 1677, 1610, 1489, 1457, 1375, 1260, 1241, 1209, 1115, 1021, 977, 769 cm$^{-1}$ $^1$H NMR (CDCl$_3$, 400 MHz) δ ppm; 9.41 (ddd, J=16.7, 11.2, 1.0 Hz, 1H), 7.43 (s, 1H), 7.37–7.05 (m, 5H), 6.66 (d, J=11.5 Hz, 1H), 6.38 (dd, J=11.5, 11.2 Hz, 1H), 6.10 (d, J=16.7 Hz, 1H), 5.87 (br d, J=9.7 Hz, 1H), 5.73 (dd, J=9.7, 1.0 Hz, 1H), 5.59 (q, J=6.6 Hz, 1H), 5.46 (br s, 1H), 4.05 (d, J=17.8 Hz, 1H), 3.78 (s, 2H), 2.52–2.25 (m, 3H), 2.29 (d, J=17.8 Hz, 1H), 2.15 (s, 3H), 1.96 (d, J=6.6 Hz, 3H), 1.85 (d, J=1.0 Hz, 3H), 1.72 (s, 3H), 1.60–1.45 (m, 1H)

FABMS m/z 743 (M+H)$^+$

HRFABMS calcd for C$_{34}$H$_{35}$N$_2$O$_{11}$S$_3$ (M+H)$^+$ 743.1403, found 743.1417

EXAMPLE 52
Synthesis of Compound 56

According to the procedure as described in Example 1, Compound 56 (15 mg, 39% yield) was obtained from Compound 35 (30 mg, 0.049 mmol), dichloromethane (3.0 ml), pyridine (1.27 ml, 15.7 mmol) and benzyl chloroformate (0.692 ml, a 30% toluene solution, 1.46 mmol).

IR (KBr) 3430, 2932, 1821, 1738, 1710, 1680, 1609, 1453, 1382, 1153, 1113, 1093, 976, 785, 768, 697 cm$^{-1}$ $^1$H NMR (CDCl$_3$, 400 MHz) δ ppm; 9.34 (ddd, J=16.8, 11.5, 1.0 Hz, 1H), 7.40 (s, 1H), 7.40–7.25 (m, 5H), 6.62 (d, J=11.5 Hz, 1H), 6.32 (dd, J=11.5, 11.5 Hz, 1H), 6.03 (dd, J=16.8, 1.0 Hz, 1H), 5.79 (br d, J=9.5 Hz, 1H), 5.61 (dd, J=9.5, 1.0 Hz, 1H), 5.54 (q, J=6.5 Hz, 1H), 5.46 (br s, 1H), 5.11 (s, 2H), 4.03 (d, J=17.7 Hz, 1H), 3.77 (s, 2H), 2.48–2.25 (m, 3H), 2.26 (d, J=17.7 Hz, 1H), 2.14 (s, 3H), 1.84 (d, J=6.5 Hz, 3H), 1.81 (d, J=1.0 Hz, 3H), 1.71 (s, 3H), 1.55–1.42 (m, 1H)

FABMS m/z 757 (M+H)$^+$

HRFABMS calcd for C$_{35}$H$_{37}$N$_2$O$_{11}$S$_3$ (M+H)$^+$ 757.1559, found 757.1538

EXAMPLE 53
Synthesis of Compound 57

According to the procedure as described in Example 1, Compound 57 (40 mg, 60% yield) was obtained from Compound 35 (50 mg, 0.080 mmol), dichloromethane (4.0 ml), pyridine (0.078 ml, 0.96 mmol ) and 9-fluorenylmethyl chloroformate (83 ml, 0.32 mmol).

IR (KBr) 3420, 2920, 1822, 1733, 1680, 1610, 1449, 1384, 1263, 1209, 1152, 1092, 976, 759, 740 cm$^{-1}$ $^1$H NMR (CDCl$_3$, 500 MHz) δ ppm; 9.48 (dd, J=16.6, 11.6 Hz, 1H), 7.66 (d, J=7.6 Hz, 1H), 7.47 (s, 1H), 7.47 (d, J=7.6 Hz, 1H), 7.43 (d, J=7.6 Hz, 1H), 7.34 (dd, J=7.6, 7.3 Hz, 1H), 7.29 (d, J=7.6, 7.3 Hz, 1H), 7.18 (dd, J=7.6, 7.3 Hz, 1H), 6.98 (dd, J=7.6, 7.3 Hz, 1H), 6.64 (d, J=11.3 Hz, 1H), 6.32 (dd, J=11.6, 11.3 Hz, 1H), 6.02 (d, J=16.6 Hz, 1H), 5.77 (br d, J=9.5 Hz, 1H), 5.57 (q, J=6.7 Hz, 1H), 5.50 (d, J=9.5 Hz, 1H), 5.49 (br s, 2H), 4.59 (dd, J=10.7, 6.7 Hz, 1H), 4.25 (dd, J=10.7, 7.0 Hz, 1H), 4.13 (br dd, J=7.0, 6.7 Hz, 1H), 4.06 (d, J=17.7 Hz, 1H), 3.79 (d, J=15.3 Hz, 1H), 3.77 (d, J=15.3 Hz, 1H), 2.53–2.29 (m, 3H), 2.26 (d, J=17.7 Hz, 1H), 2.15 (s, 3H), 1.78 (d, J=0.9 Hz, 3H), 1.77 (d, J=6.7 Hz, 3H), 1.72 (s, 3H), 1.43–1.37 (m, 1H)

FABMS m/z 845 (M+H)$^+$

HRFABMS calcd for C$_{42}$H$_{41}$N$_2$O$_{11}$S$_3$ (M+H)$^+$ 845.1872, found 845.1859

EXAMPLE 54
Synthesis of Compound 58

According to the procedure as described in Example 28, Compound 58 (18 mg, 42% yield) was obtained from Compound 35 (41 mg, 0.065 mmol), dichloromethane (2.0 ml), N,N-diisopropylethylamine (3.8 ml, 22mmol) and chloromethyl methyl ether (0.83 ml, 11 mmol).

IR (KBr) 3430, 2932, 1821, 1720, 1684, 1647, 1608, 1437, 1374, 1262, 1209, 1150, 1093, 1026, 977, 768 cm$^{-1}$ $^1$H NMR (CDCl$_3$, 500 MHz) δ ppm; 9.51 (dd, J=16.5, 11.3 Hz, 1H), 7.40 (s, 1H), 6.62 (d, J=11.3 Hz, 1H), 6.36 (dd, J=11.3, 11.3 Hz, 1H), 6.03 (d, J=16.5 Hz, 1H), 5.83 (br d, J=9.2 Hz, 1H), 5.59 (q, J=6.7 Hz, 1H), 5.50 (br s, 1H), 4.80 (dd, J=9.2, 1.2 Hz, 1H), 4.63 (d, J=6.7 Hz, 1H), 4.60 (d, J=6.7 Hz, 1H), 4.04 (d, J=17.5 Hz, 1H), 3.80 (d, J=15.3 Hz, 1H), 3.76 (d, J=15.3 Hz, 1H), 3.29 (s, 3H), 2.46–2.22 (m, 3H), 2.29 (d, J=17.5 Hz, 1H), 2.15 (s, 3H), 1.90 (d, J=6.7 Hz, 3H), 1.76 (d, J=1.2 Hz, 3H), 1.70 (s, 3H), 1.52–1.42 (m, 1H)

FABMS m/z 667 (M+H)$^+$

HRFABMS calcd for C$_{29}$H$_{35}$N$_2$O$_{10}$S$_3$ (M+H)$^+$ 667.1454, found 667.1459

EXAMPLE 55
Synthesis of Compound 59

According to the procedure as described in Example 28, Compound 59 (9.8 mg, 42% yield) was obtained from Compound 35 (21 mg, 0.034 mmol), dichloromethane (1.5 ml), N,N-diisopropylethylamine (1.1 ml, 6.4 mmol) and chloromethyl ethyl ether (0.44 ml, 4.7 mmol).

IR (KBr) 3430, 2932, 1820, 1718, 1684, 1653, 1609, 1436, 1387, 1262, 1209, 1150, 1092, 1025, 978, 768 cm$^{-1}$ $^1$H NMR (CDCl$_3$, 500 MHz) δ ppm; 9.51 (ddd, J=16.5, 11.6, 0.9 Hz, 1H), 7.40 (s, 1H), 6.62 (d, J=11.3 Hz, 1H), 6.36 (dd, J=11.6, 11.3 Hz, 1H), 6.02 (dd, J=16.5, 0.9 Hz, 1H), 5.82 (br d, J=9.5 Hz, 1H), 5.58 (q, J=6.4 Hz, 1H), 5.50 (br s, 1H), 4.82 (dd, J=9.5, 1.2 Hz, 1H), 4.68 (d, J=9.9 Hz, 1H), 4.64 (d, J=9.9 Hz, 1H), 4.04 (d, J=17.5 Hz, 1H), 3.80 (d, J=15.3 Hz, 1H), 3.76 (d, J=15.3 Hz, 1H), 3.56–3.46 (m, 2H), 2.44–2.24 (m, 3H), 2.29 (d, J=17.5 Hz, 1H), 2.15 (s, 3H), 1.90 (d, J=6.4 Hz, 3H), 1.76 (d, J=1.2 Hz, 3H), 1.70 (s, 3H), 1.52–1.41 (m, 1H), 1.14 (t, J=7.0 Hz, 3H)

FABMS m/z 681 (M+H)$^+$

HRFABMS calcd for C$_{30}$H$_{37}$N$_2$O$_{10}$S$_3$ (M+H)$^+$ 681.1610, found 681.1622

EXAMPLE 56
Synthesis of Compound 60

According to the procedure as described in Example 28, Compound 60 (17 mg, 25% yield) was obtained from Compound 35 (56 mg, 0.090 mmol), dichloromethane (4.0 ml), N,N-diisopropylethylamine (1.3 ml, 7.2mmol) and chloromethyl octyl ether (0.70 ml, 3.6 mmol).

IR (KBr) 3430, 3055, 2934, 2858, 1822, 1699, 1650, 1607, 1454, 1380, 1260, 1208, 1160, 1105, 1016, 980, 768 cm$^{-1}$ $^1$H NMR (CDCl$_3$, 500 MHz) δ ppm; 9.50 (ddd, J=16.5, 11.3, 1.0 Hz, 1H), 7.39 (s, 1H), 6.61 (d, J=11.3 Hz, 1H), 6.35 (dd, J=11.3, 11.3 Hz, 1H), 6.02 (d, J=16.5 Hz, 1H), 5.82 (dd, J=9.2, 1.0 Hz, 1H), 5.58 (q, J=6.4 Hz, 1H), 5.51 (br s, 1H), 4.81 (dd, J=9.2, 1.0 Hz, 1H), 4.67 (d, J=6.7 Hz, 1H), 4.63 (d, J=6.7 Hz, 1H), 4.04 (d, J=17.7 Hz, 1H), 3.79 (d, J=15.3 Hz, 1H), 3.76 (d, J=15.3 Hz, 1H), 3.46 (dt, J=9.5, 6.7 Hz, 1H), 3.41 (dt, J=9.5, 6.7 Hz, 1H), 2.45–2.22 (m, 3H), 2.29 (d, J=17.7 Hz, 1H), 2.15 (s, 3H), 1.89 (d, J=6.4 Hz, 3H), 1.76 (d, J=1.0 Hz, 3H), 1.70 (s, 3H), 1.55–1.43 (m, 3H), 1.31–1.20 (m, 10H), 0.88 (t, J=7.0 Hz, 3H)

FABMS m/z 765 (M+H)$^+$

HRFABMS calcd for C$_{36}$H$_{49}$N$_2$O$_{10}$S$_3$ (M+H)$^+$ 765.2549, found 765.2557

EXAMPLE 57
Synthesis of Compound 61

According to the procedure as described in Example 28, Compound 61 (16 mg, 25% yield) was obtained from Compound 35 (54 mg, 0.086 mmol), dichloromethane (4.0 ml), N,N-diisopropylethylamine (0.75 ml, 4.3 mmol) and chloromethyl benzyl ether (0.30 ml, 2.2 mmol).

IR (KBr) 3420, 2940, 1817, 1695, 1650, 1607, 1454, 1380, 1260, 1209, 1160, 1094, 1025, 980, 768, 736, 697 cm$^{-1}$ $^1$H NMR (CDCl$_3$, 500 MHz) δ ppm; 9.52 (ddd, J=16.5, 11.6, 1.0 Hz, 1H), 7.40–7.24 (m, 5H), 7.40 (s, 1H), 6.62 (d, J=11.6 Hz, 1H), 6.34 (dd, J=11.6, 11.6 Hz, 1H), 6.02 (d, J=16.5 Hz, 1H), 5.84 (dd, J=9.2, 1.0 Hz, 1H), 5.59 (q, J=6.4 Hz, 1H), 5.50 (br s, 1H), 4.89 (dd, J=6.2, 1.0 Hz, 1H), 4.76 (d, J=6.7 Hz, 1H), 4.73 (d, J=6.7 Hz, 1H), 4.56 (d, J=12.0 Hz, 1H), 4.51 (d, J=12.0 Hz, 1H), 4.04 (d, J=17.7 Hz, 1H), 3.79 (d, J=15.3 Hz, 1H), 3.76 (d, J=15.3 Hz, 1H), 2.46–2.25 (m, 3H), 2.29 (d, J=17.7 Hz, 1H), 2.15 (s, 3H), 1.91 (d, J=6.4 Hz, 3H), 1.76 (d, J=1.0 Hz, 3H), 1.70 (s, 3H), 1.54–1.45 (m, 1H)

FABMS m/z 743 (M+H)$^+$

HRFABMS calcd for $C_{35}H_{39}N_2O_{10}S_3$ (M+H)$^+$ 743.1767, found 743.1773

EXAMPLE 58
Synthesis of Compound 62

According to the procedure as described in Example 28, Compound 62 (22 mg, 38% yield) was obtained from Compound 35 (51 mg, 0.082 mmol), dichloromethane (3.0 ml), N,N-diisopropylethylamine (2.1 ml, 12 mmol) and 2-methoxyethoxymethyl chloride (0.84 ml, 7.4 mmol).

IR (KBr) 3420, 2932, 1820, 1705, 1679, 1648, 1608, 1447, 1364, 1261, 1208, 1105, 1094, 1019, 977, 768 cm$^{-1}$ $^1$H NMR (CDCl$_3$, 500 MHz) δ ppm; 9.48 (dd, J=16.8, 11.3 Hz, 1H), 7.40 (s, 1H), 6.62 (d, J=11.6 Hz, 1H), 6.36 (dd, J=11.6, 11.3 Hz, 1H), 6.02 (d, J=16.8 Hz, 1H), 5.82 (br d, J=9.2 Hz, 1H), 5.58 (q, J=6.4 Hz, 1H), 5.50 (br s, 1H), 4.84 (dd, J=9.2, 1.2 Hz, 1H), 4.72 (d, J=6.9 Hz, 1H), 4.69 (d, J=6.9 Hz, 1H), 4.04 (d, J=17.7 Hz, 1H), 3.80 (d, J=15.6 Hz, 1H), 3.76 (d, J=15.6 Hz, 1H), 3.62–3.45 (m, 4H), 3.35 (s, 3H), 2.46–2.24 (m, 3H), 2.29 (d, J=17.7 Hz, 1H), 2.15 (s, 3H), 1.89 (d, J=6.4 Hz, 3H), 1.76 (d, J=1.2 Hz, 3H), 1.70 (s, 3H), 1.50–1.42 (m, 1H)

FABMS m/z 711 (M+H)$^+$

HRFABMS calcd for $C_{31}H_{39}N_2O_{11}S_3$ (M+H)$^+$ 711.1716, found 711.1724

EXAMPLE 59
Synthesis of Compounds 63 and 64

According to the procedure as described in Example 18, Compound 35 (53 mg, 0.085 mmol) was dissolved in dichloromethane (4.7 ml), and 3,4-dihydro-2H-pyran (0.035 ml, 0.39 mmol) and camphorsulfonic acid (13.5 mg, 0.058 mmol) were added thereto, followed by stirring at 0° C. for 2 hours. After subjecting the mixture to the usual post-treatment, the mixture was purified by thin layer chromatography (developed seven times with chloroform/methanol=98/2) to obtain Compound 63 (14 mg, 23% yield) and Compound 64 (22 mg, 37% yield) as a diastereomer thereof.

Compound 63

IR (KBr) 3420, 2930, 1820, 1710, 1686, 1647, 1607, 1437, 1387, 1260, 1207, 1116, 1073, 1021, 973, 768 cm$^{-1}$ $^1$H NMR (CDCl$_3$, 400 MHz) δ ppm; 9.58 (ddd, J=16.6, 11.5, 1.0 Hz, 1H), 7.40 (s, 1H), 6.61 (d, J=11.5 Hz, 1H), 6.34 (dd, J=11.5, 11.5 Hz, 1H), 6.00 (d, J=16.6 Hz, 1H), 5.83 (br d, J=9.0 Hz, 1H), 5.59 (q, J=6.6 Hz, 1H), 5.50 (s, 1H), 5.02 (dd, J=9.0, 1.0 Hz, 1H), 4.57 (m, 1H), 4.05 (d, J=17.6 Hz, 1H), 3.88–3.80 (m, 1H), 3.78 (s, 2H), 3.53–3.47 (m, 1H), 2.46–1.40 (m, 10H), 2.30 (d, J=17.8 Hz, 1H), 2.15 (s, 3H), 1.94 (d, J=6.6 Hz, 3H), 1.77 (d, J=1.0 Hz, 3H), 1.70 (s, 3H)

FABMS m/z 707 (M+H)$^+$

HRFABMS calcd for $C_{32}H_{39}N_2O_{10}S_3$ (M+H)$^+$ 707.1767, found 707.1793

Compound 64

IR (KBr) 3420, 2940, 1822, 1715, 1690, 1650, 1610, 1441, 1375, 1262, 1207, 1117, 3073, 1028, 973, 768 cm$^{-1}$ $^1$H NMR (CDCl$_3$, 400 MHz) δ ppm; 9.39 (ddd, J=16.5, 11.2, 1.0 Hz, 1H), 7.39 (s, 1H), 6.60 (d, J=11.7 Hz, 1H), 6.37 (dd, J=11.7, 11.2 Hz, 1H), 6.05 (d, J=16.5 Hz, 1H), 5.80 (br d, J=9.2 Hz, 1H), 5.57 (q, J=6.5 Hz, 1H), 5.48 (br s, 1H), 4.74 (dd, J=9.2, 1.0 Hz, 1H), 4.70 (m, 1H), 4.04 (d, J=17.7 Hz, 1H), 3.80 (d, J=15.2 Hz, 1H), 3.83–3.72 (m, 1H), 3.75 (d, J=15.2 Hz, 1H), 3.47–3.38 (m, 1H), 2.45–1.40 (m, 10H), 2.29 (d, J=17.7 Hz, 1H), 2.15 (s, 3H), 1.88 (d, J=6.5 Hz, 3H), 1.74 (d, J=1.0 Hz, 3H), 1.69 (s, 3H)

FABMS m/z 707 (M+H)$^+$

HRFABMS calcd for $C_{32}H_{39}N_2O_{10}S_3$ (M+H)$^+$ 707.1767, found 707.1783

EXAMPLE 60
Synthesis of Compound 65

DC107 (5.8 mg, 0.011 mmol) was dissolved in methanol (0.50 ml), and then, pyridine (0.0046 ml, 0.057 mmol) and hydroxylamine hydrochloride (1.6 mg, 0.022 mmol) were added thereto, followed by stirring at 0° C. for 4 hours. The solvent was distilled off under reduced pressure, and the residue was purified by thin layer chromatography (developed with chloroform/methanol=95/5) to obtain Compound 65 (3.0 mg, 52% yield).

IR (KBr) 3370, 2932, 1713, 1641, 1527, 1449, 1376, 1298, 1211, 1094, 951, 889, 798 cm$^{-1}$ $^1$H NMR (CDCl$_3$, 400 MHz) δ ppm; 8.78 (dd, J=16.5, 11.2 Hz, 1H), 7.12 (s, 1H), 7.02 (br d, J=6.3 Hz, 1H), 6.41 (d, J=11.3 Hz, 1H), 6.34 (dd, J=11.3, 11.2 Hz, 1H), 6.20 (dd, J=9.8, 1.0 Hz, 1H), 6.18 (d, J=16.5 Hz, 1H), 6.00 (br d, J=9.8 Hz, 1H), 5.27 (br s, 1H), 5.24 (dq, J=6.6, 6.3 Hz, 1H), 3.25 (d, J=14.6 Hz, 1H), 2.85 (d, J=14.6 Hz, 1H), 2.34 (m, 4H), 1.91 (s, 3H), 1.75 (s, 3H), 1.74 (d, J=6.6 Hz, 3H)

FABMS m/z 526 (M+H)$^+$

HRFABMS calcd for $C_{22}H_{28}N_3O_6S_3$ (M+H)$^+$ 526.1140, found 526.1152

EXAMPLE 61
Synthesis of Compounds 66 and 67

According to the procedure as described in Example 60, Compound 66 (1.4 mg, 24% yield) and Compound 67 (3.6 mg, 61% yield) which is a geometrical isomer thereof were obtained from DC107 (5.7 mg, 0.011 mmol), methanol (0.5 ml), pyridine (0.030 ml, 0.37 mmol) and O-methylhydroxylamine hydrochloride (10 mg, 0.12 mmol).

Compound 66

IR (KBr) 3420, 2938, 1710, 1643, 1530, 1449, 1372, 1093, 1047, 951, 928, 795 cm$^{-1}$ $^1$H NMR (CDCl$_3$, 400 MHz) δ ppm; 8.75 (dd, J=16.5, 11.0 Hz, 1H), 7.11 (s, 1H), 6.95 (br d, J=6.5 Hz, 1H), 6.40 (d, J=11.5 Hz, 1H), 6.34 (dd, J=11.5, 11.0 Hz, 1H), 6.19 (d, J=16.5 Hz, 1H), 6.09 (dd, J=9.8, 1.0 Hz, 1H), 5.98 (br d, J=9.8 Hz, 1H), 5.24 (dq, J=6.5, 6.5 Hz, 1H), 3.93 (s, 3H), 3.27 (dd, J=14.6, 1.2 Hz, 1H), 2.84 (d, J=14.6 Hz, 1H), 2.31–1.75 (m, 4H), 1.92 (s, 3H), 1.74 (d, J=6.5 Hz, 3H), 1.72 (d, J=1.0 Hz, 3H)

FABMS m/z 540 (M+H)$^+$

HRFABMS calcd for $C_{23}H_{30}N_3O_6S_3$ (M+H)$^+$ 540.1297, found 540.1284

Compound 67

IR (KBr) 3420, 2938, 1705, 1643, 1530, 1450, 1374, 1096, 1052, 949, 889,799 cm$^{-1}$ $^1$H NMR (CDCl$_3$, 400 MHz) δ ppm; 8.13 (dd, J=16.6, 11.5 Hz, 1H), 7.14 (s, 1H), 6.99 (br d, J=6.6 Hz, 1H), 6.78 (d, J=16.6 Hz, 1H), 6.51 (d, J=11.5 Hz, 1H), 6.39 (dd, J=11.5, 11.5 Hz, 1H), 5.86 (br d, J=9.4 Hz, 1H), 5.32 (dq, J=6.6, 6.6 Hz, 1H), 5.13 (d, J=9.4 Hz, 1H), 3.93 (s, 3H), 3.11 (d, J=15.3 Hz, 1H), 3.01 (d, J=15.3 Hz, 1H), 2.32 (dt, J=12.5, 4.1 Hz, 1H), 1.99–1.80 (m, 3H), 1.81 (s, 3H), 1.74 (d, J=6.6 Hz, 3H), 1.66 (d, J=1.2 Hz, 3H)

FABMS m/z 540 (M+H)$^+$

HRFABMS calcd for $C_{23}H_{30}N_3O_6S_3$ (M+H)$^+$ 540.1297, found 540.1284

EXAMPLE 62
Synthesis of Compounds 68 and 69

According to the procedure as described in Example 60, Compound 68 (29 mg, 47% yield) and Compound 69 (26 mg, 43% yield) which is a geometrical isomer thereof were obtained from DC107 (50 mg, 0.10 mmol), methanol (5.0 ml), pyridine (0.040 ml, 0.50 mmol) and O-benzylhydroxylamine hydrochloride (32 mg, 0.20 mmol).

Compound 68

IR (KBr) 3420, 2924, 1719, 1648, 1540, 1451, 1363, 1084, 1015, 952, 795, 698 cm$^{-1}$ $^1$H NMR (CDCl$_3$, 400 MHz) δ ppm; 8.78 (dd, J=16.8, 11.0 Hz, 1H), 7.37–7.30 (m, 5H), 7.10 (s, 1H), 6.97 (d, J=6.2 Hz, 1H), 6.39 (d, J=11.5 Hz, 1H), 6.33 (dd, J=11.5, 11.0 Hz, 1H), 6.20 (d, J=16.8 Hz, 1H), 6.14 (dd, J=9.7, 1.2 Hz, 1H), 5.97 (br d, J=9.7 Hz, 1H), 5.23 (dq, J=6.3, 6.0 Hz, 1H), 5.17 (d, J=12.0 Hz, 1H), 5.13 (d, J=12.0 Hz, 1H), 3.26 (dd, J=14.6, 1.4 Hz, 1H), 2.83 (d, J=14.6 Hz, 1H), 2.27 (dt, J=12.7, 2.9 Hz, 1H), 2.06 (dt, J=12.7, 6.3 Hz, 1H), 1.92 (s, 3H), 1.92 (ddd, J=14.7, 12.7, 2.9 Hz, 1H), 1.82 (ddd, J=14.7, 12.7, 6.3 Hz, 1H), 1.73 (d, J=6.3 Hz, 3H), 1.63 (s, 3H)

FABMS m/z 616 (M+H)$^+$

HRFABMS calcd for C$_{29}$H$_{34}$N$_3$O$_6$S$_3$ (M+H)$^+$ 616.1610, found 616.1612

Compound 69

IR (KBr) 3400, 2930, 1720, 1652, 1539, 1451, 1369, 1209, 1097, 1016, 952, 878, 799, 730, 697 cm$^{-1}$ $^1$H NMR (CDCl$_3$, 400 MHz) δ ppm; 8.25 (dd, J=16.3, 11.2 Hz, 1H), 7.38–7.28 (m, 5H), 7.11 (s, 1H), 6.83 (d, J=16.3 Hz, 1H), 6.82 (br d, J=6.6 Hz, 1H), 6.50 (d, J=11.3 Hz, 1H), 6.36 (dd, J=11.3, 11.2 Hz, 1H), 5.91 (br d, J=9.4 Hz, 1H), 5.29 (dq, J=6.9, 6.6 Hz, 1H), 5.16 (br s, 2H), 5.15 (d, J=9.4 Hz, 1H), 4.59 (br s, 1H), 3.10 (d, J=15.0 Hz, 1H), 2.98 (d, J=15.0 Hz, 1H), 2.38 (br s, 1H), 2.36–2.26 (m, 1H), 2.01–1.82 (m, 3H), 1.82 (s, 3H), 1.73 (d, J=6.9 Hz, 3H), 1.64 (d, J=1.2 Hz, 3H)

FABMS m/z 616 (M+H)$^+$

HRFABMS calcd for C$_{29}$H$_{34}$N$_3$O$_6$S$_3$ (M+H)$^+$ 616.1610, found 616.1605

EXAMPLE 63

Synthesis of Compounds 70 and 71

According to the procedure as described in Example 60, Compound 70 (27 mg, 49% yield) and Compound 71 (14 mg, 26% yield) which is a geometrical isomer thereof were obtained from DC107 (51 mg, 0.10 mmol), methanol (5.0 ml), pyridine (0.040 ml, 0.50 mmol) and O-allylhydroxylamine hydrochloride (33 mg, 0.30 mmol).

Compound 70

IR (KBr) 3420, 2926, 1719, 1647, 1539, 1448, 1370, 1096, 1025, 1001, 945, 888, 798 cm$^{-1}$ $^1$H NMR (CDCl$_3$, 400 MHz) δ ppm; 8.79 (dd, J=16.4, 11.2 Hz, 1H), 7.11 (s, 1H), 6.92 (d, J=6.1 Hz, 1H), 6.40 (d, J=11.2 Hz, 1H), 6.33 (dd, J=11.2, 11.2 Hz, 1H), 6.20 (d, J=16.4 Hz, 1H), 6.14 (dd, J=10.0, 2.0 Hz, 1H), 6.02–5.91 (m, 1H), 5.99 (br d, J=10.0 Hz, 1H), 5.31–5.20 (m, 3H), 5.23 (br s, 1H), 4.62 (dd, J=5.6, 1.2 Hz, 2H), 3.26 (d, J=14.7 Hz, 1H), 2.83 (d, J=14.7 Hz, 1H), 2.28 (dt, J=12.7, 3.0 Hz, 1H), 2.09 (dt, J=12.7, 6.3 Hz, 1H), 1.98–1.78 (m, 3H), 1.92 (s, 3H), 1.74 (d, J=6.6 Hz, 3H), 1.73 (br s, 3H)

FABMS m/z 566 (M+H)$^+$

HRFABMS calcd for C$_{25}$H$_{32}$N$_3$O$_6$S$_3$ (M+H)$^+$ 566.1453, found 566.1438

Compound 71

IR (KBr) 3420, 2928, 1711, 1647, 1538, 1447, 1369, 1097, 1032, 996, 949, 924, 887, 799 cm$^{-1}$ $^1$H NMR (CDCl$_3$, 500 MHz) δ ppm; 8.26 (dd, J=16.5, 11.6 Hz, 1H), 7.12 (s, 1H), 6.82 (d, J=16.5 Hz, 1H), 6.75 (d, J=6.7 Hz, 1H), 6.51 (d, J=11.3 Hz, 1H), 6.38 (dd, J=11.6, 11.3 Hz, 1H), 6.01 (ddt, J=17.4, 10.4, 5.5 Hz, 1H), 5.91 (br d, J=9.5 Hz, 1H), 5.31 (dq, J=17.4, 1.5 Hz, 1H), 5.30 (dq, J=6.7, 6.4 Hz, 1H), 5.23 (dq, J=10.4, 1.5 Hz, 1H), 5.15 (dd, J=9.5, 2.8 Hz, 1H), 4.63 (dt, J=5.5, 1.5 Hz, 2H), 4.58 (br s, 1H), 3.11 (d, J=15.0 Hz, 1H), 2.98 (d, J=15.0 Hz, 1H), 2.37–1.82 (m, 5H), 1.83 (s, 3H), 1.74 (d, J=6.4 Hz, 3H), 1.68 (d, J=1.0 Hz, 3H)

FABMS m/z 566 (M+H)$^+$

HRFABMS calcd for C$_{25}$H$_{32}$N$_3$O$_6$S$_3$ (M+H)$^+$ 566.1453, found 566.1464

EXAMPLE 64

Synthesis of Compounds 72 and 73

According to the procedure as described in Example 60, Compound 72 (16 mg, 23% yield) and Compound 73 (15 mg, 22% yield) which is a geometrical isomer thereof were obtained from Compound 35 (60 mg, 0.096 mmol), methanol (3.0 ml), pyridine (0.039 ml, 0.48 mmol) and O-benzylhydroxylamine hydrochloride (47 mg, 0.29 mmol).

Compound 72

IR (KBr) 3440, 2928, 1820, 1720, 1684, 1452, 1364, 1263, 1208, 1147, 1017, 983, 871, 797, 768, 732, 699 cm$^{-1}$ $^1$H NMR (CDCl$_3$, 400 MHz) δ ppm; 8.94 (dd, J=16.6, 11.2 Hz, 1H), 7.37–7.25 (m, 5H), 7.25 (s, 1H), 6.38 (d, J=11.2 Hz, 1H), 6.31 (dd, J=11.2, 11.2 Hz, 1H), 6.21 (d, J=16.6 Hz, 1H), 6.12 (dd, J=8.6, 5.6 Hz, 1H), 5.86 (br d, J=8.6 Hz, 1H), 5.58 (br s, 1H), 5.54 (q, J=6.6 Hz, 1H), 5.18 (br s, 2H), 4.03 (d, J=17.6 Hz, 1H), 3.78 (br s, 2H), 2.38–1.40 (m, 4H), 2.30 (d, J=17.6 Hz, 1H), 2.15 (s, 3H), 1.88 (d, J=6.6 Hz, 3H), 1.72 (d, J=1.2 Hz, 3H), 1.70 (s, 3H)

FABMS m/z 728 (M+H)$^+$

HRFABMS calcd for C$_{34}$H$_{38}$N$_3$O$_9$S$_3$ (M+H)$^+$ 728.1770, found 728.1768

Compound 73

IR (KBr) 3440, 2930, 1820, 1720, 1684, 1451, 1363, 1262, 1207, 1150, 1012, 980, 928, 877, 799, 767, 732, 698 cm$^{-1}$ $^1$H NMR (CDCl$_3$, 400 MHz) δ ppm; 8.89 (dd, J=16.6, 11.5 Hz, 1H), 7.42–7.25 (m, 5H), 7.28 (s, 1H), 6.83 (d, J=16.6 Hz, 1H), 6.47 (d, J=11.5 Hz, 1H), 6.34 (dd, J=11.5, 11.5 Hz, 1H), 5.98 (br d, J=8.3 Hz, 1H), 5.57 (br s, 1H), 5.55 (q, J=6.6 Hz, 1H), 5.17 (br s, 2H), 5.11 (dd, J=8.3, 5.9 Hz, 1H), 4.02 (d, J=17.5 Hz, 1H), 3.78 (br s, 2H), 2.40–1.45 (m, 4H), 2.35 (d, J=17.5 Hz, 1H), 2.14 (s, 3H), 1.98 (d, J=3.9 Hz, 1H), 1.89 (d, J=6.6 Hz, 3H), 1.74 (s, 3H), 1.71 (s, 3H)

FABMS m/z 728 (M+H)$^+$

HRFABMS calcd for C$_{34}$H$_{38}$N$_3$O$_9$S$_3$ (M+H)$^+$ 728.1770, found 728.1768

EXAMPLE 65

Synthesis of Compound 74

DC107 (20 mg, 0.039 mmol) was dissolved in methanol (3.0 ml), and p-toluenesulfonyl hydrazide (102 mg, 0.55 mmol) was added thereto, followed by stirring at 25° C. for 5.5 hours. After distilling off the solvent under reduced pressure, the residue was purified by thin layer chromatography (developed with chloroform/methanol=95/5) to obtain Compound 74 (14 mg, 53% yield).

IR (KBr) 3400, 2930, 2930, 1707, 1647, 1597, 1558, 1449, 1375, 1334, 1292, 1209, 1186, 1092, 999, 949, 886, 811, 704, 662 cm$^{-1}$ $^1$H NMR (CDCl$_3$, 500 MHz) δ ppm; 8.18 (dd, J=15.6, 11.3 Hz, 1H), 7.82 (d, J=8.0 Hz, 2H), 7.30 (d, J=8.0 Hz, 2H), 7.16 (s, 1H), 6.82 (br d, J=6.7 Hz, 1H), 6.56 (d, J=11.6 Hz, 1H), 6.31 (dd, J=11.6, 11.3 Hz, 1H), 6.22 (d, J=15.6 Hz, 1H), 5.65 (br d, J=9.2 Hz, 1H), 5.31 (dq, J=6.7, 6.7 Hz, 1H), 5.07 (d, J=9.2 Hz, 1H), 4.30 (br s, 1H), 3.06 (d, J=15.3 Hz, 1H), 3.00 (d, J=15.3 Hz, 1H), 2.46–2.21 (m, 2H), 2.43 (s, 3H), 1.90–1.60 (m, 2H), 1.74 (s, 3H), 1.71 (d, J=6.7 Hz, 3H), 1.48 (s, 3H)

FABMS m/z 679 (M+H)$^+$

HRFABMS calcd for C$_{29}$H$_{35}$N$_4$O$_7$S$_4$ (M+H)$^+$ 679.1388, found 679.1379

EXAMPLE 66

Synthesis of Compound 75

DC107 (50 mg, 0.098mmol) was dissolved in methanol (10 ml), and methyl hydrazinocarboxylate (44 mg, 0.49 mmol) and pyridinium p-toluenesulfonate (74 mg, 0.29 mmol) were added thereto, followed by stirring at 25° C. for 40 minutes. After distilling off the solvent under reduced pressure, the residue was purified by thin layer chromatography (developed with chloroform/methanol=94/6) to obtain Compound 75 (8.8 mg, 15% yield).

IR (KBr) 3400, 2932, 1721, 1650, 1527, 1449, 1374, 1241, 1095, 950, 894, 799, 767 cm$^{-1}$ $^1$H NMR (CDOD$_3$, 400 MHz) δ ppm; 8.95 (br d, J=6.8 Hz, 1H), 8.03 (br dd, J=15.9, 11.7 Hz, 1H), 7.45 (s, 1H), 6.59 (d, J=11.5 Hz, 1H), 6.53 (d, J=15.9 Hz, 1H), 6.38 (dd, J=11.7, 11.5 Hz, 1H), 5.65 (br d, J=9.0 Hz, 1H), 5.32 (dq, J=6.8, 6.6 Hz, 1H), 5.15 (d, J=9.0 Hz, 1H), 3.79 (s, 3H), 3.21 (d, J=15.8 Hz, 1H), 2.98 (d, J=15.8 Hz, 1H), 2.45–1.78 (m, 4H), 1.70 (d, J=6.8 Hz, 3H), 1.68 (s, 3H), 1.61 (s, 3H)

FABMS m/z 583 (M+H)$^+$

HRFABMS calcd for $C_{24}H_{31}N_4O_7S_3$ (M+H)$^+$ 583.1355, found 583.1371

EXAMPLE 67

Synthesis of Compound 76

According to the procedure as described in Example 22, Compound 76 (11 mg, 26% yield) was obtained from DC107 (30 mg, 0.058 mmol), pyridine (0.72 ml, 8.8 mmol), benzoyl chloride (0.30 ml, 2.6 mmol) and 4-dimethylaminopyridine (2.1 mg, 0.017 mmol).

IR (KBr) 3400, 2928, 1721, 1670, 1614, 1517, 1450, 1375, 1316, 1267, 1176, 1096, 1068, 1025, 996, 952, 853, 799, 711 cm$^{-1}$ $^1$H NMR (CDCl$_3$, 400 MHz) δ ppm; 8.60 (br s, 1H), 8.02–7.95 (m, 4H), 7.65–7.34 (m, 6H), 7.28 (s, 1H), 6.58 (d, J=11.2 Hz, 1H), 6.47 (br s, 1H), 6.17 (d, J=9.5 Hz, 1H), 6.16 (br s, 1H), 6.01 (d, J=16.6 Hz, 1H), 5.78 (br d, J=9.5 Hz, 1H), 5.46 (dq, J=7.0, 6.8 Hz, 1H), 3.49 (d, J=16.1 Hz, 1H), 3.16 (br s, 1H), 2.32–1.90 (m, 4H), 2.06 (s, 3H), 1.75 (s, 3H), 1.68 (d, J=6.8 Hz, 3H)

FABMS m/z 719 (M+H)$^+$

HRFABMS calcd for $C_{36}H_{35}N_2O_8S_3$ (M+H)$^+$ 719.1555, found 719.1564

EXAMPLE 68

Synthesis of Compound 77

According to the procedure as described in Example 32, Compound 77 (24 mg, 25% yield) was obtained from DC107 (82 mg, 0.16 mmol), potassium carbonate (220 mg, 1.6 mmol), chloromethyl cyclopropanecarboxylate (280 mg, 2.1 mmol) and potassium iodide (26 mg, 0.16 mmol).

IR (KBr) 3408, 3100, 2936, 1725, 1693, 1649, 1611, 1453, 1414, 1387, 1264, 1154, 1099, 1063, 979, 887, 809, 750 cm$^{-1}$ $^1$H NMR (CDCl$_3$, 400 MHz) δ ppm; 8.46 (ddd, J=16.3, 11.5, 1.0 Hz, 1H), 7.35 (s, 1H), 6.58 (d, J=12.0 Hz, 1H), 6.23 (dd, J=12.0, 11.5 Hz, 1H), 6.17 (d, J=16.3 Hz, 1H), 5.73, (br d, J=8.5 Hz, 1H), 5.44 (br s, 1H), 5.41 (q, J=7.0 Hz, 1H), 5.41 (d, J=11.0 Hz, 1H), 5.37 (d, J=11.0 Hz, 1H), 4.94 (dd, J=8.5, 3.9 Hz, 1H), 3.90 (d, J=17.8 Hz, 1H), 3.73 (d, J=3.9 Hz, 1H), 2.37–1.55 (m, 5H), 2.28 (d, J=17.8 Hz, 1H), 2.02 (d, J=7.0 Hz, 3H), 1.80 (s, 3H), 1.75 (d, J=1.2 Hz, 3H), 1.05–0.85 (m, 4H)

FABMS m/z 609 (M+H)$^+$

HRFABMS calcd for $C_{27}H_{33}N_2O_8S_3$ (M+H)$^+$ 609.1399, found 609.1399

EXAMPLE 69

Synthesis of Compound 78

According to the procedure as described in Example 32, Compound 78 (27 mg, 43% yield) was obtained from DC107 (51 mg, 0.10 mmol), potassium carbonate (140 mg, 1.0 mmol), chloromethyl cyclobutanecarboxylate (250 mg, 1.7 mmol) and potassium iodide (17 mg, 0.10 mmol).

IR (KBr) 3430, 2950, 1730, 1694, 1648, 1610, 1450, 1365, 1254, 1154, 1090, 1051, 986, 730 cm$^{-1}$ $^1$H NMR (CDCl$_3$, 500 MHz) δ ppm; 8.46 (ddd, J=16.3, 11.3, 1.0 Hz, 1H), 7.34 (s, 1H), 6.58 (d, J=11.6 Hz, 1H), 6.23 (dd, J=11.6, 11.3 Hz, 1H), 6.17 (d, J=16.3 Hz, 1H), 5.73 (dd, J=8.5, 1.0 Hz, 1H), 5.51 (br s, 1H), 5.41 (q, J=7.0 Hz, 1H), 5.41 (d, J=11.0 Hz, 1H), 5.36 (d, J=11.0 Hz, 1H), 4.94 (dd, J=8.5, 3.7 Hz, 1H), 3.89 (d, J=17.7 Hz, 1H), 3.73 (d, J=3.7 Hz, 1H), 3.17–3.08 (m, 1H), 2.36–1.80 (m, 10H), 2.26 (d, J=17.7 Hz, 1H), 2.02 (d, J=7.0 Hz, 3H), 1.78 (s, 3H), 1.74 (d, J=1.0 Hz, 3H)

FABMS m/z 623 (M+H)$^+$

HRFABMS calcd for $C_{28}H_{35}N_2O_8S_3$ (M+H)$^+$ 623.1555, found 623.1569

EXAMPLE 70

Synthesis of Compound 79

According to the procedure as described in Example 32, Compound 79 (24 mg, 26% yield) was obtained from DC107 (75 mg, 0.15 mmol), potassium carbonate (250 mg, 1.8 mmol), chloromethyl cyclopentanecarboxylate (330 mg, 2.0 mmol) and potassium iodide (30 mg, 0.18 mmol).

IR (KBr) 3420, 3106, 2960, 2874, 1720, 1691, 1648, 1610, 1452, 1411, 1372, 1263, 1143, 1105, 1087, 980, 859, 807, 730 cm$^{-1}$ $^1$H NMR (CDCl$_3$, 500 MHz) δ ppm; 8.47 (ddd, J=16.5, 11.5, 1.2 Hz, 1H), 7.35 (s, 1H), 6.58 (d, J=11.9 Hz, 1H), 6.23 (dd, J=11.9, 11.5 Hz, 1H), 6.17 (d, J=16.5 Hz, 1H), 5.74 (br d, J=8.8 Hz, 1H), 5.51 (br s, 1H), 5.41 (q, J=7.0 Hz, 1H), 5.41 (d, J=11.0 Hz, 1H), 5.35 (d, J=11.0 Hz, 1H), 4.94 (br d, J=8.8 Hz, 1H), 3.89 (d, J=17.7 Hz, 1H), 3.74 (br s, 1H), 2.77–2.66 (m, 1H), 2.36–1.50 (m, 12H), 2.25 (d, J=17.7 Hz, 1H), 2.02 (d, J=7.0 Hz, 3H), 1.78 (s, 3H), 1.75 (d, J=1.2 Hz, 3H)

FABMS m/z 637 (M+H)$^+$

HRFABMS calcd for $C_{29}H_{37}N_2O_8S_3$ (M+H)$^+$ 637.1712, found 637.1695

EXAMPLE 71

Synthesis of Compound 80

According to the procedure as described in Example 32, Compound 80 (37 mg, 35% yield) was obtained from DC107 (84 mg, 0.16 mmol), potassium carbonate (220 mg, 1.6 mmol), chloromethyl cyclohexanecarboxylate (280 mg, 1.6 mmol) and potassium iodide (26 mg, 0.16 mmol).

IR (KBr) 3420, 3106, 2936, 2858, 1725, 1692, 1648, 1610, 1451, 1376, 1267, 1157, 1120, 1090, 1020, 974, 804, 728 cm$^{-1}$ $^1$H NMR (CDCl$_3$, 400 MHz) δ ppm; 8.47 (ddd, J=16.3, 11.5, 1.0 Hz, 1H), 7.35 (s, 1H), 6.58 (d, J=12.0 Hz, 1H), 6.23 (dd, J=12.0, 11.5 Hz, 1H), 6.17 (d, J=16.3 Hz, 1H), 5.74 (br d, J=8.5 Hz, 1H), 5.50 (br s, 1H), 5.41 (q, J=6.8 Hz, 1H), 5.40 (d, J=11.0 Hz, 1H), 5.35 (d, J=11.0 Hz, 1H), 4.94 (br d, J=8.5 Hz, 1H), 3.89 (d, J=17.8 Hz, 1H), 3.75 (br s, 1H), 2.35–1.20 (m, 15H), 2.26 (d, J=17.8 Hz, 1H), 2.20 (d, J=6.8 Hz, 3H), 1.78 (s, 3H), 1.75 (d, J=1.2 Hz, 3H)

FABMS m/z 651 (M+H)$^+$

HRFABMS calcd for $C_{30}H_{39}N_2O_8S_3$ (M+H)$^+$ 651.1868, found 651.1868

EXAMPLE 72
Synthesis of Compound 81

According to the procedure as described in Example 32, Compound 81 (25 mg, 35% yield) was obtained from DC107 (60 mg, 0.12 mmol), potassium carbonate (290 mg, 2.1 mmol), chloromethyl isobutyrate (320 mg, 2.3 mmol) and potassium iodide (58 mg, 0.35 mmol).

IR (KBr) 3420, 3106, 2980, 2936, 1720, 1694, 1648, 1611, 1469, 1454, 1373, 1265, 1183, 1146, 1101, 974, 807, 754 cm$^{-1}$ $^1$H NMR (CDCl$_3$, 400 MHz) δ ppm; 8.47 (ddd, J=16.4, 11.2, 1.0 Hz, 1H), 7.35 (s, 1H), 6.58 (d, J=11.7 Hz, 1H), 6.23 (dd, J=11.7, 11.2 Hz, 1H), 6.17 (d, J=16.4 Hz, 1H), 5.74 (br d, J=16.4 Hz, 1H), 5.52 (br s, 1H), 5.41 (q, J=7.0 Hz, 1H), 5.41 (d, J=11.0 Hz, 1H), 5.36 (d, J=11.0 Hz, 1H), 4.94 (dd, J=8.5, 3.9 Hz, 1H), 3.89 (d, J=17.8 Hz, 1H), 3.74 (d, J=3.9 Hz, 1H), 2.60–2.45 (m, 1H), 2.35–1.90 (m, 4H), 2.26 (d, J=17.8 Hz, 1H), 2.02 (d, J=7.0 Hz, 3H), 1.78 (s, 3H), 1.74 (d, J=1.2 Hz, 3H), 1.13 (d, J=7.1 Hz, 6H)

FABMS m/z 611 (M+H)$^+$

HRFABMS calcd for C$_{27}$H$_{35}$N$_2$O$_8$S$_3$ (M+H)$^+$ 611.1555, found 611.1547

EXAMPLE 73
Synthesis of Compound 82

According to the procedure as described in Example 32, Compound 82 (22 mg, 28% yield) was obtained from DC107 (65 mg, 0.13 mmol), potassium carbonate (170 mg, 1.2 mmol), chloromethyl isovalerate (320 mg, 2.1 mmol) and potassium iodide (30 mg, 0.18 mmol).

IR (KBr) 3430, 3105, 2936, 2880, 1720, 1697, 1650, 1611, 1453, 1408, 1371, 1265, 1160, 1091, 979, 804, 730 cm$^{-1}$ $^1$H NMR (CDCl$_3$, 500 MHz) δ ppm; 8.47 (ddd, J=16.3, 11.3, 1.0 Hz, 1H), 7.35 (s, 1H), 6.58 (d, J=11.9 Hz, 1H), 6.23 (dd, J=11.9, 11.3 Hz, 1H), 6.17 (d, J=16.3 Hz, 1H), 5.74 (br d, J=8.5 Hz, 1H), 5.53 (br d, 1H), 5.41 (q, J=7.0 Hz, 1H), 5.41 (d, J=11.0 Hz, 1H), 5.36 (d, J=11.0 Hz, 1H), 4.94 (dd, J=8.5, 3.7 Hz, 1H), 3.88 (d, J=17.7 Hz, 1H), 3.73 (d, J=3.7 Hz, 1H), 2.41–1.92 (m, 7H), 2.26 (d, J=17.7 Hz, 1H), 2.02 (d, J=7.0 Hz, 3H), 1.78 (s, 3H), 1.75 (d, J=1.0 Hz, 3H), 0.93 (d, J=6.4 Hz, 6H)

FABMS m/z 625 (M+H)$^+$

HRFABMS calcd for C$_{28}$H$_{37}$N$_2$O$_8$S$_3$ (M+H)$^+$ 625.1712, found 625.1732

EXAMPLE 74
Synthesis of Compound 83

According to the procedure as described in Example 32, Compound 83 (23 mg, 38% yield) was obtained from DC107 (50 mg, 0.098 mmol), potassium carbonate (244 mg, 1.8 mmol), chloromethyl n-valerinate (300 mg, 2.0 mmol) and potassium iodide (50 mg, 0.30 mmol).

IR (KBr) 3430, 2960, 2936, 1720, 1693, 1650, 1611, 1452, 1374, 1260, 1154, 1105, 1089, 1018, 981, 727 cm$^{-1}$ $^1$H NMR (CDCl$_3$, 400 MHz) δ ppm; 8.46 (ddd, J=16.3, 11.3, 1.0 Hz, 1H), 7.35 (s, 1H), 6.58 (d, J=11.7 Hz, 1H), 6.23 (dd, J=11.7, 11.3 Hz, 1H), 6.17 (d, J=16.3 Hz, 1H), 5.73 (br d, J=8.5 Hz, 1H), 5.52 (br s, 1H), 5.41 (q, J=6.8 Hz, 1H), 5.40 (d, J=11.0 Hz, 1H), 5.35 (d, J=11.0 Hz, 1H), 4.94 (dd, J=8.5, 3.9 Hz, 1H), 3.89 (d, J=17.8 Hz, 1H), 3.73 (d, J=3.9 Hz, 1H), 2.38–1.23 (m, 10H), 2.26 (d, J=17.8 Hz, 1H), 2.02 (d, J=6.8 Hz, 3H), 1.79 (s, 3H), 1.75 (d, J=1.2 Hz, 3H), 0.89 (t, J=7.3 Hz, 3H)

FABMS m/z 625 (M+H)$^+$

HRFABMS calcd for C$_{28}$H$_{37}$N$_2$O$_8$S$_3$ (M+H)$^+$ 625.1712, found 625.1741

EXAMPLE 75
Synthesis of Compound 84

According to the procedure as described in Example 32, Compound 84 (30 mg, 36% yield) was obtained from DC107 (63 mg, 0.12 mmol), potassium carbonate (310 mg, 2.2 mmol), chloromethyl n-octanoate (240 mg, 1.2 mmol) and potassium iodide (61 mg, 0.37 mmol).

IR (KBr) 3420, 2930, 2858, 1721, 1698, 1650, 1612, 1456, 1411, 1375, 1264, 1153, 1107, 1018, 978, 807, 727 cm$^{-1}$ $^1$H NMR (CDCl$_3$, 400 MHz) δ ppm; 8.47 (ddd, J=16.3, 11.2, 0.8 Hz, 1H), 7.35 (s, 1H), 6.58 (d, J=11.7 Hz, 1H), 6.23 (dd, J=11.7, 11.2 Hz, 1H), 6.17 (d, J=16.3 Hz, 1H), 5.74 (br d, J=8.5 Hz, 1H), 5.52 (br s, 1H), 5.41 (q, J=7.0 Hz, 1H), 5.39 (d, J=11.0 Hz, 1H), 5.36 (d, J=11.0 Hz, 1H), 4.94 (dd, J=8.5, 3.7 Hz, 1H), 3.89 (d, J=17.8 Hz, 1H), 3.73 (d, J=3.9 Hz, 1H), 2.36–1.20 (m, 14H), 2.29 (t, J=7.3 Hz, 2H), 2.27 (d, J=17.8 Hz, 1H), 2.02 (d, J=7.0 Hz, 3H), 1.79 (s, 3H), 1.75 (d, J=1.2 Hz, 3H), 0.87 (t, J=6.8 Hz, 3H)

FABMS m/z 667 (M+H)$^+$

HRFABMS calcd for C$_{31}$H$_{43}$N$_2$O$_8$S$_3$ (M+H)$^+$ 667.2181, found 667.2172

EXAMPLE 76
Synthesis of Compound 85

According to the procedure as described in Example 32, Compound 85 (29 mg, 28% yield) was obtained from Compound 18 (85 mg, 0.14 mmol), potassium carbonate (197 mg, 1.4 mmol), chloromethyl cyclohexanecarboxylate (250 mg, 1.4 mmol) and potassium iodide (25 mg, 0.14 mmol). From $^1$H NMR data, Compound 85 was found to be a mixture of diastereomers at about 1:1 due to the asymmetric carbon of the tetrahydropyranyl group.

IR (KBr) 3420, 2936, 2858, 1730, 1698, 1651, 1609, 1452, 1375, 1262, 1156, 1123, 1074, 1020, 971, 869 cm$^{-1}$ $^1$H NMR (CDCl$_3$, 400 MHz) δ ppm; 9.59, 9.39 (dd, J=16.4, 11.2 Hz, 1H), 7.40, 7.39 (s, 1H), 6.61, 6.60 (d, J=11.5 Hz, 1H), 6.37, 6.60 (dd, J=11.5, 11.2 Hz, 1H), 6.04, 6.00 (d, J=16.4 Hz, 1H), 5.83, 5.80 (d, J=9.3 Hz, 1H), 5.58, 5.56 (q, J=6.6 Hz, 1H), 5.52, 5.50 (br s, 1H), 5.42 (d, J=11.0 Hz, 1H), 5.35 (d, J=11.0 Hz, 1H), 5.02, 4.74 (dd, J=9.3, 1.0 Hz, 1H), 4.72–4.53 (m, 1H), 4.04, 4.03 (d, J=17.8 Hz, 1H), 3.88–3.70 (m, 1H), 3.54–3.40 (m, 1H), 2.45–1.20 (m, 21H), 2.29, 2.28 (d, J=17.8 Hz, 1H), 1.94, 1.88 (d, J=6.6 Hz, 3H), 1.77, 1.74 (d, J=1.2 Hz, 3H), 1.70, 1.69 (s, 3H)

FABMS m/z 735 (M+H)$^+$

HRFABMS calcd for C$_{35}$H$_{47}$N$_2$O$_9$S$_3$ (M+H)$^+$ 735.2443, found 735.2463

EXAMPLE 77
Synthesis of Compound 86

According to the procedure as described in Example 32, Compound 86 (34 mg, 34% yield) was obtained from Compound 18 (85 mg, 0.14 mmol), potassium carbonate (197 mg, 1.4 mmol), chloromethyl isovalerinate (323 mg, 2.1 mmol) and potassium iodide (25 mg, 0.14 mmol). From $^1$H NMR data, Compound 86 was found to be a mixture of diastereomers at about 1:1 due to the asymmetric carbon of the tetrahydropyranyl group.

IR (KBr) 3420, 2960, 2930, 1740, 1700, 1649, 1609, 1454, 1370, 1262, 1155, 1115, 1074, 1019, 974, 868 cm$^{-1}$ $^1$H NMR (CDCl$_3$, 500 MHz) δ ppm; 9.59, 9.40 (dd, J=16.6, 11.7 Hz, 1H), 7.40, 7.39 (s, 1H), 6.61, 6.60 (d, J=11.5 Hz, 1H), 6.37, 6.35 (dd, J=11.7, 11.5 Hz, 1H), 6.05, 6.00 (d, J=16.6 Hz, 1H), 5.83, 5.80 (d, J=9.3 Hz, 1H), 5.59, 5.57 (q, J=6.6 Hz, 1H), 5.55, 5.53 (br s, 1H), 5.42 (d, J=11.0 Hz, 1H), 5.36 (d, J=11.0 Hz, 1H), 5.02, 4.74 (dd, J=9.3, 1.2 Hz, 1H), 4.73–4.55 (m, 1H), 4.04, 4.02 (d, J=17.7 Hz, 1H), 3.87–3.70 (m, 1H), 3.54–3.40 (m, 1H), 2.45–1.40 (m, 13H), 2.30, 2.29 (d, J=17.7 Hz, 1H), 1.94, 1.88 (d, J=6.6 Hz, 3H), 1.77, 1.74 (d, J=1.2 Hz, 3H), 1.71, 1.70 (s, 3H), 0.96, 0.95 (d, J=6.6 Hz, 6H)

FABMS m/z 709 (M+H)$^+$

HRFABMS calcd for $C_{33}H_{45}N_2O_9S_3$ (M+H)$^+$ 709.2287, found 709.2289

EXAMPLE 78
Synthesis of Compound 87

According to the procedure as described in Example 19, Compound 87 (37 mg, 54% yield) was obtained from Compound 35 (61 mg, 0.098 mmol), ethyl vinyl ether (0.056 ml, 0.59 mmol) and camphorsulfonic acid (22 mg, 0.098 mmol). From $^1$H NMR data, Compound 87 was found to be a mixture of diastereomers at about 10:9 due to the asymmetric carbon of the 1-ethoxyethyl group.

IR (KBr) 3420, 3096, 2984, 2934, 1820, 1705, 1688, 1648, 1608, 1447, 1391, 1377, 1308, 1263, 1208, 1090, 1054, 976, 784 cm$^{-1}$ $^1$H NMR (CDCl$_3$, 400 MHz) δ ppm; major isomer: 9.49 (dd, J=16.5, 11.5 Hz, 1H), 7.38 (s, 1H), 6.60 (d, J=11.2 Hz, 1H), 6.35 (dd, J=11.5, 11.2 Hz, 1H), 6.02 (d, J=16.5 Hz, 1H), 5.80 (br d, J=9.0 Hz, 1H), 5.57 (q, J=6.3 Hz, 1H), 5.52 (br s, 1H), 4.68 (dd, J=9.0, 1.0 Hz, 1H), 4.66 (q, J=5.5 Hz, 1H), 4.04 (d, J=17.6 Hz, 1H), 3.83–3.72 (m, 2H), 3.58–3.31 (m, 2H), 2.46–1.40 (m, 4H), 2.28 (d, J=17.6 Hz, 1H), 2.15 (s, 3H), 1.90 (d, J=6.3 Hz, 3H), 1.74 (d, J=1.0 Hz, 3H), 1.69 (s, 3H), 1.25 (d, J=5.5 Hz, 3H), 1.90 (t, J=7.1 Hz, 3H); minor isomer: 9.63 (dd, J=16.3, 11.5 Hz, 1H), 7.40 (s, 1H), 6.62 (d, J=11.2 Hz, 1H), 6.35 (dd, J=11.5, 11.2 Hz, 1H), 6.00 (d, J=16.3 Hz, 1H), 5.82 (br d, J=9.3 Hz, 1H), 5.58 (q, J=6.3 Hz, 1H), 5.55 (br s, 1H), 4.91 (dd, J=9.0, 1.0 Hz, 1H), 4.72 (q, J=5.5 Hz, 1H), 4.04 (d, J=17.6 Hz, 1H), 3.83–3.72 (m, 2H), 3.58–3.31 (m, 2H), 2.46–1.40 (m, 4H), 2.27 (d, J=17.6 Hz, 1H), 2.15 (s, 3H), 1.92 (d, J=6.3 Hz, 3H), 1.75 (d, J=1.0 Hz, 3H), 1.69 (s, 3H), 1.21 (d, J=5.5 Hz, 3H), 1.17 (t, J=7.1 Hz, 3H).

FABMS m/z 695 (M+H)$^+$

HRFABMS calcd for $C_{31}H_{39}N_2O_{10}S_3$ (M+H)$^+$ 695.1767, found 695.1761

EXAMPLE 79
Synthesis of Compounds 88 and 89

According to the procedure as described in Example 60, Compound 88 (14 mg, 45% yield) and its geometrical isomer, Compound 89 (7.4 mg, 24% yield) were obtained from Compound 63 (30 mg, 0.042 mmol), methanol (4.0 ml), pyridine (0.034 ml, 0.42 mmol) and O-methylhydroxylamine hydrochloride (17.5 mg, 0.21 mmol).

Compound 88

IR (KBr) 3420, 2940, 1822, 1720, 1686, 1440, 1376, 1262, 1208, 1047, 973, 928, 871, 799, 766, 730 cm$^{-1}$ $^1$H NMR (CDCl$_3$, 400 MHz) δ ppm; 8.99 (dd, J=16.4, 11.0 Hz, 1H), 7.24 (s, 1H), 6.35 (d, J=11.5 Hz, 1H), 6.29 (dd, J=11.5, 11.0 Hz, 1H), 6.17 (d, J=16.4 Hz, 1H), 6.11 (dd, J=9.2, 1.2 Hz, 1H), 5.82 (br d, J=9.2 Hz, 1H), 5.58 (br s, 1H), 5.58 (q, J=6.6 Hz, 1H), 4.47 (br s, 1H), 4.05 (d, J=17.6 Hz, 1H), 3.93 (s, 3H), 3.88–3.72 (m, 3H), 3.55–3.47 (m, 1H), 2.44–1.30 (m, 10H), 2.27 (d, J=17.6 Hz, 1H), 2.15 (s, 3H), 1.90 (d, J=6.6 Hz, 3H), 1.79 (d, J=1.0 Hz, 3H), 1.70 (s, 3H)

FABMS m/z 736 (M+H)$^+$

HRFABMS calcd for $C_{33}H_{42}N_3O_{10}S_3$ (M+H)$^+$ 736.2032, found 736.2015

Compound 89

IR (KBr) 3420, 2938, 1823, 1715, 1683, 1441, 1377, 1262, 1208, 1048, 973, 887, 798, 769 cm$^{-1}$ $^1$H NMR (CDCl$_3$, 400 MHz) δ ppm; 9.00 (dd, J=16.6, 11.5 Hz, 1H), 7.28 (s, 1H), 6.76 (d, J=16.6 Hz, 1H), 6.44 (d, J=11.3 Hz, 1H), 6.33 (dd, J=11.5, 11.3 Hz, 1H), 5.96 (br d, J=9.0 Hz, 1H), 5.58 (br s, 1H), 5.58 (q, J=6.6 Hz, 1H), 5.11 (dd, J=9.0, 1.0 Hz, 1H), 4.61 (br s, 1H), 4.04 (d, J=17.6 Hz, 1H), 3.94 (s, 3H), 3.90–3.81 (m, 1H), 3.78 (br s, 2H), 3.58–3.50 (m, 1H), 2.45–1.30 (m, 10H), 2.26 (d, J=17.6 Hz, 1H), 2.15 (s, 3H), 1.90 (d, J=6.6 Hz, 3H), 1.78 (d, J=1.0 Hz, 3H), 1.70 (s, 3H)

FABMS m/z 736 (M+H)$^+$

HRFABMS calcd for $C_{33}H_{42}N_3O_{10}S_3$ (M+H)$^+$ 736.2032, found 736.2020

EXAMPLE 80
Synthesis of Compound 90

According to the procedure as described in Example 18, Compound 90 (30 mg, 49% yield) was obtained from DC107 (50 mg, 0.1 mmol), 5,6-dihydro-4-methoxy-2H-pyran (0.056 ml, 0.50 mmol) and camphorsulfonic acid (23 mg, 0.1 mmol).

IR (KBr) 3420, 3330, 2944, 1726, 1642, 1609, 1529, 1453, 1357, 1306, 1261, 1231, 1142, 1097, 1048, 949, 886, 807, 732 cm$^{-1}$ $^1$H NMR (CDCl$_3$, 400 MHz) δ ppm; 9.31 (ddd, J=16.5, 11.5, 1.0 Hz, 1H), 7.29 (s, 1H), 6.88 (br d, J=6.3 Hz, 1H), 6.65 (d, J=11.5 Hz, 1H), 6.39 (t, J=11.5 Hz, 1H), 6.01 (d, J=16.5 Hz, 1H), 5.95 (br d, J=9.8 Hz, 1H), 5.26 (dq, J=6.3, 6.5 Hz, 1H), 5.22 (br s, 1H), 5.03 (dd, J=9.8, 1.2 Hz, 1H), 3.64–3.44 (m, 4H), 3.24 (d, J=14.8 Hz, 1H), 3.06 (s, 3H), 2.86 (d, J=14.8 Hz, 1H), 2.35–1.50 (m, 8H), 1.90 (s, 3H), 1.80 (d, J=6.5 Hz, 3H), 1.74 (d, J=1.2 Hz, 3H)

FABMS m/z 625 (M+H)$^+$

HRFABMS calcd for $C_{28}H_{37}N_2O_8S_3$ (M+H)$^+$ 625.1712, found 625.1738

EXAMPLE 81
Synthesis of Compound 91

According to the procedure as described in Example 18, Compound 91 (40 mg, 58% yield) was obtained from DC107 (58 mg, 0.11 mmol), 1-methoxy-1-cyclohexene (64 mg, 0.56 mmol) and camphorsulfonic acid (5 mg, 0.02 mmol).

IR (KBr) 3400, 2938, 2938, 1720, 1644, 1610, 1525, 1450, 1369, 1270, 1247, 1180, 1153, 1091, 1022, 926, 800 cm$^{-1}$ $^1$H NMR (CDCl$_3$, 400 MHz) δ ppm; 9.29 (dd, J=16.6, 11.5 Hz, 1H), 7.27 (s, 1H), 6.94 (br d, J=5.9 Hz, 1H), 6.64 (d, J=11.3 Hz, 1H), 6.38 (dd, J=11.5, 11.3 Hz, 1H), 5.98 (d, J=16.6 Hz, 1H), 5.93 (br d, J=9.8 Hz, 1H), 5.26 (br s, 1H), 5.26 (dq, J=5.9, 6.6 Hz, 1H), 5.01 (dd, J=9.8, 1.2 Hz, 1H), 3.24 (d, J=14.5 Hz, 1H), 3.02 (s, 3H), 2.85 (d, J=14.5 Hz, 1H), 2.35–1.20 (m, 14H), 1.90 (s, 3H), 1.81 (d, J=6.6 Hz, 3H), 1.73 (d, J=1.2 Hz, 3H)

FABMS m/z 623 (M+H)$^+$

HRFABMS calcd for $C_{29}H_{39}N_2O_7S_3$ (M+H)$^+$ 623.1919, found 623.1890

EXAMPLE 82
Synthesis of Compound 92

According to the procedure as described in Example 18, Compound 93 (15 mg, 30% yield) was obtained from DC107 (41 mg, 0.08 mmol), 5,6-dihydro-4-methoxy-2H-thiopyran (52 mg, 0.40 mmol) and camphorsulfonic acid (4.6 mg, 0.02 mmol).

IR (KBr) 3322, 2928, 1721, 1642, 1611, 1530, 1452, 1362, 1247, 1208, 1096, 1031, 950, 881, 799 cm$^{-1}$ $^1$H NMR (CDCl$_3$, 500 MHz) δ ppm; 9.27 (ddd, J=16.5, 11.5, 1.0 Hz, 1H), 7.29 (s, 1H), 6.87 (br d, J=6.2 Hz, 1H), 6.65 (d, J=11.3 Hz, 1H), 6.39 (dd, J=11.5, 11.3 Hz, 1H), 6.00 (d, J=16.5 Hz, 1H), 5.94 (br d, J=9.8 Hz, 1H), 5.26 (dq, J=6.2, 6.5 Hz, 1H), 5.22 (br s, 1H), 5.00 (dd, J=9.8, 1.2 Hz, 1H), 3.25 (d, J=14.8 Hz, 1H), 3.03 (s, 3H), 2.85 (d, J=14.8 Hz, 1H), 2.70–1.60 (m, 12H), 1.91 (s, 3H), 1.81 (d, J=6.5 Hz, 3H), 1.74 (d, J=1.0 Hz, 3H)

FABMS m/z 641 (M+H)$^+$

HRFABMS calcd for $C_{28}H_{37}N_2O_7S_4$ (M+H)$^+$ 641.1483, found 641.1483

EXAMPLE 83
Synthesis of Compound 93

According to the procedure as described in Example 18, Compound 93 (33 mg, 76% yield) was obtained from DC107 (32 mg, 0.063 mmol), 1-ethoxycarbonyl-4-methoxy-1,2,5,6-tetrahydropyridine (58 mg, 0.31 mmol) and camphorsulfonic acid (7 mg, 0.031 mmol).

IR (KBr) 3290, 2934, 1680, 1642, 1611, 1637, 1442, 1354, 1240, 1100, 1025, 951, 892, 799, 766 cm$^{-1}$ $^1$H NMR (CDCl$_3$, 400 MHz) δ ppm; 9.28 (dd, J=16.6, 11.5 Hz, 1H), 7.29 (s, 1H), 6.95 (br d, J=5.8 Hz, 1H), 6.64 (d, J=11.2 Hz, 1H), 6.37 (dd, J=11.5, 11.2 Hz, 1H), 5.99 (d, J=16.6 Hz, 1H), 5.95 (br d, J=9.8 Hz, 1H), 5.27 (br s, 1H), 5.25 (dq, J=5.8, 6.4 Hz, 1H), 5.03 (br d, J=9.8 Hz, 1H), 4.05 (q, J=7.1 Hz, 2H), 3.58–3.45 (m, 2H), 3.24 (d, J=14.8 Hz, 1H), 3.25–3.03 (m, 2H), 3.06 (s, 3H), 2.87 (d, J=14.8 Hz, 1H), 2.36–1.35 (m, 8H), 1.90 (s, 3H), 1.79 (d, J=6.4 Hz, 3H), 1.74 (s, 3H), 1.20 (t, J=7.1 Hz, 3H)

FABMS m/z 696 (M+H)$^+$

HRFABMS calcd for $C_{31}H_{42}N_3O_9S_3$ (M+H)$^+$ 696.2083, found 696.2065

EXAMPLE 84
Synthesis of Compound 94

DC107 (51 mg, 0.099mmol) and 2-pyrazinecarboxylic acid (55 mg, 0.44 mmol) were dissolved in dichloromethane (10 ml), and 1-ethyl-3-(3-dimethylaminopropyl) carbodiimide hydrochloride (86 mg, 0.44 mmol) and 4-dimethylaminopyridine (3.6 mg, 0.029 mmol) were added thereto, followed by stirring at room temperature for 30 minutes. After subjecting the mixture to the usual post-treatment, the mixture was purified by thin layer chromatography (developed with chloroform/methanol=95/5) to obtain Compound 94 (45 mg, 74% yield).

IR (KBr) 3400, 2930, 1721, 1661, 1613, 1529, 1447, 1371, 1308, 1274, 1200, 1134, 1100, 1048, 1017, 895, 806, 771 cm$^{-1}$ $^1$H NMR (CDCl$_3$, 500 MHz) δ ppm; 9.20 (d, J=1.2 Hz, 1H), 8.70 (d, J=2.4 Hz, 1H), 8.69 (dd, J=16.5, 11.6 Hz, 1H), 8.59 (dd, J=2.4, 1.2 Hz, 1H), 7.29 (s, 1H), 6.67 (d, J=11.3 Hz, 1H), 6.57 (br d, J=6.7 Hz, 1H), 6.38 (dd, J=11.6, 11.3 Hz, 1H), 6.22 (d, J=9.8 Hz, 1H), 6.11 (d, J=16.5 Hz, 1H), 5.90 (d, J=9.8 Hz, 1H), 5.40 (dq, J=6.7, 6.7 Hz, 1H), 4.05 (br s, 1H), 3.16 (d, J=15.5 Hz, 1H), 2.99 (d, J=15.5 Hz, 1H), 2.42 (dt, J=13.0, 4.3 Hz, 1H), 2.09 (td, J=12.5, 4.3 Hz, 1H), 1.93 (dt, J=4.6, 13.0 Hz, 1H), 1.82–1.72 (m, 1H), 1.81 (d, J=1.2 Hz, 3H), 1.73 (s, 3H), 1.69 (d, J=6.7 Hz, 3H)

FABMS m/z 617 (M+H)$^+$

HRFABMS calcd for $C_{27}H_{29}N_4O_7S_3$ (M+H)$^+$ 617.1198, found 617.1218

EXAMPLE 85
Synthesis of Compound 95

According to the procedure as described in Example 45, Compound 95 (51 mg, 91% yield) was obtained from DC107 (41 mg, 0.080 mmol), N-Boc-L-proline (173 mg, 0.80mmol), 1-ethyl-3-(3-dimethylaminopropyl) carbodiimide hydrochloride (154 mg, 0.80 mmol), dichloromethane (4 ml) and 4-dimethylaminopyridine (3 mg, 0.025 mmol).

IR (KBr) 3430, 3300, 2980, 2936, 1740, 1700, 1674, 1610, 1537, 1476, 1408, 1367, 1257, 1200, 1164, 1128, 1090, 999, 891, 854, 771 cm$^{-1}$ $^1$H NMR (CDCl$_3$, 500 MHz) δ ppm; 8.53, 8.45 (dd, J=16.5, 11.6 Hz, 1H), 7.28 (s, 1H), 6.65, 6.63 (d, J=11.3 Hz, 1H), 6.57, 6.71 (br d, J=6.4 Hz, 1H), 6.34 (dd, J=11.6, 11.3 Hz, 1H), 6.03, 6.04 (d, J=16.5 Hz, 1H), 5.91, 5.85 (d, J=9.5 Hz, 1H), 5.79, 5.73 (br d, J=9.5 Hz, 1H), 5.42, 5.43 (dq, J=6.4, 6.4 Hz, 1H), 4.25 (dd, J=8.5, 4.0 Hz, 1H), 4.00, 4.04 (br s, 1H), 3.42–3.28 (m, 2H), 3.17, 3.20 (d, J=15.6 Hz, 1H), 2.97, 2.95 (d, J=15.6 Hz, 1H), 2.45–1.60 (m, 8H), 1.77, 1.75 (d, J=6.4 Hz, 3H), 1.70 (s, 3H), 1.70 (s, 3H), 1.36 (s, 9H).

FABMS m/z 708 (M+H)$^+$

HRFABMS calcd for $C_{32}H_{42}N_3O_9S_3$ (M+H)$^+$ 708.2083, found 708.2108

EXAMPLE 86
Synthesis of Compound 96

According to the procedure as described in Example 45, Compound 96 (42 mg, 78% yield) was obtained from DC107 (41 mg, 0.080 mmol), N-Boc-glycine (43 mg, 0.24 mmol), 1-ethyl-3-(3-dimethylaminopropyl)carbodiimide hydrochloride (46 mg, 0.24 mmol), dichloromethane (5 ml) and 4-dimethylaminopyridine (2 mg, 0.016 mmol).

IR (KBr) 3400, 2980, 2936, 1711, 1695, 1660, 1615, 1531, 1452, 1368, 1256, 1162, 1102, 1055, 997, 949, 896, 859, 799 cm$^{-1}$ $^1$H NMR (CDCl$_3$, 400 MHz) δ ppm; 8.79 (dd, J=16.6, 11.2 Hz, 1H), 7.30 (s, 1H), 6.97 (br d, J=6.6 Hz, 1H), 6.64 (d, J=11.2 Hz, 1H), 6.32 (dd, J=11.5, 11.2 Hz, 1H), 6.03 (d, J=16.6 Hz, 1H), 5.80 (br s, 2H), 5.43 (dq, J=6.6, 6.8 Hz, 1H), 5.03 (br s, 1H), 4.25 (br s, 1H), 3.97 (dd, J=18.2, 5.3 Hz, 1H), 3.77 (dd, J=18.2, 5.3 Hz, 1H), 3.08 (br s, 2H), 2.40–1.35 (m, 4H), 1.75 (d, J=6.8 Hz, 3H), 1.73 (d, J=1.4 Hz, 3H), 1.73 (s, 3H), 1.42 (s, 9H)

FABMS m/z 668 (M+H)$^+$

HRFABMS calcd for $C_{29}H_{38}N_3O_9S_3$ (M+H)$^+$ 668.1770, found 668.1790

EXAMPLE 87
Synthesis of Compound 97

According to the procedure as described in Example 45, Compound 97 (43 mg, 80% yield) was obtained from DC107 (40 mg, 0.077 mmol), N-Cbz-glycine (82 mg, 0.39 mmol), 1-ethyl-3-(3-dimethylaminopropyl)carbodiimide hydrochloride (75 mg, 0.39 mmol), dichloromethane (5 ml) and 4-dimethylaminopyridine (3 mg, 0.025 mmol).

IR (KBr) 3380, 2932, 1712, 1660, 1614, 1543, 1454, 1373, 1264, 1188, 1102, 1055, 998, 896 cm$^{-1}$ $^1$H NMR (CDCl$_3$, 400 MHz) δ ppm; 8.76 (dd, J=16.6, 11.5 Hz, 1H), 7.37–7.26 (m, 5H), 7.28 (s, 1H), 6.98 (br d, J=6.6 Hz, 1H), 6.63 (d, J=11.5 Hz, 1H), 6.33 (t, J=11.5 Hz, 1H), 6.04 (d, 16.6 Hz, 1H), 5.84 (d, J=9.7 Hz, 1H), 5.80 (d, J=9.7 Hz, 1H), 5.43 (dq, J=6.6, 6.6 Hz, 1H), 5.26 (br dd, J=5.9, 5.4 Hz, 1H), 5.01 (d, J=12.3 Hz, 1H), 4.96 (d, J=12.3 Hz, 1H), 4.25 (br s, 1H), 4.00 (dd, J=18.2, 5.9 Hz, 1H), 3.90 (dd, J=18.2, 5.4 Hz, 1H), 3.12 (d, J=16.1 Hz, 1H), 3.07 (d, J=16.1 Hz, 1H), 2.41–2.30 (m, 1H), 2.15–2.06 (m, 1H), 1.93–1.52 (m, 2H), 1.74 (d, J=6.6 Hz, 3H), 1.73 (s, 3H), 1.73 (s, 3H)

FABMS m/z 702 (M+H)$^+$

HRFABMS calcd for $C_{32}H_{36}N_3O_9S_3$ (M+H)$^+$ 702.1634, found 702.1631

EXAMPLE 88
Synthesis of Compound 98

According to the procedure as described in Example 45, Compound 98 (60 mg, 76% yield) was obtained from DC107 (51 mg, 0.10 mmol), N-Fmoc-glycine (44 mg, 0.15 mmol), 1-ethyl-3-(3-dimethylaminopropyl)carbodiimide hydrochloride (28 mg, 0.15 mmol), dichloromethane (6 ml) and 4-dimethylaminopyridine (1.2 mg, 0.01 mmol).

IR (KBr) 3400, 2932, 1711, 1661, 1613, 1523, 1449, 1373, 1266, 1189, 1102, 1051, 996, 940, 896,799, 759,740 cm$^{-1}$ $^1$H NMR (CDCl$_3$, 500 MHz) δ ppm; 8.70 (dd, J=16.5, 11.5 Hz, 1H), 7.80–7.28 (m, 8H), 7.12 (s, 1H), 7.03 (br d, J=7.0 Hz, 1H), 6.47 (d, J=11.3 Hz, 1H), 6.22 (dd, J=11.5, 11.3 Hz, 1H), 6.03 (d, J=16.5 Hz, 1H), 5.83 (d, J=9.0 Hz, 1H), 5.79 (d, J=9.0 Hz, 1H), 5.42 (dq, J=7.0, 6.7 Hz, 1H), 5.31 (br t, J=5.5 Hz, 1H), 4.32 (dd, J=10.4, 6.7 Hz, 1H), 4.22 (br s, 1H), 4.15 (br t, J=6.7 Hz, 1H), 4.03 (dd, J=10.4, 6.7 Hz, 1H), 3.98 (dd, J=18.0, 5.8 Hz, 1H), 3.93 (dd, J=18.0, 5.5 Hz, 1H), 3.13 (d, J=16.3 Hz, 1H), 3.07 (d, J=16.3 Hz, 1H), 2.40–2.30 (m, 1H), 2.15–2.06 (m, 1H), 1.93–1.72 (m, 2H), 1.74 (s, 3H), 1.72 (s, 3H), 1.68 (d, J=6.7 Hz, 3H)

FABMS m/z 790 (M+H)$^+$

HRFABMS calcd for C$_{39}$H$_{40}$N$_3$O$_9$S$_3$ (M+H)$^+$ 790.1926, found 790.1933

EXAMPLE 89

Synthesis of Compound 99

According to the procedure as described in Example 45, Compound 99 (34 mg, 57% yield) was obtained from DC107 (51 mg, 0.10 mmol), N-formylglycine (31 mg, 0.30 mmol), 1-ethyl-3-(3-dimethylaminopropyl)carbodiimide hydrochloride (58 mg, 0.30 mmol), dichloromethane (10 ml) and 4-dimethylaminopyridine (2.4 mg, 0.02 mmol).

IR (KBr) 3330, 2932, 1748, 1665, 1612, 1529, 1447, 1376, 1265, 1187, 1097, 999, 949, 896, 799 cm$^{-1}$ $^1$H NMR (CDCl$_3$, 500 MHz) δ ppm; 8.55 (dd, J=16.5, 11.5 Hz, 1H), 8.03 (s, 1H), 6.60 (d, J=11.3 Hz, 1H), 6.27 (dd, J=11.5, 11.3 Hz, 1H), 5.96 (d, J=16.5 Hz, 1H), 5.87 (d, J=9.8 Hz, 1H), 5.68 (br d, J=9.8 Hz, 1H), 5.30 (q, J=6.7 Hz, 1H), 4.02 (d, J=18.3 Hz, 1H), 3.96 (d, J=18.3 Hz, 1H), 3.13 (d, J=16.2 Hz, 1H), 2.85 (d, J=16.2 Hz, 1H), 2.33 (dt, J=6.1, 12.2 Hz, 1H), 1.96 (td, J=12.2, 3.1 Hz, 1H), 1.85–1.50 (m, 2H), 1.66 (d, J=6.7 Hz, 3H), 1.62 (s, 3H), 1.58 (s, 3H)

FABMS m/z 596 (M+H)$^+$

HRFABMS calcd for C$_{25}$H$_{30}$N$_3$O$_8$S$_3$ (M+H)$^+$ 596.1195, found 596.1199

Anal calcd for C$_{25}$H$_{29}$N$_3$O$_8$S$_3$·1.4H$_2$O: C, 48.36; H, 5.16; N, 6.77; found: C, 48.44; H, 4.95; N, 6.43

EXAMPLE 90

Synthesis of Compound 100

According to the procedure as described in Example 45, Compound 100 (34 mg, 56% yield) was obtained from DC107 (51 mg, 0.10 mmol), N-acetylglycine (117 mg, 1.0 mmol), 1-ethyl-3-(3-dimethylaminopropyl)carbodiimide hydrochloride (192 mg, 1.0 mmol), dichloromethane (10 ml) and 4-dimethylaminopyridine (7.3 mg, 0.06 mmol).

IR (KBr) 3400, 2936, 1715, 1557, 1612, 1540, 1446, 1375, 1270, 1189, 1100, 1034, 999, 894, 799 cm$^{-1}$ $^1$H NMR (CDCl$_3$, 400 MHz) δ ppm; 8.69 (dd, J=16.6, 11.5 Hz, 1H), 8.24 (br d, J=7.1 Hz, 1H), 7.32 (s, 1H), 6.61 (d, J=11.7 Hz, 1H), 6.28 (dd, J=11.7, 11.5 Hz, 1H), 6.09 (br dd, J=4.9, 5.5 Hz, 1H), 6.05 (d, J=16.6 Hz, 1H), 5.82 (d, J=8.5 Hz, 1H), 5.74 (d, J=8.5 Hz, 1H), 5.49 (dq, J=6.8, 7.1 Hz, 1H), 4.24 (br s, 1H), 3.95 (dd, J=17.3, 4.9 Hz, 1H), 3.86 (dd, J=17.3, 5.5 Hz, 1H), 3.18 (br s, 2H), 2.43–1.65 (m, 4H), 1.77 (s, 3H), 1.75 (s, 3H), 1.74 (d, J=6.8 Hz, 3H), 1.70 (s, 3H)

FABMS m/z 610 (M+H)$^+$

HRFABMS calcd for C$_{26}$H$_{32}$N$_3$O$_8$S$_3$ (M+H)$^+$ 610.1351, found 610.1357

EXAMPLE 91

Synthesis of Compound 101

According to the procedure as described in Example 45, Compound 101 (31 mg, 55% yield) was obtained from DC107 (41 mg, 0.080 mmol), N-Cbz-sarcosine (89.mg, 0.40 mmol), 1-ethyl-3-(3-dimethylaminopropyl)carbodiimide hydrochloride (77 mg, 0.40 mmol), dichloromethane (5 ml) and 4-dimethylaminopyridine (2 mg, 0.016 mmol).

IR (KBr) 3400, 2938, 1701, 1687, 1655, 1612, 1528, 1482, 1449, 1404, 1364, 1194, 1151, 1100, 1000, 947, 895, 799, 770, 698 cm$^{-1}$ $^1$H NMR (CDCl$_3$, 500 MHz) δ ppm; major isomer 8.75 (dd, J=16.5, 11.6 Hz, 1H), 7.38–7.24 (m, 6H), 6.60 (d, J=11.3 Hz, 1H), 6.31 (dd, J=11.6, 11.3 Hz, 1H), 6.06 (d, J=16.5 Hz, 1H), 5.81 (d, J=9.0 Hz, 1H), 5.80 (d, J=9.0 Hz, 1H), 5.50 (dq, J=7.0, 6.7 Hz, 1H), 4.97 (d, J=12.2 Hz, 1H), 4.87 (d, J=12.2 Hz, 1H), 4.13 (br s, 1H), 4.09 (d, J=17.7 Hz, 1H), 3.92 (d, J=17.7 Hz, 1H), 3.14 (d, J=16.5 Hz, 1H), 3.09 (d, J=16.5 Hz, 1H), 2.99 (s, 3H), 2.42–1.70 (m, 4H), 1.75 (s, 3H), 1.74 (d, J=6.8 Hz, 3H), 1.68 (s, 3H); minor isomer 8.62 (dd, J=16.5, 11.6 Hz, 1H), 7.38–7.24 (m, 6H), 6.61 (d, J=11.5 Hz, 1H), 6.55 (br d, J=6.4 Hz, 1H), 6.30 (dd, J=11.6, 11.3 Hz, 1H), 6.00 (d, J=16.5 Hz, 1H), 5.87 (d, J=10.0 Hz, 1H), 5.79 (d, J=10.0 Hz, 1H), 5.40 (dq, J=6.4, 6.8 Hz, 1H), 5.06 (s, 2H), 4.03 (br s, 1H), 4.02 (d, J=17.7 Hz, 1H), 3.96 (d, J=17.7 Hz, 1H), 3.1–2.977 (m, 2H), 2.93 (s, 3H), 2.42–1.70 (m, 4H), 1.74 (s, 3H), 1.73 (d, J=6.8 Hz, 3H), 1.67 (s, 3H)

FABMS m/z 716 (M+H)$^+$

HRFABMS calcd for C$_{33}$H$_{38}$N$_3$O$_3$ (M+H)$^+$ 716.1770, found 716.1770

EXAMPLE 92

Synthesis of Compound 102

According to the procedure as described in Example 45, Compound 102 (45 mg, 67% yield) was obtained from DC107 (51 mg, 0.10 mmol), N-Boc-L-alanine (95 mg, 0.50 mmol), 1-ethyl-3-(3-dimethylaminopropyl)carbodiimide hydrochloride (96 mg, 0.50 mmol), dichloromethane (5 ml) and 4-dimethylaminopyridine (6 mg, 0.050 mmol).

IR (KBr) 3400, 2982, 2936, 1711, 1660, 1616, 1522, 1452, 1368, 1256, 1165, 1102, 1067, 996, 894, 856, 799 cm$^{-1}$ $^1$H NMR (CDCl$_3$, 500 MHz) δ ppm; 8.08 (br, 1H), 7.29 (s, 1H), 6.67 (br d, J=6.4 Hz, 1H), 6.64 (d, J=11.3 Hz, 1H), 6.34 (dd, J=11.3, 11.3 Hz, 1H), 6.03 (d, J=16.8 Hz, 1H), 5.81 (m, 2H), 5.40 (dq, J=6.7, 6.4 Hz, 1H), 5.01 (br, 1H), 4.30 (br, 1H), 4.23 (br, 1H), 3.09 (br d, J=15.6 Hz, 1H), 3.04 (br d, J=15.6 Hz, 1H), 2.37 (dt, J=12.5, 4.6 Hz, 1H), 2.08 (dt, J=12.5, 4.6 Hz, 1H), 1.91–1.75 (m, 2H), 1.77 (d, J=6.7 Hz, 3H), 1.75 (br s, 3H), 1.72 (s, 3H), 1.38 (s, 9H), 1.33 (d, J=7.3 Hz, 3H)

FABMS m/z 682 (M+H)$^+$

HRFABMS calcd for C$_{30}$H$_{40}$N$_3$O$_9$S$_3$ (M+H)$^+$ 682.1926, found 682.1926

EXAMPLE 93

Synthesis of Compound 103

According to the procedure as described in Example 45, Compound 103 (53 mg, 76% yield) was obtained from DC107 (51 mg, 0.10 mmol), N-Cbz-L-alanine (66 mg, 0.30 mmol), 1-ethyl-3-(3-dimethylaminopropyl)carbodiimide hydrochloride (57 mg, 0.30 mmol), dichloromethane (5 ml) and 4-dimethylaminopyridine (2.4 mg, 0.020 mmol).

IR (KBr) 3324, 3068, 2984, 2938, 1705, 1658, 1613, 1528, 1452, 1375, 1342, 1260, 1202, 1098, 1068, 996, 947, 896, 858, 807, 777, 733, 697 cm$^{-1}$ $^1$H NMR (CDCl$_3$, 500 MHz) δ ppm; 8.73 (br dd, J=16.8, 11.3 Hz, 1H), 7.36–7.18 (m, 5H), 7.32 (s, 1H), 7.20 (br d, J=6.7 Hz, 1H), 6.59 (d, J=11.6 Hz, 1H), 6.31 (dd, J=11.6, 11.3 Hz, 1H), 6.06 (d, J=16.8 Hz, 1H), 5.84 (br d, J=8.8 Hz, 1H), 5.76 (d, J=8.8 Hz, 1H), 5.47 (dq, J=6.7, 6.7 Hz, 1H), 5.21 (br d, J=6.0 Hz, 1H), 4.89 (d, J=12.2 Hz, 1H), 4.60 (d, J=12.2 Hz, 1H), 4.33 (br s, 1H), 4.28 (dq, J=7.0, 6.0 Hz, 1H), 3.17 (d, J=16.2 Hz, 1H), 3.12 (d, J=16.2 Hz, 1H), 2.43–1.70 (m, 4H), 1.74 (d, J=6.7 Hz, 3H), 173 (s, 3H), 1.73 (s, 3H), 1.40 (d, J=7.0 Hz, 3H)

FABMS m/z 716 (M+H)$^+$

HRFABMS calcd for $C_{33}H_{38}N_3O_9S_3$ (M+H)$^+$ 716.1770, found 716.1770

EXAMPLE 94
Synthesis of Compound 104

According to the procedure as described in Example 45, tert-butyldimethylsilyl ether compound of Compound 104 (59 mg, 88% yield) was obtained from DC107 (41 mg, 0.080 mmol), N-Cbz-O-tert-butyldimethylsilyl-L-serine (351 mg, 0.97 mmol), 1-ethyl-3-(3-dimethylaminopropyl) carbodiimide (185 mg, 0.97 mmol), tetrahydrofuran (8 ml) and 4-dimethylaminopyridine (6.8 mg, 0.06 mmol).

The obtained tert-butyldimethylsilyl ether compound (50 mg, 0.059 mmol) was dissolved in methanol (5 ml), and 3N hydrochloric acid (0.2 ml) was added thereto, followed by stirring for 1.5 hours. After subjecting the mixture to the usual post-treatment, the mixture was purified by thin layer chromatography (developed with chloroform/methanol=95/5) to obtain Compound 104 (19 mg, 44% yield).

IR (KBr) 3400, 2930, 1718, 1708, 1654, 1611, 1529, 1452, 1375, 1340, 1261, 1199, 1083, 995, 892 cm$^{-1}$ $^1$H NMR (CDCl$_3$, 400 MHz) δ ppm; 8.61 (br dd, J=16.6, 11.7 Hz, 1H), 7.43–7.25 (m, 7H), 6.64 (d, J=11.5 Hz, 1H), 6.32 (dd, J=11.7, 11.5 Hz, 1H), 6.07 (d, J=16.6 Hz, 1H), 5.89 (d, J=8.5 Hz, 1H), 5.78 (br d, J=8.5 Hz, 1H), 5.65 (br d, J=7.1 Hz, 1H), 5.48 (dq, J=7.1, 6.6 Hz, 1H), 5.06 (d, J=12.2 Hz, 1H), 4.97 (br d, J=12.2 Hz, 1H), 4.40–4.13 (m, 1H), 4.04 (br d, J=11.0 Hz, 1H), 3.91 (br d, J=11.0 Hz, 1H), 3.79 (br s, 1H), 3.72 (br s, 1H), 3.22 (d, J=16.6 Hz, 1H), 3.02 (br d, J=16.6 Hz, 1H), 2.43–1.50 (m, 4H), 1.72 (d, J=6.6 Hz, 3H), 1.71 (s, 3H), 1.63 (s, 3H)

FABMS m/z 732 (M+H)$^+$

HRFABMS calcd for $C_{33}H_{38}N_3O_{10}S_3$ (M+H)$^+$ 732.1719, found 732.1726

EXAMPLE 95
Synthesis of Compound 105

According to the procedure as described in Example 45, Compound 105 (55 mg, 77% yield) was obtained from DC107 (50 mg, 0.099 mmol), N-Cbz-β-alanine (66 mg, 0.30 mmol), 1-ethyl-3-(3-dimethylaminopropyl)carbodiimide hydrochloride (57 mg, 0.30 mmol), dichloromethane (5 ml) and 4-dimethylaminopyridine (2.4 mg, 0.020 mmol).

IR (KBr) 3330, 2934, 1709, 1658, 1614, 1524, 1454, 1373, 1255, 1179, 1101, 1000, 947, 896, 858, 799, 697 cm$^{-1}$ $^1$H NMR (CDCl$_3$, 400 MHz) δ ppm; 8.67 (br dd, J=16.7, 11.6 Hz, 1H), 7.38–7.26 (m, 5H), 7.27 (s, 1H), 6.63 (d, J=11.3 Hz, 1H), 6.51 (br d, J=6.6 Hz, 1H), 6.33 (dd, J=11.6, 11.3 Hz, 1H), 6.03 (d, J=16.8 Hz, 1H), 5.88 (d, J=9.8 Hz, 1H), 5.76 (br d, J=9.8 Hz, 1H), 5.50 (m, 1H), 5.39 (dq, J=6.6, 6.6 Hz, 1H), 5.07 (s, 2H), 4.11 (br s, 1H), 3.44 (m, 2H), 3.13 (d, J=15.4 Hz, 1H), 2.98 (d, J=15.4 Hz, 1H), 2.50 (m, 2H), 2.35 (dt, J=13.0, 4.3 Hz, 1H), 2.06 (dt, J=13.0, 4.3 Hz, 1H), 1.96–1.65 (m, 2H), 1.75 (d, J=6.6 Hz, 3H), 1.73 (s, 3H), 1.69 (d, J=1.2 Hz, 3H)

FABMS m/z 716 (M+H)$^+$

HRFABMS calcd for $C_{33}H_{38}N_3O_9S_3$ (M+H)$^+$ 716.1770, found 716.1794

EXAMPLE 96
Synthesis of Compound 106

According to the procedure as described in Example 45, Compound 106 (39 mg, 54% yield) was obtained from DC107 (51 mg, 0.10 mmol), N-Cbz-γ-amino-n-butyric acid (71 mg, 0.30 mmol), 1-ethyl-3-(3-dimethylaminopropyl) carbodiimide hydrochloride (57 mg, 0.30 mmol), dichloromethane (5 ml) and 4-dimethylaminopyridine (2.4 mg, 0.020 mmol).

IR (KBr) 3332, 3300, 2936, 1710, 1656, 1614, 1527, 1454, 1373, 1250, 1167, 1000, 948, 896, 858, 799, 775, 737, 697 cm$^{-1}$ $^1$H NMR (CDCl$_3$, 500 MHz) δ ppm; 8.73 (br dd, J=16.8, 11.9 Hz, 1H), 7.38–7.26 (m, 5H), 7.22 (br s, 1H), 6.79 (br d, J=6.7 Hz, 1H), 6.61 (d, J=11.3 Hz, 1H), 6.33 (dd, J=11.9, 11.3 Hz, 1H), 6.03 (d, J=16.8 Hz, 1H), 5.79 (br s, 2H), 5.37 (dq, J=6.7, 6.7 Hz, 1H), 4.98 (m, 2H), 4.83 (br, 1H), 4.34 (br, 1H), 3.25–3.33 (m, 4H), 2.42–2.30 (m, 3H), 2.12–1.70 (m, 5H), 1.75 (s, 3H), 1.74 (d, J=6.7 Hz, 3H), 1.71 (br s, 3H)

FABMS m/z 730 (M+H)$^+$

HRFABMS calcd for $C_{34}H_{40}N_3O_9S_3$ (M+H)$^+$ 730.1926, found 730.1946

EXAMPLE 97
Synthesis of Compound 107

According to the procedure as described in Example 45, Compound 107 (42 mg, 55% yield) was obtained from DC107 (60 mg, 0.11mmol), N-Boc-glycylglycine (167 mg, 0.72 mmol), 1-ethyl-3-(3-dimethylaminopropyl) carbodiimide hydrochloride (113 mg, 0.72 mmol), dichloromethane (6 ml) and 4-dimethylaminopyridine (7.2 mg, 0.059 mmol).

IR (KBr) 3292, 1707, 1686, 1656, 1544, 1369, 1169, 1103, 945, 895, 859 cm$^{-1}$ $^1$H NMR (CDCl$_3$, 500 MHz) δ ppm; 8.67 (dd, J=16.5, 11.6 Hz, 1H), 7.87 (br, 1H), 7.34 (s, 1H), 6.87 (br, 1H), 6.63 (d, J=11.6 Hz, 1H), 6.31 (t, J=11.6 Hz, 1H), 6.05 (d, J=16.5 Hz, 1H), 5.79 (d, J=9.2 Hz, 1H), 5.77 (d, J=9.2 Hz, 1H), 5.48 (dq, J=7.0, 6.7 Hz, 1H), 4.90 (br, 1H), 4.29 (br, 1H), 3.98 (dd, J=17.4, 5.5 Hz, 1H), 3.95 (dd, J=17.4, 5.5 Hz, 1H), 3.61 (dd, J=17.0, 6.1 Hz, 1H), 3.59 (dd, J=17.0, 6.1 Hz, 1H), 3.18 (d, J=16.5 Hz, 1H), 3.12 (d, J=16.5 Hz, 1H), 2.36 (m, 1H), 2.12 (m, 1H), 1.92–1.75 (m, 2H), 1.74 (d, J=6.71 Hz, 3H), 1.74 (s, 3H), 1.71 (s, 3H), 1.43 (s, 9H)

FABMS m/z 725 (M+H)$^+$

HRFABMS calcd for $C_{31}H_{41}N_4O_{10}S_3$ (M+H)$^+$ 725.1985, found 725.2009

EXAMPLE 98
Synthesis of Compound 108

According to the procedure as described in Example 45, Compound 108 (53 mg, 47% yield) was obtained from DC107 (81 mg, 0.15 mmol), N-Cbz-glycylglycine (420 mg, 1.5 mmol), 1-ethyl-3-(3-dimethylaminopropyl) carbodiimide hydrochloride (303 mg, 1.58 mmol), tetrahydrofuran (17 ml) and 4-dimethylaminopyridine (11 mg, 0.090 mmol).

IR (KBr) 3400, 2930, 1710, 1662, 1614, 1526, 1452, 1378, 1257, 1190, 1100, 1049, 990, 893 cm$^{-1}$ $^1$H NMR (CDCl$_3$, 500 MHz) δ ppm; 8.65 (dd, J=16.8, 11.6 Hz, 1H), 7.74 (br, 1H), 7.40–7.30 (m, 5H), 7.30 (s, 1H), 6.73 (br, 1H), 6.61 (d, J=11.5 Hz, 1H), 6.29 (dd, J=11.6, 11.5 Hz, 1H), 6.03 (d, J=16.8 Hz, 1H), 5.78 (br s, 2H), 5.47 (dq, J=7.0, 7.0 Hz, 1H), 5.17 (br, 1H), 5.10 (d, J=12.2 Hz, 1H), 5.08 (d, J=12.2 Hz, 1H), 4.24 (br s, 1H), 3.98 (dd, J=18.5, 5.2 Hz, 1H), 3.93 (dd, J=18.0, 4.9 Hz, 1H), 3.69 (d, J=5.8 Hz, 2H), 3.18 (d, J=16.5 Hz, 1H), 3.10 (d, J=16.5 Hz, 1H), 2.39–2.32 (m, 1H), 2.14–2.08 (m, 1H), 1.92–1.70 (m, 2H), 1.73 (s, 3H), 1.71 (d, J=7.0 Hz, 3H), 1.70 (s, 3H)

FABMS m/z 759 (M+H)⁺

HRFABMS calcd for $C_{34}H_{39}N_4O_{10}S_3$ (M+H)⁺ 759.1828, found 759.1810

EXAMPLE 99
Synthesis of Compound 109

According to the procedure as described in Example 45, Compound 109 (42 mg, 55% yield) was obtained from DC107 (60 mg, 0.11 mmol), N-benzoylglycylglycine (418 mg, 1.77 mmol), 1-ethyl-3-(3-dimethylaminopropyl) carbodiimide hydrochloride (339 mg, 1.77 mmol), dichloromethane (15 ml) and 4-dimethylaminopyridine (13 mg, 0.11 mmol).

IR (KBr) 3340, 3064, 2936, 2472, 1759, 1711, 1655, 1641, 1616, 1576, 1544, 1528, 1451, 1377, 1290, 1189, 997, 970, 932, 908, 799, 727 cm⁻¹

¹H NMR (CDCl₃, 400 MHz) δ ppm; 8.68 (dd, J=16.5, 11.5 Hz, 1H), 7.75–7.40 (m, 5H), 7.63 (br d, J=7.0 Hz, 1H), 7.32 (s, 1H), 6.89 (br t, J=5.4 Hz, 1H), 6.67 (br t, J=5.4 Hz, 1H), 6.64 (d, J=11.7 Hz, 1H), 6.30 (dd, J=11.7, 11.5 Hz, 1H), 6.04 (d, J=16.5 Hz, 1H), 5.79 (br s, 2H), 5.46 (dq, J=7.0, 6.8 Hz, 1H), 4.22 (br s, 1H), 4.00 (d, J=5.4 Hz, 2H), 3.98 (d, J=5.4 Hz, 2H), 3.18 (d, J=16.4 Hz, 1H), 3.11 (d, J=16.4 Hz, 1H), 2.42–1.50 (m, 4H), 1.74 (s, 3H), 1.71 (d, J=6.8 Hz, 3H), 1.71 (s, 3H)

FABMS m/z 729 (M+H)⁺

HRFABMS calcd for $C_3H_{37}N_4O_9S_3$ (M+H)⁺ 729.1722, found 729.1735

EXAMPLE 100
Synthesis of Compound 110

According to the procedure as described in Example 45, Compound 110 (39 mg, 50% yield) was obtained from DC107 (51 mg, 0.10 mmol), N-Cbz-L-alanylglycine (280 mg, 1.0 mmol), 1-ethyl-3-(3-dimethylaminopropyl) carbodiimide hydrochloride (192 mg, 1.0 mmol), tetrahydrofuran (9 ml) and 4-dimethylaminopyridine (7.3 mg, 0.06 mmol).

IR (KBr) 3420, 2938, 1704, 1658, 1612, 1529, 1453, 1376, 1255, 1188, 1099, 997, 947, 897, 859, 799, 739, 698 cm⁻¹

¹H NMR (CDCl₃, 400 MHz) δ ppm; 8.65 (dd, J=16.5, 11.2 Hz, 1H), 7.45 (br d, J=6.3 Hz, 1H), 7.38–7.25 (m, 5H), 7.28 (s, 1H), 6.83 (br, 1H), 6.62 (d, J=11.4 Hz, 1H), 6.31 (dd, J=11.4, 11.2 Hz, 1H), 6.04 (d, J=16.5 Hz, 1H), 5.80 (d, J=9.3 Hz, 1H), 5.78 (d, J=9.3 Hz, 1H), 5.45 (dq, J=6.3, 6.8 Hz, 1H), 5.24 (d, J=7.6 Hz, 1H), 5.12 (d, J=12.0 Hz, 1H), 5.07 (br s, 1H), 5.06 (d, J=12.2 Hz, 1H), 4.19 (m, 1H), 4.02 (dd, J=17.8, 5.6 Hz, 1H), 3.89 (dd, J=17.8, 4.6 Hz, 1H), 3.13 (d, J=16.1 Hz, 1H), 3.04 (d, J=16.1 Hz, 1H), 2.42–1.50 (m, 4H), 1.72 (d, J=6.8 Hz, 3H), 1.71 (s, 3H), 1.68 (s, 3H), 1.29 (d, J=7.0 Hz, 3H)

FABMS m/z 773 (M+H)⁺

HRFABMS calcd for $C_{35}H_{41}N_4O_{10}S_3$ (M+H)⁺ 773.1985, found 773.1982

EXAMPLE 101
Synthesis of Compound 111

According to the procedure as described in Example 45, Compound 111 (38 mg, 41% yield) was obtained from DC107 (62 mg, 0.12 mmol), N-Cbz-β-alanylglycine (339 mg, 1.2 mmol), 1-ethyl-3-(3-dimethylaminopropyl) carbodiimide hydrochloride (232 mg, 1.2 mmol), tetrahydrofuran (11 ml) and 4-dimethylaminopyridine (8.8 mg, 0.07 mmol).

IR (KBr) 3312, 2934, 1702, 1660, 1613, 1528, 1452, 1374, 1258, 1183, 1099, 996, 948, 895, 858, 799, 774, 739, 697 cm⁻¹

¹H NMR (CDCl₃+CD₃OD, 500 MHz) δ ppm; 8.61 (br dd, J=16.5, 11.6 Hz, 1H), 7.37–7.28 (m, 5H), 7.33 (s, 1H), 6.66 (d, J=11.3 Hz, 1H), 6.33 (d, J=11.6, 11.3 Hz, 1H), 6.03 (d, J=16.5 Hz, 1H), 5.89 (d, J=9.5 Hz, 1H), 5.74 (br d, J=9.5 Hz, 1H), 5.38 (q, J=6.7 Hz, 1H), 5.07 (br s, 2H), 3.99 (d, J=18.0 Hz, 1H), 3.94 (d, J=18.0 Hz, 1H), 3.35 (dd, J=5.9, 5.3 Hz, 2H), 3.18 (d, J=16.2 Hz, 1H), 2.96 (d, J=16.2 Hz, 1H), 2.43–2.28 (m, 3H), 2.05–1.55 (m, 3H), 1.73 (d, J=6.7 Hz, 3H), 1.70 (d, J=0.7 Hz, 3H), 1.68 (s, 3H)

FABMS m/z 773 (M+H)⁺

HRFABMS calcd for $C_{35}H_{41}N_4O_{10}S_3$ (M+H)⁺ 773.1985, found 773.1990

EXAMPLE 102
Synthesis of Compound 112

According to the procedure as described in Example 45, Compound 112 (31 mg, 42% yield) was obtained from DC107 (51 mg, 0.10 mmol), N-Boc-β-alanylglycine (244 mg, 1.0 mmol), 1-ethyl-3-(3-dimethylaminopropyl) carbodiimide hydrochloride (191 mg, 1.0 mmol), tetrahydrofuran (9 ml) and 4-dimethylaminopyridine (12 mg, 0.10 mmol).

IR (KBr) 3400, 2980, 2932, 1704, 1656, 1615, 1545, 1450, 1368, 1270, 1254, 1181, 1098, 997, 894, 857, 799 cm⁻¹

¹H NMR (CDCl₃, 400MHz) δ ppm; 8.65 (dd, J=16.9, 11.2 Hz, 1H), 8.11 (br s, 1H), 7.33 (s, 1H), 7.16 (br, 1H), 6.63 (d, J=11.5 Hz, 1H), 6.30 (dd, J=11.5, 11.2 Hz, 1H), 6.05 (d, J=16.9 Hz, 1H), 5.79 (d, J=8.8 Hz, 1H), 5.75 (d, J=8.8 Hz, 1H), 5.49 (dq, J=6.8, 6.5 Hz, 1H), 4.86 (br, 1H), 4.29 (br s, 1H), 3.95 (dd, J=17.6, 5.1 Hz, 1H), 3.90 (dd, J=17.6, 5.3 Hz, 1H), 3.44–3.19 (m, 2H), 3.18 (d, J=16.5 Hz, 1H), 3.14 (d, J=16.5 Hz, 1H), 2.42–1.70 (m, 6H), 1.74 (s, 3H), 1.73 (d, J=6.5 Hz, 3H), 1.70 (s, 3H), 1.41 (s, 9H)

FABMS m/z 739 (M+H)⁺

HRFABMS calcd for $C_{32}H_{43}N_4O_{10}S_3$ (M+H)⁺ 739.2141, found 739.2168

EXAMPLE 103
Synthesis of Compound 113

According to the procedure as described in Example 45, Compound 113 (16 mg, 20% yield) was obtained from DC107 (51 mg, 0.12 mmol), N-Cbz-γ-aminobutyrylglycine (295 mg, 1.0 mmol), 1-ethyl-3-(3-dimethylaminopropyl) carbodiimide hydrochloride (192 mg, 1.0 mmol), tetrahydrofuran (9 ml) and 4-dimethylaminopyridine (7.3 mg, 0.06 mmol).

IR (KBr) 3350, 2932, 1718, 1658, 1544, 1452, 1375, 1260, 1186, 1098, 998, 945, 896, 799, 698 cm⁻¹

¹H NMR (CDCl₃, 400 MHz) δ ppm; 8.67 (dd, J=16.8, 11.2 Hz, 1H), 8.13 (br s, 1H), 7.39–7.26 (m, 5H), 7.30 (s, 1H), 6.92 (br, 1H), 6.59 (d, J=11.5 Hz, 1H), 6.27 (dd, J=11.5, 11.2 Hz, 1H), 6.05 (d, J=16.8 Hz, 1H), 5.81 (br d, J=8.8 Hz, 1H), 5.74 (d, J=8.8 Hz, 1H), 5.49 (dq, J=7.0, 6.6 Hz, 1H), 5.08 (br s, 2H), 4.89 (br t, J=4.6 Hz, 1H), 4.27 (br s, 1H), 3.90 (br d, J=4.6 Hz, 2H), 3.20–3.10 (m, 4H), 2.43–1.50 (m, 8H), 1.74 (s, 3H), 1.73 (d, J=6.6 Hz, 3H), 1.69 (s, 3H)

FABMS m/z 787 (M+H)⁺

HRFABMS calcd for $C_{36}H_{43}N_4O_{10}S_3$ (M+H)⁺ 787.2141, found 787.2137

EXAMPLE 104
Synthesis of Compound 114

According to the procedure as described in Example 45, Compound 114 (41 mg, 54% yield) was obtained from DC107 (51 mg, 0.10 mmol), N-Cbz-sarcosylglycine (278 mg, 1.0 mmol), 1-ethyl-3-(3-dimethylaminopropyl) carbodiimide hydrochloride (191 mg, 1.0 mmol), tetrahydrofuran (9 ml) and 4-dimethylaminopyridine (7.2 mg, 0.06 mmol).

IR (KBr) 3400, 2938, 1700, 1688, 1665, 1534, 1451, 1405, 1365, 1189, 1153, 1103, 989, 939, 895, 799, 769, 697 cm$^{-1}$ $^1$H NMR (CDCl$_3$, 400 MHz) δ ppm; 8.67 (br dd, J=16.5, 11.3 Hz, 1H), 7.69 (br s, 1H), 7.34 (br s, 5H), 7.31 (s, 1H), 6.69 (br, 1H), 6.61 (d, J=11.5 Hz, 1H), 6.29 (dd, J=11.5, 11.3 Hz, 1H), 6.04 (d, J=16.5 Hz, 1H), 5.80 (br d, J=9.5 Hz, 1H), 5.77 (d, J=9.5 Hz, 1H), 5.47 (dq, J=6.8, 6.6 Hz, 1H), 5.13 (s, 2H), 4.20 (br s, 1H), 4.02–3.55 (m, 4H), 3.18 (d, J=16.4 Hz, 1H), 3.11 (d, J=16.4 Hz, 1H), 2.93 (s, 3H), 2.42–1.70 (m, 4H), 1.74 (s, 3H), 1.73 (d, J=6.6 Hz, 3H), 1.71 (s, 3H)

FABMS m/z 773 (M+H)$^+$

HRFABMS calcd for C$_{35}$H$_{41}$N$_4$O$_{10}$S$_3$ (M+H)$^+$ 773.1985, found 773.1997

Anal calcd for C$_{35}$H$_{40}$N$_4$O$_{10}$S$_3$·1.0H$_2$O: C, 53.15; H, 5.35; N, 7.08; found: C, 53.22; H, 5.21; N, 7.10

EXAMPLE 105
Synthesis of Compound 115

According to the procedure as described in Example 45, Compound 115 (39 mg, 43% yield) was obtained from DC107 (60 mg, 0.11 mmol), N-Cbz-leucylglycine (380 mg, 1.2 mmol), 1-ethyl-3-(3-dimethylaminopropyl) carbodiimide hydrochloride (226 mg, 1.2 mmol), tetrahydrofuran (11 ml) and 4-dimethylaminopyridine (8.6 mg, 0.07 mmol).

IR (KBr) 3400, 2960, 1706, 1664, 1615, 1528, 1452, 1370, 1261, 1190, 1100, 1043, 996, 896 cm$^{-1}$ $^1$H NMR (CDCl$_3$, 500 MHz) δ ppm; 8.73 (dd, J=16.8, 11.3 Hz, 1H), 7.38–7.27 (m, 6H), 7.30 (s, 1H), 6.78 (br, 1H), 6.63 (d, J=11.6 Hz, 1H), 6.31 (dd, J=11.6, 11.3 Hz, 1H), 6.03 (d, J=16.8 Hz, 1H), 5.81 (d, J=9.2 Hz, 1H), 5.79 (d, J=9.2 Hz, 1H), 5.46 (dq, J=7.0, 6.7 Hz, 1H), 5.12 (d, J=12.2 Hz, 1H), 5.08 (d, J=12.2 Hz, 1H), 5.00 (br, 1H), 4.21 (br s, 1H), 4.11 (m, 1H), 4.01 (dd, J=18.0, 5.5 Hz, 1H), 3.89 (br dd, J=18.0, 4.9 Hz, 1H), 3.12 (d, J=16.5 Hz, 1H), 3.07 (d, J=16.5 Hz, 1H), 2.40–2.31 (m, 1H), 2.34 (m, 1H), 1.93–1.45 (m, 5H), 1.73 (d, J=6.7 Hz, 3H), 1.72 (s, 3H), 1.70 (s, 3H), 0.89 (d, J=7.0 Hz, 3H), 0.85 (d, J=7.0 Hz, 3H)

FABMS m/z 815 (M+H)$^+$

HRFABMS calcd for C$_{38}$H$_{47}$N$_4$O$_{10}$S$_3$ (M+H)$^+$ 815.2454, found 815.2435

EXAMPLE 106
Synthesis of Compound 116

According to the procedure as described in Example 45, tert-butyldimethylsilyl ether compound of Compound 116 (74 mg, 68% yield) was obtained from DC107 (60 mg, 0.12 mmol), N-Cbz-O-tert-butyldimethylsilyl-L-serylglycine (485 mg, 0.97 mmol), 1-ethyl-3-(3-dimethylaminopropyl) carbodiimide hydrochloride (226 mg, 0.97 mmol), tetrahydrofuran (10 ml) and 4-dimethylaminopyridine (8.6 mg, 0.07 mmol).

The obtained tert-butyldimethylsilyl ether compound (74 mg, 0.081 mmol) was dissolved in methanol (7.4 ml), and 3N hydrochloric acid (0.3 ml) was added thereto, followed by stirring for 1 hour. After subjecting the mixture to the usual post-treatment, the mixture was purified by thin layer chromatography (developed with chloroform/methanol=95/5) to obtain Compound 116 (22 mg, 34% yield).

IR (KBr) 3402, 2926, 1719, 1655, 1539, 1448, 1384, 1260, 1194, 1090, 892 cm$^{-1}$ $^1$H NMR (CDCl$_3$, 400 MHz) δ ppm; 8.61 (dd, J=16.6, 11.2 Hz, 1H), 7.40–7.10 (m, 7H), 7.25 (s, 1H), 6.62 (d, J=11.5 Hz, 1H), 6.31 (dd, J=11.5, 11.2 Hz, 1H), 6.03 (d, J=16.6 Hz, 1H), 5.82 (d, J=9.3 Hz, 1H), 5.81 (br s, 1H), 5.75 (br d, J=9.3 Hz, 1H), 5.46 (dq, J=7.0, 6.9 Hz, 1H), 5.10 (d, J=12.0 Hz, 1H), 5.07 (d, J=12.0 Hz, 1H), 4.26–3.58 (m, 6H), 3.19 (d, J=16.2 Hz, 1H), 3.02 (d, J=16.2 Hz, 1H), 2.94 (br s, 1H), 2.40–1.60 (m, 4H), 1.71 (d, J=6.9 Hz, 3H), 1.70 (s, 3H), 1.68 (s, 3H)

FABMS m/z 789 (M+H)$^+$.

HRFABMS calcd for C$_{35}$H$_{41}$N$_4$O$_{11}$S$_3$ (M+H)$^+$ 789.1934, found 789.1918

EXAMPLE 107
Synthesis of Compound 117

According to the procedure as described in Example 45, Compound 117 (32 mg, 42% yield) was obtained from DC107 (50 mg, 0.098 mmol), N-Cbz-β-alanylsarcosine (148 mg, 0.50 mmol), 1-ethyl-3-(3-dimethylaminopropyl) carbodiimide hydrochloride (94 mg, 0.50 mmol), tetrahydrofuran (15 ml) and 4-dimethylaminopyridine (3.6 mg, 0.03 mmol).

IR (KBr) 3400, 2938, 1709, 1656, 1647, 1527, 1511, 1453, 1405, 1372, 1255, 1187, 1101, 997, 942, 895 cm$^{-1}$ $^1$H NMR (CDCl$_3$, 500 MHz) δ ppm; 8.65 (dd, J=16.5, 11.6 Hz, 1H), 7.55 (br d, J=6.7 Hz, 1H), 7.39–7.27 (m, 5H), 7.29 (s, 1H), 6.60 (d, J=11.3 Hz, 1H), 6.30 (dd, J=11.6, 11.3 Hz, 1H), 6.05 (d, J=16.5 Hz, 1H), 5.80–5.73 (m, 2H), 5.47 (dq, J=7.0, 6.7 Hz, 1H), 5.17 (br, 1H), 5.06 (br s, 2H), 4.15 (br s, 1H), 4.10–3.90 (m, 2H), 3.30–3.00 (m, 2H), 3.16 (d, J=16.8 Hz, 1H), 3.07 (d, J=16.8 Hz, 1H), 3.03 (s, 3H), 2.60–1.70 (m, 6H), 1.74 (d, J=7.0 Hz, 3H), 1.73 (s, 3H), 1.67 (s, 3H)

FABMS m/z 787 (M+H)$^+$

HRFABMS calcd for C$_{36}$H$_{43}$N$_4$O$_{10}$S$_3$ (M+H)$^+$ 787.2141, found 787.2163

EXAMPLE 108
Synthesis of Compound 118

According to the procedure as described in Example 45, Compound 118 (45 mg, 53% yield) was obtained from DC107 (51 mg, 0.10mmol), N-Cbz-glycyl-β-alanine (282 mg, 1.1 mmol), 1-ethyl-3-(3-dimethylaminopropyl) carbodiimide hydrochloride (193 mg, 1.1 mmol), tetrahydrofuran (9 ml) and 4-dimethylaminopyridine (7.3 mg, 0.06 mmol).

IR (KBr) 3330, 3072, 2936, 1720, 1658, 1613, 1537, 1454, 1375, 1255, 1175, 1098, 1060, 998, 946, 896, 859, 799, 776, 737, 697 cm$^{-1}$ $^1$H NMR (CDCl$_3$, 500 MHz) δ ppm; 8.45 (br dd, J=16.5, 11.6 Hz, 1H), 7.38–7.28 (m, 5H), 7.27 (s, 1H), 6.99 (br, 1H), 6.73 (br d, J=6.7 Hz, 1H), 6.66 (d, J=11.6 Hz, 1H), 6.32 (t, J=11.6 Hz, 1H), 6.02 (d, J=16.5 Hz, 1H), 5.98 (d, J=9.5 Hz, 1H), 5.70 (br d, J=9.5 Hz, 1H), 5.60 (br, 1H), 5.43 (dq, J=6.7, 6.7 Hz, 1H), 5.10 (s, 2H), 4.02 (br, 1H), 3.84 (br, 2H), 3.59–3.48 (m, 2H), 3.25 (d, J=15.9 Hz, 1H), 2.90 (d, J=15.9 Hz, 1H), 2.57–2.47 (m, 2H), 2.37 (dt, J=4.8, 12.8 Hz, 1H), 2.04–1.60 (m, 3H), 1.74 (d, J=6.7 Hz, 3H), 1.65 (s, 3H), 1.65 (s, 3H)

FABMS m/z 773 (M+H)$^+$

HRFABMS calcd for C$_{35}$H$_{41}$N$_4$O$_{10}$S$_3$ (M+H)$^+$ 773.1985, found 773.2009

EXAMPLE 109
Synthesis of Compound 119

According to the procedure as described in Example 45, Compound 119 (42 mg, 53% yield) was obtained from DC107 (51 mg, 0.10 mmol), N-Cbz-β-alanyl-β-alanine (205 mg, 0.70 mmol), 1-ethyl-3-(3-dimethylaminopropyl) carbodiimide hydrochloride (134 mg, 0.70 mmol), tetrahydrofuran (9 ml) and 4-dimethylaminopyridine (4.9 mg, 0.040 mmol).

IR (KBr) 3400, 2936, 1720, 1656, 1531, 1454, 1373, 1259, 1174, 1098, 896, 859, 799, 738, 697 cm$^{-1}$

¹H NMR (CDCl₃, 400 MHz) δ ppm; 8.51 (dd, J=16.6, 11.5 Hz, 1H), 7.37–7.21 (m, 5H), 7.34 (s, 1H), 6.70 (br t, J=8.0 Hz, 1H), 6.66 (d, J=11.5 Hz, 1H), 6.57 (d, J=6.8 Hz, 1H), 6.34 (t, J=11.5 Hz, 1H), 6.05 (d, J=16.6 Hz, 1H), 5.98 (d, J=9.5 Hz, 1H), 5.73 (br d, J=9.5 Hz, 1H), 5.50 (br, 1H), 5.43 (dq, J=6.8, 6.8 Hz, 1H), 5.07 (br s, 2H), 3.92 (br s, 1H), 3.58–3.40 (m, 4H), 3.24 (d, J=16.1 Hz, 1H), 2.90 (d, J=16.1 Hz, 1H), 2.57–2.30 (m, 5H), 2.08–1.70 (m, 3H), 1.75 (d, J=6.8 Hz, 3H), 1.67 (d, J=1.2 Hz, 3H), 1.66 (s, 3H)

FABMS m/z 787 (M+H)⁺

HRFABMS calcd for $C_{36}H_{43}N_4O_{10}S_3$ (M+H)⁺ 787.2141, found 787.2153

EXAMPLE 110
Synthesis of Compound 120

According to the procedure as described in Example 18, Compound 120 (7.6 mg, 17% yield) was obtained from Compound 80 (40 mg, 0.062 mmol), 2-methoxypropene (0.029 ml, 0.31mmol) and camphorsulfonic acid (14 mg, 0.062 mmol).

IR (KBr) 3420, 2938, 1720, 1649, 1609, 1452, 1374, 1256, 1211, 1154, 1124, 1070, 1021, 975, 887 cm⁻¹

¹H NMR (CDCl₃, 400 MHz) δ ppm; 9.51 (ddd, J=16.4, 11.5, 1.0 Hz, 1H), 7.41 (s, 1H), 6.61 (d, J=11.3 Hz, 1H), 6.36 (dd, J=11.5, 11.3 Hz, 1H), 5.98 (d, J=16.4 Hz, 1H), 5.81 (dd, J=9.5, 1.2 Hz, 1H), 5.57 (q, J=6.6 Hz, 1H), 5.47 (br s, 1H), 5.41 (d, J=11.0 Hz, 1H), 5.35 (d, J=11.0 Hz, 1H), 4.92 (dd, J=9.5, 1.2 Hz, 1H), 4.04 (d, J=17.8 Hz, 1H), 3.09 (s, 3H), 2.29 (d, J=17.8 Hz, 1H), 2.42–1.20 (m, 15H), 1.97 (d, J=6.6 Hz, 3H), 1.77 (d, J=1.2 Hz, 3H), 1.69 (s, 3H), 1.28 (s, 6H)

FABMS m/z 723 (M+H)⁺

EXAMPLE 111
Synthesis of Compound 121

According to the procedure as described in Example 18, Compound 121 (12 mg, 66% yield) was obtained from Compound 35 (16 mg, 0.026mmol), 2-methoxypropene (0.012 ml, 0.13 mmol) and camphorsulfonic acid (3 mg, 0.013 mmol).

IR (KBr) 3400, 3224, 2938, 1819, 1730, 1705, 1680, 1642, 1608, 1448, 1374, 1258, 1208, 1146, 1070, 1029, 977, 888, 769, 732 cm⁻¹

¹H NMR (CDCl₃, 400 MHz) δ ppm; 9.50 (ddd, J=16.6, 11.5, 1.0 Hz, 1H), 7.41 (s, 1H), 6.61 (d, J=11.5 Hz, 1H), 6.36 (t, J=11.5 Hz, 1H), 5.99 (d, J=16.6 Hz, 1H), 5.82 (br d, J=9.2 Hz, 1H), 5.57 (q, J=6.6 Hz, 1H), 5.46 (br s, 1H), 4.92 (dd, J=9.5, 1.2 Hz, 1H), 4.05 (d, J=17.6 Hz, 1H), 3.80 (d, J=15.1 Hz, 1H), 3.75 (d, J=15.1 Hz, 1H), 3.10 (s, 3H), 2.43–1.35 (m, 4H), 2.29 (d, J=17.6 Hz, 1H), 2.15 (s, 3H), 1.97 (d, J=6.6 Hz, 3H), 1.78 (d, J=1.4 Hz, 3H), 1.69 (s, 3H), 1.28 (s, 3H), 1.28 (s, 3H)

FABMS m/z 695 (M+H)⁺

HRFABMS calcd for $C_{31}H_{39}N_2O_{10}S_3$ (M+H)⁺ 695.1767, found 695.1757

EXAMPLE 112
Synthesis of Compound 122

According to the procedure as described in Example 18, Compound 122 (54 mg, 81% yield) was obtained from Compound 35 (56 mg, 0.090 mmol), 5,6-dihydro-4-methoxy-2H-pyran (0.030 ml, 0.27 mmol) and camphorsulfonic acid (9.3 mg, 0.045 mmol).

IR (KBr) 3412, 2938, 2870, 1818, 1710, 1685, 1642, 1608, 1450, 1356, 1262, 1233, 1208, 1141, 1095, 977, 768 cm⁻¹

¹H NMR (CDCl₃, 400 MHz) δ ppm; 9.53 (dd, J=16.5, 11.3 Hz, 1H), 7.43 (s, 1H), 6.63 (d, J=11.5 Hz, 1H), 6.37 (dd, J=11.5, 11.3 Hz, 1H), 6.00 (d, J=16.5 Hz, 1H), 5.86 (br d, J=9.5 Hz, 1H), 5.57 (q, J=6.6 Hz, 1H), 5.44 (br s, 1H), 4.98 (dd, J=9.5, 1.2 Hz, 1H), 4.05 (d, J=17.6 Hz, 1H), 3.81 (d, J=15.4 Hz, 1H), 3.74 (d, J=15.4 Hz, 1H), 3.70–3.49 (m, 4H), 3.11 (s, 3H), 2.44–2.23 (m, 3H), 2.29 (d, J=17.6 Hz, 1H), 2.15 (s, 3H), 1.95 (d, J=6.6 Hz, 3H), 1.79 (d, J=1.2 Hz, 3H), 1.80–1.35 (m, 5H), 1.68 (s, 3H)

FABMS m/z 737 (M+H)⁺

HRFABMS calcd for $C_{33}H_{41}N_2O_{11}S_3$ (M+H)⁺ 737.1872, found 737.1848

EXAMPLE 113
Synthesis of Compounds 123 and 124

According to the procedure as described in Example 60, Compound 123 (13 mg, 33% yield) and its geometrical isomer, Compound 124 (13 mg, 33% yield), were obtained from Compound 122 (38 mg, 0.052 mmol), methanol (3 ml), pyridine (0.05 mol) and hydroxylamine hydrochloride (18 mg, 0.26 mmol).

Compound 123

IR (KBr) 3400, 2932, 1817, 1720, 1680, 1448, 1355, 1263, 1207, 1140, 1094, 886, 838 cm⁻¹

¹H NMR (CDCl₃, 400 MHz) δ ppm; 9.05 (dd, J=16.6, 11.3 Hz, 1H), 7.32 (s, 1H), 6.87 (d, J=16.6 Hz, 1H), 6.50 (d, J=11.6 Hz, 1H), 6.39 (dd, J=11.6, 11.3 Hz, 1H), 6.03 (br d, J=9.8 Hz, 1H), 5.55 (q, J=6.6 Hz, 1H), 5.51 (br s, 1H), 5.28 (dd, J=9.8, 1.2 Hz, 1H), 4.06 (d, J=17.6 Hz, 1H), 3.80 (d, J=15.1 Hz, 1H), 3.75 (d, J=15.1 Hz 1H), 3.65–3.54 (m, 4H), 3.13 (s, 3H), 2.35–1.20 (m, 8H), 2.20 (d, J=17.6 Hz, 1H), 2.08 (s, 3H), 1.85 (d, J=6.6 Hz, 3H), 1.75 (d, J=1.2 Hz, 3H), 1.62 (s, 3H)

FABMS m/z 752 (M+H)⁺

HRFABMS calcd for $C_{33}H_{42}N_3O_{11}S_3$ (M+H)⁺ 752.1981, found 752.1957

Compound 124

IR (KBr) 3400, 2940, 1819, 1720, 1687, 1444, 1356, 1262, 1208, 1141, 1094, 837 cm⁻¹

¹H NMR (CDCl₃, 400 MHz) δ ppm; 9.03 (dd, J=16.6, 11.0 Hz, 1H), 7.22 (s, 1H), 6.33 (d, J=11.3 Hz, 1H), 6.27 (dd, J=11.3, 11.0 Hz, 1H), 6.14 (dd, J=9.8, 1.2 Hz, 1H), 6.09 (d, J=16.6 Hz, 1H), 5.84 (br d, J=9.8 Hz, 1H), 5.49 (q, J=6.6 Hz, 1H), 5.44 (br s, 1H), 3.98 (d, J=17.6 Hz, 1H), 3.74 (d, J=15.1 Hz, 1H), 3.67 (d, J=15.1 Hz, 1H), 3.60–3.45 (m, 4H), 3.07 (s, 3H), 2.42–1.25 (m, 8H), 2.30 (d, J=17.6 Hz, 1H), 2.14 (s, 3H), 1.92 (d, J=6.6 Hz, 3H), 1.76 (d, J=1.2 Hz, 3H), 1.68 (s, 3H)

FABMS m/z 752 (M+H)⁺

HRFABMS calcd for $C_{33}H_{42}N_3O_{11}S_3$ (M+H)⁺ 752.1981, found 752.1973

EXAMPLE 114
Synthesis of Compound 125

According to the procedure as described in Example 60, Compound 125 (13 mg, 91% yield) was obtained from Compound 63 (14 mg, 0.020mmol), methanol (1.0 ml), pyridine (0.020 ml) and hydroxylamine hydrochloride (6.9 mg, 0.10 mmol). From ¹H NMR, Compound 125 was found to be a mixture of geometrical isomers at a ratio of about 3:2.

IR (KBr) 3400, 2932, 1820, 1720, 1680, 1440, 1370, 1261, 1207, 975, 769 cm⁻¹

¹H NMR (CDCl₃, 400 MHz) δ ppm; major isomer 8.96 (dd, J=16.6, 11.5 Hz, 1H), 7.19 (s, 1H), 6.36–6.15 (m, 2H), 6.17 (dd, J=9.3, 1.5 Hz, 1H), 6.10 (d, J=16.6 Hz, 1H), 5.79 (br d, J=9.3 Hz, 1H), 5.51 (br s, 1H), 5.51 (q, J=6.6 Hz, 1H), 4.45 (br s, 1H), 3.98 (d, J=17.6 Hz, 1H), 3.85–3.45 (m, 4H), 2.40–1.30 (m, 10H), 2.08 (s, 3H), 1.84 (d, J=6.6 Hz, 3H), 1.75 (d, J=1.2 Hz, 3H), 1.63 (s, 3H); minor isomer 8.97 (dd, J=16.6, 11.5 Hz, 1H), 7.23 (s, 1H), 6.79 (d, J=16.6 Hz, 1H), 6.41 (d, 11.7 Hz, 1H), 6.23 (dd, J=11.7, 11.0 Hz, 1H), 5.90

(br d, J=9.3 Hz, 1H), 5.51 (br s, 1H), 5.51 (q, J=6.6 Hz, 1H), 5.06 (dd, J=9.0, 1.2 Hz, 1H), 4.54 (br s, 1H), 4.00 (d, J=17.6 Hz, 1H), 3.85–3.45 (m, 4H), 2.40–1.30 (m, 10H), 2.08 (s, 3H), 1.83 (d, J=6.6 Hz, 3H), 1.70 (d, J=1.2 Hz, 3H), 1.62 (s, 3H)

FABMS m/z 722 (M+H)$^+$

HRFABMS calcd for $C_{32}H_{39}N_3O_{10}S_3$ (M+H)$^+$ 722.1876, found 722.1881

EXAMPLE 115
Synthesis of Compound 126

According to the procedure as described in Example 18, Compound 126 (25 mg, 71% yield) was obtained from Compound 35 (30 mg, 0.048mmol), 1-methoxy-1-cyclohexene (27 mg, 0.24 mmol) and camphorsulfonic acid (2.2 mg, 0.01 mmol).

IR (KBr) 3420, 2940, 2860, 1820, 1720, 1680, 1649, 1609, 1450, 1369, 1255, 1208, 1152, 1090, 1017, 977, 926, 769 cm$^{-1}$ $^1$H NMR (CDCl$_3$, 400 MHz) δ ppm; 9.52 (ddd, J=16.6, 11.5, 1.0 Hz, 1H), 7.41 (s, 1H), 6.61 (d, J=11.5 Hz, 1H), 6.36 (t, J=11.5 Hz, 1H), 5.99 (d, J=16.6 Hz, 1H), 5.84 (br dd, J=9.8, 1.2 Hz, 1H), 5.57 (q, J=6.6 Hz, 1H), 5.46 (dd, J=9.8, 1.4 Hz, 1H), 4.05 (d, J=17.8 Hz, 1H), 3.80 (dd, J=15.1, 0.7 Hz, 1H), 3.75 (dd, J=15.1, 0.7 Hz, 1H), 3.07 (s, 3H), 2.41–1.20 (m, 14H), 2.28 (d, J=17.8 Hz, 1H), 2.15 (s, 3H), 1.97 (d, J=6.6 Hz, 3H), 1.78 (d, J=1.4 Hz, 3H), 1.68 (s, 3H)

FABMS m/z 735 (M+H)$^+$

HRFABMS calcd for $C_{34}H_{43}N_2O_{10}S_3$ (M+H)$^+$ 735.2080, found 735.2067

EXAMPLE 116
Synthesis of Compound 127

According to the procedure as described in Example 18, Compound 127 (32 mg, 91% yield) was obtained from Compound 35 (29 mg, 0.047 mmol), 5,6-dihydro-4-methoxy-2H-thiopyran (60 mg, 0.46 mmol) and camphorsulfonic acid (8 mg, 0.034 mmol).

IR (KBr) 3400, 3090, 2930, 1820, 1710, 1678, 1642, 1609, 1427, 1376, 1248, 1207, 1147, 1094, 1030, 978, 879, 809, 768 cm$^{-1}$ $^1$H NMR (CDCl$_3$, 400 MHz) δ ppm; 9.49 (ddd, J=16.6, 11.5, 1.0 Hz, 1H), 7.43 (s, 1H), 6.62 (d, J=11.5 Hz, 1H), 6.37 (t, J=11.5 Hz, 1H), 6.00 (s, J=16.6 Hz, 1H), 5.84 (dd, J=9.8, 1.0 Hz, 1H), 5.57 (q, J=6.6 Hz, 1H), 5.43 (br s, 1H), 4.95 (dd, J=9.8, 1.2 Hz, 1H), 4.04 (d, J=17.8 Hz, 1H), 3.81 (d, J=15.4 Hz, 1H), 3.74 (d, J=15.4 Hz, 1H), 3.08 (s, 3H), 2.72–1.35 (m, 12H), 2.30 (d, J=17.6 Hz, 1H), 2.14 (s, 3H), 1.96 (d, J=6.6 Hz, 3H), 1.78 (d, J=1.2 Hz, 3H), 1.68 (s, 3H)

FABMS m/z 753 (M+H)$^+$

HRFABMS calcd for $C_{33}H_{41}N_2O_{10}S_4$ (M+H)$^+$ 753.1644, found 753.1618

EXAMPLE 117
Synthesis of Compounds 128 and 129

Compound 127 (80 mg, 0.11 mmol) was dissolved in dichloromethane (7 ml), and m-chloroperbenzoic acid (40 mg, 0.16 mmol) was gradually added thereto at 0° C. After subjecting the mixture to the usual post-treatment, the mixture was purified by thin layer chromatography (developed with chloroform/methanol=97/3) to obtain Compound 128 (16 mg, 20% yield) and Compound 129 (44 mg, 53% yield).

Compound 128

IR (KBr) 3450, 2936, 1817, 1710, 1680, 1643, 1608, 1450, 1362, 1263, 1205, 1095, 1035, 982, 769 cm$^{-1}$ $^1$H NMR (CDCl$_3$, 400 MHz) δ ppm; major isomer 9.51 (ddd, J=16.6, 11.5, 0.7 Hz, 1H), 7.43 (s, 1H), 6.62 (d, J=11.2 Hz, 1H), 6.35 (dd, J=11.5, 11.2 Hz, 1H), 6.00 (d, J=16.6 Hz, 1H), 5.86 (br d, J=9.0 Hz, 1H), 5.56 (q, J=6.6 Hz, 1H), 5.46 is, 1H), 4.99 (dd, J=9.0, 1.2 Hz, 1H), 4.05 (d, J=17.8 Hz, 1H), 3.82 (dd, J=15.4, 1.0 Hz, 1H), 3.73 (d, J=15.4 Hz, 1H), 3.13 is, 3H), 2.92–1.35 (m, 12H), 2.31 (d, J=17.8 Hz, 1H), 2.14 (s, 3H), 1.97 (d, J=6.6 Hz, 3H), 1.79 (d, J=1.2 Hz, 3H), 1.68 (s, 3H); minor isomer 9.45 (ddd, J=16.6, 11.5, 0.7 Hz, 1H), 7.46 (s, 1H), 6.65 (d, J=11.2 Hz, 1H), 6.35 (dd, J=11.5, 11.2 Hz, 1H), 6.02 (d, J=16.6 Hz, 1H), 5.85 (br d, J=9.0 Hz, 1H), 5.57 (q, J=6.6 Hz, 1H), 5.40 (s, 1H), 4.97 (dd, J=9.0, 1.2 Hz, 1H), 4.05 (d, J=17.8 Hz, 1H), 3.81 (dd, J=15.4, 0.7 Hz, 1H), 3.74 (d, J=15.4 Hz, 1H), 3.17 (s, 3H), 2.92–1.35 (m, 12H), 2.29 (d, J=17.8 Hz, 1H), 2.14 (s, 3H), 1.95 (d, J=6.6 Hz, 3H), 1.80 (d, J=1.2 Hz, 3H), 1.67 (s, 3H)

FABMS m/z 769 (M+H)$^+$

HRFABMS calcd for $C_{33}H_{41}N_2O_{11}S_4$ (M+H)$^+$ 769.1593, found 769.1584

Compound 129

IR (KBr) 3420, 2944, 1819, 1720, 1679, 1645, 1608, 1450, 1290, 1267, 1205, 1095, 1032, 978, 851 cm$^{-1}$ $^1$H NMR (CDCl$_3$, 400 MHz) δ ppm; 9.46 (ddd, J=16.6, 11.5, 0.8 Hz, 1H), 7.46 (s, 1H), 6.66 (d, J=11.5 Hz, 1H), 6.37 (t, J=11.5 Hz, 1H), 6.01 (d, J=16.6 Hz, 1H), 5.86 (br dd, J=9.5, 1.0 Hz, 1H), 5.57 (q, J=6.4 Hz, 1H), 5.38 (br s, 1H), 4.95 (dd, J=9.5, 1.2 Hz, 1H), 4.05 (d, J=17.6 Hz, 1H), 3.83 (d, J=15.3 Hz, 1H), 3.73 (d, J=15.3 Hz, 1H), 3.15 (s, 3H), 3.15–2.80 (m, 4H), 2.45–1.40 (m, 8H), 2.31 (d, J=17.6 Hz, 1H), 2.15 (s, 3H), 1.94 (d, J=6.4 Hz, 3H), 1.79 (d, J=1.2 Hz, 3H), 1.68 (s, 3H)

FABMS m/z 785 (M+H)$^+$

HRFABMS calcd for $C_{33}H_{41}N_2O_{12}S_4$ (M+H)$^+$ 785.1542, found 785.1564

EXAMPLE 118
Synthesis of Compound 130

According to the procedure as described in Example 18, Compound 130 (37 mg, 71% yield) was obtained from Compound 35 (40 mg, 0.064 mmol), 1-ethoxycarbonyl-4-methoxy-1,2,5,6-tetrahydropyridine (59 mg, 0.32 mmol) and camphorsulfonic acid (7.4 mg, 0.032 mmol).

IR (KBr) 3420, 2936, 1821, 1667, 1640, 1608, 1440, 1381, 1354, 1241, 1208, 1143, 1105, 1019, 976, 769 cm$^{-1}$ $^1$H NMR (CDCl$_3$, 500 MHz) δ ppm; 9.50 (dd, J=16.4, 11.5 Hz, 1H), 7.42 (s, 1H), 6.62 (d, J=11.5 Hz, 1H), 6.36 (t, J=11.5 Hz, 1H), 5.99 (d, J=16.6 Hz, 1H), 5.85 (br d, J=9.7 Hz, 1H), 5.56 (q, J=6.6 Hz, 1H), 5.43 (br s, 1H), 4.98 (dd, J=9.7, 1.3 Hz, 1H), 4.08 (q, J=7.0 Hz, 2H), 4.04 (d, J=17.8 Hz, 1H), 3.81 (d, J=15.4 Hz, 1H), 3.74 (d, J=15.4 Hz, 1H), 3.61–3.50 (m, 2H), 3.27 (m, 2H), 3.11 (s, 3H), 2.44–1.35 (m, 8H), 2.29 (d, J=17.8 Hz, 1H), 2.14 (s, 3H), 1.94 (d, J=6.6 Hz, 3H), 1.78 (d, J=1.3 Hz, 3H), 1.68 (s, 3H), 1.22 (t, J=7.0 Hz, 3H)

FABMS m/z 808 (M+H)$^+$

HRFABMS calcd for $C_{36}H_{46}N_2O_{12}S_3$ (M+H)$^+$ 808.2243, found 808.2223

EXAMPLE 119
Synthesis of Compound 131

According to the procedure as described in Example 18, Compound 131 (20 mg, 31% yield) was obtained from Compound 35 (50 mg, 0.080 mmol), 1-phenyl-4-methoxy-1,2,5,6-tetrahydropyridine (150 mg, 0.80mmol) and trifluoroacetic acid (0.055 mg, 0.70 mmol).

IR (KBr) 3400, 2936, 1821, 1720, 1680, 1648, 1598, 1496, 1451, 1339, 1260, 1209, 1092, 1031, 977, 760 cm$^{-1}$ $^1$H NMR (CDCl$_3$, 400 MHz) δ ppm; 9.52 (dd, J=16.5, 11.5 Hz, 1H), 7.41 (s, 1H), 7.25–7.18 (m, 2H), 6.89–6.76 (m, 3H), 6.61 (d, J=11.5 Hz, 1H), 6.34 (t, J=11.5 Hz, 1H), 6.00 (d, J=16.6 Hz, 1H), 5.87 (br d, J=9.8 Hz, 1H), 5.57 (q, J=6.6

Hz, 1H), 5.45 (br s, 1H), 5.02 (dd, J=9.8, 1.2 Hz, 1H), 4.05 (d, J=17.8 Hz, 1H), 3.81 (d, J=15.2 Hz, 1H), 3.74 (d, J=15.2 Hz, 1H), 3.30–2.93 (m, 4H), 3.14 (s, 3H), 2.43–1.40 (m, 8H), 2.15 (s, 3H), 1.96 (d, J=6.6 Hz, 3H), 1.80 (d, J=1.2 Hz, 3H), 1.68 (s, 3H)

FABMS m/z 812 (M+H)$^+$

HRFABMS calcd for $C_{39}H_{45}N_3O_{10}S_3$ (M+H)$^+$ 812.2345, found 812.2333

EXAMPLE 120

Synthesis of Compound 132

DC107 (110 mg, 0.22 mmol) was dissolved in acetonitrile (10 ml), and p-nitrobenzylbromide (140 mg, 0.64 mmol) and potassium carbonate (150 mg, 1.1 mmol) were added thereto, followed by stirring at room temperature for 14 hours. After subjecting the mixture to the usual post-treatment, the mixture was purified by thin layer chromatography (developed with chloroform/methanol=97/3) to obtain Compound 132 (90 mg, 65% yield).

$^1$H NMR (CDCl$_3$, 400 MHz) δ ppm; 8.44 (ddd, J=16.3, 11.5, 1.0 Hz, 1H), 8.15 (br d, J=8.8 Hz, 2H), 7.45 (br d, J=8.8 Hz, 2H), 7.34 (s, 1H), 6.58 (d, J=11.5 Hz, 1H), 6.23 (t, J=11.5 Hz, 1H), 6.17 (d, J=16.3 Hz, 1H), 5.72 (br d, J=9.0 Hz, 1H), 5.47 (br s, 1H), 5.40 (q, J=6.8 Hz, 1H), 4.94 (dd, J=9.0, 3.7 Hz, 1H), 4.12–4.03 (m, 2H), 3.88 (d, J=17.6 Hz, 1H), 3.75 (br d, J=3.7 Hz, 1H), 2.18 (d, J=17.6 Hz, 1H), 2.35–1.85 (m, 4H), 2.01 (d, J=6.8 Hz, 3H), 1.76 (s, 3H), 1.74 (d, J=1.2 Hz, 3H)

FABMS m/z 646 (M+H)$^+$

HRFABMS calcd for $C_{29}H_{32}N_3O_8S_3$ (M+H)$^+$ 646.1351, found 646.1350

EXAMPLE 121

Synthesis of Compound 133

According to the procedure as described in Example 18, Compound 133 (49 mg, 74% yield) was obtained from Compound 132 (56 mg, 0.087 mmol), 5,6-dihydro-4-methoxy-2H-pyran (0.029 ml, 0.26 mmol) and camphorsulfonic acid (10 mg, 0.044 mmol).

IR (KBr) 3400, 3088, 2938, 2870, 1720, 1680, 1640, 1607, 1519, 1491, 1453, 1345, 1260, 1140, 1100, 988, 840, 810, 730 cm$^{-1}$ $^1$H NMR (CDCl$_3$, 400 MHz) δ ppm; 9.52 (ddd, J=16.6, 11.5, 1.0 Hz, 1H), 8.16 (br d, J=8.8 Hz, 2H), 7.46 (br d, J=8.8 Hz, 2H), 7.42 (s, 1H), 6.62 (d, J=11.5 Hz, 1H), 6.36 (t, J=11.5 Hz, 1H), 6.00 (d, J=16.6 Hz, 1H), 5.84 (br d, J=9.8 Hz, 1H), 5.56 (q, J=6.3 Hz, 1H), 5.46 (br s, 1H), 4.97 (dd, J=9.8, 1.5 Hz, 1H), 4.08 (br s, 2H), 4.03 (d, J=17.6 Hz, 1H), 3.70–3.48 (m, 4H), 3.10 (s, 3H), 2.41–1.60 (m, 8H), 2.19 (d, J=17.6 Hz, 1H), 1.94 (d, J=6.6 Hz, 3H), 1.77 (d, J=1.2 Hz, 3H), 1.67 (s, 3H)

FABMS m/z 760 (M+H)$^+$

HRFABMS calcd for $C_{35}H_{42}N_3O_{10}S_3$ (M+H)$^+$ 760.2032, found 760.2033

EXAMPLE 122

Synthesis of Compound 134

DC107 (100 mg, 0.20 mmol) was dissolved in acetonitrile (10 ml), and p-acetoxybenzylchloride (110 mg, 0.59 mmol), potassium carbonate (150 mg, 1.1 mmol) and potassium iodide (17 mg, 0.10 mmol) were added thereto, followed by stirring at room temperature for 12 hours. After subjecting the mixture to the usual post-treatment, the mixture was purified by thin layer chromatography (developed with chloroform/methanol=97/3) to obtain Compound 134 (71 mg, 54% yield).

IR (KBr) 3420, 2930, 1760, 1720, 1670, 1647, 1710, 1610, 1505, 1460, 1370, 1260, 1192, 1052, 985, 913, 731 cm$^{-1}$ $^1$H NMR (CDCl$_3$, 400 MHz) δ ppm; 8.45 (ddd, J=16.3, 11.0, 1.0 Hz, 1H), 7.27 (s, 1H), 7.28–7.25 (m, 2H), 7.05–6.95 (m, 2H), 6.58 (d, J=11.7 Hz, 1H), 6.23 (dd, J=11.7, 11.0 Hz, 1H), 6.17 (d, J=16.3 Hz, 1H), 5.71 (br d, J=8.6 Hz, 1H), 5.41 (br s, 1H), 5.40 (q, J=6.8 Hz, 1H), 4.94 (dd, J=8.6, 3.7 Hz, 1H), 4.01 (br s, 2H), 3.90 (d, J=17.8 Hz, 1H), 3.72 (d, J=3.7 Hz, 1H), 2.28 (s, 3H), 2.35–1.85 (m, 4H), 2.21 (d, J=17.8 Hz, 1H), 2.01 (d, J=6.8 Hz, 3H), 1.78 (s, 3H), 1.73 (d, J=1.2 Hz, 3H)

FABMS m/z 659 (M+H)$^+$

HRFABMS calcd for $C_{31}H_{35}N_2O_8S_3$ (M+H)$^+$ 659.1555, found 659.1553

EXAMPLE 123

Synthesis of Compound 135

Compound 134 (23 mg, 0.035 mmol) obtained in Example 122 was dissolved in dichloromethane (4.0 ml), and 3,4-dihydro-2H-pyran (0.10 ml) and camphorsulfonic acid (3 mg) were added thereto, followed by stirring at 20° C. for 15 minutes. After subjecting the mixture to the usual post-treatment, the mixture was purified by thin layer chromatography (developed with chloroform/methanol=30/1) to obtain Compound 135 (10 mg, 38% yield). From $^1$H NMR, Compound 135 was found to be a mixture of diastereomers at a ratio of about 1:1.

IR (KBr) 2922, 1763, 1718, 1676, 1655, 1610, 1508, 1371, 1259, 1203, 1117, 1018, 980 cm$^{-1}$ $^1$H NMR (CDCl$_3$, 270 MHz) δ ppm; 9.59 (dd, J=11.6, 16.1 Hz) and 9.40 (dd, J=11.4, 16.3 Hz) (total 1H), 7.29 (m, 2H), 7.40 (s) and 7.39 (s) (total 1H), 6.61 (d, J=11.4 Hz) and 6.60 (d, J=11.4 Hz) (total 1H), 7.02 (m, 2H), 6.36 (t, J=11.4 Hz) and 6.34 (t, J=11.4 Hz) (total 1H), 6.04 (d, J=16.8 Hz) and 6.00 (d, J=16.3 Hz) (total 1H), 5.82 (br d, J=9.4 Hz) and 5.79 (br d, J=9.4 Hz) (total 1H), 5.58 (q, J=6.9 Hz) and 5.56 (q, J=6.9 Hz) (total 1H), 5.46 (br s) and 5.43 (br s) (total 1H), 5.02 (d, J=9.4 Hz) and 4.74 (d, J=9.4 Hz) (total 1H), 4.71 (br s) and 4.57 (br s) (total 1H), 4.04 (d, J=17.8 Hz) and 4.03 (d, J=17.8 Hz) (total 1H), 4.01 (s, 2H), 3.9–3.3 (m, 2H), 2.5–1.3 (m, 10H), 2.33 (s, 3H), 2.21 (d, J=17.8 Hz, 1H), 1.93 (d, J=6.9 Hz) and 1.87 (d, J=6.9 Hz) (total 3H), 1.76 (d, J=1.0 Hz) and 1.72 (d, J=1.0 Hz) (total 3H), 1.69 (s, 3H)

FABMS m/z 743 (M+H)$^+$

EXAMPLE 124

Synthesis of Compound 136

According to the procedure as described in Example 18, Compound 136 (48 mg, 82% yield) was obtained from Compound 134 (50 mg, 0.076 mmol), 5,6-dihydro-4-methoxy-2H-pyran (0.042 ml, 0.38 mmol) and camphorsulfonic acid (8.8 mg, 0.038 mmol).

IR (KBr) 3400, 2970, 1760, 1720, 1680, 1610, 1510, 1450, 1370, 1260, 1190, 1160, 1100, 1005, 910 cm$^{-1}$ $^1$H NMR (CDCl$_3$, 400 MHz) δ ppm; 9.45 (dd, J=16.6, 11.5 Hz, 1H), 7.42 (s, 1H), 7.32–7.26 (m, 2H), 7.06–6.97 (m, 2H), 6.62 (d, J=11.5 Hz, 1H), 6.36 (t, J=11.5 Hz, 1H), 6.00 (d, J=16.0 Hz, 1H), 5.84 (br d, J=9.5 Hz, 1H), 5.56 (q, J=6.3 Hz, 1H), 5.37 (br s, 1H), 4.97 (dd, J=9.5, 1.2 Hz, 1H), 4.06–3.95 (m, 2H), 4.03 (d, J=17.6 Hz, 1H), 3.70–3.46 (m, 4H), 3.10 (s, 3H), 2.36–1.25 (m, 8H), 2.28 (s, 3H), 2.21 (d, J=17.6 Hz, 1H), 1.94 (d, J=6.3 Hz, 3H), 1.77 (d, J=1.3 Hz, 3H), 1.67 (s, 3H)

FABMS m/z 773 (M+H)$^+$

HRFABMS calcd for $C_{37}H_{45}N_2O_{10}S_3$ (M+H)$^+$ 773.2236, found 773.2211

EXAMPLE 125

Synthesis of Compound 137

Compound 134 (185 mg, 0.281 mmol) produced in Example 122 was dissolved in methanol (20 ml), and hydrochloric acid (2M, 6.0 ml) was added thereto, followed by stirring at 20° C. for 4 hours. A phosphoric acid buffer (pH 7) was added to the reaction mixture and extracted with chloroform. After subjecting the mixture to the usual post-treatment, the mixture was purified by fractional HPLC (acetonitrile/water=45/5) to obtain Compound 137 (57 mg, 33% yield).

IR (KBr) 2933, 1734, 1701, 1670, 1612, 1516, 1458, 1267, 1099, 991 $cm^{-1}$ $^1$H NMR ($CDCl_3$, 270 MHz) δ ppm; 8.06 (dd, J=11.1, 16.2 Hz, 1H), 7.27 (s, 1H), 7.16 (d, J=8.4 Hz, 2H), 6.70 (d, J=8.4 Hz, 2H), 6.61 (d, J=11.9 Hz, 1H), 6.25 (t, J=11.4 Hz, 1H), 6.2–6.1 (br, 1H), 6.18 (d, J=16.2 Hz, 1H), 5.39 (br d, J=9.0 Hz, 1H), 5.36 (q, J=6.9 Hz, 1H), 4.88 (dd, J=3.2, 9.0 Hz, 1H), 4.7 (br s, 1H), 4.18 (br s, 1H), 4.04 (d, J=13.7 Hz, 1H), 3.89 (d, J=13.7 Hz, 1H), 3.76 (br d, J=17.6 Hz, 1H), 2.17 (d, J=17.6 Hz, 1H), 2.02 (d, J=6.9 Hz, 3H), 2.0–1.5 (m, 4H), 1.76 (s, 3H), 1.62 (d, J=1.0 Hz, 3H)

FABMS m/z 617 $(M+H)^+$

EXAMPLE 126
Synthesis of Compound 138

DC107 (57 mg, 0.11 mmol) was dissolved in acetonitrile (6 ml), and p-(N,N-dimethylcarbamoyloxy)benzyl chloride (48 mg, 0.23 mmol), potassium carbonate (31 mg, 0.23 mmol) and potassium iodide (9 mg, 0.057 mmol) were added thereto, followed by stirring at room temperature for 15 hours. After subjecting the mixture to the usual post-treatment, the mixture was purified by thin layer chromatography (developed with chloroform/methanol=97/3) to obtain Compound 138 (22 mg, 54% yield).

$^1$H NMR ($CDCl_3$, 400 MHz) δ ppm; 8.45 (ddd, J=16.4, 11.5, 1.0 Hz, 1H), 7.33 (s, 1H), 7.28–7.23 (m, 2H), 7.04–6.98 (m, 2H), 6.58 (d, J=11.5 Hz, 1H), 6.23 (t, J=11.5 Hz, 1H), 6.17 (d, J=6.3 Hz, 1H), 5.72 (br d, J=8.8 Hz, 1H), 5.40 (q, J=6.8 Hz, 1H), 5.39 (br s, 1H), 4.93 (dd, J=8.8, 3.9 Hz, 1H), 4.00 (br s, 2H), 3.90 (d, J=17.8 Hz, 1H), 3.72 (d, J=3.9 Hz, 1H), 3.08 (s, 3H), 2.99 (s, 3H), 2.33–1.70 (m, 4H), 2.22 (d, J=17.8 Hz, 1H), 2.01 (d, J=6.8 Hz, 3H), 1.77 (s, 3H), 1.73 (d, J=1.2 Hz, 3H)

FABMS m/z 688 $(M+H)^+$

HRFABMS calcd for $C_{32}H_{38}N_3O_8S_3$ $(M+H)^+$ 688.1821, found 688.1814

EXAMPLE 127
Synthesis of Compound 139

According to the procedure as described in Example 18, Compound 139 (20 mg, 84% yield) was obtained from Compound 138 (20 mg, 0.029 mmol), 5,6-dihydro-4-methoxy-2H-pyran (0.016 ml, 0.15 mmol) and camphorsulfonic acid (3.4 mg, 0.015 mmol).

IR (KBr) 3400, 3092, 2938, 1720, 1680, 1643, 1609, 1445, 1386, 1210, 1175, 910, 753 $cm^{-1}$ $^1$H NMR ($CDCl_3$, 400 MHz) δ ppm; 9.54, (dd, J=16.3, 11.5 Hz, 1H), 7.42 (s, 1H), 7.30–7.24 (m, 2H), 7.07–7.01 (m, 2H), 6.62 (d, J=11.5 Hz, 1H), 6.36 (t, J=11.5 Hz, 1H), 6.00 (d, J=16.6 Hz, 1H), 5.85 (br d, J=9.8 Hz, 1H), 5.56 (q, J=6.6 Hz, 1H), 5.39 (br s, 1H), 4.97 (dd, J=9.8, 1.5 Hz, 1H), 4.05 (d, J=17.8 Hz, 1H), 4.05–3.96 (m, 2H), 3.70–3.48 (m, 4H), 3.10 (s, 3H), 3.09 (s, 3H), 3.00 (s, 3H), 2.39–1.20 (m, 8H), 2.24 (d, J=17.8 Hz, 1H), 1.94 (d, J=6.6 Hz, 3H), 1.78 (d, J=1.2 Hz, 3H), 1.68 (s, 3H)

FABMS m/z 802 $(M+H)^+$

HRFABMS calcd for $C_{38}H_{48}N_3O_{10}S_3$ $(M+H)^+$ 802.2502, found 802.2472

EXAMPLE 128
Synthesis of Compound 140

DC107 (26 mg, 0.051 mmol) was dissolved in dimethylformamide (0.50 ml), and 4-(chloromethyl)phenyl N-acetylhexahydroisonicotinate [a total amount of 4-(hydroxymethyl)phenyl N-acetylhexahydroisonicotinate (54 mg, 0.19 mmol) treated with thionyl chloride (0.50 ml)], N,N-diisopropylethylamine (0.10 ml) and potassium iodide (26 mg, 0.16 mmol) were added thereto, followed by stirring at 20° C. for 8 hours. After subjecting the mixture to the usual post-treatment, the mixture was purified by thin layer chromatography (developed with chloroform/methanol=20/1) to obtain Compound 140 (9.3 mg, 24% yield).

IR (KBr) 2933, 1751, 1718, 1655, 1618, 1508, 1458, 1273, 1167 $cm^{-1}$ $^1$H NMR ($CDCl_3$, 270 MHz) δ ppm; 8.44 (dd, J=11.4, 16.8 Hz, 1H), 7.35 (s, 1H), 7.28 (d, J=8.4 Hz, 2H), 6.98 (d, J=8.4 Hz, 2H), 6.59 (d, J=11.4 Hz, 1H), 6.25 (t, J=11.4 Hz, 1H), 6.17 (d, J=16.8 Hz, 1H), 5.71 (d, J=8.7 Hz, 1H), 5.44 (br s, 1H), 5.40 (q, J=6.9 Hz, 1H), 4.94 (dd, J=3.0, 8.7 Hz, 1H), 4.46 (br d, J=13.9 Hz, 1H), 4.01 (s, 2H), 3.90 (d, J=17.8 Hz, 1H), 3.79 (d, J=13.9 Hz, 1H), 3.76 (br d, J=3.0 Hz, 1H), 3.21 (ddd, J=3.0, 10.9, 13.9 Hz, 1H), 2.9–2.7 (m, 1H), 2.89 (ddd, J=3.0, 10.9, 13.9 Hz, 1H), 2.4–1.7 (m, 8H), 2.19 (d, J=17.8 Hz, 1H), 2.12 (s, 3H), 2.01 (d, J=6.9 Hz, 3H), 1.78 (s, 3H), 1.73 (s, 3H)

FABMS m/z 770 $(M+H)^+$

EXAMPLE 129
Synthesis of Compound 141

According to the procedure as described in Example 18, Compound 140 (20 mg, 0.026 mmol) was dissolved in dichloromethane (2.0 ml), and 3,4-dihydro-2H-pyran (0.050 ml) and camphorsulfonic acid (10 mg) were added thereto, followed by stirring at 20° C. for 5 hours. After subjecting the mixture to the usual post-treatment, the mixture was purified by thin layer chromatography (developed with chloroform/methanol=20/1) to obtain Compound 141 (20 mg, 89% yield). From $^1$H NMR, Compound 141 was found to be a mixture of diastereomers at a ratio of about 1:1.

IR (KBr) 1751, 1718, 1676, 1653, 1618, 1508, 1450, 1273, 1203, 1167, 1151, 1132, 1028, 980 $cm^{-1}$ $^1$H NMR ($CDCl_3$, 270 MHz) δ ppm; 9.60 (dd, J=11.4, 16.8 Hz) and 9.40 (dd, J=11.4, 16.8 Hz) (total 1H), 7.40 (s) and 7.39 (s) (total 1H), 7.30 (d, J=8.4 Hz, 2H), 7.00 (d, J=8.4 Hz, 2H), 6.61 (br d, J=11.4 Hz, 1H), 6.37 (t, J=11.4 Hz) and 6.34 (t, J=11.4 Hz) (total 1H), 6.04 (d, J=16.8 Hz) and 6.00 (d, J=16.8 Hz) (total 1H), 5.82 (br d, J=ca. 10 Hz) and 5.79 (br d, J=ca. 10 Hz) (total 1H), 5.58 (q, J=6.4 Hz) and 5.56 (q, J=6.4 Hz) (total 1H), 5.48 (s) and 5.45 (s) (total 1H), 5.02 (d, J=ca. 10 Hz) and 4.74 (br d, J=ca. 10 Hz) (total 1H), 4.70 (br s) and 4.56 (br s) (total 1H), 4.47 (br d, J=10.4 Hz, 1H), 4.03 (d, J=17.6 Hz) and 4.02 (d, J=17.6 Hz) (total 1H), 4.02 (s, 2H), 3.9–3.4 (m, 2H), 3.85 (br d, J=14.8 Hz, 1H), 3.21 (br t, J=11.4 Hz, 1H), 2.89 (br t, J=11.4 Hz, 1H), 2.80 (m, 1H), 2.4–1.4 (m, 14H), 2.21 (d, J=17.6 Hz) and 2.20 (d, J=17.6 Hz) (total 1H), 2.12 (s, 3H), 1.93 (d, J=6.4 Hz) and 1.87 (d, J=6.4 Hz) (total 3H), 1.76 (s) and 1.73 (s) (total 3H), 1.69 (s, 3H)

FABMS m/z 877 $(M+Na)^+$

EXAMPLE 130
Synthesis of Compound 142

According to the procedure as described in Example 18, Compound 140 (10 mg, 0.013 mmol) was dissolved in dichloromethane (1.0 ml), and 5,6-dihydro-4-methoxy-2H-pyran (0.030 ml) and camphorsulfonic acid (8.0 mg) were added thereto, followed by stirring at 0° C. for 0.5 hours.

After subjecting the mixture to the usual post-treatment, the mixture was purified by thin layer chromatography (developed with chloroform/methanol=20/1) to obtain Compound 142 (11 mg, 100% yield).

IR (KBr) 2930, 1750, 1716, 1676, 1647, 1618, 1508, 1450, 1271, 1167, 1144, 1109, 985 cm$^{-1}$ $^1$H NMR (CDCl$_3$, 270 MHz) δ ppm; 9.56 (dd, J=11.4, 16.8 Hz, 1H), 7.43 (s, 1H), 7.29 (d, J=8.7 Hz, 2H), 6.99 (d, J=8.7 Hz, 2H), 6.63 (d, J=11.9 Hz, 1H), 6.37 (t, J=11.7 Hz, 1H), 6.01 (d, J=16.8 Hz, 1H), 5.85 (d, J=9.7 Hz, 1H), 5.56 (q, J=6.7 Hz, 1H), 5.43 (s, 1H), 4.97 (dd, J=1.0, 9.7 Hz, 1H), 4.47 (br d, J=13.9 Hz, 1H), 4.05 (d, J=17.8 Hz, 1H), 4.01 (s, 2H), 3.85 (br d, J=13.9 Hz, 1H), 3.7–3.5 (m, 4H), 3.21 (ddd, J=2.5, 11.4, 13.9 Hz, 1H), 3.10 (s, 3H), 2.89 (ddd, J=2.5, 11.4, 13.9 Hz, 1H), 2.79 (m, 1H), 2.4–1.6 (m, 12H), 2.23 (d, J=17.8 Hz, 1H), 2.12 (s, 3H), 1.94 (d, J=6.7 Hz, 3H), 1.77 (d, J=1.0 Hz, 3H), 1.68 (s, 3H)

FABMS m/z 852 [(M—CH$_3$O)+H]$^+$

EXAMPLE 131
Synthesis of Compound 143

According to the procedure as described in Example 45, Compound 143 (32 mg, 74% yield) was obtained from Compound 35 (37 mg, 0.059 mmol), picolinic acid (22 mg, 0.18 mmol), 1-ethyl-3-(3-dimethylaminopropyl) carbodiimide hydrochloride (35 mg, 0.18 ml), dichloromethane (3 ml) and 4-dimethylaminopyridine (7 mg, 0.059 mmol).

IR (KBr) 3420, 3104, 2930, 1820, 1720, 1680, 1649, 1610, 1439, 1380, 1205, 1130, 970, 863, 747 cm$^{-1}$ $^1$H NMR (CDCl$_3$, 400 MHz) δ ppm; 9.19 (ddd, J=16.6, 11.5, 1.0 Hz, 1H), 8.68 (m, 1H), 8.04 (m, 1H), 7.73 (m, 1H), 7.42 (m, 1H), 7.41 (s, 1H), 6.62 (d, J=11.5 Hz, 1H), 6.34 (t, J=11.5 Hz, 1H), 6.12 (dd, J=16.6, 1.0 Hz, 1H), 6.07 (dd, J=9.5, 1.0 Hz, 1H), 5.88 (br d, J=9.5 Hz, 1H), 5.46 (q, J=6.6 Hz, 1H), 5.42 (br s, 1H), 3.99 (d, J=17.8 Hz, 1H), 3.82–3.74 (m, 2H), 2.48–1.52 (m, 4H), 2.27 (d, J=17.8 Hz, 1H), 2.15 (s, 3H), 1.91 (br s, 3H), 1.72 (s, 3H), 1.71 (d, J=6.6 Hz, 3H)

FABMS m/z 728 (M+H)$^+$

HRFABMS calcd for C$_{33}$H$_{34}$N$_3$O$_{10}$S$_3$ (M+H)$^+$ 728.1406, found 728.1408

EXAMPLE 132
Synthesis of Compound 144

According to the procedure as described in Example 45, Compound 144 (26 mg, 56% yield) was obtained from Compound 35 (40 mg, 0.064 mmol), nicotinic acid (23 mg, 0.19 mmol), 1-ethyl-3-(3-dimethylaminopropyl) carbodiimide hydrochloride (37 mg, 0.19 mmol), dichloromethane (3 ml) and 4-dimethylaminopyridine (8 mg, 0.064 mmol).

IR (KBr) 3400, 3200, 2932, 1820, 1720, 1680, 1649, 1610, 1589, 1422, 1380, 1270, 1205, 1100, 971, 863, 768, 740, 701 cm$^{-1}$ $^1$H NMR (CDCl$_3$, 400 MHz) δ ppm; 9.35 (ddd, J=16.6, 11.5, 1.0 Hz, 1H), 9.17 (m, 1H), 8.73 (dd, J=4.9 Hz, 1H), 8.26 (ddd, J=7.8, 2.2, 1.7 Hz, 1H), 7.45 (s, 1H), 7.34 (ddd, J=7.8, 4.9, 1.0 Hz, 1H), 6.65 (d, J=11.5 Hz, 1H), 6.36 (t, J=11.5 Hz, 1H), 6.10 (d, J=16.6 Hz, 1H), 6.09 (dd, J=9.5, 1.0 Hz, 1H), 5.92 (br d, J=9.5 Hz, 1H), 5.47 (q, J=6.6 Hz, 1H), 5.44 (br s, 1H), 4.01 (d, J=17.6 Hz, 1H), 3.78 (br s, 2H), 2.50–1.50 (m, 4H), 2.28 (d, J=17.6 Hz, 1H), 2.14 (s, 3H), 1.90 (d, J=1.2 Hz, 3H), 1.71 (s, 3H), 1.66 (d, J=6.6 Hz, 3H)

FABMS m/z 728 (M+H)$^+$

HRFABMS calcd for C$_{33}$H$_{34}$N$_3$O$_{10}$S$_3$ (M+H)$^+$ 728.1406, found 728.1414

EXAMPLE 133
Synthesis of Compound 145

According to the procedure as described in Example 45, Compound 145 (26 mg, 54% yield) was obtained from Compound 35 (42 mg, 0.067 mmol), 2-pyrazinecarboxylic acid (25 mg, 0.20 mmol), 1-ethyl-3-(3-dimethylaminopropyl)carbodiimide hydrochloride (39 mg, 0.20 ml), dichloromethane (8 ml) and 4-dimethylaminopyridine (1.7 mg, 0.013 mmol).

IR (KBr) 3420, 2930, 1819, 1717, 1678, 1609, 1448, 1395, 1374, 1270, 1208, 1133, 1047, 1017, 978, 864, 769 cm$^{-1}$ $^1$H NMR (CDCl$_3$, 400 MHz) δ ppm; 9.25 (d, J=1.5 Hz, 1H), 9.23 (ddd, J=16.6, 11.2, 1.0 Hz, 1H), 8.72 (d, J=2.7 Hz, 1H), 8.69 (dd, J=2.7, 1.5 Hz, 1H), 7.44 (s, 1H), 6.65 (d, J=11.5 Hz, 1H), 6.35 (dd, J=11.5, 11.2 Hz, 1H), 6.14 (dd, J=16.6, 1.0 Hz, 1H), 6.13 (d, J=9.5 Hz, 1H), 5.93 (br d, J=9.5 Hz, 1H), 5.49 (q, J=6.6 Hz, 1H), 5.40 (br s, 1H), 4.02 (d, J=17.5 Hz, 1H), 3.79 (s, 2H), 2.50–1.50 (m, 4H), 2.29 (d, J=17.5 Hz, 1H), 2.16 (s, 3H), 1.92 (d, J=1.0 Hz, 3H), 1.74 (d, J=6.0 Hz, 3H), 1.74 (s, 3H)

FABMS m/z 729 (M+H)$^+$

HRFABMS calcd for C$_{32}$H$_{33}$N$_3$O$_{10}$S$_3$ (M+H)$^+$ 729.1359, found 729.1377

EXAMPLE 134
Synthesis of Compound 146

Compound 35 (40 mg, 0.064 mmol) and phthalic anhydride (28 mg, 0.19 mmol) were dissolved in dichloromethane (4 ml), and 4-dimethylaminopyridine (23 mg, 0.19 mmol) was added thereto, followed by stirring at room temperature for 4 hours. After subjecting the mixture to the usual post-treatment, the mixture was purified by thin layer chromatography (developed with chloroform/methanol=95/5) to obtain Compound 146 (16 mg, 32% yield).

IR (KBr) 3420, 2928, 1820, 1720, 1680, 1648, 1610, 1448, 1380, 1250, 1205, 1071, 977, 748 cm$^{-1}$ $^1$H NMR (CDCl$_3$, 400 MHz) δ ppm; 9.18 (br dd, J=16.6, 11.2 Hz, 1H), 7.83–7.30 (m, 4H), 7.37 (s, 1H), 6.60 (d, J=11.5 Hz, 1H), 6.31 (dd, J=11.5, 11.2 Hz, 1H), 6.07 (d, J=16.6 Hz, 1H), 5.96 (br d, J=9.3 Hz, 1H), 5.78 (br d, J=9.3 Hz, 1H), 5.39 (q, J=6.5 Hz, 1H), 3.99 (d, J=17.8 Hz, 1H), 3.74 (br s, 2H), 2.50–1.60 (m, 4H), 2.26 (d, J=17.8 Hz, 1H), 2.12 (s, 3H), 1.75 (br s, 3H), 1.64 (s, 3H), 1.45 (br d, J=6.5 Hz, 3H)

FABMS m/z 771 (M+H)$^+$

HRFABMS calcd for C$_{35}$H$_{35}$N$_2$O$_{12}$S$_3$ (M+H)$^+$ 771.1352, found 771.1382

EXAMPLE 135
Synthesis of Compound 147

According to the procedure as described in Example 45, Compound 147 (28 mg, 47% yield) was obtained from Compound 35 (50 mg, 0.080 mmol), 3-pyridylacetic acid hydrochloride (42 mg, 0.24 mmol), 1-ethyl-3-(3-dimethylaminopropyl)carbodiimide hydrochloride (46 mg, 0.24 mmol), dichloromethane (4 ml) and 4-dimethylaminopyridine (10 mg, 0.080 mmol).

IR (KBr) 3400, 2932, 1810, 1720, 1680, 1611, 1429, 1370, 1265, 978, 862, 769 cm$^{-1}$ $^1$H NMR (CDCl$_3$, 400 MHz) δ ppm; 9.06 (ddd, J=16.6, 11.5, 1.0 Hz, 1H), 8.43 (dd, J=4.9, 1.5 Hz, 1H), 8.39 (d, J=2.0 Hz, 1H), 7.56 (ddd, J=7.3, 4.9, 2.0 Hz, 1H), 7.43 (s, 1H), 7.15 (dd, J=7.3, 4.9 Hz, 1H), 6.60 (d, J=11.5 Hz, 1H), 6.25 (t, J=11.5 Hz, 1H), 5.96 (d, J=16.6 Hz, 1H), 5.76 (br d, J=9.3 Hz, 1H), 5.71 (dd, J=9.3, 1.0 Hz, 1H), 5.60 (br s, 1H), 5.57 (q, J=6.6 Hz, 1H), 4.03 (d, J=17.8 Hz, 1H), 3.77 (br s, 2H), 3.61 (br s, 2H), 2.46–1.55 (m, 4H), 2.30 (d, J=17.8 Hz, 1H), 2.14 (s, 3H), 1.94 (d, J=6.6 Hz, 3H), 1.77 (d, J=1.0 Hz, 3H), 1.69 (s, 3H)

FABMS m/z 742 (M+H)$^+$

HRFABMS calcd for $C_{34}H_{36}N_3O_{10}S_3$ (M+H)$^+$ 742.1563, found 742.1591

EXAMPLE 136
Synthesis of Compound 148

According to the procedure as described in Example 45, Compound 148 (41 mg, 61% yield) was obtained from Compound 35 (51 mg, 0.081 mmol), N-Boc-L-proline (350 mg, 1.63 mmol), 1-ethyl-3-(3-dimethylaminopropyl)carbodiimide hydrochloride (311 mg, 1.63 mmol), dichloromethane (5 ml) and 4-dimethylaminopyridine (6 mg, 0.049 mmol).

IR (KBr) 3420, 2970, 1821, 1735, 1685, 1400, 1369, 1263, 1208, 1161, 1120, 1089, 977 cm$^{-1}$ $^1$H NMR (CDCl$_3$, 500 MHz) δ ppm; major isomer 8.91 (dd, J=16.5, 11.3 Hz, 1H), 7.40 (s, 1H), 6.60 (d, J=11.3 Hz, 1H), 6.27 (dd, J=11.3, 11.3 Hz, 1H), 6.03 (d, J=16.5 Hz, 1H), 5.77 (br s, 2H), 5.53 (q, J=6.7 Hz, 1H), 5.43 (br s, 1H), 4.25 (dd, J=8.7, 3.5 Hz, 1H), 3.98 (d, J=17.8 Hz, 1H), 3.78 (d, J=15.6 Hz, 1H), 3.76 (d, J=15.6 Hz, 1H), 3.51–3.30 (m, 2H), 2.38–1.40 (m, 8H), 2.32 (d, J=14.8 Hz, 1H), 2.14 (s, 3H), 1.96 (d, J=6.7 Hz, 3H), 1.78 (s, 3H), 1.70 (s, 3H), 1.36 (s, 9H); minor isomer (main peaks); 8.83 (dd, J=16.5, 11.3 Hz, 1H), 7.37 (s, 1H), 6.58 (d, J=11.3 Hz, 1H), 6.29 (dd, J=11.3, 11.3 Hz, 1H), 6.04 (d, J=16.5 Hz, 1H), 5.73 (br, 2H), 4.33 (m, 1H), 1.42 (s, 9H)

FABMS m/z 820 (M+H)$^+$

HRFABMS calcd for $C_{37}H_{46}N_3O_{12}S_3$ (M+H)$^+$ 820.2243, found 820.2251

EXAMPLE 137
Synthesis of Compound 149

According to the procedure as described in Example 45, Compound 149 (23 mg, 42% yield) was obtained from Compound 35 (46 mg, 0.074 mmol), pyroglutamic acid (47 mg, 0.37 mmol), 1-ethyl-3-(3-dimethylaminopropyl)carbodiimide hydrochloride (71 mg, 0.37 mmol), dichloromethane (5 ml) and 4-dimethylaminopyridine (9 mg, 0.074 mmol).

IR (KBr) 3400, 3220, 2932, 1813, 1740, 1720, 1680, 1649, 1610, 1450, 1377, 1260, 1200, 1105, 977, 863, 769 cm$^{-1}$ $^1$H NMR (CDCl$_3$, 400 MHz) δ ppm; 8.94 (dd, J=16.6, 11.5 Hz, 1H), 7.44 (s, 1H), 6.65 (d, J=11.7 Hz, 1H), 6.31 (dd, J=11.7, 11.5 Hz, 1H), 6.02 (d, J=16.6 Hz, 1H), 5.91 (br s, 1H), 5.74 (br s, 2H), 5.56 (q, J=6.6 Hz, 1H), 5.41 (br s, 1H), 4.25–4.20 (m, 1H), 3.99 (d, J=17.6 Hz, 1H), 3.83–3.70 (m, 2H), 2.48–1.60 (m, 8H), 2.32 (d, J=17.6 Hz, 1H), 2.14 (s, 3H), 1.94 (d, J=6.6 Hz, 3H), 1.79 (s, 3H), 1.71 (s, 3H)

FABMS m/z 734 (M+H)$^+$

HRFABMS calcd for $C_{32}H_{36}N_3O_{11}S_3$ (M+H)$^+$ 734.1512, found 734.1541

EXAMPLE 138
Synthesis of Compound 150

Compound 35 (50 mg, 0.080 mmol) and phthalic anhydride (32 mg, 0.32 mmol) were dissolved in dichloromethane (4 ml), and 4-dimethylaminopyridine (10 mg, 0.080 mmol) was added thereto, followed by stirring at room temperature for 10 hours. After subjecting the mixture to the usual post-treatment, the mixture was purified by thin layer chromatography (developed with chloroform/methanol=95/5) to obtain Compound 150 (35 mg, 61% yield).

IR (KBr) 3400, 2936, 1820, 1735, 1670, 1609, 1372, 979, 755 cm$^{-1}$ $^1$H NMR (CDCl$_3$, 400 MHz) δ ppm; 9.20 (dd, J=16.6, 11.5 Hz, 1H), 7.42 (s, 1H), 6.62 (d, J=11.5 Hz, 1H), 6.32 (t, J=11.5 Hz, 1H), 6.00 (d, J=16.6 Hz, 1H), 5.77 (br d, J=9.4 Hz, 1H), 5.72 (d, J=9.4 Hz, 1H), 5.58 (q, J=6.6 Hz, 1H), 4.05 (d, J=17.6 Hz, 1H), 3.78 (br s, 2H), 2.74–1.48 (m, 8H), 2.30 (d, J=17.6 Hz, 1H), 2.14 (s, 3H), 1.93 (d, J=6.6 Hz, 3H), 1.78 (br s, 3H), 1.67 (s, 3H)

FABMS m/z 723 (M+H)$^+$

HRFABMS calcd for $C_{31}H_{35}N_2O_{12}S_3$ (M+H)$^+$ 723.1352, found 723.1378

EXAMPLE 139
Synthesis of Compound 151

Compound 35 (35 mg, 0.056 mmol) was dissolved in dichloromethane (3 ml), and pyridine (0.20 ml, 0.28 mmol) and methylmalonyl chloride (0.009 ml, 0.084 mmol) were added thereto, followed by stirring at room temperature for 50 minutes. After subjecting the mixture to the usual post-treatment, the mixture was purified by thin layer chromatography (developed with chloroform/methanol=97/3) to obtain Compound 151 (12 mg, 29% yield).

IR (KBr) 3420, 2934, 1814, 1720, 1680, 1648, 1609, 1438, 1260, 1205, 1145, 977, 768 cm$^{-1}$ $^1$H NMR (CDCl$_3$, 400 MHz) δ ppm; 9.18 (ddd, J=16.6, 11.5, 1.0 Hz, 1H), 7.42 (s, 1H), 6.62 (d, J=11.5 Hz, 1H), 6.34 (t, J=11.5 Hz, 1H), 6.03 (d, J=16.6 Hz, 1H), 5.57 (br d, J=9.3 Hz, 1H), 5.73 (dd, J=9.3, 1.0 Hz, 1H), 5.57 (q, J=6.6 Hz, 1H), 5.42 (br s, 1H), 4.03 (d, J=17.6 Hz, 1H), 3.78 (br s, 2H), 3.63 (s, 3H), 3.35 (br s, 2H), 2.47–1.45 (m, 4H), 2.28 (d, J=17.6 Hz, 1H), 2.14 (s. 3H), 1.88 (d, J=6.6 Hz, 3H), 1.79 (d, J=1.0 Hz, 3H), 1.71 (s, 3H)

FABMS m/z 723 (M+H)$^+$

HRFABMS calcd for $C_{31}H_{35}N_2O_{12}S_3$ (M+H)$^+$ 723.1352, found 723.1322

EXAMPLE 140
Synthesis of Compound 152

According to the procedure as described in Example 45, tert-butyl ester of Compound 151 (30 mg, 41% yield) was obtained from Compound 35 (60 mg, 0.096 mmol), mono-tert-butyl malonate (77 mg, 0.48 mmol), 1-ethyl-3-(3-dimethylaminopropyl)carbodiimide hydrochloride (92 mg, 0.48 mmol), dichloromethane (3 ml) and 4-dimethylaminopyridine (12 mg, 0.096 mmol).

The obtained tert-butyl ester (26 mg, 0.034 mmol) was dissolved in dichloromethane (4 ml), and trifluoroacetic acid (0.5 ml) was added thereto, followed by stirring at room temperature for 40 minutes. After condensing the reaction mixture, the mixture was purified by thin layer chromatography (developed with ether/methanol=9/1) to obtain Compound 152 (7.5 mg, 31% yield).

IR (KBr) 3420, 2930, 1819, 1720, 1680, 1609, 1380, 1260, 1204, 977, 770 cm$^{-1}$ $^1$H NMR (CDCl$_3$+CD$_3$OD, 400 MHz) δ ppm; 8.99 (dd, J=16.6, 11.5 Hz, 1H), 7.42 (s, 1H), 6.61 (d, J=11.5 Hz, 1H), 6.26 (t, J=11.5 Hz, 1H), 6.00 (d, J=16.6 Hz, 1H), 5.75 (br d, J=9.5 Hz, 1H), 5.71 (br d, J=9.5 Hz, 1H), 5.50 (q, J=6.8 Hz, 1H), 4.03 (d, J=17.6 Hz, 1H), 3.75 (br s, 2H), 3.27 (br, 2H), 2.54–1.45 (m, 4H), 2.31 (d, J=17.6 Hz, 1H), 2.13 (s, 3H), 1.90 (d, J=6.6 Hz, 3H), 1.74 (s, 3H), 1.61 (s, 3H)

FABMS m/z 709 (M+H)$^+$

HRFABMS calcd for $C_{30}H_{33}N_2O_{12}S_3$ (M+H)$^+$ 709.1195, found 709.1184

EXAMPLE 141
Synthesis of Compound 153

According to the procedure as described in Example 45, Compound 153 (43 mg, 48% yield) was obtained from Compound 35 (70 mg, 0.11 mmol), p-methoxybenzyloxyacetic acid (66 mg, 0.34 mmol), 1-ethyl-3-(3-dimethylaminopropyl)carbodiimide hydrochloride (65 mg, 0.34 mmol), dichloromethane (5 ml) and 4-dimethylaminopyridine (14 mg, 0.11 mmol).

IR (KBr) 3400, 3294, 2938, 1820, 1720, 1680, 1647, 1608, 1513, 1443, 1378, 1250, 1110, 971, 815, 768, 730 cm$^{-1}$ $^1$H NMR (CDCl$_3$, 400 MHz) δ ppm; 9.17 (ddd, J=16.6, 11.5, 1.0 Hz, 1H), 7.41 (s, 1H), 7.20–7.15 (m, 2H), 6.82–6.75 (m, 2H), 6.61 (d, J=11.5 Hz, 1H), 6.32 (t, J=11.5 Hz, 1H), 6.05 (d, J=16.6 Hz, 1H), 5.77 (br s, 2H), 5.54 (q, J=6.6 Hz, 1H), 5.41 (br s, 1H), 4.50 (d, J=11.4 Hz, 1H), 4.48 (d, J=11.4 Hz, 1H), 4.03 (bs, 2H), 4.02 (d, J=17.8 Hz, 1H), 3.78 (s, 3H), 3.77 (br s, 2H), 2.46–1.45 (m, 4H), 2.27 (d, J=17.8 Hz, 1H), 2.14 (s, 3H), 1.82 (d, J=6.6 Hz, 3H), 1.79 (s, 3H), 1.71 (s, 3H)

FABMS m/z 801 (M+H)$^+$

HRFABMS calcd for C$_{37}$H$_{41}$N$_2$O$_{12}$S$_3$ (M+H)$^+$ 801.1821, found 801.1808

EXAMPLE 142
Synthesis of Compound 154

Compound 153 (40 mg, 0.050 mmol) obtained in Example 141 was dissolved in dichloromethane (3 ml), and 2,3-dichloro-5,6-dicyano-p-benzoquinone (86 mg, 0.44 mmol) and water (0.2 ml) were added thereto, followed by stirring at room temperature for 24 hours. After subjecting the mixture to the usual post-treatment, the mixture was purified by thin layer chromatography (developed with chloroform/methanol=97/3) to obtain Compound 154 (20 mg, 59% yield).

IR (KBr) 3420, 2932, 1816, 1720, 1680, 1648, 1609, 1440, 1375, 1266, 1195, 1075, 976, 863, 768 cm$^{-1}$ $^1$H NMR (CDCl$_3$, MHz) δ ppm; 9.19 (ddd, J=16.6, 11.5, 1.0 Hz, 1H), 7.43 (s, 1H), 6.63 (d, J=11.5 Hz, 1H), 6.32 (t, J=11.5 Hz, 1H), 6.04 (d, J=16.6 Hz, 1H), 5.78 (br s, 2H), 5.58 (q, J=6.6 Hz, 1H), 5.39 (br s, 1H), 5.12 (d, J=5.6 Hz, 2H), 4.02 (d, J=17.6 Hz, 1H), 3.78 (br s, 2H), 2.50–1.45 (m, 4H), 2.31 (d, J=5.6 Hz, 1H), 2.29 (d, J=17.6 Hz, 1H), 2.14 (s, 3H), 1.88 (d, J=6.6 Hz, 3H), 1.80 (s, 3H), 1.71 (s, 3H)

FABMS m/z 681 (M+H)$^+$

HRFABMS calcd for C$_{29}$H$_{33}$N$_2$O$_{11}$S$_3$ (M+H)$^+$ 681.1246, found 681.1230

EXAMPLE 143
Synthesis of Compound 155

According to the procedure as described in Example 28, Compound 155 (11 mg, 30% yield) was obtained from Compound 35 (30 mg, 0.048 mmol), dichloromethane (2.0 ml), N,N-diisopropylethylamine (0.084 ml, 0.48 mmol) and 2-(2-methoxyethoxy)ethoxymethyl chloride (81 mg, 0.48 mmol).

IR (KBr) 3420, 2930, 1818, 1705, 1685, 1644, 1608, 1451, 1261, 1207, 1093, 1022, 970, 769 cm$^{-1}$ $^1$H NMR (CDCl$_3$, 400 MHz) δ ppm; 9.48 (ddd, J=16.6, 11.5, 1.0 Hz, 1H), 7.40 (s, 1H), 6.61 (d, J=11.5 Hz, 1H), 6.35 (t, J=11.5 Hz, 1H), 6.01 (d, J=16.6 Hz, 1H), 5.81 (br d, J=9.3 Hz, 1H), 5.57 (q, J=6.6 Hz, 1H), 5.50 (br s, 1H), 4.83 (dd, J=9.3, 1.2 Hz, 1H), 4.71 (d, J=6.8 Hz, 1H), 4.69 (d, J=6.8 Hz, 1H), 4.03 (d, J=17.6 Hz, 1H), 3.78 (br s, 2H), 3.70–3.48 (m, 8H), 3.36 (s, 3H), 2.45–1.42 (m, 4H), 2.28 (d, J=17.6 Hz, 1H), 2.15 (s, 3H), 1.88 (d, J=6.6 Hz, 3H), 1.75 (d, J=1.2 Hz, 3H), 1.70 (s, 3H)

FABMS m/z 755 (M+H)$^+$

HRFABMS calcd for C$_{33}$H$_{43}$N$_2$O$_{12}$S$_3$ (M+H)$^+$ 755.1978, found 755.1984

EXAMPLE 144
Synthesis of Compound 156

According to the procedure as described in Example 45, Compound 156 (32 mg, 47% yield) was obtained from Compound 35 (54 mg, 0.086 mmol), N-Boc-glycine (60 mg, 0.34 mmol), 1-ethyl-3-(3-dimethylaminopropyl) carbodiimide hydrochloride (66 mg, 0.34 mmol), dichloromethane (5 ml) and 4-dimethylaminopyridine (3.1 mg, 0.025 mmol).

IR (KBr) 3420, 2936, 1820, 1755, 1708, 1694, 1647, 1610, 1448, 1368, 1259, 1161, 977, 769 cm$^{-1}$ $^1$H NMR (CDCl$_3$, 400 MHz) δ ppm; 9.23 (dd, J=16.6, 11.5, 1H), 7.43 (s, 1H), 6.63 (d, J=11.5 Hz, 1H), 6.32 (t, J=11.5 Hz, 1H), 6.02 (d, J=16.6 Hz, 1H), 5.77 (br d, J=9.5 Hz, 1H), 5.72 (d, J=9.5 Hz, 1H), 5.58 (q, J=6.6 Hz, 1H), 5.42 (br s, 1H), 4.96 (br, 1H), 4.03 (d, J=17.5 Hz, 1H), 3.96 (br dd, J=18.5, 6.6 Hz, 1H), 3.83 (dd, J=18.5, 5.1 Hz, 1H), 3.78 (br s, 2H), 2.50–2.22 (m, 3H), 2.29 (d, J=17.5 Hz, 1H), 2.14 (s, 3H), 1.91 (d, J=6.6 Hz, 3H), 1.79 (d, J=1.0 Hz, 3H), 1.71 (s, 3H), 1.55–1.42 (m, 1H), 1.40 (s, 9H)

FABMS m/z 780 (M+H)$^+$

HRFABMS calcd for C$_{34}$H$_{42}$N$_3$O$_{12}$S$_3$ (M+H)$^+$ 780.1930, found 780.1926

EXAMPLE 145
Synthesis of Compound 157

According to the procedure as described in Example 45, Compound 157 (36 mg, 54% yield) was obtained from Compound 35 (50 mg, 0.080 mmol), N-Cbz-glycine (84 mg, 0.40 mmol), 1-ethyl-3-(3-dimethylaminopropyl) carbodiimide hydrochloride (77 mg, 0.40 mmol), dichloromethane (5 ml) and 4-dimethylaminopyridine (3 mg, 0.025 mmol).

IR (KBr) 3400, 2940, 1821, 1722, 1692, 1650, 1610, 1527, 1453, 1371, 1265, 1207, 1178, 1055, 981, 770 cm$^{-1}$ $^1$H NMR (CDCl$_3$, 400 MHz) δ ppm; 9.19 (dd, J=16.5, 11.2 Hz, 1H), 7.41 (s, 1H), 7.39–7.25 (m, 5H), 6.61 (d, J=11.4 Hz, 1H), 6.31 (dd, J=11.4, 11.2 Hz, 1H), 6.02 (d, J=16.5 Hz, 1H), 5.81–5.70 (m, 2H), 5.57 (q, J=6.6 Hz, 1H), 5.41 (br s, 1H), 5.21 (br s, 1H), 5.07 (br s, 2H), 4.02 (d, J=17.7 Hz, 1H), 4.07–3.85 (m, 2H), 3.78 (br s, 2H), 2.50–2.01 (m, 3H), 2.29 (d, J=17.7 Hz, 1H), 2.14 (s, 3H), 1.91 (d, J=6.6 Hz, 3H), 1.79 (s, 3H), 1.71 (s, 3H), 1.55–1.47 (m, 1H)

FABMS m/z 814 (M+H)$^+$

HRFABMS calcd for C$_{37}$H$_{40}$N$_3$O$_{12}$S$_3$ (M+H)$^+$ 814.1774, found 814.1766

EXAMPLE 146
Synthesis of Compound 158

According to the procedure as described in Example 45, Compound 158 (25 mg, 60% yield) was obtained from Compound 35 (30 mg, 0.047 mmol), Fmoc-glycine (19 mg, 0.094 mmol), 1-ethyl-3-(3-dimethylaminopropyl) carbodiimide hydrochloride (18 mg, 0.094 mmol), dichloromethane (3.5 ml) and 4-dimethylaminopyridine (1.0 mg, 0.008 mmol).

IR (KBr) 3406, 2930, 1819, 1725, 1685, 1609, 1518, 1450, 1390, 1374, 1261, 1204, 1182, 1104, 1051, 979, 760, 740 cm$^{-1}$ $^1$H NMR (CDCl$_3$, 400 MHz) δ ppm; 9.19 (dd, J=16.6, 11.7 Hz, 1H), 7.75 (d, J=7.5 Hz, 2H), 7.55 (d, J=7.2 Hz, 2H), 7.41 (s, 1H), 7.38 (dd, J=7.5, 7.2 Hz, 2H), 7.30 (dd, J=7.5, 7.2 Hz, 2H), 6.61 (d, J=11.5 Hz, 1H), 6.31 (dd, J=11.7, 11.5 Hz, 1H), 6.03 (d, J=16.6 Hz, 1H), 5.77 (s, 2H), 5.58 (q, J=6.6 Hz, 1H), 5.40 (br s, 1H), 5.23 (br, 1H), 4.35 (d, J=7.2 Hz, 2H), 4.18 (t, J=7.2 Hz, 1H), 4.04 (dd, J=18.5, 5.8 Hz, 1H), 4.02 (d, J=17.5 Hz, 1H), 3.92 (dd, J=18.5, 4.7 Hz, 1H), 3.78

(s, 2H), 2.58–1.50 (m, 4H), 2.29 (d, J=17.5 Hz, 1H), 2.14 (s, 3H), 1.91 (d, J=6.6 Hz, 3H), 1.80 (s, 3H), 1.71 (s, 3H)

FABMS m/z 902 (M+H)$^+$

HRFABMS calcd for $C_{44}H_{44}N_3O_{12}S_3$ (M+H)$^+$ 902.2087, found 902.2072

EXAMPLE 147
Synthesis of Compound 159

According to the procedure as described in Example 45, Compound 159 (16 mg, 35% yield) was obtained from Compound 35 (40 mg, 0.064 mmol), N-formylglycine (67 mg, 0.64 mmol), 1-ethyl-3-(3-dimethylaminopropyl)carbodiimide hydrochloride (123 mg, 0.64 mmol), dichloromethane (8 ml) and 4-dimethylaminopyridine (4.6 mg, 0.038 mmol).

IR (KBr) 3400, 2986, 2932, 1818, 1750, 1677, 1610, 1516, 1443, 1376, 1266, 1206, 1186, 1108, 1094, 976, 859, 807, 768, 731, 669 cm$^{-1}$ $^1$H NMR (CDCl$_3$, 400 MHz) δ ppm; 9.19 (ddd, J=16.6, 11.2, 1.0 Hz, 1H), 8.19 (d, J=1.0 Hz, 1H), 7.45 (s, 1H), 6.65 (d, J=11.5 Hz, 1H), 6.33 (dd, J=11.5, 11.2 Hz, 1H), 6.08 (br, 1H), 6.04 (d, J=16.6 Hz, 1H), 5.79 (br d, J=9.5 Hz, 1H), 5.77 (dd, J=9.5, 1.0 Hz, 1H), 5.59 (q, J=6.6 Hz, 1H), 5.41 (br s, 1H), 4.16 (dd, J=18.5, 5.6, 1.0 Hz, 1H), 4.02 (d, J=17.8 Hz, 1H), 4.00 (ddd, J=18.5, 4.6, 1.0 Hz, 1H), 3.79 (br s, 2H), 2.50–2.25 (m, 3H), 2.32 (d, J=17.8 Hz, 1H), 2.16 (s, 3H), 1.93 (s, J=6.6 Hz, 3H), 1.81 (d, J=1.0 Hz, 3H), 1.72 (s, 3H), 1.61–1.50 (m, 1H)

FABMS m/z 708 (M+H)$^+$

HRFABMS calcd for $C_{30}H_{34}N_3O_{11}S_3$ (M+H)$^+$ 708.1355, found 708.1373

EXAMPLE 148
Synthesis of Compound 160

According to the procedure as described in Example 45, Compound 160 (22 mg, 32% yield) was obtained from Compound 35 (59 mg, 0.1095 mmol), N-acetylglycine (166 mg, 1.4 mmol), 1-ethyl-3-(3-dimethylaminopropyl)carbodiimide hydrochloride (273 mg, 1.4 mmol), dichloromethane (12 ml) and 4-dimethylaminopyridine (10 mg, 0.085 mmol).

IR (KBr) 3394, 2932, 1820, 1720, 1678, 1609, 1534, 1447, 1376, 1266, 1206, 1108, 1035, 978, 768 cm$^{-1}$ $^1$H NMR (CDCl$_3$, 400 MHz) δ ppm; 9.21 (ddd, J=1608, 11.5, 1.0 Hz, 1H), 7.43 (s, 1H), 6.63 (d, J=11.5 Hz, 1H), 6.32 (t, J=11.5 Hz, 1H), 6.02 (dd, J=1.0, 16.8 Hz, 1H), 5.91 (m, 1H), 5.79 (br d, J=9.5 Hz, 1H), 5.74 (dd, J=9.5, 1.0 Hz, 1H), 5.57 (q, J=6.6 Hz, 1H), 5.43 (br s, 1H), 4.08 (dd, J=18.5, 5.4 Hz, 1H), 4.02 (d, J=17.6 Hz, 1H), 3.93 (dd, J=18.5, 4.7 Hz, 1H), 3.77 (br s, 2H), 2.48–1.50 (m, 4H), 2.29 (d, J=17.6 Hz, 1H), 2.14 (s, 3H), 1.98 (s, 3H), 1.90 (d, J=6.6 Hz, 3H), 1.79 (d, J=1.0 Hz, 3H), 1.70 (s, 3H)

FABMS m/z 722 (M+H)$^+$

HRFABMS calcd for $C_{31}H_{36}N_3O_{11}S_3$ (M+H)$^+$ 722.1512, found 722.1508

EXAMPLE 149
Synthesis of Compound 161

According to the procedure as described in Example 45, Compound 161 (46 mg, 72% yield) was obtained from Compound 35 (50 mg, 0.080 mmol), N-Boc-sarcosine (46 mg, 0.24 mmol), 1-ethyl-3-(3-dimethylaminopropyl)carbodiimide hydrochloride (45 mg, 0.24 mmol), dichloromethane (3 ml) and 4-dimethylaminopyridine (10 mg, 0.080 mmol).

IR (KBr) 3420, 2932, 1820, 1720, 1680, 1657, 1612, 1452, 1367, 1260, 1140, 977, 879, 769, 731 cm$^{-1}$ $^1$H NMR (CDCl$_3$, 400 MHz) δ ppm; 9.20–9.06 (m, 1H), 7.41 (s, 1H), 6.61 (d, J=11.5 Hz, 1H), 6.03 (br d, J=16.6 Hz, 1H), 5.80–5.70 (m, 2H), 5.57 (q, J=6.6 Hz, 1H), 5.44, 5.41 (br s, 1H), 4.20–3.75 (m, 3H), 3.77 (br s, 2H), 2.86, 2.84 (br s, 3H), 2.45–1.50 (m, 5H), 2.14 (s, 3H), 1.93 (d, J=6.6 Hz, 3H), 1.79 (s, 3H), 1.71 (s, 3H), 1.43, 1.37 (s, 9H)

FABMS m/z 794 (M+H)$^+$

HRFABMS calcd for $C_{35}H_{44}N_3O_{12}S_3$ (M+H)$^+$ 794.2087, found 794.2097

EXAMPLE 150
Synthesis of Compound 162

According to the procedure as described in Example 45, Compound 162 (49 mg, 73% yield) was obtained from Compound 35 (51 mg, 0.081 mmol), N-Cbz-sarcosine (189 mg, 0.81 mmol), 1-ethyl-3-(3-dimethylaminopropyl)carbodiimide hydrochloride (156 mg, 0.81 mmol), dichloromethane (6 ml) and 4-dimethylaminopyridine (6 mg, 0.048 mmol).

IR (KBr) 3420, 2934, 1819, 1750, 1705, 1690, 1609, 1451, 1400, 1364, 1263, 1206, 1149, 1115, 977, 769, 698 cm$^{-1}$ $^1$H NMR (CDCl$_3$, 500 MHz) δ ppm; major isomer 9.14 (dd, J=16.7, 11.3 Hz, 1H), 7.41 (s, 1H), 7.38–7.22 (m, 5H), 6.61 (d, J=11.6 Hz, 1H), 6.32 (dd, J=11.6, 11.3 Hz, 1H), 6.04 (d, J=16.7 Hz, 1H), 5.77 (br s, 2H), 5.57 (q, J=6.7 Hz, 1H), 5.43 (br s, 1H), 5.09 (s, 2H), 4.17 (d, J=17.7 Hz, 1H), 4.02 (d, J=17.7 Hz, 1H), 3.90 (d, J=17.7 Hz, 1H), 3.77 (br s, 2H), 2.94 (s, 3H), 2.46–1.95 (m, 3H), 2.29 (d, J=17.7 Hz, 1H), 2.14 (s, 3H), 1.93 (d, J=6.6 Hz, 3H), 1.79 (s, 3H), 1.71 (s, 3H), 1.62–1.48 (m, 1H); minor isomer 9.06 (dd, J=16.5, 11.3 Hz, 1H), 7.41 (s, 1H), 7.38–7.22 (m, 5H), 6.58 (d, J=11.6 Hz, 1H), 6.23 (dd, J=11.6, 11.3 Hz, 1H), 5.97 (d, J=16.5 Hz, 1H), 5.72 (s, 2H), 5.54 (q, J=6.7 Hz, 1H), 5.40 (br s, 1H), 5.07 (br s, 2H), 4.01 (d, J=17.7 Hz, 1H), 3.98 (d, J=17.7 Hz, 1H), 3.94 (d, J=17.7 Hz, 1H), 3.77 (br s, 2H), 2.95 (s, 3H), 2.46–1.95 (m, 3H), 2.28 (d, J=17.7 Hz, 1H), 2.14 (s, 3H), 1.87 (d, J=6.6 Hz, 3H), 1.74 (s, 3H), 1.70 (s, 3H), 1.62–1.48 (m, 1H)

FABMS m/z 828 (M+H)$^+$

HRFABMS calcd for $C_{38}H_{42}N_3O_{12}S_3$ (M+H)$^+$ 828.1930, found 828.1939

Anal calcd for $C_{38}H_{41}N_3O_{12}S_3 \cdot 0.5H_2O$: C, 54.54; H, 5.06; N, 5.02; found: C, 54.67; H, 5.13; N, 4.94

EXAMPLE 151
Synthesis of Compound 163

According to the procedure as described in Example 45, Compound 163 (25 mg, 53% yield) was obtained from Compound 35 (35 mg, 0.056 mmol), N-Cbz-L-alanine (38 mg, 0.17 mmol), 1-ethyl-3-(3-dimethylaminopropyl)carbodiimide hydrochloride (32 mg, 0.17 mmol), dichloromethane (5 ml) and 4-dimethylaminopyridine (1.4 mg, 0.011 mmol).

IR (KBr) 3400, 2984, 2932, 1820, 1712, 1690, 1610, 1524, 1454, 1374, 1264, 1208, 1159, 1113, 1070, 977, 770, 697 cm$^{-1}$ $^1$H NMR (CDCl$_3$, 500 MHz) δ ppm; 9.06 (br dd, J=17.1, 11.0 Hz, 1H), 7.39 (s, 1H), 7.37–7.25 (m, 5H), 6.59 (d, J=11.6 Hz, 1H), 6.30 (br dd, J=11.6, 11.0 Hz, 1H), 6.01 (d, J=17.1 Hz, 1H), 5.76 (br d, J=9.2 Hz, 1H), 5.64 (d, J=9.2 Hz, 1H), 5.55 (q, J=6.7 Hz, 1H), 5.42 (br, 1H), 5.29 (br, 1H), 5.04 (br d, J=12.2 Hz, 1H), 5.00 (br d, J=12.2 Hz, 1H), 4.36 (m, 1H), 4.01 (d, J=17.7 Hz, 1H), 3.79 (d, J=15.3 Hz, 1H), 3.76 (d, J=15.3 Hz, 1H), 2.46–2.20 (m, 3H), 2.32 (d, J=17.7 Hz, 1H), 2.14 (s, 3H), 1.93 (d, J=6.7 Hz, 3H), 1.77 (br s, 3H), 1.70 (s, 3H), 1.68–1.60 (m, 1H), 1.37 (d, J=7.0 Hz, 3H)

FABMS m/z 828 (M+H)$^+$

HRFABMS calcd for $C_{38}H_{42}N_3O_{12}S_3$ (M+H)$^+$ 828.1930, found 828.1932

EXAMPLE 152
Synthesis of Compound 164

According to the procedure as described in Example 45, tert-butyldimethylsilyl ether compound of Compound 164 (90 mg, 86% yield) was obtained from Compound 35 (69 mg, 0.11 mmol), N-Cbz-O-tert-butyldimethylsilyl-L-serine (473 mg, 1.33 mmol), 1-ethyl-3-(3-dimethylaminopropyl) carbodiimide hydrochloride (257 mg, 1.33 mmol), tetrahydrofuran (14 ml) and 4-dimethylaminopyridine (9.5 mg, 0.077 mmol).

The obtained tert-butyldimethylsilyl ether compound (90 mg, 0.094 mmol) was dissolved in methanol (5 ml), and 3N hydrochloric acid (0.2 ml) was added thereto, followed by stirring for 1 hour. After subjecting the mixture to the usual post-treatment, the mixture was purified by thin layer chromatography (developed with chloroform/methanol=95/5) to obtain Compound 164 (12 mg, 15% yield).

IR (KBr) 3430, 2934, 1818, 1719, 1706, 1682, 1609, 1521, 1453, 1375, 1341, 1267, 1209, 1155, 1059, 979, 769 cm$^{-1}$ $^1$H NMR (CDCl$_3$, 400 MHz) δ ppm; 8.76 (br dd, J=16.6, 11.5 Hz, 1H), 7.38 (s, 1H), 7.40–7.26 (m, 5H), 6.60 (d, J=11.7 Hz, 1H), 6.27 (dd, J=11.7, 11.5 Hz, 1H), 6.06 (d, J=16.6 Hz, 1H), 5.84 (br d, J=8.5 Hz, 1H), 5.73 (br d, J=8.5 Hz, 1H), 5.71 (br, 1H), 5.47 (br q, J=6.6 Hz, 1H), 5.37 (br s, 1H), 5.15–5.00 (m, 2H), 4.46–3.98 (m, 1H), 3.98–3.80 (m, 2H), 3.96 (d, J=17.8 Hz, 1H), 3.77 (br s, 2H), 2.45–1.50 (m, 4H), 2.30 (d, J=17.8 Hz, 1H), 2.14 (s, 3H), 1.97 (d, J=6.6 Hz, 3H), 1.77 (br s, 3H), 1.74 (s, 3H)

FABMS m/z 844 (M+H)$^+$

HRFABMS calcd for C$_{38}$H$_{42}$N$_3$O$_{13}$S$_3$ (M+H)$^+$ 844.1880, found 844.1872

EXAMPLE 153
Synthesis of Compound 165

According to the procedure as described in Example 45, Compound 165 (18 mg, 22% yield) was obtained from Compound 35 (61 mg, 0.097 mmol), N-Boc-glycylglycine (208 mg, 0.90 mmol), 1-ethyl-3-(3-dimethylaminopropyl) carbodiimide hydrochloride (280 mg, 1.46 mmol), dichloromethane (6 ml) and 4-dimethylaminopyridine (18 mg, 0.15 mmol).

IR (KBr) 3400, 2984, 2938, 1819, 1773, 1703, 1685, 1610, 1534, 1369, 1267, 1169, 1109, 979, 770 cm$^{-1}$ $^1$H NMR (CDCl$_3$, 400 MHz) δ ppm; 9.21 (dd, J=16.6, 11.7 Hz, 1H), 7.44 (s, 1H), 6.63 (d, J=11.4 Hz, 1H), 6.55 (br dd, J=5.2, 4.9 Hz, 1H), 6.32 (dd, J=11.7, 11.4 Hz, 1H), 6.02 (dd, J=16.6, 0.8 Hz, 1H), 5.80 (br d, J=9.3 Hz, 1H), 5.76 (dd, J=9.3, 0.8 Hz, 1H), 5.57 (q, J=6.6 Hz, 1H), 5.46 (br s, 1H), 5.06 (br, 1H), 4.11 (dd, J=18.4, 11.4 Hz, 1H), 4.04 (d, J=17.8 Hz, 1H), 3.95 (dd, J=18.4, 4.9 Hz, 1H), 3.85–3.70 (m, 4H), 2.49–2.25 (m, 3H), 2.30 (d, J=17.8 Hz, 1H), 2.14 (s, 3H), 1.92 (d, J=6.6 Hz, 3H), 1.79 (d, J=1.0 Hz, 3H), 1.70 (s, 3H), 1.62–1.50 (m, 1H), 1.44 (s, 9H)

FABMS m/z 837 (M+H)$^+$

HRFABMS calcd for C$_{36}$H$_{45}$N$_4$O$_{13}$S$_3$ (M+H)$^+$ 837.2145, found 837.2169

EXAMPLE 154
Synthesis of Compound 166

According to the procedure as described in Example 45, Compound 166 (2.3 mg, 29% yield) was obtained from Compound 35 (5.6 mg, 0.0090 mmol), N-Cbz-glycylglycine (24 mg, 0.090 mmol), 1-ethyl-3-(3-dimethylaminopropyl) carbodiimide hydrochloride (18 mg, 0.090 mmol), dichloromethane (3 ml) and 4-dimethylaminopyridine (1 mg, 0.090 mmol).

IR (KBr) 3370, 2928, 1818, 1721, 1710, 1684, 1675, 1609, 1527, 1451, 1375, 1264, 1176, 1092, 977, 769 cm$^{-1}$ $^1$H NMR (CDCl$_3$, 500 MHz) δ ppm; 9.19 (dd, J=16.5, 11.6 Hz, 1H), 7.42 (s, 1H), 7.38–7.20 (m, 5H), 6.63 (d, J=11.3 Hz, 1H), 6.44 (br, 1H), 6.32 (dd, J=11.6, 11.3 Hz, 1H), 6.02 (d, J=16.5 Hz, 1H), 5.81 (d, J=9.5 Hz, 1H), 5.79 (d, J=9.5 Hz, 1H), 5.56 (q, J=6.7 Hz, 1H), 5.44 (br s, 1H), 5.33 (br, 1H), 5.12 (br s, 2H), 4.16–3.84 (m, 4H), 4.02 (d, J=17.7 Hz, 1H), 3.79 (d, J=15.3 Hz, 1H), 3.75 (d, J=15.3 Hz, 1H), 2.47–2.26 (m, 3H), 2.30 (d, J=17.7 Hz, 1H), 2.14 (s, 3H), 1.90 (d, J=6.7 Hz, 3H), 1.80 (d, J=1.0 Hz, 3H), 1.70 (s, 3H), 1.62–1.52 (m, 1H)

FABMS m/z 871 (M+H)$^+$

HRFABMS calcd for C$_{39}$H$_{43}$N$_4$O$_{13}$S$_3$ (M+H)$^+$ 871.1989, found 871.2014

EXAMPLE 155
Synthesis of Compound 167

According to the procedure as described in Example 45, Compound 167 (47 mg, 62% yield) was obtained from Compound 35 (59 mg, 0.090 mmol), N-benzoylglycylglycine (337 mg, 1.42 mmol), 1-ethyl-3-(3-dimethylaminopropyl)carbodiimide hydrochloride (272 mg, 1.42 mmol), dichloromethane (15 ml) and 4-dimethylaminopyridine (10 mg, 0.08 mmol).

IR (KBr) 3400, 2936, 1816, 1685, 1656, 1609, 1529, 1488, 1447, 1374, 1268, 1202, 1108, 978, 769, 714 cm$^{-1}$ $^1$H NMR (CDCl$_3$, 500 MHz) δ ppm; 9.17 (ddd, J=16.8, 11.5, 0.6 Hz, 1H), 7.84–7.76 (m, 2H), 7.54–7.40 (m, 3H), 7.42 (s, 1H), 7.06 (br t, J=5.2 Hz, 1H), 6.77 (br t, J=5.2 Hz, 1H), 6.62 (d, J=11.3 Hz, 1H), 6.31 (dd, J=11.5, 11.3 Hz, 1H), 6.00 (d, J=16.8 Hz, 1H), 5.80 (br s, 2H), 5.55 (q, J=6.7 Hz, 1H), 5.53 (br s, 1H), 4.20–3.92 (m, 4H), 4.04 (d, J=17.7 Hz, 1H), 3.80–3.70 (m, 2H), 2.48–2.28 (m, 3H), 2.31 (d, J=17.7 Hz, 1H), 2.14 (s, 3H), 1.92 (d, J=6.7 Hz, 3H), 1.78 (d, J=0.6 Hz, 3H), 1.67 (s, 3H), 1.65–1.55 (m, 1H)

FABMS m/z 841 (M+H)$^+$

HRFABMS calcd for C$_{38}$H$_{41}$N$_4$O$_{12}$S$_3$ (M+H)$^+$ 841.1883, found 841.1862

EXAMPLE 156
Synthesis of Compound 168

According to the procedure as described in Example 45, Compound 168 (27 mg, 30% yield) was obtained from Compound 35 (62 mg, 0.10 mmol), N-Cbz-L-alanylglycine (418 mg, 1.5 mmol), 1-ethyl-3-(3-dimethylaminopropyl) carbodiimide hydrochloride (287 mg, 1.5 mmol), tetrahydrofuran (10 ml) and 4-dimethylaminopyridine (11 mg, 0.090 mmol).

IR (KBr) 3400, 2982, 3942, 1818, 1717, 1686, 1677, 1609, 1521, 1452, 1376, 1262, 1205, 1130, 1000, 790, 718 cm$^{-1}$ $^1$H NMR (CDCl$_3$, 500 MHz) δ ppm; 9.19 (dd, J=16.4, 11.5 Hz, 1H), 7.43 (s, 1H), 7.38–7.26 (m, 5H), 6.63 (d, J=11.3 Hz, 1H), 6.53 (br, 1H), 6.32 (dd, J=11.5, 11.3 Hz, 1H), 6.02 (d, J=16.4 Hz, 1H), 5.79 (br d, J=9.8 Hz, 1H), 5.76 (d, J=9.8 Hz, 1H), 5.56 (q, J=6.7 Hz, 1H), 5.41 (br s, 1H), 5.23 (br, 1H), 5.11 (d, J=12.2 Hz, 1H), 5.09 (d, J=12.2 Hz, 1H), 4.28–4.20 (m, 1H), 4.11 (dd, J=18.3, 5.5 Hz, 1H), 4.02 (d, J=17.7 Hz, 1H), 3.89 (br d, J=18.3 Hz, 1H), 3.77 (s, 2H), 2.47–2.26 (m, 3H), 2.29 (d, J=17.7 Hz, 1H), 2.14 (s, 3H), 1.90 (d, J=6.7 Hz, 3H), 1.79 (d, J=1.0 Hz, 3H), 1.70 (s, 3H), 1.60–1.50 (m, 1H), 1.36 (d, J=7.3 Hz, 3H)

FABMS m/z 885 (M+H)$^+$

HRFABMS calcd for C$_{40}$H$_{45}$N$_4$O$_{13}$S$_3$ (M+H)$^+$ 885.2145, found 885.2125

EXAMPLE 157
Synthesis of Compound 169

According to the procedure as described in Example 45, Compound 169 (39 mg, 40% yield) was obtained from Compound 35 (70 mg, 0.11 mmol), N-Cbz-β-alanylglycine (316 mg, 1.12 mmol), 1-ethyl-3-(3-dimethylaminopropyl)carbodiimide hydrochloride (216 mg, 1.12 mmol), tetrahydrofuran (14 ml) and 4-dimethylaminopyridine (8.2 mg, 0.06 mmol).

IR (KBr) 3356, 2940, 1820, 1707, 1669, 1610, 1522, 1452, 1376, 1263, 1206, 1182, 1111, 979, 769, 735, 697 cm$^{-1}$ $^1$H NMR (CDCl$_3$, 400 MHz) δ ppm; 9.18 (dd, J=16.4, 11.3 Hz, 1H), 7.42 (s, 1H), 7.35–7.25 (m, 5H), 6.62 (d, J=11.5 Hz, 1H), 6.31 (dd, J=11.5, 11.3 Hz, 1H), 6.09 (m, 1H), 6.02 (d, J=16.4 Hz, 1H), 5.79 (br d, J=10.0 Hz, 1H), 5.77 (d, J=10.0 Hz, 1H), 5.55 (q, J=6.6 Hz, 1H), 5.42 (br s, 1H), 5.39 (m, 1H), 5.07 (br s, 2H), 4.09 (dd, J=18.3, 5.6 Hz, 1H), 4.02 (d, J=17.6 Hz, 1H), 3.90 (dd, J=18.3, 4.9 Hz, 1H), 3.79 (d, J=15.0 Hz, 1H), 3.75 (d, J=15.0 Hz, 1H), 3.52–3.40 (m, 2H), 2.50–2.25 (m, 5H), 2.30 (d, J=17.6 Hz, 1H), 2.14 (s, 3H), 1.90 (d, J=6.6 Hz, 3H), 1.79 (d, J=1.0 Hz, 3H), 1.70 (s, 3H), 1.60–1.48 (m, 1H)

FABMS m/z 885 (M+H)$^+$

HRFABMS calcd for C$_{40}$H$_{45}$N$_4$O$_{13}$S$_3$ (M+H)$^+$ 885.2145, found 885.2164

EXAMPLE 158
Synthesis of Compound 170

According to the procedure as described in Example 45, Compound 170 (14 mg, 21% yield) was obtained from Compound 35 (50 mg, 0.080 mmol), N-Boc-β-alanylglycine (198 mg, 0.80 mmol), 1-ethyl-3-(3-dimethylaminopropyl)carbodiimide hydrochloride (154 mg, 0.80 mmol), tetrahydrofuran (9 ml) and 4-dimethylaminopyridine (5.9 mg, 0.048 mmol).

IR (KBr) 3400, 2982, 2936, 1819, 1702, 1673, 1610, 1542, 1511, 1450, 1390, 1367, 1267, 1205, 1172, 1107, 978, 769 cm$^{-1}$ $^1$H NMR (CDCl$_3$, 400 MHz) δ ppm; 9.19, (dd, J=16.6, 11.5 Hz, 1H), 7.43 (s, 1H), 6.63 (d, J=11.5 Hz, 1H), 6.32 (t, J=11.5 Hz, 1H), 6.12 (br, 1H), 6.02 (d, J=16.6 Hz, 1H), 5.79 (d, J=9.5 Hz, 1H), 5.75 (d, J=9.5 Hz, 1H), 5.57 (q, J=6.8 Hz, 1H), 5.44 (br s, 1H), 5.10 (br s, 1H), 4.09 (dd, J=18.6, 5.6 Hz, 1H), 4.02 (d, J=17.8 Hz, 1H), 3.93 (dd, J=18.6, 4.8 Hz, 1H), 3.78 (br s, 2H), 3.45–3.30 (m, 2H), 2.50–1.45 (m, 6H), 2.30 (d, J=17.8 Hz, 1H), 2.14 (s, 3H), 1.92 (d, J=6.8 Hz, 3H), 1.79 (s, 3H), 1.71 (s, 3H), 1.43 (s, 9H)

FABMS m/z 851 (M+H)$^+$

HRFABMS calcd for C$_{37}$H$_{47}$N$_4$O$_{13}$S$_3$ (M+H)$^+$ 851.2302, found 851.2302

EXAMPLE 159
Synthesis of Compound 171

According to the procedure as described in Example 45, Compound 171 (16 mg, 16% yield) was obtained from Compound 35 (70 mg, 0.11 mmol), N-Cbz-γ-aminobutyrylglycine (498 mg, 1.7 mmol), 1-ethyl-3-(3-dimethylaminopropyl)carbodiimide hydrochloride (325 mg, 1.7 mmol), tetrahydrofuran (15 ml) and 4-dimethylaminopyridine (12 mg, 0.10 mmol).

IR (KBr) 3380, 2942, 1819, 1703, 1691, 1678, 1610, 1528, 1454, 1376, 1264, 1207, 1179, 1114, 979, 770, 739, 698 cm$^{-1}$ $^1$H NMR (CDCl$_3$, 500 MHz) δ ppm; 9.20 (dd, J=16.6, 11.2 Hz, 1H), 7.42 (s, 1H), 7.38–7.27 (m, 5H), 6.62 (d, J=11.5 Hz, 1H), 6.39 (br, 1H), 6.31 (dd, J=11.5, 11.2 Hz, 1H), 6.02 (d, J=16.6 Hz, 1H), 5.79 (d, J=9.5 Hz, 1H), 5.75 (d, J=9.5 Hz, 1H), 5.57 (q, J=6.7 Hz, 1H), 5.46 (br s, 1H), 5.08 (br s, 2H), 4.99 (br s, 1H), 4.07 (dd, J=18.1, 5.4 Hz, 1H), 4.02 (d, J=17.8 Hz, 1H), 3.92 (dd, J=18.1, 5.0 Hz, 1H), 3.77 (br s, 2H), 3.28–3.20 (m, 4H), 2.40–1.50 (m, 6H), 2.29 (d, J=17.8 Hz, 1H), 2.14 (s, 3H), 1.91 (d, J=6.7 Hz, 3H), 1.79 (d, J=1.0 Hz, 3H), 1.70 (s, 3H)

FABMS m/z 899 (M+H)$^+$

HRFABMS calcd for C$_{41}$H$_{47}$N$_4$O$_{13}$S$_3$ (M+H)$^+$ 899.2302, found 899.2315

EXAMPLE 160
Synthesis of Compound 172

According to the procedure as described in Example 45, Compound 172 (43 mg, 60% yield) was obtained from Compound 35 (51 mg, 0.081 mmol), N-Cbz-sarcosylglycine (229 mg, 0.81 mmol), 1-ethyl-3-(3-dimethylaminopropyl)carbodiimide hydrochloride (156 mg, 0.81 mmol), tetrahydrofuran (9 ml) and 4-dimethylaminopyridine (5.9 mg, 0.048 mmol).

IR (KBr) 3400, 3090, 2938, 1817, 1700, 1687, 1671, 1610, 1530, 1453, 1402, 1366, 1263, 1207, 1152, 1111, 1030, 978, 862, 808, 769, 734, 698 cm$^{-1}$ $^1$H NMR (CDCl$_3$, 400 MHz) δ ppm; 9.20 (br dd, J=16.5, 11.2 Hz, 1H), 7.43 (s, 1H), 7.40–7.25 (m, 5H), 6.63 (d, J=11.5 Hz, 1H), 6.47 (br, 1H), 6.32 (dd, J=11.5, 11.2 Hz, 1H), 6.02 (d, J=16.5 Hz, 1H), 5.78 (br d, J=9.3 Hz, 1H), 5.74 (d, J=9.3 Hz, 1H), 5.58 (q, J=6.6 Hz, 1H), 5.43 (br s, 1H), 5.14 (s, 2H), 4.12–3.88 (m, 2H), 4.03 (d, J=17.6 Hz, 1H), 3.96 (d, 16.6 Hz, 1H), 3.91 (d, J=16.6 Hz, 1H), 3.78 (s, 2H), 3.00 (s, 3H), 2.50–2.26 (m, 3H), 2.29 (d, J=17.6 Hz, 1H), 2.14 (s, 3H), 1.91 (d, J=6.6 Hz, 3H), 1.70 (d, J=1.0 Hz, 3H), 1.71 (s, 3H), 1.57–1.45 (m, 1H)

FABMS m/z 885 (M+H)$^+$

HRFABMS calcd for C$_{40}$H$_{45}$N$_4$O$_{13}$S$_3$ (M+H)$^+$ 885.2145, found 885.2135

Anal calcd for C$_{40}$H$_{44}$N$_4$O$_{13}$S$_3$·1.0H$_2$O: C, 53.20; H, 5.13; N, 6.20; found: C, 53.38; H, 5.20; N, 6.07

EXAMPLE 161
Synthesis of Compound 173

According to the procedure as described in Example 45, Compound 173 (37 mg, 36% yield) was obtained from Compound 35 (70 mg, 0.11 mmol), N-Cbz-leucylglycine (364 mg, 1.1 mmol), 1-ethyl-3-(3-dimethylaminopropyl)carbodiimide hydrochloride (217 mg, 1.1 mmol), tetrahydrofuran (14 ml) and 4-dimethylaminopyridine (8.3 mg, 0.06 mmol).

IR (KBr) 3400, 2960, 2932, 1819, 1715, 1680, 1610, 1516, 1452, 1375, 1264, 1208, 1110, 1039, 981, 768 cm$^{-1}$ $^1$H NMR (CDCl$_3$, 500 MHz) δ ppm; 9.21 (dd, J=16.6, 11.2 Hz, 1H), 7.43 (s, 1H), 7.36–7.26 (m, 5H), 6.63 (d, J=11.5 Hz, 1H), 6.52 (br, 1H), 6.32 (dd, J=11.5, 11.2 Hz, 1H), 6.02 (d, J=16.6 Hz, 1H), 5.80 (br d, J=9.5 Hz, 1H), 5.77 (d, J=9.5 Hz, 1H), 5.54 (q, J=6.7 Hz, 1H), 5.42 (br s, 1H), 5.13 (br, 1H), 5.10 (br s, 2H), 4.20 (br, 1H), 4.10 (dd, J=18.3, 5.8 Hz, 1H), 4.02 (d, J=18.0 Hz, 1H), 3.90 (br d, J=18.3 Hz, 1H), 3.77 (br s, 2H), 2.47–1.43 (m, 7H), 2.29 (d, J=18.0 Hz, 1H), 2.14 (s, 3H), 1.89 (d, J=6.7 Hz, 3H), 1.79 (d, J=1.0 Hz, 3H), 1.70 (s, 3H), 0.91 (d, J=6.3 Hz, 6H)

FABMS m/z 927 (M+H)$^+$

HRFABMS calcd for C$_{43}$H$_{51}$N$_4$O$_{13}$S$_3$(M+H)$^+$ 927.2414, found 927.2614

EXAMPLE 162
Synthesis of Compound 174

According to the procedure as described in Example 45, tert-butyldimethylsilyl ether compound of Compound 174 (90 mg, 68% yield) was obtained from Compound 35 (84 mg, 0.13 mmol), N-Cbz-O-tert-butyldimethylsilyl-L-serylglycine (712 mg, 1.74 mmol), 1-ethyl-3-(3-dimethylaminopropyl)carbodiimide hydrochloride (334 mg, 1.74 mmol), tetrahydrofuran (14 ml) and 4-dimethylaminopyridine (13 mg, 0.11 mmol).

The obtained tert-butyldimethylsilyl ether compound (85 mg, 0.084 mmol) was dissolved in methanol (5.0 ml), and 3N hydrochloric acid (0.5 ml) was added thereto, followed by stirring for 30 minutes. After subjecting the mixture to the usual post-treatment, the mixture was purified by thin layer chromatography (developed with chloroform/methanol=95/5) to obtain Compound 174 (13 mg, 17% yield).

IR (KBr) 3400, 2934, 1818, 1717, 1677, 1608, 1526, 1448, 1375, 1265, 1205, 1105, 975 $cm^{-1}$ $^1$H NMR (CDCl$_3$, 400 MHz) δ ppm; 9.11 (dd, J=16.4, 11.3 Hz, 1H), 7.42 (s, 1H), 7.38–7.28 (m, 5H), 6.95 (br, 1H), 6.63 (d, J=11.7 Hz, 1H), 6.31 (dd, J=11.7, 11.5 Hz, 1H), 6.02 (d, J=16.4 Hz, 1H), 5.78 (br s, 2H), 5.76 (br, 1H), 5.55 (q, J=6.8 Hz, 1H), 5.37 (br s, 1H), 5.12 (br s, 2H), 4.30–3.63 (m, 7H), 4.01 (d, J=17.8 Hz, 1H), 2.47–1.50 (m, 4H), 2.30 (d, J=17.8 Hz, 1H), 2.14 (s, 3H), 1.92 (d, J=6.8 Hz, 3H), 1.78 (s, 3H), 1.70 (s, 3H)

FABMS m/z 901 (M+H)$^+$

HRFABMS calcd for C$_{40}$H$_{45}$N$_4$O$_{14}$S$_3$ (M+H)$^+$ 901.2094, found 901.2068

EXAMPLE 163
Synthesis of Compound 175

According to the procedure as described in Example 45, Compound 175 (55 mg, 66% yield) was obtained from Compound 35 (58 mg, 0.093 mmol), N-Cbz-β-alanylsarcosine (330 mg, 1.12 mmol), 1-ethyl-3-(3-dimethylaminopropyl)carbodiimide hydrochloride (180 mg, 0.93 mmol), tetrahydrofuran (17 ml) and 4-dimethylaminopyridine (6.8 mg, 0.056 mmol).

IR (KBr) 3400, 2934, 1818, 1708, 1689, 1656, 1511, 1452, 1403, 1372, 1264, 1206, 1115, 978, 769, 698 $cm^{-1}$ $^1$H NMR (CDCl$_3$, 500 MHz) δ ppm; 9.11 (dd, J=16.5, 11.6 Hz, 1H), 7.41 (s, 1H), 7.36–7.20 (m, 5H), 6.61 (d, J=11.6 Hz, 1H), 6.31 (t, J=11.6 Hz, 1H), 6.03 (d, J=16.5 Hz, 1H), 5.77 (br s, 2H), 5.55 (q, J=6.7 Hz, 1H), 5.52–5.40 (m, 2H), 5.07 (br s, 2H), 4.28 (d, J=17.1 Hz, 1H), 4.02 (d, J=17.7 Hz, 1H), 3.91 (d, J=17.1 Hz, 1H), 3.77 (br s, 2H), 3.50–3.40 (m, 2H), 2.97 (s, 3H), 2.62–2.10 (m, 6H), 2.29 (d, J=17.7 Hz, 1H), 2.14 (s, 3H), 1.93 (d, J=6.7 Hz, 3H), 1.78 (s, 3H), 1.70 (s, 3H)

FABMS m/z 899 (M+H)$^+$

HRFABMS calcd for C$_{41}$H$_{47}$N$_4$O$_{13}$S$_3$ (M+H)$^+$ 899.2302, found 899.0309

EXAMPLE 164
Synthesis of Compound 176

According to the procedure as described in Example 45, Compound 176 (34 mg, 48% yield) was obtained from Compound 35 (50 mg, 0.080 mmol), N-Cbz-glycyl-β-alanine (272 mg, 0.97 mmol), 1-ethyl-3-(3-dimethylaminopropyl)carbodiimide hydrochloride (186 mg, 0.97 mmol), tetrahydrofuran (9 ml) and 4-dimethylaminopyridine (6.9 mg, 0.056 mmol).

IR (KBr) 3400, 2938, 1820, 1720, 1678, 1610, 1531, 1454, 1374, 1261, 1208, 1170, 1090, 979, 769, 699 $cm^{-1}$ $^1$H NMR (CDCl$_3$, 500 MHz) δ ppm; 8.99 (d, J=16.5, 11.8 Hz, 1H), 7.39 (s, 1H), 7.38–7.29 (m, 5H), 6.66 (br t, J=8.2 Hz, 1H), 6.60 (d, J=11.6 Hz, 1H), 6.27 (dd, J=11.8, 11.6 Hz, 1H), 6.03 (d, J=16.5 Hz, 1H), 5.76 (s, 2H), 5.52 (q, J=6.7 Hz, 1H), 5.42 (br s, 1H), 5.41 (br, 1H), 5.12 (s, 2H), 4.00 (d, J=17.7 Hz, 1H), 3.83 (d, J=8.2 Hz, 2H), 3.77 (s, 2H), 3.59–3.46 (m, 2H), 2.54 (t, J=5.8 Hz, 2H), 2.46–2.24 (m, 3H), 2.28 (d, J=17.7 Hz, 1H), 2.14 (s, 3H), 1.93 (s, 3H), 1.77 (s, 3H), 1.72 (s, 3H), 1.65–1.55 (m, 1H)

FABMS m/z 885 (M+H)$^+$

HRFABMS calcd for C$_{40}$H$_{45}$N$_4$O$_{13}$S$_3$ (M+H)$^+$ 885.2145, found 885.2133

EXAMPLE 165
Synthesis of Compound 177

According to the procedure as described in Example 45, Compound 177 (60 mg, 61% yield) was obtained from Compound 35 (71 mg, 0.11 mmol), N-Cbz-β-alanyl-β-alanine (503 mg, 1.7 mmol), 1-ethyl-3-(3-dimethylaminopropyl)carbodiimide hydrochloride (327 mg, 1.7 mmol), tetrahydrofuran (17 ml) and 4-dimethylaminopyridine (12 mg, 0.10 mmol).

IR (KBr) 3382, 2942, 1818, 1710, 1690, 1678, 1648, 1610, 1531, 1453, 1373, 1264, 1208, 1168, 1094, 977, 769, 698 $cm^{-1}$ $^1$H NMR (CDCl$_3$, 400 MHz) δ ppm; 9.01 (dd, J=16.6, 11.2 Hz, 1H), 7.38 (s, 1H), 7.38–7.25 (m, 5H), 6.60 (d, J=11.5 Hz, 1H), 6.33 (br, 1H), 6.27 (dd, J=11.5, 11.2 Hz, 1H), 6.03 (d, J=16.6 Hz, 1H), 5.76 (s, 2H), 5.52 (q, J=6.6 Hz, 1H), 5.43 (br, 1H), 5.42 (br s, 1H), 5.09 (br s, 2H), 4.00 (d, J=17.6 Hz, 1H), 3.77 (br s, 2H), 3.55–3.40 (m, 4H), 2.55–1.55 (m, 8H), 2.27 (d, J=17.6 Hz, 1H), 2.14 (s, 3H), 1.92 (d, J=6.6 Hz, 3H), 1.77 (s, 3H), 1.72 (s, 3H)

FABMS m/z 899 (M+H)$^+$

HRFABMS calcd for C$_{41}$H$_{47}$N$_4$O$_{13}$S$_3$ (M+H)$^+$ 899.2302, found 899.2291

INDUSTRIAL APPLICABILITY

The present invention provides DC107 derivatives having an antibacterial activity and an antitumor activity or pharmacologically acceptable slats thereof.

What is claimed is:

1. A compound represented by formula (I):

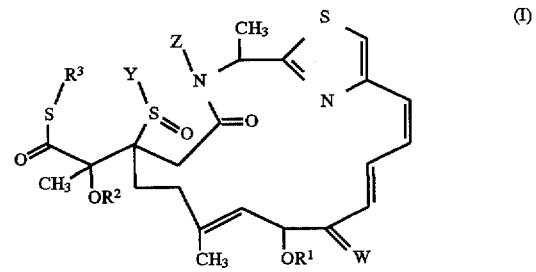

wherein

R$^1$ represents hydrogen, a lower alkoxyalkyl group, an aralkyloxyalkyl group, a lower alkoxyalkoxyalkyl group, a lower alkoxyalkoxyalkoxyalkyl group, an aralkyl group, a tetrahydropyranyl group,

{wherein Q$^1$ represents CH$_2$, O, S, SO, SO$_2$ or N—Q$^3$ (wherein Q$^3$ represents a substituted or unsubstituted aryl group or a lower alkoxycarbonyl group), and Q$^2$ represents a lower alkyl group}, or COR$^4$ {wherein R$^4$ represents an alkyl group, an alicyclic alkyl group, an aralkyl group, a substituted or unsubstituted aryl group, a substituted or unsubstituted heterocyclic group, a lower alkoxy group, an alicyclic alkoxy group, a 9-fluorenylmethoxy group, an aralkyloxy group, a substituted or unsubstituted aryloxy group, (CH$_2$)$_m$R$^{4A}$ (wherein m represents an integer of from 1 to 6, R$^{4A}$ represents hydroxy, a lower alkoxy group, a carboxyl group, a lower alkoxycarbonyl group, a substituted or unsubstituted aryl group, a substituted or unsubstituted heterocyclic group, a substituted or unsubstituted aralkyloxy group, or NR$^{4B}$COR$^{4C}$ {wherein R$^{4B}$ represents hydrogen or a lower alkyl group, and R$^{4C}$ represents hydrogen, a lower alkyl group, a lower alkoxy group, an aralkyloxy group, an aryl group, an aryloxy group, a 9-fluorenylmethoxy group, (CH$_2$)$_n$NHCOR$^{4D}$ (wherein n represents an integer of from 1 to 6, R$^{4D}$ represents an alkyl group, a lower alkoxy group, an aralkyloxy group, an aryl group, an aryloxy group or a 9-fluorenylmethyloxy group) or CHR$^{4E}$NHCOR$^{4F}$ (wherein R$^{4E}$ represents a lower alkyl group or a hydroxy lower alkyl group, and R$^{4F}$ has the same meaning as R$^{4D}$)}) or CHR$^{4G}$NHCOR$^{4H}$ (wherein R$^{4G}$ has the same meaning as R$^{4E}$, and R$^{4H}$ has the same meaning as R$^{4C}$)};

R$^2$ represents hydrogen or COR$^5$ (wherein R$^5$ represents a lower alkyl group, an aralkyl group, a substituted or unsubstituted aryl group, or a substituted or unsubstituted heterocyclic group);

R$^3$ represents a lower alkyl group, a lower alkenyl group, a substituted or unsubstituted aralkyl group, in which aryl may be substituted, a lower alkoxyalkyl group, an aralkyloxyalkyl group, a substituted or unsubstituted aryloxyalkyl group, a lower alkoxycarbonylalkyl group, a lower alkanoyloxyalkyl group, an alicyclic alkanoyloxyalkyl group, or

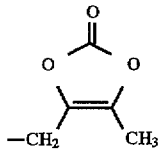

or R$^3$ bonds to Y to represent a single bond;

Y bonds to R$^3$ to represent a single bond or bonds to Z to represent a single bond;

Z represents hydrogen or bonds to Y to represent a single bond;

W represents oxygen or NR$^6$ (wherein R$^6$ represents a hydroxyl group, a lower alkoxy group, a lower alkenyloxy group, an aralkyloxy group, a substituted or unsubstituted arylsulfonylamino group or a lower alkoxycarbonylamino group), with the proviso that when R$^1$, R$^2$ and Z each represent hydrogen and R$^3$ bonds to Y to represent a single bond, then W cannot represent oxygen or a pharmacologically acceptable salt thereof.

2. The compound or the pharmacologically acceptable salt thereof according to claim 1, wherein Y bonds to Z to represent a single bond.

3. The compound or the pharmacologically acceptable salt thereof according to claim 1, wherein Y bonds to R$^3$ to represent a single bond.

4. The compound or the pharmacologically acceptable salt thereof according to claim 1, wherein W is oxygen.

5. The compound or the pharmacologically acceptable salt thereof according to claim 1, wherein W is NR$^6$ (wherein R$^6$ represents hydroxy, a lower alkoxy group, a lower alkenyloxy group, an aralkyloxy group, a substituted or unsubstituted arylsulfonylamino group or a lower alkoxycarbonylamino group.

6. The compound or the pharmacologically acceptable salt thereof according to claim 2, wherein W is oxygen.

7. The compound or the pharmacologically acceptable salt thereof according to claim 6, wherein R$^1$ is a tetrahydropyranyl group or

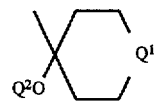

{wherein Q$^1$ represents CH$_2$, O, S, SO, SO$_2$ or N—Q$^{13}$ (wherein Q$^3$ represents a substituted or unsubstituted aryl group or a lower alkoxycarbonyl group) and Q$^2$ represents a lower alkyl group}.

8. The compound or the pharmacologically acceptable salt thereof according to claim 6 wherein R$^1$ is CO(CH$_2$)$_m$R$^{4A}$, wherein m represents an integer of from 1 to 6; R$^{4A}$ represents hydroxy, a lower alkoxy group, a carboxyl group, a lower alkoxycarbonyl group, a substituted or unsubstituted aryl group, a substituted or unsubstituted heterocyclic group, a substituted or unsubstituted aralkyloxy group, or NR$^{4B}$COR$^{4C}$ {wherein R$^{4B}$ represents hydrogen or a lower alkyl group; and R$^{4C}$ represents hydrogen, a lower alkyl group, a lower alkoxy group, an aralkyloxy group, an aryl group, an aryloxy group, a 9-fluorenylmethoxy group, (CH$_2$)$_n$NHCOR$^{4D}$ (wherein n represents an integer of from 1 to 6, R$^{4D}$ represents an alkyl group, a lower alkoxy group or a 9-fluorenylmethoxy group) or CHR$^{4E}$NHCOR$^{4F}$ (wherein R$^{4E}$ represents a lower alkyl group or a hydroxy lower alkyl group, and R$^{4F}$ has the same meaning as R$^{4D}$)}, or COCHR$^{4G}$NHCOR$^{4H}$ (wherein R$^{4G}$ has the same meaning as R$^{4E}$, and R$^{4H}$ has the same meaning as R$^{4C}$).

9. The compound or the pharmacologically acceptable salt thereof according to claim 7, wherein R$^3$ is

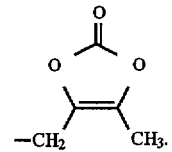

10. An antibacterial agent comprising a compound or the pharmacologically acceptable salt thereof according to claim 1 as an active ingredient.

11. An antitumor agent comprising a compound or the pharmacologically acceptable salt thereof according to claim 1 as an active ingredient.

12. A pharmaceutical composition comprising a therapeutically effective amount of a compound represented by formula (I):

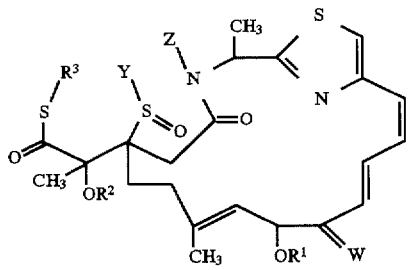

or a pharmacologically acceptable salt thereof, wherein $R^1$ represents hydrogen, a lower alkoxyalkyl group, an aralkyloxyalkyl group, a lower alkoxyalkoxyalkyl group, a lower alkoxyalkoxyalkoxyalkyl group, an aralkyl group, a tetrahydropyranyl group,

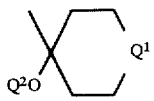

{wherein $Q^1$ represents $CH_2$, O, S, SO, $SO_2$ or $N-Q^3$ (wherein $Q^3$ represents a substituted or unsubstituted aryl group or a lower alkoxycarbonyl group), and $Q^2$ represents a lower alkyl group}, or $COR^4$ {wherein $R^4$ represents an alkyl group, an alicyclic alkyl group, an aralkyl group, a substituted or unsubstituted aryl group, a substituted or unsubstituted heterocyclic group, a lower alkoxy group, an alicyclic alkoxy group, a 9-fluorenylmethoxy group, an aralkyloxy group, a substituted or unsubstituted aryloxy group, $(CH_2)_m R^{4A}$ (wherein m represents an integer of from 1 to 6, $R^{4A}$ represents hydroxy, a lower alkoxy group, a carboxyl group, a lower alkoxycarbonyl group, a substituted or unsubstituted aryl group, a substituted or unsubstituted heterocyclic group, a substituted or unsubstituted aralkyloxy group, or $NR^{4B}COR^{4C}$ {wherein $R^{4B}$ represents hydrogen or a lower alkyl group, and $R^{4C}$ represents hydrogen, a lower alkyl group, a lower alkoxy group, an aralkyloxy group, an aryl group, an aryloxy group, a 9-fluorenylmethoxy group, $(CH_2)_n NHCOR^{4D}$ (wherein n represents an integer of from 1 to 6, $R^{4D}$ represents an alkyl group, a lower alkoxy group, an aralkyloxy group, an aryl group, an aryloxy group or a 9-fluorenylmethyloxy group) or $CHR^{4E}NHCOR^{4F}$ (wherein $R^{4E}$ represents a lower alkyl group or a hydroxy lower alkyl group, and $R^{4F}$ has the same meaning as $R^{4D}$)}} or $CHR^{4G}NHCOR^{4H}$ (wherein $R^{4G}$ has the same meaning as $R^{4E}$, and $R^{4H}$ has the same meaning as $R^{4C}$)};

$R^2$ represents hydrogen or $COR^5$ (wherein $R^5$ represents a lower alkyl group, an aralkyl group, a substituted or unsubstituted aryl group, or a substituted or unsubstituted heterocyclic group);

$R^3$ represents a lower alkyl group, a lower alkenyl group, a substituted or unsubstituted aralkyl group, in which aryl may be substituted, a lower alkoxyalkyl group, an aralkyloxyalkyl group, a substituted or unsubstituted aryloxyalkyl group, a lower alkoxycarbonylalkyl group, a lower alkanoyloxyalkyl group, an alicyclic alkanoyloxyalkyl group, or

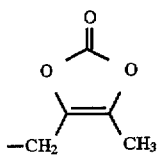

or $R^3$ bonds to Y to represent a single bond;

Y bonds to $R^3$ to represent a single bond or bonds to Z to represent a single bond;

Z represents hydrogen or bonds to Y to represent a single bond;

W represents oxygen or $NR^6$ (wherein $R^6$ represents a hydroxyl group, a lower alkoxy group, a lower alkenyloxy group, an aralkyloxy group, a substituted or unsubstituted arylsulfonylamino group or a lower alkoxycarbonylamino group), with the proviso that when $R^1$, $R^2$ and Z each represent hydrogen and $R^3$ bonds to Y to represent a single bond, then W cannot represent oxygen, and a pharmacologically acceptable carrier therefor.

13. A method for treating a patient exhibiting symptoms of bacterial activity comprising:

administering an effective antibacterial amount of a compound or a pharmacologically acceptable salt thereof, as defined in claim 1.

14. A method for treating a patient exhibiting symptoms of tumor activity comprising:

administering an effective antitumor amount of a compound or a pharmacologically acceptable salt thereof, as defined in claim 1.

* * * * *

UNITED STATES PATENT AND TRADEMARK OFFICE
CERTIFICATE OF CORRECTION

PATENT NO. : 5,733,924

DATED : March 31, 1998

INVENTOR(S) : YUTAKA KANDA, ET AL.

It is certified that error appears in the above-identified patent and that said Letters Patent is hereby corrected as shown below:

On title page, item

[87] PCT Pub. Date change "March 1, 1997" to --Jan. 3, 1997--.

[57] ABSTRACT, line 2, change "slats" to --salts--.

COLUMN 50

Line 9, "chloroform/methanol=7/" should read --chloroform/methanol=97/--.

COLUMN 100

Line 39, "slats" should read --salts--.

COLUMN 102

Line 20, "N-Q$^{13}$" should read --N-Q$^3$--; and
Line 26, "claim 6" should read --claim 6,--.

Signed and Sealed this

Twenty-ninth Day of December, 1998

Attest:

BRUCE LEHMAN

*Attesting Officer*    *Commissioner of Patents and Trademarks*